United States Patent
Arora et al.

(10) Patent No.: US 9,309,230 B2
(45) Date of Patent: *Apr. 12, 2016

(54) OLIGOOXOPIPERAZINES AND METHODS OF MAKING AND USING THEM

(71) Applicant: New York University, New York, NY (US)

(72) Inventors: Paramjit S. Arora, Cold Spring Harbor, NY (US); Petra Tošovská, New York, NY (US); Danielle Guarracino, Princeton, NJ (US); Brooke Bullock Lao, Leesville, SC (US)

(73) Assignee: New York University, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/304,304

(22) Filed: Jun. 13, 2014

(65) Prior Publication Data

US 2015/0072991 A1    Mar. 12, 2015

Related U.S. Application Data

(63) Continuation of application No. 12/917,176, filed on Nov. 1, 2010, now Pat. No. 8,791,121.

(60) Provisional application No. 61/373,108, filed on Aug. 12, 2010.

(51) Int. Cl.
| | |
|---|---|
| *A61K 31/496* | (2006.01) |
| *C07D 403/06* | (2006.01) |
| *C07D 403/14* | (2006.01) |
| *C07D 241/08* | (2006.01) |

(52) U.S. Cl.
CPC ............ *C07D 403/14* (2013.01); *C07D 241/08* (2013.01); *C07D 403/06* (2013.01); *A61K 31/496* (2013.01)

(58) Field of Classification Search
CPC .. A61K 31/496; C07D 403/06; C07D 403/14; C07D 241/08
See application file for complete search history.

(56) References Cited

U.S. PATENT DOCUMENTS

| | | | |
|---|---|---|---|
| 4,758,652 A | 7/1988 | Heitz et al. | |
| 5,369,103 A | 11/1994 | Cliffe et al. | |
| 6,841,675 B1 | 1/2005 | Schmidt et al. | |
| 8,791,121 B2 * | 7/2014 | Arora et al. | 514/252.11 |
| 2012/0040992 A1 | 2/2012 | Arora et al. | |

FOREIGN PATENT DOCUMENTS

| | | |
|---|---|---|
| WO | 03-062212 A1 | 7/2003 |
| WO | 2009/097486 A1 | 6/2009 |

OTHER PUBLICATIONS

Tosovska, et al., Oligooxopiperazines as Nonpeptidic α-Helix Mimetics, Organic Letters, 12(7), 1588-1591 (2010).*
Arora, "Non-Peptidic α-Helix and β-Strand Mimetics," Award Abstract No. 0848410 (National Science Foundation, Feb. 1, 2009).
Arora, Synthetic Strategies for Targeting Protein Interfaces (Nov. 2, 2009).
European Patent Application No. 10855990.7, Extended European Search Report (Jan. 15, 2014).
PCT US/2010/054983, International Search Report (Oct. 20, 2011).
PCT US/2010/054983, Written Opinion (Oct. 20, 2011).
Tošovská & Arora, "Oligooxopiperazines as Nonpeptidic Alpha-Helix Mimetics," Org. Lett. 12:1588-91 (2010).
Extended European Search Report for corresponding European Patent Application No. 14181686.8 (Apr. 14, 2015).
International Preliminary Report on Patentability for corresponding International Application No. PCT/US2010/054983 (Feb. 12, 2013).

* cited by examiner

*Primary Examiner* — Erich A Leeser
(74) *Attorney, Agent, or Firm* — LeClairRyan, a Professional Corporation

(57) ABSTRACT

The present invention relates to oligooxopiperazines and their use. Methods for preparing oligooxopiperazines are also disclosed.

41 Claims, 76 Drawing Sheets

ALKYLATING AGENT A (X-CH$_2$-CH=CH)

| SOLID PHASE | SOLUTION PHASE |
|---|---|
| STEP A: ALKYLATE 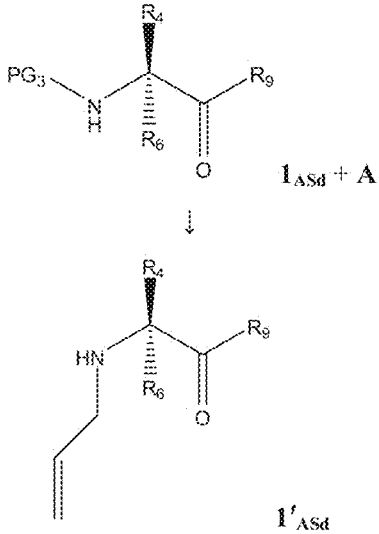 | STEP A: ALKYLATE 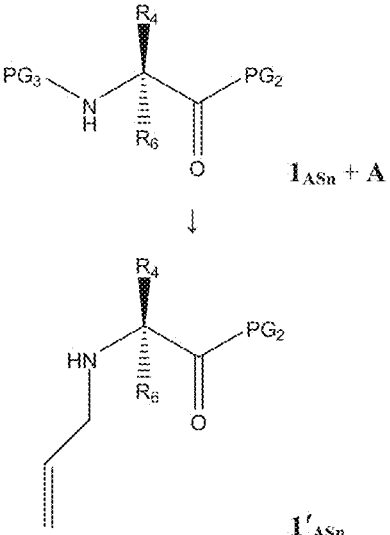 |
| PG$_2$ = protecting group for protecting carboxylic acid<br>PG$_3$ = protecting group for protecting amine that allows for alkylation<br>R$_9$ = –O-Res or –NH-Res, Res = solid phase peptide synthesis resin<br>A = Alkylating agent A | |
| STEP B: COUPLE 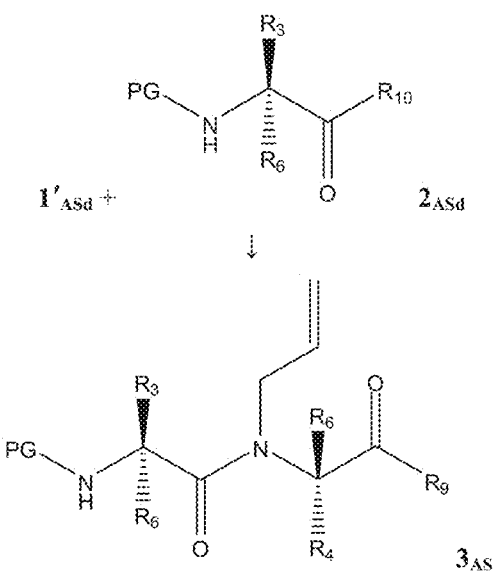 | STEP B: COUPLE 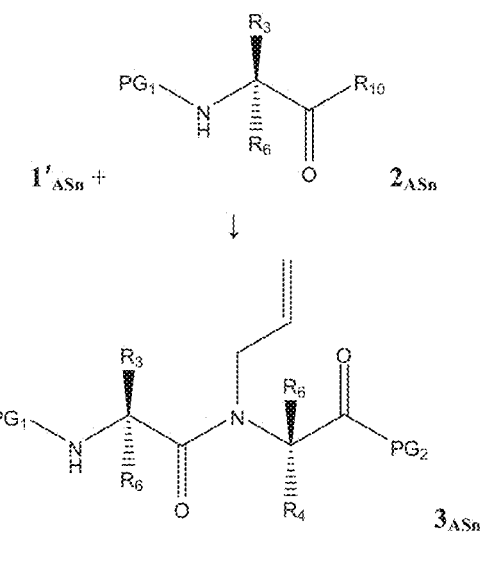 |
| PG, PG$_1$ = protecting group for protecting amine<br>R$_9$ = –O-Res or –NH-Res, Res = solid phase peptide synthesis resin<br>R$_{10}$ = –OH or a halide | |

*FIG. 1A*

ALKYLATING AGENT B (X-CH$_2$-CH(OR$_{11}$)$_2$)

| SOLID PHASE | SOLUTION PHASE |
|---|---|
| STEP A: ALKYLATE | STEP A: ALKYLATE |
| $1_{BSd}$ + B → $1'_{BSd}$ | $1_{BSn}$ + B → $1'_{BSn}$ |

PG$_2$ = protecting group for protecting carboxylic acid
PG$_3$ = protecting group for protecting amine that allows for alkylation
R$_9$ = –O-Res or –NH-Res, Res = solid phase peptide synthesis resin
R$_{11}$ = alkyl
B = Alkylating agent B

| STEP B: COUPLE | STEP B: COUPLE |
|---|---|
| $1'_{BSd}$ + $2_{BSd}$ → $3_{BSd}$ | $1'_{BSn}$ + $2_{BSn}$ → $3_{BSn}$ |

PG, PG$_1$ = protecting group for protecting amine
PG$_2$ = protecting group for protecting carboxylic acid
R$_9$ = –O-Res or –NH-Res, Res = solid phase peptide synthesis resin
R$_{10}$ = –OH or a halide
R$_{11}$ = alkyl

*FIG. 1C*

ALKYLATING AGENT D (X-(CH$_2$)$_2$-OH)

| SOLID PHASE | SOLUTION PHASE |
|---|---|
| STEP A: COUPLE | STEP A: COUPLE |

PG, PG$_1$ = protecting group for protecting amine
PG$_2$ = protecting group for protecting carboxylic acid
PG$_3$ = protecting group for protecting amine that allows for alkylation
R$_9$ = –O-Res or –NH-Res, Res = solid phase peptide synthesis resin
R$_{10}$ = –OH or a halide

| STEP B: ALKYLATE | STEP B: ALKYLATE |
|---|---|
| 3$_{DSd}$ + D | 3$_{DSn}$ + D |

PG$_2$ = protecting group for protecting carboxylic acid
PG$_3$ = protecting group for protecting amine that allows for alkylation
R$_9$ = –O-Res or –NH-Res, Res = solid phase peptide synthesis resin
D = Alkylating agent D

*FIG. 1G* half-chair
ΔG ~ −3.0 Kcal/mol boat trans amide
ΔG ~ −1.0 Kcal/mol cis amide

TRIMER

| oxopiperazine position | $R_1$ | $R_2$ | $R_3$ | $R_4$ | $R_5$ |
|---|---|---|---|---|---|
| helix position | i | i+4 | -- | i+6 | i+7 |

| DIMER A | | | | |
|---|---|---|---|---|
| oxopiperazine position | $R_1$ | $R_2$ | $R_3$ | $R_4$ |
| helix position | i | i+4 | -- | i+7 |

| oxopiperazine position | DIMER B | | | |
|---|---|---|---|---|
| | R₁ | R₂ | R₃ | R₄ |
| helix position | i | i+4 | -- | i+6 |

DIMER C

| oxopiperazine position | R₀ | R₁ | R₂ | R₃ | R₄ |
|---|---|---|---|---|---|
| helix position | i | i+2 | i+3 | i+4 | i+7 |

| A. PDB Code | B. Interface Chains | C. Chain | D. Title | E. Function | F. $G_{AVG,HELIX}$ (Kcal/mol) | G. $G_{SEM,HELIX}$ (Kcal/mol) | H. $G_{SEM,CHAIN}$ (Kcal/mol) | I. Helix Contribution | J. # Hotspot Residues | K. Hotspot Residues Residue #, $G_{(KCAL/MOL)}$ |
|---|---|---|---|---|---|---|---|---|---|---|
| 1A00 | AB | A | CHEY-BINDING DOMAIN OF CHEA IN COMPLEX WITH CHEY | CHEMOTAXIS | 2.0 | 4.1 | 4.1 | 100% | 2 | K122, 2.0; E125, 2.0; |
| 1A00 | CD | D | CHEY-BINDING DOMAIN OF CHEA IN COMPLEX WITH CHEY | CHEMOTAXIS | 2.2 | 4.4 | 4.4 | 100% | 2 | V211, 1.1; F214, 3.3; |
| 1A4Y | DE | E | RIBONUCLEASE INHIBITOR-ANGIOGENIN COMPLEX | COMPLEX (INHIBITOR/NUCLEASE) | 2.0 | 3.9 | 5.1 | 76% | 2 | R5, 1.9; H8, 2.0; |
| 1A9N | AB | B | CRYSTAL STRUCTURE OF THE SPLICEOSOMAL U2B"-U2A' PROTEIN COMPLEX BOUND TO A FRAGMENT OF U2 SMALL NUCLEAR RNA | RNA BINDING PROTEIN/RNA | 2.0 | 3.9 | 3.9 | 100% | 2 | R28, 1.8; Y31, 2.1; |
| 1AY7 | AB | B | RIBONUCLEASE SA COMPLEX WITH BARSTAR | COMPLEX (ENZYME/INHIBITOR) | 2.2 | 4.4 | 7.7 | 57% | 2 | D35, 1.5; D39, 2.9; |
| 1B0N | AB | B | SINR PROTEIN/SINI PROTEIN COMPLEX | TRANSCRIPTION REGULATOR | 2.0 | 5.9 | 27.4 | 22% | 3 | I32, 1.1; Y35, 2.6; L36, 2.2; |
| 1B27 | BE | E | STRUCTURAL RESPONSE TO MUTATION AT A PROTEIN-PROTEIN INTERFACE | HYDROLASE/HYDROLASE INHIBITOR | 3.2 | 6.3 | 11.2 | 56% | 2 | D36, 1.5; D40, 4.8; |
| 1B9X | AB | B | STRUCTURAL ANALYSIS OF PHOSDUCIN AND ITS PHOSPHORYLATION-REGULATED INTERACTION WITH TRANSDUCIN | SIGNALING PROTEIN | 2.4 | 7.2 | 18.4 | 39% | 3 | F540, 3.8; Y543, 2.4; V544, 1.0; |
| 1BDJ | AB | B | COMPLEX STRUCTURE OF HPT DOMAIN AND CHEY | COMPLEX (CHEMOTAXIS TRANSFERASE) | 2.1 | 4.1 | 8.0 | 51% | 2 | E750, 1.3; E754, 2.8; |

FIG. 11A1

| A. | B. | C. | D. | L. | M. | N. | O. | P. | Q. | R. | S. |
|---|---|---|---|---|---|---|---|---|---|---|---|
| PDB Code | Interface Chains | Chain | Title | Hotspot Residue Helix Positions | Hotspot Residue End to End Length | Helix Length | Helix Start Residue # | Helix End Residue # | Helix Sequence | SEQ ID NO: | Resolution |
| 1A0O | AB | A | CHEY-BINDING DOMAIN OF CHEA IN COMPLEX WITH CHEY | i; i+3; | 4 | 14 | 113 | 126 | AATLEEKLNKIFEK | 1 | 2.95 |
| 1A0O | CD | D | CHEY-BINDING DOMAIN OF CHEA IN COMPLEX WITH CHEY | i; i+3; | 4 | 12 | 205 | 216 | EDDITAVLCFVI | 2 | 2.95 |
| 1A4Y | DE | E | RIBONUCLEASE INHIBITOR-ANGIOGENIN COMPLEX | i; i+3; | 4 | 9 | 5 | 13 | RYTHFLTQH | 3 | 2.00 |
| 1A9N | AB | B | CRYSTAL STRUCTURE OF THE SPLICEOSOMAL U2B"-U2A' PROTEIN COMPLEX BOUND TO A FRAGMENT OF U2 SMALL NUCLEAR RNA | i; i+3; | 4 | 12 | 23 | 34 | KEELKRSLYALF | 4 | 2.38 |
| 1AY7 | AB | B | RIBONUCLEASE SA COMPLEX WITH BARSTAR | i; i+4; | 5 | 9 | 34 | 42 | LDALWDCLT | 5 | 1.70 |
| 1B0N | AB | B | SINR PROTEIN/SINI PROTEIN COMPLEX | i; i+3; i+4; | 5 | 11 | 29 | 39 | PEEIRKYLLLN | 6 | 1.90 |
| 1B27 | BE | E | STRUCTURAL RESPONSE TO MUTATION AT A PROTEIN-PROTEIN INTERFACE | i; i+4; | 5 | 9 | 35 | 43 | LDALWDALT | 7 | 2.10 |
| 1B9X | AB | B | STRUCTURAL ANALYSIS OF PHOSDUCIN AND ITS PHOSPHORYLATION- REGULATED INTERACTION WITH TRANSDUCIN | i; i+3; i+4; | 5 | 14 | 533 | 546 | VSKCCEEFRDYVEE | 8 | 3.00 |
| 1BDJ | AB | B | COMPLEX STRUCTURE OF HPT DOMAIN AND CHEY | i; i+4; | 5 | 15 | 744 | 758 | WEDNVGEWIEEMK EE | 9 | 2.68 |

FIG. 11A2

| A. PDB Code | B. Interface Chains | C. Chain | D. Title | E. Function | F. $G_{AVG,HELIX}$ (Kcal/mol) | G. $G_{SEM,HELIX}$ (Kcal/mol) | H. $G_{SEM,CHAIN}$ (Kcal/mol) | I. Helix Contribution | J. # Hotspot Residues | K. Hotspot Residues Residue #, $G_{(KCAL/MOL)}$ |
|---|---|---|---|---|---|---|---|---|---|---|
| 1BXL | AB | B | STRUCTURE OF BCL-XL/BAK PEPTIDE COMPLEX, NMR, MINIMIZED AVERAGE STRUCTURE | COMPLEX (APOPTOSIS/PEPTIDE) | 2.4 | 4.8 | 7.1 | 68% | 2 | L78, 2.7; I81, 2.1; |
| 1D2Z | CB | C | THREE-DIMENSIONAL STRUCTURE OF A COMPLEX BETWEEN THE DEATH DOMAINS OF PELLE AND TUBE | APOPTOSIS | 2.0 | 4.0 | 5.7 | 70% | 2 | N112, 1.6; R115, 2.4; |
| 1DE4 | GI | G | HEMOCHROMATOSIS PROTEIN HFE COMPLEXED WITH TRANSFERRIN RECEPTOR | METAL TRANSPORT INHIBITOR/ RECEPTOR | 2.0 | 3.9 | 14.5 | 27% | 2 | E146, 1.6; H150, 2.3; |
| 1DML | CD | D | CRYSTAL STRUCTURE OF HERPES SIMPLEX UL42 BOUND TO THE C-TERMINUS OF HSV POL | DNA BINDING PROTEIN/ TRANSFERASE | 3.8 | 7.6 | 14.4 | 53% | 2 | F1231, 5.2; L1234, 2.4; |
| 1DOA | AB | A | STRUCTURE OF THE RHO FAMILY GTP-BINDING PROTEIN CDC42 IN COMPLEX WITH THE MULTIFUNCTIONAL REGULATOR RHOGDI | CELL CYCLE | 2.0 | 6.0 | 8.4 | 71% | 3 | R66, 2.8; L67, 2.2; R68, 1.0; |
| 1DOA | AB | B | STRUCTURE OF THE RHO FAMILY GTP-BINDING PROTEIN CDC42 IN COMPLEX WITH THE MULTIFUNCTIONAL REGULATOR RHOGDI | CELL CYCLE | 2.3 | 4.3 | 10.4 | 43% | 2 | Y51, 2.8; L53, 1.7; |

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 1BXL | AB | B | STRUCTURE OF BCL-XL/BAK PEPTIDE COMPLEX, NMR, MINIMIZED AVERAGE STRUCTURE | i; i+3; | 4 | 9 | 576 | 584 | RQLAIIGDD | 10 | NOT APP |
| 1D2Z | CB | C | THREE-DIMENSIONAL STRUCTURE OF A COMPLEX BETWEEN THE DEATH DOMAINS OF PELLE AND TUBE | i; i+3; | 4 | 7 | 111 | 117 | HNAMRLI | 11 | 2.00 |
| 1DE4 | GI | G | HEMOCHROMATOSIS PROTEIN HFE COMPLEXED WITH TRANSFERRIN RECEPTOR | i; i+4; | 5 | 12 | 140 | 151 | AWPIKLEWERHK | 12 | 2.80 |
| 1DML | CD | D | CRYSTAL STRUCTURE OF HERPES SIMPLEX UL42 BOUND TO THE C-TERMINUS OF HSV POL | i; i+3; | 4 | 16 | 1220 | 1235 | AEETRMLHHRAFD TLA | 13 | 2.70 |
| 1DOA | AB | A | STRUCTURE OF THE RHO FAMILY GTP-BINDING PROTEIN CDC42 IN COMPLEX WITH THE MULTIFUNCTIONAL REGULATOR RHOGDI | i; i+1; i+2; | 3 | 5 | 65 | 69 | DRLRP | 14 | 2.60 |
| 1DOA | AB | B | STRUCTURE OF THE RHO FAMILY GTP-BINDING PROTEIN CDC42 IN COMPLEX WITH THE MULTIFUNCTIONAL REGULATOR RHOGDI | i; i+4; | 5 | 12 | 46 | 57 | ESLRKYKEALLG | 15 | 2.60 |

| A. PDB Code | B. Interface Chains | C. Chain | D. Title | E. Function | F. $G_{AVG,HELIX}$ (Kcal/mol) | G. $G_{SEM,HELIX}$ (Kcal/mol) | H. $G_{SEM,CHAIN}$ (Kcal/mol) | I. Helix Contribution | J. # Hotspot Residues | K. Hotspot Residues Residue #, $G_{(KCAL/MOL)}$ |
|---|---|---|---|---|---|---|---|---|---|---|
| 1DS6 | A B | A | CRYSTAL STRUCTURE OF A RAC-RHOGDI COMPLEX | SIGNALING PROTEIN | 2.5 | 4.9 | 13.4 | 37% | 2 | R66, 1.6; L67, 3.3; |
| 1E44 | B A | B | RIBONUCLEASE DOMAIN OF COLICIN E3 IN COMPLEX WITH ITS IMMUNITY PROTEIN | RIBONUCLEASE | 4.0 | 8.0 | 11.4 | 70% | 2 | F2, 5.4; Y5, 2.6; |
| 1EM8 | A B | B | CRYSTAL STRUCTURE OF CHI AND PSI SUBUNIT HETERODIMER FROM DNA POL III | GENE REGULATION | 3.5 | 7.0 | 11.5 | 61% | 2 | R118, 1.6; W122, 5.4; |
| 1ES7 | A D | D | COMPLEX BETWEEN BMP-2 AND TWO BMP RECEPTOR IA ECTODOMAINS | CYTOKINE | 2.5 | 4.9 | 4.9 | 100% | 2 | F285, 3.3; K288, 1.6; |
| 1ES7 | C B | B | COMPLEX BETWEEN BMP-2 AND TWO BMP RECEPTOR IA ECTODOMAINS | CYTOKINE | 2.1 | 4.2 | 4.2 | 100% | 2 | F285, 2.6; K288, 1.6; |
| 1EUV | A B | A | X-RAY STRUCTURE OF THE C-TERMINAL ULP1 PROTEASE DOMAIN IN COMPLEX WITH SMT3, THE YEAST ORTHOLOG OF SUMO | HYDROLASE | 3.5 | 6.9 | 23.4 | 29% | 2 | D451, 4.6; E455, 2.3; |
| 1EUV | A B | A | X-RAY STRUCTURE OF THE C-TERMINAL ULP1 PROTEASE DOMAIN IN COMPLEX WITH SMT3, THE YEAST ORTHOLOG OF SUMO | HYDROLASE | 2.6 | 5.1 | 23.4 | 22% | 2 | F474, 3.3; T477, 1.8; |

*FIG. 11C1*

| A. | B. | C. | D. | L. | M. | N. | O. | P. | Q. | R. | S. |
|---|---|---|---|---|---|---|---|---|---|---|---|
| PDB Code | Interface Chains | Chain | Title | Hotspot Residue Helix Positions | Hotspot Residue End to End Length | Helix Length | Helix Start Residue # | Helix End Residue # | Helix Sequence | SEQ ID NO: | Resolution |
| 1DS6 | A B | A | CRYSTAL STRUCTURE OF A RAC-RHOGDI COMPLEX | i;i+1; | 2 | 5 | 65 | 69 | DRLRP | 16 | 2.35 |
| 1E44 | B A | B | RIBONUCLEASE DOMAIN OF COLICIN E3 IN COMPLEX WITH ITS IMMUNITY PROTEIN | i;i+3; | 4 | 6 | 2 | 7 | FKDYGH | 17 | 2.40 |
| 1EM8 | A B | B | CRYSTAL STRUCTURE OF CHI AND PSI SUBUNIT HETERODIMER FROM DNA POL III | i;i+4; | 5 | 14 | 115 | 128 | PTARAALWQQICTY | 18 | 2.10 |
| 1ES7 | A D | D | COMPLEX BETWEEN BMP-2 AND TWO BMP RECEPTOR IA ECTODOMAINS | i;i+3; | 4 | 7 | 783 | 789 | SDFQCKD | 19 | 2.90 |
| 1ES7 | C B | B | COMPLEX BETWEEN BMP-2 AND TWO BMP RECEPTOR IA ECTODOMAINS | i;i+3; | 4 | 7 | 283 | 289 | SDFQCKD | 20 | 2.90 |
| 1EUV | A B | A | X-RAY STRUCTURE OF THE C-TERMINAL ULP1 PROTEASE DOMAIN IN COMPLEX WITH SMT3, THE YEAST ORTHOLOG OF SUMO. | i;i+4; | 5 | 14 | 451 | 464 | DTIIEFFMKYIEKS | 21 | 1.60 |
| 1EUV | A B | A | X-RAY STRUCTURE OF THE C-TERMINAL ULP1 PROTEASE DOMAIN IN COMPLEX WITH SMT3, THE YEAST ORTHOLOG OF SUMO. | i;i+3; | 4 | 10 | 473 | 482 | SFFYTNLSER | 22 | 1.60 |

FIG. 11C2

| A. PDB Code | B. Interface Chains | C. Chain | D. Title | E. Function | F. $G_{AVG,HELIX}$ (Kcal/mol) | G. $G_{SUM,HELIX}$ (Kcal/mol) | H. $G_{SUM,CHAIN}$ (Kcal/mol) | I. Helix Contribution | J. # Hotspot Residues | K. Hotspot Residues Residue #, $G_{(KCAL/MOL)}$ |
|---|---|---|---|---|---|---|---|---|---|---|
| 1F47 | BA | A | THE BACTERIAL CELL-DIVISION PROTEIN ZIPA AND ITS INTERACTION WITH AN FTSZ FRAGMENT REVEALED BY X-RAY CRYSTALLOGRAPHY | CELL CYCLE | 2.3 | 4.5 | 7.4 | 61% | 2 | F11, 2.1; I8, 2.4; |
| 1FM6 | UX | U | THE 2.1 ANGSTROM RESOLUTION CRYSTAL STRUCTURE OF THE HETERODIMER OF THE HUMAN RXRALPHA AND PPARGAMMA LIGAND BINDING DOMAINS RESPECTIVELY BOUND WITH 9-CIS RETINOIC ACID AND ROSIGLITAZONE AND CO-ACTIVATOR PEPTIDES. | TRANSCRIPTION | 2.1 | 4.2 | 5.6 | 75% | 2 | E394, 1.2; Y397, 3.0; |
| 1FOE | CD | C | CRYSTAL STRUCTURE OF RAC1 IN COMPLEX WITH THE GUANINE NUCLEOTIDE EXCHANGE REGION OF TIAM1 | SIGNALING PROTEIN, IMMUNE SYSTEM/ SIGNALING | 3.5 | 10.6 | 24.2 | 44% | 3 | K1195, 4.4; L1198, 5.0; L1199, 1.2; |
| 1FOE | CD | C | CRYSTAL STRUCTURE OF RAC1 IN COMPLEX WITH THE GUANINE NUCLEOTIDE EXCHANGE REGION OF TIAM1 | SIGNALING PROTEIN, IMMUNE SYSTEM/ SIGNALING | 2.9 | 8.6 | 24.2 | 36% | 3 | I1187, 1.2; I1190, 3.6; Q1191, 3.8; |

*FIG. 11D1*

| A. | B. | C. | D. | L. | M. | N. | O. | P. | Q. | R. | S. |
|---|---|---|---|---|---|---|---|---|---|---|---|
| PDB Code | Interface Chains | Chain | Title | Hotspot Residue Helix Positions | Hotspot Residue End to End Length | Helix Length | Helix Start Residue # | Helix End Residue # | Helix Sequence | SEQ ID NO: | Resolution |
| 1F47 | BA | A | THE BACTERIAL CELL-DIVISION PROTEIN ZIPA AND ITS INTERACTION WITH AN FTSZ FRAGMENT REVEALED BY X-RAY CRYSTALLOGRAPHY | i; i+3; | 4 | 9 | 8 | 16 | IPAFLRKQA | 23 | 1.95 |
| 1FM6 | UX | U | THE 2.1 ANGSTROM RESOLUTION CRYSTAL STRUCTURE OF THE HETERODIMER OF THE HUMAN RXRALPHA AND PPARGAMMA LIGAND BINDING DOMAINS RESPECTIVELY BOUND WITH 9-CIS RETINOIC ACID AND ROSIGLITAZONE AND CO-ACTIVATOR PEPTIDES. | i; i+3; | 4 | 23 | 386 | 408 | PAEVEALREKVAS LEAYCKHKY | 24 | 2.10 |
| 1FOE | CD | C | CRYSTAL STRUCTURE OF RAC1 IN COMPLEX WITH THE GUANINE NUCLEOTIDE EXCHANGE REGION OF TIAM1 | i; i+3; i+4; | 5 | 12 | 1195 | 1206 | KYPLLLRELFAL | 25 | 2.80 |
| 1FOE | CD | C | CRYSTAL STRUCTURE OF RAC1 IN COMPLEX WITH THE GUANINE NUCLEOTIDE EXCHANGE REGION OF TIAM1 | i; i+3; i+4; | 5 | 8 | 1187 | 1194 | IKPIQRVL | 26 | 2.80 |

FIG. 11D2

| A. | B. | C. | D. | E. | F. | G. | H. | I. | J. | K. | |
|---|---|---|---|---|---|---|---|---|---|---|---|
| PDB Code | Interface Chains | Chain | Title | Function | $G_{AVG,HELIX}$ (Kcal/mol) | $G_{SEM,HELIX}$ (Kcal/mol) | $G_{SEM,CHAIN}$ (Kcal/mol) | Helix Contribution | # Hotspot Residues | Hotspot Residues | |
| | | | | | | | | | | Residue #, $G_{(KCAL/MOL)}$ | |
| 1F0E | CD | C | CRYSTAL STRUCTURE OF RAC1 IN COMPLEX WITH THE GUANINE NUCLEOTIDE EXCHANGE REGION OF TIAM1 | SIGNALING PROTEIN, IMMUNE SYSTEM/ SIGNALING | 4.0 | 7.8 | 24.2 | 32% | 2 | I1231, 3.7; N1232, 4.1; | |
| 1F0E | CD | D | CRYSTAL STRUCTURE OF RAC1 IN COMPLEX WITH THE GUANINE NUCLEOTIDE EXCHANGE REGION OF TIAM1 | SIGNALING PROTEIN, IMMUNE SYSTEM/SIGNALING | 2.0 | 4.0 | 32.8 | 12% | 2 | R66, 2.1; L67, 1.9; | |
| 1FQV | AB | A | INSIGHTS INTO SCF UBIQUITIN LIGASES FROM THE STRUCTURE OF THE SKP1-SKP2 COMPLEX | LIGASE | 2.0 | 8.1 | 11.7 | 69% | 4 | K137, 1.9; R138, 1.2; W139, 2.5; Y140, 2.5; | |
| 1FQV | EF | E | INSIGHTS INTO SCF UBIQUITIN LIGASES FROM THE STRUCTURE OF THE SKP1-SKP2 COMPLEX | LIGASE | 3.3 | 6.6 | 12.5 | 53% | 2 | K131, 2.8; S133, 3.8; | |
| 1H2M | AS | S | FACTOR INHIBITING HIF-1 ALPHA IN COMPLEX WITH HIF-1 ALPHA FRAGMENT PEPTIDE | TRANSCRIPTION ACTIVATOR/INHIBITOR | 2.3 | 4.5 | 5.5 | 82% | 2 | L818, 2.1; L819, 2.4; | |
| 1H3O | AB | B | CRYSTAL STRUCTURE OF THE HUMAN TAF4-TAF12 (TAFII35-TAFII20) COMPLEX | TRANSCRIPTION/ TBP-ASSOCIATED FACTORS | 2.1 | 4.1 | 14.3 | 29% | 2 | L66, 2.6; V70, 1.5; | |
| 1H4L | AD | D | STRUCTURE AND REGULATION OF THE CDK5-P25(NCK5A) COMPLEX | KINASE/KINASE ACTIVATOR | 2.8 | 5.6 | 11.7 | 48% | 2 | W258, 3.2; L262, 2.4; | |

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 1FOE | CD | C | CRYSTAL STRUCTURE OF RAC1 IN COMPLEX WITH THE GUANINE NUCLEOTIDE EXCHANGE REGION OF TIAM1 | i; i+1; | 2 | 8 | 1226 | 1233 | KVASHIVE | 27 | 2.80 |
| 1FOE | CD | D | CRYSTAL STRUCTURE OF RAC1 IN COMPLEX WITH THE GUANINE NUCLEOTIDE EXCHANGE REGION OF TIAM1 | i; i+1; | 2 | 5 | 65 | 69 | DRLRP | 28 | 2.80 |
| 1FQV | AB | A | INSIGHTS INTO SCF UBIQUITIN LIGASES FROM THE STRUCTURE OF THE SKP1-SKP2 COMPLEX | i; i+1; i+2; i+3; | 4 | 8 | 137 | 144 | KPWYRLAS | 29 | 2.80 |
| 1FQV | EF | E | INSIGHTS INTO SCF UBIQUITIN LIGASES FROM THE STRUCTURE OF THE SKP1-SKP2 COMPLEX | i; i+2; | 3 | 9 | 126 | 134 | LPELLKVSG | 30 | 2.80 |
| 1H2M | AS | S | FACTOR INHIBITING HIF-1 ALPHA IN COMPLEX WITH HIF-1 ALPHA FRAGMENT PEPTIDE | i; i+1; | 2 | 7 | 816 | 822 | EELLRAL | 31 | 2.50 |
| 1H3O | AB | B | CRYSTAL STRUCTURE OF THE HUMAN TAF4-TAF12 (TAFII135-TAFII20) COMPLEX | i; i+4; | 5 | 12 | 60 | 71 | KKKLQDLVREVD | 32 | 2.30 |
| 1H4L | AD | D | STRUCTURE AND REGULATION OF THE CDK5-P25(NCK5A) COMPLEX | i; i+4; | 5 | 15 | 254 | 268 | KEAFWDRCLSVINLM | 33 | 2.65 |

| A. PDB Code | B. Interface Chains | C. Chain | D. Title | E. Function | F. $G_{AVG,HELIX}$ (Kcal/mol) | G. $G_{SUM,HELIX}$ (Kcal/mol) | H. $G_{SUM,CHAIN}$ (Kcal/mol) | I. Helix Contribution | J. # Hotspot Residues | K. Hotspot Residues Residue #, $G_{(KCAL/MOL)}$ |
|---|---|---|---|---|---|---|---|---|---|---|
| 1H59 | AB | B | COMPLEX OF IGFBP-5 WITH IGF-I | INSULIN | 2.2 | 4.4 | 6.1 | 72% | 2 | L70, 3.1; L74, 1.3; |
| 1H6K | AX | X | NUCLEAR CAP BINDING COMPLEX | NUCLEAR PROTEIN | 2.2 | 4.3 | 9.4 | 46% | 2 | Y100, 2.6; R99, 1.7; |
| 1HE1 | AC | A | CRYSTAL STRUCTURE OF THE COMPLEX BETWEEN THE GAP DOMAIN OF THE PSEUDOMONAS AERUGINOSA EXOS TOXIN AND HUMAN RAC | SIGNALING PROTEIN | 2.4 | 4.7 | 9.5 | 49% | 2 | Q182, 2.0; Q183, 2.7; |
| 1HH4 | AD | A | RAC1-RHOGDI COMPLEX INVOLVED IN NADPH OXIDASE ACTIVATION | SIGNALING PROTEIN/ INHIBITOR | 2.6 | 5.1 | 9.1 | 56% | 2 | H103, 3.1; H104, 2.0; |
| 1HH4 | BE | B | RAC1-RHOGDI COMPLEX INVOLVED IN NADPH OXIDASE ACTIVATION | SIGNALING PROTEIN/ INHIBITOR | 2.2 | 4.3 | 13.6 | 32% | 2 | R66, 2.4; L67, 1.9; |
| 1HH4 | BE | E | RAC1-RHOGDI COMPLEX INVOLVED IN NADPH OXIDASE ACTIVATION | SIGNALING PROTEIN/ INHIBITOR | 2.2 | 4.3 | 7.1 | 61% | 2 | Y351, 2.5; L355, 1.8; |
| 1HV2 | AB | B | SOLUTION STRUCTURE OF YEAST ELONGIN C IN COMPLEX WITH A VON HIPPEL-LINDAU PEPTIDE | SIGNALING PROTEIN | 2.2 | 4.3 | 4.3 | 100% | 2 | L158, 3.2; R161, 1.1; |
| 1HWM | AB | A | EBULIN, ORTHORHOMBIC CRYSTAL FORM MODEL | HYDROLASE | 2.1 | 4.1 | 9.2 | 45% | 2 | E223, 2.8; I239, 1.3; |
| 1I7W | CD | D | BETA-CATENIN/PHOSPHORYLATED E-CADHERIN COMPLEX | CELL ADHESION | 2.1 | 4.1 | 22.7 | 18% | 2 | K717, 1.1; L718, 3.0; |
| 1IWQ | AB | A | CRYSTAL STRUCTURE OF MARCKS CALMODULIN BINDING DOMAIN PEPTIDE COMPLEXED WITH CA2+/CALMODULIN | METAL BINDING PROTEIN/ PROTEIN BINDING | 2.5 | 4.9 | 22.1 | 22% | 2 | L105, 1.2; M109, 3.7; |

*FIG. 11F1*

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 1H59 | AB | B | COMPLEX OF IGFBP-5 WITH IGF-I | i;i+4; | 5 | 7 | 69 | 75 | PLHALLH | 34 | 2.10 |
| 1H6K | AX | X | NUCLEAR CAP BINDING COMPLEX | i;i+1; | 2 | 12 | 91 | 102 | RADAENAMRYIN | 35 | 2.00 |
| 1HE1 | AC | A | CRYSTAL STRUCTURE OF THE COMPLEX BETWEEN THE GAP DOMAIN OF THE PSEUDOMONAS AERUGINOSA EXOS TOXIN AND HUMAN RAC | i;i+1; | 2 | 5 | 181 | 185 | LQQWG | 36 | 2.00 |
| 1HH4 | AD | A | RAC1-RHOGDI COMPLEX INVOLVED IN NADPH OXIDASE ACTIVATION | i;i+1; | 2 | 13 | 93 | 105 | VRAKWYPEVRHHC | 37 | 2.70 |
| 1HH4 | BE | B | RAC1-RHOGDI COMPLEX INVOLVED IN NADPH OXIDASE ACTIVATION | i;i+1; | 2 | 5 | 65 | 69 | DRLRP | 38 | 2.70 |
| 1HH4 | BE | E | RAC1-RHOGDI COMPLEX INVOLVED IN NADPH OXIDASE ACTIVATION | i;i+4; | 5 | 12 | 346 | 357 | ESLRKYKEALLG | 39 | 2.70 |
| 1HV2 | AB | B | SOLUTION STRUCTURE OF YEAST ELONGIN C IN COMPLEX WITH A VON HIPPEL-LINDAU PEPTIDE | i;i+3; | 4 | 14 | 158 | 171 | LKERCLQVVRSLVK | 40 | NOT APP |
| 1HWM | AB | A | EBULIN ORTHORHOMBIC CRYSTAL FORM MODEL | i;i+4; | 5 | 9 | 233 | 241 | FHELYKITG | 41 | 2.80 |
| 1I7W | CD | D | BETA-CATENIN/PHOSPHORYLATED E-CADHERIN COMPLEX | i;i+1; | 2 | 7 | 716 | 722 | KKLADMY | 42 | 2.00 |
| 1IWQ | AB | A | CRYSTAL STRUCTURE OF MARCKS CALMODULIN BINDING DOMAIN PEPTIDE COMPLEXED WITH CA2+/CALMODULIN | i;i+4; | 5 | 11 | 102 | 112 | AAEERHVMTNL | 43 | 2.00 |

FIG. 11F2

| A. PDB Code | B. Interface Chains | C. Chain | D. Title | E. Function | F. $G_{AVG,HELIX}$ (Kcal/mol) | G. $G_{SUM,HELIX}$ (Kcal/mol) | H. $G_{SUM,CHAIN}$ (Kcal/mol) | I. Helix Contribution | J. # Hotspot Residues | K. Hotspot Residues Residue #, $G$ (KCAL/MOL) |
|---|---|---|---|---|---|---|---|---|---|---|
| 1J1D | B,C | C | CRYSTAL STRUCTURE OF THE 46KDA DOMAIN OF HUMAN CARDIAC TROPONIN IN THE CA2+ SATURATED FORM | CONTRACTILE PROTEIN | 2.0 | 4.0 | 19.6 | 20% | 2 | K72, 2.9; L76, 1.1; |
| 1J2J | A,B | A | CRYSTAL STRUCTURE OF GGA1 GAT N-TERMINAL REGION IN COMPLEX WITH ARF1 GTP FORM | PROTEIN TRANSPORT | 2.4 | 4.7 | 8.3 | 57% | 2 | L77, 2.7; H80, 2.0; |
| 1JPW | B,E | E | CRYSTAL STRUCTURE OF A HUMAN TCF-4 /BETA-CATENIN COMPLEX | CELL ADHESION | 2.1 | 4.1 | 14.0 | 29% | 2 | V44, 2.0; K45, 2.1; |
| 1KBH | A,B | A | MUTUAL SYNERGISTIC FOLDING IN THE INTERACTION BETWEEN NUCLEAR RECEPTOR COACTIVATORS CBP AND ACTR | TRANSCRIPTION | 2.2 | 4.3 | 7.8 | 55% | 2 | I34, 3.0; V38, 1.3; |
| 1KI1 | A,B | A | GUANINE NUCLEOTIDE EXCHANGE REGION OF INTERSECTIN IN COMPLEX WITH CDC42 | SIGNALING PROTEIN | 2.7 | 5.3 | 7.3 | 73% | 2 | L67, 3.0; L70, 2.3; |
| 1L2W | A,I | I | CRYSTAL STRUCTURE OF THE YERSINIA VIRULENCE EFFECTOR YOPE CHAPERONE-BINDING DOMAIN IN COMPLEX WITH ITS SECRETION CHAPERONE, SYCE | CHAPERONE | 2.1 | 4.1 | 8.3 | 49% | 2 | Y39, 1.9; L43, 2.2; |

*FIG. 11G1*

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 1J1D | B C | C | CRYSTAL STRUCTURE OF THE 46KDA DOMAIN OF HUMAN CARDIAC TROPONIN IN THE CA2+ SATURATED FORM | i; i+4; | 5 | 18 | 63 | 80 | REAEERRGEKGRA LSTRA | 44 | 2.61 |
| 1J2J | A B | A | CRYSTAL STRUCTURE OF GGA1 GAT N-TERMINAL REGION IN COMPLEX WITH ARF1 GTP FORM | i; i+3; | 4 | 7 | 75 | 81 | RPLWRHY | 45 | 1.60 |
| 1JPW | B E | E | CRYSTAL STRUCTURE OF A HUMAN TCF-4 /BETA-CATENIN COMPLEX | i; i+1; | 2 | 6 | 42 | 47 | ADVKSS | 46 | 2.50 |
| 1KBH | A B | A | MUTUAL SYNERGISTIC FOLDING IN THE INTERACTION BETWEEN NUCLEAR RECEPTOR COACTIVATORS CBP AND ACTR | i; i+4; | 5 | 8 | 34 | 41 | IPELYNQG | 47 | NOT APP |
| 1KI1 | A B | A | GUANINE NUCLEOTIDE EXCHANGE REGION OF INTERSECTIN IN COMPLEX WITH CDC42 | i; i+3; | 4 | 7 | 67 | 73 | LRPLSYP | 48 | 2.30 |
| 1L2W | A I | I | CRYSTAL STRUCTURE OF THE YERSINIA VIRULENCE EFFECTOR YOPE CHAPERONE-BINDING DOMAIN IN COMPLEX WITH ITS SECRETION CHAPERONE. SYCE | i; i+4; | 5 | 8 | 38 | 45 | QYANNLAG | 49 | 2.00 |

*FIG. 11G2*

| A. | B. | C. | D. | E. | F. | G. | H. | I. | J. | K. |
|---|---|---|---|---|---|---|---|---|---|---|
| PDB Code | Interface Chains | Chain | Title | Function | $G_{AVG,HELIX}$ (Kcal/mol) | $G_{SUM,HELIX}$ (Kcal/mol) | $G_{SUM,CHAIN}$ (Kcal/mol) | Helix Contribution | # Hotspot Residues | Hotspot Residues Residue #, $G_{(KCAL/MOL)}$ |
| 1L8C | AB | B | STRUCTURAL BASIS FOR HIF-1ALPHA/CBP RECOGNITION IN THE CELLULAR HYPOXIC RESPONSE | GENE REGULATION | 2.3 | 4.6 | 16.8 | 27% | 2 | L141, 2.4; L145, 2.2; |
| 1LB1 | CD | D | CRYSTAL STRUCTURE OF THE DBL AND PLECKSTRIN HOMOLOGY DOMAINS OF DBS IN COMPLEX WITH RHOA | SIGNALING PROTEIN | 2.1 | 4.1 | 16.3 | 25% | 2 | L69, 1.9; L72, 2.2; |
| 1LB1 | EF | F | CRYSTAL STRUCTURE OF THE DBL AND PLECKSTRIN HOMOLOGY DOMAINS OF DBS IN COMPLEX WITH RHOA | SIGNALING PROTEIN | 2.0 | 3.9 | 10.6 | 37% | 2 | H105, 2.0; F106, 1.9; |
| 1LQB | BC | B | CRYSTAL STRUCTURE OF A HYDROXYLATED HIF-1 ALPHA PEPTIDE BOUND TO THE PVHL/ELONGIN-C/ELONGIN-B COMPLEX | GENE REGULATION | 2.3 | 4.5 | 13.8 | 33% | 2 | L101, 1.4; L104, 3.1; |
| 1LQB | BC | C | CRYSTAL STRUCTURE OF A HYDROXYLATED HIF-1 ALPHA PEPTIDE BOUND TO THE PVHL/ELONGIN-C/ELONGIN-B COMPLEX | GENE REGULATION | 2.5 | 7.6 | 10.6 | 72% | 3 | L158, 3.5; K159, 1.2; R161, 2.9; |
| 1LTX | AR | A | STRUCTURE OF RAB ESCORT PROTEIN-1 IN COMPLEX WITH RAB GERANYLGERANYL TRANSFERASE AND ISOPRENOID | TRANSFERASE/PROTEIN BINDING | 2.4 | 4.7 | 6.6 | 71% | 2 | Q216, 2.4; F20, 2.3; |

*FIG. 11H1*

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 1L8C | AB | B | STRUCTURAL BASIS FOR HIF-1 ALPHA/CBP RECOGNITION IN THE CELLULAR HYPOXIC RESPONSE | i; i+4; | 5 | 11 | 139 | 149 | EELLRALDQVN | 50 | NOT APP |
| 1LB1 | CD | D | CRYSTAL STRUCTURE OF THE DBL AND PLECKSTRIN HOMOLOGY DOMAINS OF DBS IN COMPLEX WITH RHOA | i; i+3; | 4 | 7 | 69 | 75 | LRPLSYP | 51 | 2.81 |
| 1LB1 | EF | F | CRYSTAL STRUCTURE OF THE DBL AND PLECKSTRIN HOMOLOGY DOMAINS OF DBS IN COMPLEX WITH RHOA | i; i+1; | 2 | 19 | 89 | 107 | PDSLENPEKWTPEVKHFC | 52 | 2.81 |
| 1LQB | BC | B | CRYSTAL STRUCTURE OF A HYDROXYLATED HIF-1 ALPHA PEPTIDE BOUND TO THE PVHL/ELONGIN-C/ELONGIN-B COMPLEX | i; i+3; | 4 | 11 | 100 | 110 | ALELLMAANFL | 53 | 2.00 |
| 1LQB | BC | C | CRYSTAL STRUCTURE OF A HYDROXYLATED HIF-1 ALPHA PEPTIDE BOUND TO THE PVHL/ELONGIN-C/ELONGIN-B COMPLEX | i; i+1; i+3; | 4 | 11 | 158 | 168 | LKERCLQVVRS | 54 | 2.00 |
| 1LTX | AR | A | STRUCTURE OF RAB ESCORT PROTEIN-1 IN COMPLEX WITH RAB GERANYLGERANYL TRANSFERASE AND ISOPRENOID | i; i+4; | 5 | 18 | 205 | 222 | ENVLLKELELVQNAFFTD | 55 | 2.70 |

FIG. 11H2

| A. | B. | C. | D. | E. | F. | G. | H. | I. | J. | K. | |
|---|---|---|---|---|---|---|---|---|---|---|---|
| PDB Code | Interface Chains | Chain | Title | Function | G_AVG,HELIX (Kcal/mol) | G_SUM,HELIX (Kcal/mol) | G_SUM,CHAIN (Kcal/mol) | Helix Contribution | # Hotspot Residues | Hotspot Residues | |
| | | | | | | | | | | Residue #, G (KCAL/MOL) | |
| 1LTX | AR | R | STRUCTURE OF RAB ESCORT PROTEIN-1 IN COMPLEX WITH RAB GERANYLGERANYL TRANSFERASE AND ISOPRENOID | TRANSFERASE/ PROTEIN BINDING | 3.2 | 6.3 | 9.7 | 65% | 2 | R275, 3.5; F279, 2.8; | |
| 1MDU | AB | A | CRYSTAL STRUCTURE OF THE CHICKEN ACTIN TRIMER COMPLEXED WITH HUMAN GELSOLIN SEGMENT 1 (GS-1) | STRUCTURAL PROTEIN | 2.2 | 6.5 | 11.0 | 59% | 3 | I79, 2.3; F80, 3.2; V82, 1.0; | |
| 1MF8 | AB | A | CRYSTAL STRUCTURE OF HUMAN CALCINEURIN COMPLEXED WITH CYCLOSPORIN A AND HUMAN CYCLOPHILIN | HYDROLASE, LIGASE | 2.9 | 8.6 | 33.6 | 26% | 3 | F350, 4.8; W352, 1.4; L354, 2.4; | |
| 1MZN | CD | D | CRYSTAL STRUCTURE AT 1.9 ANGSTROEMS RESOLUTION OF THE HOMODIMER OF HUMAN RXR ALPHA LIGAND BINDING DOMAIN BOUND TO THE SYNTHETIC AGONIST COMPOUND BMS 649 AND A COACTIVATOR PEPTIDE | TRANSCRIPTION | 2.1 | 6.2 | 7.8 | 79% | 3 | L1475, 2.2; L1478, 1.4; L1479, 2.6; | |
| 1NIJ | AB | B | CRYSTAL STRUCTURE OF THE NF-YB/NF-YC HISTONE PAIR | DNA BINDING PROTEIN | 2.6 | 5.1 | 43.7 | 12% | 2 | R47, 1.5; I51, 3.6; | |
| 1NRL | BD | D | CRYSTAL STRUCTURE OF THE HUMAN PXR-LBD IN COMPLEX WITH AN SRC-1 | TRANSCRIPTION | 2.0 | 6.0 | 6.0 | 100% | 3 | L690, 2.6; H691, 1.0; L694, 2.4; | |

FIG. 11I1

| A. | B. | C. | D. | L. | M. | N. | O. | P. | Q. | R. | S. |
|---|---|---|---|---|---|---|---|---|---|---|---|
| PDB Code | Interface Chains | Chain | Title | Hotspot Residue Helix Positions | Hotspot Residue End to End Length | Helix Length | Helix Start Residue # | Helix End Residue # | Helix Sequence | SEQ ID NO: | Resolution |
| 1LTX | AR | R | STRUCTURE OF RAB ESCORT PROTEIN-1 IN COMPLEX WITH RAB GERANYLGERANYL TRANSFERASE AND ISOPRENOID | i;i+4; | 5 | 7 | 275 | 281 | RADVFNS | 56 | 2.70 |
| 1MDU | AB | A | CRYSTAL STRUCTURE OF THE CHICKEN ACTIN TRIMER COMPLEXED WITH HUMAN GELSOLIN SEGMENT 1 (GS-1) | i;i+1;i+3; | 4 | 18 | 71 | 88 | QDESGAAAHFTVQL DDYL | 57 | 2.20 |
| 1MF8 | AB | A | CRYSTAL STRUCTURE OF HUMAN CALCINEURIN COMPLEXED WITH CYCLOSPORIN A AND HUMAN CYCLOPHILIN | i;i+2;i+4; | 5 | 10 | 349 | 358 | VFTWSLPFVG | 58 | 3.10 |
| 1M2N | CD | D | CRYSTAL STRUCTURE AT 1.9 ANGSTROEMS RESOLUTION OF THE HOMODIMER OF HUMAN RXR ALPHA LIGAND BINDING DOMAIN BOUND TO THE SYNTHETIC AGONIST COMPOUND BMS 649 AND A COACTIVATOR PEPTIDE | i;i+3;i+4; | 5 | 9 | 1473 | 1481 | KILHRLLQD | 59 | 1.90 |
| 1NLJ | AB | B | CRYSTAL STRUCTURE OF THE NF-YB/NF-YC HISTONE PAIR | i;i+4; | 5 | 9 | 45 | 53 | LARIKKIMK | 60 | 1.67 |
| 1NRL | BD | D | CRYSTAL STRUCTURE OF THE HUMAN PXR-LBD IN COMPLEX WITH AN SRC-1 | i;i+1;i+4; | 5 | 9 | 688 | 696 | KILHRLLQE | 61 | 2.00 |

FIG. 11I2

| A. | B. | C. | D. | E. | F. | G. | H. | I. | J. | K. |
|---|---|---|---|---|---|---|---|---|---|---|
| PDB Code | Interface Chains | Chain | Title | Function | $G_{AVG,HELIX}$ (Kcal/mol) | $G_{SUM,HELIX}$ (Kcal/mol) | $G_{SUM,CHAIN}$ (Kcal/mol) | Helix Contribution | # Hotspot Residues | Hotspot Residues Residue #, $G_{(KCAL/MOL)}$ |
| 1NU7 | EF | E | STAPHYLOCOAGULASE-THROMBIN COMPLEX | HYDROLASE/ PROTEIN BINDING | 2.2 | 4.3 | 5.3 | 81% | 2 | E14, 2.6; L14, 1.7; |
| 1OL5 | AB | B | STRUCTURE OF AURORA-A 122-403, PHOSPHORYLATED ON THR287, THR288 AND BOUND TO TPX2 1-43 | TRANSFERASE/ CELL CYCLE | 3.0 | 6.0 | 18.6 | 32% | 2 | W34, 2.8; F55, 3.2; |
| 1OOK | AB | A | CRYSTAL STRUCTURE OF THE COMPLEX OF PLATELET RECEPTOR GPIB- ALPHA AND HUMAN ALPHA-THROMBIN | HYDROLASE | 2.1 | 6.2 | 15.3 | 41% | 3 | E14, 1.9; E14, 2.3; L14, 2.0; |
| 1OR7 | AC | A | CRYSTAL STRUCTURE OF ESCHERICHIA COLI SIGMAE WITH THE CYTOPLASMIC DOMAIN OF ITS ANTI-SIGMA RSEA | TRANSCRIPTION | 2.2 | 4.4 | 31.9 | 14% | 2 | R171, 1.3; F175, 3.1; |
| 1OR7 | AC | A | CRYSTAL STRUCTURE OF ESCHERICHIA COLI SIGMAE WITH THE CYTOPLASMIC DOMAIN OF ITS ANTI-SIGMA RSEA | TRANSCRIPTION | 2.0 | 4.0 | 31.9 | 13% | 2 | F22, 1.3; L24, 2.7; |
| 1OSV | BD | D | STRUCTURAL BASIS FOR BILE ACID BINDING AND ACTIVATION OF THE NUCLEAR RECEPTOR FXR | DNA BINDING PROTEIN | 2.3 | 4.6 | 4.6 | 100% | 2 | L5, 3.3; R6, 1.3; |
| 1QLS | AD | D | S100C (S100A11), OR CALGIZZARIN, IN COMPLEX WITH ANNEXIN I N-TERMINUS | METAL-BINDING PROTEIN/ INHIBITOR | 7.8 | 15.5 | 15.5 | 100% | 2 | F6, 1.0; L7, 14.5; |

*FIG. 11J1*

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 1NU7 | EF | E | STAPHYLOCOAGULASE-THROMBIN COMPLEX | i; i+1; | 2 | 8 | 14 | 14 | ERELLESY | 62 | 2.20 |
| 1OL5 | AB | B | STRUCTURE OF AURORA-A 122-403, PHOSPHORYLATED ON THR287, THR288 AND BOUND TO TPX2 1-43 | i; i+1; | 2 | 9 | 33 | 41 | SWFEEKANL | 63 | 2.50 |
| 1OOK | AB | A | CRYSTAL STRUCTURE OF THE COMPLEX OF PLATELET RECEPTOR GPIB-ALPHA AND HUMAN ALPHA-THROMBIN | i; i+1; i; | 4 | 7 | 14 | 14 | ERELLES | 64 | 2.30 |
| 1OR7 | AC | A | CRYSTAL STRUCTURE OF ESCHERICHIA COLI SIGMAE WITH THE CYTOPLASMIC DOMAIN OF ITS ANTI-SIGMA RSEA | i; i+4; | 5 | 20 | 167 | 186 | VGTVRSRHPRAREA IDNKVQ | 65 | 2.00 |
| 1OR7 | AC | A | CRYSTAL STRUCTURE OF ESCHERICHIA COLI SIGMAE WITH THE CYTOPLASMIC DOMAIN OF ITS ANTI-SIGMA RSEA | i; i+2; | 3 | 11 | 19 | 29 | QKAFNLLVVRY | 66 | 2.00 |
| 1OSV | BD | D | STRUCTURAL BASIS FOR BILE ACID BINDING AND ACTIVATION OF THE NUCLEAR RECEPTOR FXR | i; i+1; | 2 | 8 | 3 | 10 | ALLRYLLD | 67 | 2.50 |
| 1QLS | AD | D | S100C (S100A11), OR CALGIZZARIN, IN COMPLEX WITH ANNEXIN I N-TERMINUS | i; i+1; | 2 | 9 | 2 | 10 | MVSAFLKQA | 68 | 2.30 |

FIG. 11J2

| A. PDB Code | B. Interface Chains | C. Chain | D. Title | E. Function | F. $G_{AVG,HELIX}$ (Kcal/mol) | G. $G_{SEM,HELIX}$ (Kcal/mol) | H. $G_{SEM,CHAIN}$ (Kcal/mol) | I. Helix Contribution | J. # Hotspot Residues | K. Hotspot Residues Residue #, $G$ (KCAL/MOL) |
|---|---|---|---|---|---|---|---|---|---|---|
| 1R4A | A E | E | CRYSTAL STRUCTURE OF GTP-BOUND ADP-RIBOSYLATION FACTOR LIKE PROTEIN 1 (ARL1) AND GRIP DOMAIN OF GOLGIN245 COMPLEX | PROTEIN TRANSPORT | 2.1 | 4.2 | 10.5 | 40% | 2 | E2174, 1.3; Y2177, 2.9; |
| 1R8Q | A E | A | FULL-LENGTH ARF1-GDP-MG IN COMPLEX WITH BREFELDIN A AND A SEC7 DOMAIN | PROTEIN TRANSPORT/ EXCHANGE FACTOR | 2.5 | 4.9 | 14.3 | 34% | 2 | L77, 3.0; Y81, 1.9; |
| 1RP3 | A B | B | COCRYSTAL STRUCTURE OF THE FLAGELLAR SIGMA/ANTI-SIGMA COMPLEX, SIGMA-28FLGM | TRANSCRIPTION | 2.2 | 4.4 | 31.0 | 14% | 2 | V60, 1.6; K64, 2.8; |
| 1T0F | B D | D | CRYSTAL STRUCTURE OF THE TNSA/TNSC(504-555) COMPLEX | DNA BINDING PROTEIN | 2.2 | 4.4 | 18.9 | 23% | 2 | L521, 1.5; R522, 2.9; |
| 1TTW | A B | B | CRYSTAL STRUCTURE OF THE YERSINIA PESTIS TYPE III SECRETION CHAPERONE SYCH IN COMPLEX WITH A STABLE FRAGMENT OF YSCM2 | CHAPERONE | 2.2 | 4.3 | 11.4 | 38% | 2 | F45, 1.9; V49, 2.4; |
| 1TUE | A B | B | THE X-RAY STRUCTURE OF THE PAPILLOMAVIRUS HELICASE IN COMPLEX WITH ITS MOLECULAR MATCHMAKER E2 | REPLICATION | 2.7 | 8.1 | 13.8 | 59% | 3 | I20, 1.7; Y23, 4.9; E24, 1.5; |
| 1TUE | H J | H | THE X-RAY STRUCTURE OF THE PAPILLOMAVIRUS HELICASE IN COMPLEX WITH ITS MOLECULAR MATCHMAKER E2 | REPLICATION | 2.5 | 5.0 | 16.6 | 30% | 2 | F460, 2.8; I461, 2.2; |

*FIG. 11K1*

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 1R4A | A E | E | CRYSTAL STRUCTURE OF GTP-BOUND ADP-RIBOSYLATION FACTOR LIKE PROTEIN 1 (ARL1) AND GRIP DOMAIN OF GOLGIN245 COMPLEX | i; i+3; | 4 | 15 | 2173 | 2187 | TEFEYLRKVLFEYMM | 69 | 2.30 |
| 1R8Q | A E | A | FULL-LENGTH ARF1-GDP-MG IN COMPLEX WITH BREFELDIN A AND A SEC7 DOMAIN | i; i+4; | 5 | 8 | 75 | 82 | RPLWRHYF | 70 | 1.86 |
| 1RP3 | A B | B | COCRYSTAL STRUCTURE OF THE FLAGELLAR SIGMA/ANTI-SIGMA COMPLEX, SIGMA-28/FLGM | i; i+4; | 5 | 14 | 56 | 69 | LEKKVKELKEKIEK | 71 | 2.30 |
| 1T0F | B D | D | CRYSTAL STRUCTURE OF THE TNSA/TNSC(504-555) COMPLEX | i; i+1; | 2 | 7 | 521 | 527 | LRYHYSQ | 72 | 1.85 |
| 1TTW | A B | B | CRYSTAL STRUCTURE OF THE YERSINIA PESTIS TYPE III SECRETION CHAPERONE SYCH IN COMPLEX WITH A STABLE FRAGMENT OF YSCM2 | i; i+4; | 5 | 7 | 44 | 50 | RFAYAVL | 73 | 2.38 |
| 1TUE | A B | B | THE X-RAY STRUCTURE OF THE PAPILLOMAVIRUS HELICASE IN COMPLEX WITH ITS MOLECULAR MATCHMAKER E2 | i; i+3; i+4; | 5 | 23 | 4 | 26 | PKETLSERLSALQDKIDHYEND | 74 | 2.10 |
| 1TUE | H J | H | THE X-RAY STRUCTURE OF THE PAPILLOMAVIRUS HELICASE IN COMPLEX WITH ITS MOLECULAR MATCHMAKER E2 | i; i+1; | 2 | 14 | 460 | 473 | FITFLGALKSFLKG | 75 | 2.10 |

*FIG. 11K2*

| A. PDB Code | B. Interface Chains | C. Chain | D. Title | E. Function | F. $G_{AV,HELIX}$ (Kcal/mol) | G. $G_{SUM,HELIX}$ (Kcal/mol) | H. $G_{SUM,CHAIN}$ (Kcal/mol) | I. Helix Contribution | J. # Hotspot Residues | K. Hotspot Residues Residue #, $G$ (KCAL/MOL) |
|---|---|---|---|---|---|---|---|---|---|---|
| 1TY4 | A C | C | CRYSTAL STRUCTURE OF A CED-9/EGL-1 COMPLEX | APOPTOSIS | 2.0 | 6.0 | 13.8 | 43% | 3 | D63, 2.5; F65, 2.5; D66, 1.0; |
| 1U0S | Y A | A | CHEMOTAXIS KINASE CHEA P2 DOMAIN IN COMPLEX WITH RESPONSE REGULATOR CHEY FROM THE THERMOPHILE THERMOTOGA MARITIMA | SIGNALING PROTEIN | 2.5 | 7.4 | 7.4 | 100% | 3 | R195, 2.5; Y197, 2.9; L198, 2.0; |
| 1U0S | Y A | Y | CHEMOTAXIS KINASE CHEA P2 DOMAIN IN COMPLEX WITH RESPONSE REGULATOR CHEY FROM THE THERMOPHILE THERMOTOGA MARITIMA | SIGNALING PROTEIN | 2.1 | 4.1 | 13.7 | 30% | 2 | I91, 2.2; I94, 1.9; |
| 1U7B | A B | B | CRYSTAL STRUCTURE OF HPCNA BOUND TO RESIDUES 331-350 OF THE FLAP ENDONUCLEASE-1 (FEN1) | REPLICATION | 3.0 | 6.0 | 6.0 | 100% | 2 | L340, 2.8; F343, 3.2; |
| 1U8T | B F | F | CRYSTAL STRUCTURE OF CHEY D13K Y106W ALONE AND IN COMPLEX WITH A FLIM PEPTIDE | SIGNALING PROTEIN | 2.0 | 5.9 | 7.6 | 78% | 3 | I11, 2.0; D12, 1.5; Q8, 2.4; |
| 1VCB | B C | B | THE VHL-ELONGINC-ELONGINB STRUCTURE | TRANSCRIPTION | 2.1 | 4.1 | 10.1 | 41% | 2 | L101, 1.5; L104, 2.6; |

FIG. 11L1

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 1TY4 | AC | C | CRYSTAL STRUCTURE OF A CED-9/EGL-1 COMPLEX | i;i+2;i+3; | 4 | 6 | 63 | 68 | DDFDAQ | 76 | 2.20 |
| 1U0S | YA | A | CHEMOTAXIS KINASE CHEA P2 DOMAIN IN COMPLEX WITH RESPONSE REGULATOR CHEY FROM THE THERMOPHILE THERMOTOGA MARITIMA | i;i+2;i+3; | 4 | 15 | 192 | 206 | KSARIYLVFHKLEEL | 77 | 1.90 |
| 1U0S | YA | Y | CHEMOTAXIS KINASE CHEA P2 DOMAIN IN COMPLEX WITH RESPONSE REGULATOR CHEY FROM THE THERMOPHILE THERMOTOGA MARITIMA | i;i+3; | 4 | 10 | 87 | 96 | QAMVIEAIKA | 78 | 1.90 |
| 1U7B | AB | B | CRYSTAL STRUCTURE OF HPCNA BOUND TO RESIDUES 331-350 OF THE FLAP ENDONUCLEASE-1 (FEN1) | i;i+3; | 4 | 5 | 340 | 344 | LDDFF | 79 | 1.88 |
| 1U8T | BF | F | CRYSTAL STRUCTURE OF CHEY D13K Y106W ALONE AND IN COMPLEX WITH A FLIM PEPTIDE | i;i+3;i+4; | 5 | 7 | 8 | 14 | QAEIDAL | 80 | 1.50 |
| 1VCB | BC | B | THE VHL-ELONGINC-ELONGINB STRUCTURE | i;i+3; | 4 | 15 | 97 | 111 | PEIALELLMAANFLD | 81 | 2.70 |

*FIG. 11L2*

| A. | B. | C. | D. | E. | F. | G. | H. | I. | J. | K. |
|---|---|---|---|---|---|---|---|---|---|---|
| PDB Code | Interface Chains | Chain | Title | Function | G_{AVG,HELIX} (Kcal/mol) | G_{SEM,HELIX} (Kcal/mol) | G_{SEM,CHAIN} (Kcal/mol) | Helix Contribution | #Hotspot Residues | Hotspot Residues Residue #; G_{(KCAL/MOL)} |
| 1X86 | G H | H | CRYSTAL STRUCTURE OF THE DH/PH DOMAINS OF LEUKEMIA-ASSOCIATED RHOGEF IN COMPLEX WITH RHOA | SIGNALING PROTEIN/ MEMBRANE PROTEIN | 3.1 | 6.1 | 14.8 | 41% | 2 | D67, 3.5; L69, 2.6; |
| 1XCG | A B | B | CRYSTAL STRUCTURE OF HUMAN RHOA IN COMPLEX WITH DH/PH FRAGMENT OF PDZRHOGEF | SIGNALING PROTEIN ACTIVATOR/ SIGNALING PR | 2.9 | 5.8 | 18.5 | 31% | 2 | L69, 3.7; L72, 2.1; |
| 1XIU | A E | E | CRYSTAL STRUCTURE OF THE AGONIST-BOUND LIGAND-BINDING DOMAIN OF BIOMPHALARIA GLABRATA RXR | TRANSCRIPTION/ TRANSFERASE | 2.2 | 8.8 | 8.8 | 100% | 4 | L690, 1.8; H691, 2.2; L693, 1.9; L634, 2.9; |
| 1XL3 | A C | A | COMPLEX STRUCTURE OF Y.PESTIS VIRULENCE FACTORS YOPN AND TYEA | CELL INVASION | 4.0 | 12.0 | 16.6 | 72% | 3 | F278, 4.7; W279, 4.4; F282, 2.9; |
| 1XLS | A E | A | CRYSTAL STRUCTURE OF THE MOUSE CAR/RXR LBD HETERODIMER BOUND TO TCPOBOP AND 9CRA AND A TIF2 PEPTIDE CONTAING THE THIRD LXXLL MOTIFS | TRANSCRIPTION | 3.3 | 6.6 | 9.5 | 69% | 2 | R426, 2.0; S427, 4.6; |
| 1XV9 | C G | G | CRYSTAL STRUCTURE OF CAR/RXR HETERODIMER BOUND WITH SRC1 PEPTIDE, FATTY ACID, AND 5B-PREGNANE-3,20-DIONE. | DNA BINDING PROTEIN | 2.7 | 5.4 | 6.4 | 84% | 2 | I632, 4.3; L633, 1.1; |

FIG. 11M1

| A. | B. | C. | D. | L. | M. | N. | O. | P. | Q. | R. | S. |
|---|---|---|---|---|---|---|---|---|---|---|---|
| PDB Code | Interface Chains | Chain | Title | Hotspot Residue Helix Positions | Hotspot Residue End to End Length | Helix Length | Helix Start Residue # | Helix End Residue # | Helix Sequence | SEQ ID NO: | Resolution |
| 1X86 | GH | H | CRYSTAL STRUCTURE OF THE DH/PH DOMAINS OF LEUKEMIA-ASSOCIATED RHOGEF IN COMPLEX WITH RHOA | i; i+2; | 3 | 5 | 67 | 71 | DRLRP | 82 | 3.22 |
| 1XCG | AB | B | CRYSTAL STRUCTURE OF HUMAN RHOA IN COMPLEX WITH DH/PH FRAGMENT OF PDZRHOGEF | i; i+3; | 4 | 7 | 69 | 75 | LRPLSYP | 83 | 2.50 |
| 1XIU | AE | E | CRYSTAL STRUCTURE OF THE AGONIST-BOUND LIGAND-BINDING DOMAIN OF BIOMPHALARIA GLABRATA RXR | i; i+1; i+3; i+4; | 5 | 10 | 688 | 697 | KILHRLLQEG | 84 | 2.50 |
| 1XL3 | AC | A | COMPLEX STRUCTURE OF Y.PESTIS VIRULENCE FACTORS YOPN AND TYEA | i; i+1; i+4; | 5 | 6 | 278 | 283 | FWQFFS | 85 | 2.20 |
| 1XLS | AE | A | CRYSTAL STRUCTURE OF THE MOUSE CAR/RXR LBD HETERODIMER BOUND TO TCPOBOP AND 9CRA AND A TIF2 PEPTIDE CONTAING THE THIRD LXXLL MOTIFS | i; i+1; | 2 | 29 | 414 | 442 | REAKLLLRLPALRSI GLKCLEHLFFFKLI | 86 | 2.96 |
| 1XV9 | CG | G | CRYSTAL STRUCTURE OF CAR/RXR HETERODIMER BOUND WITH SRC1 PEPTIDE, FATTY ACID, AND 5B-PREGNANE-3,20-DIONE. | i; i+1; | 2 | 7 | 631 | 637 | KILHRLL | 87 | 2.70 |

FIG. 11M2

| A. PDB Code | B. Interface Chains | C. Chain | D. Title | E. Function | F. $G_{AVG,HELIX}$ (Kcal/mol) | G. $G_{SUM,HELIX}$ (Kcal/mol) | H. $G_{SUM,CHAIN}$ (Kcal/mol) | I. Helix Contribution | J. # Hotspot Residues | K. Hotspot Residues Residue #, $G$ (KCAL/MOL) |
|---|---|---|---|---|---|---|---|---|---|---|
| 1Y3A | AE | E | STRUCTURE OF G-ALPHA-I1 BOUND TO A GDP-SELECTIVE PEPTIDE PROVIDES INSIGHT INTO GUANINE NUCLEOTIDE EXCHANGE | SIGNALING PROTEIN | 3.1 | 9.3 | 9.3 | 100% | 3 | W5, 4.2; F8, 3.3; L9, 1.8; |
| 1YCR | AB | B | MDM2 BOUND TO THE TRANSACTIVATION DOMAIN OF P53 | COMPLEX (ONCOGENE PROTEIN/PEPTIDE) | 3.7 | 11.1 | 12.9 | 86% | 3 | F19, 2.5; L22, 2.5; W23, 6.1; |
| 1YOK | AB | B | CRYSTAL STRUCTURE OF HUMAN LRH-1 BOUND WITH TIF-2 PEPTIDE AND PHOSPHATIDYLGLYCEROL | TRANSCRIPTION | 2.8 | 8.3 | 8.3 | 100% | 3 | L745, 2.9; L748, 2.7; L749, 2.7; |
| 1Z2C | AB | A | CRYSTAL STRUCTURE OF MDIA1 GBD-FH3 IN COMPLEX WITH RHOC-GMPPNP | SIGNALING PROTEIN | 2.6 | 5.1 | 15.1 | 34% | 2 | R68, 4.0; L69, 1.1; |
| 1Z56 | AC | A | CO-CRYSTAL STRUCTURE OF LIF1P-LIG4P | LIGASE | 4.3 | 12.9 | 12.9 | 100% | 3 | R209, 1.4; M211, 1.3; M212, 10.2; |
| 1ZNV | CD | C | HOW A HIS-METAL FINGER ENDONUCLEASE COLE7 BINDS AND CLEAVES DNA WITH A TRANSITION METAL ION COFACTOR | HYDROLASE/PROTEIN BINDING | 2.5 | 4.9 | 9.5 | 52% | 2 | D52, 1.3; Y55, 3.6; |
| 1ZOQ | AC | C | IRF3-CBP COMPLEX | TRANSCRIPTION/TRANSFERASE | 2.1 | 4.2 | 7.6 | 55% | 2 | Q2085, 2.2; I2089, 2.0; |
| 1ZOQ | BD | D | IRF3-CBP COMPLEX | TRANSCRIPTION/TRANSFERASE | 2.0 | 4.0 | 8.2 | 49% | 2 | L2096, 1.6; F2100, 2.4; |
| 1ZVV | BP | P | CRYSTAL STRUCTURE OF A CCPA-CRH-DNA COMPLEX | TRANSCRIPTION/DNA | 2.2 | 4.4 | 4.4 | 100% | 2 | H7, 2.4; M51, 2.0; |

*FIG. 11N1*

| A. | B. | C. | D. | L. | M. | N. | O. | P. | Q. | R. | S. |
|---|---|---|---|---|---|---|---|---|---|---|---|
| PDB Code | Interface Chains | Chain | Title | Hotspot Residue Helix Positions | Hotspot Residue End to End Length | Helix Length | Helix Start Residue # | Helix End Residue # | Helix Sequence | SEQ ID NO: | Resolution |
| 1Y3A | A E | E | STRUCTURE OF G-ALPHA-I1 BOUND TO A GDP-SELECTIVE PEPTIDE PROVIDES INSIGHT INTO GUANINE NUCLEOTIDE EXCHANGE | i;i+3;i+4; | 5 | 6 | 5 | 10 | WYDFLM | 88 | 2.50 |
| 1YCR | A B | B | MDM2 BOUND TO THE TRANSACTIVATION DOMAIN OF P53 | i;i+3;i+4; | 5 | 6 | 19 | 24 | FSDLWK | 89 | 2.60 |
| 1YOK | A B | B | CRYSTAL STRUCTURE OF HUMAN LRH-1 BOUND WITH TIF-2 PEPTIDE AND PHOSPHATIDYLGLYCEROL | i;i+3;i+4; | 5 | 9 | 743 | 751 | ALLRYLLDK | 90 | 2.50 |
| 1Z2C | A B | A | CRYSTAL STRUCTURE OF MDIA1 GBD-FH3 IN COMPLEX WITH RHOC - GMPPNP | i;i+1; | 2 | 5 | 67 | 71 | DRLRP | 91 | 3.00 |
| 1Z56 | A C | A | CO-CRYSTAL STRUCTURE OF LIF1P-LIG4P | i;i+2;i+3; | 3 | 6 | 209 | 214 | RAMMVT | 92 | 3.92 |
| 1ZNV | C D | C | HOW A HIS-METAL FINGER ENDONUCLEASE COLE7 BINDS AND CLEAVES DNA WITH A TRANSITION METAL ION COFACTOR | i;i+3; | 4 | 6 | 51 | 56 | TDLIYY | 93 | 2.00 |
| 1ZOQ | A C | C | IRF3-CBP COMPLEX | i;i+4; | 5 | 13 | 2080 | 2092 | PQQQQQVLNILKS | 94 | 2.37 |
| 1ZOQ | B D | D | IRF3-CBP COMPLEX | i;i+4; | 5 | 12 | 2094 | 2105 | PQLMAAFIKQRT | 95 | 2.37 |
| 1ZVV | B P | P | CRYSTAL STRUCTURE OF A CCPA-CRH-DNA COMPLEX | i;i+4; | 5 | 8 | 47 | 54 | IMGLMSLA | 96 | 2.98 |

*FIG. 11N2*

| A. PDB Code | B. Interface Chains | C. Chain | D. Title | E. Function | F. $G_{AVG,HELIX}$ (Kcal/mol) | G. $G_{SUM,HELIX}$ (Kcal/mol) | H. $G_{SUM,CHAIN}$ (Kcal/mol) | I. Helix Contribution | J. # Hotspot Residues | K. Hotspot Residues Residue #, $G_{(KCAL/MOL)}$ |
|---|---|---|---|---|---|---|---|---|---|---|
| 2A19 | A B | B | PKR KINASE DOMAIN- EIF2ALPHA- AMP-PNP COMPLEX. | PROTEIN SYNTHESIS/ TRANSFERASE | 3.4 | 6.7 | 6.7 | 100% | 2 | F489, 5.3; E490, 1.4; |
| 2A45 | A B | A | CRYSTAL STRUCTURE OF THE COMPLEX BETWEEN THROMBIN AND THE CENTRAL "E" REGION OF FIBRIN | BLOOD CLOTTING | 2.1 | 4.1 | 4.1 | 100% | 2 | E14, 1.6; L14, 2.5; |
| 2A4J | A B | B | SOLUTION STRUCTURE OF THE C-TERMINAL DOMAIN (T94-Y172) OF THE HUMAN CENTRIN 2 IN COMPLEX WITH A 17 RESIDUES PEPTIDE (P1-XPC) FROM XERODERMA PIGMENTOSUM GROUP C PROTEIN | STRUCTURAL PROTEIN | 3.1 | 6.2 | 14.7 | 42% | 2 | 2, 4.2; 5, 2.0; |
| 2AGH | B C | C | STRUCTURAL BASIS FOR COOPERATIVE TRANSCRIPTION FACTOR BINDING TO THE CBP COACTIVATOR | TRANSCRIPTION | 2.3 | 6.9 | 8.2 | 84% | 3 | I849, 2.0; F852, 3.8; V853, 1.1; |
| 2B5L | A C | C | CRYSTAL STRUCTURE OF DDB1 IN COMPLEX WITH SIMIAN VIRUS 5 V PROTEIN | PROTEIN BINDING/ VIRAL PROTEIN | 2.4 | 4.7 | 8.4 | 56% | 2 | V24, 2.1; F27, 2.6; |
| 2C9W | A C | C | CRYSTAL STRUCTURE OF SOCS-2 IN COMPLEX WITH ELONGIN-B AND ELONGIN REGULATION CAT 1.9A RESOLUTION | TRANSCRIPTION | 2.1 | 6.3 | 9.1 | 69% | 3 | L101, 2.2; L103, 1.0; L104, 3.1; |

FIG. 1101

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 2A19 | AB | B | PKR KINASE DOMAIN- EIF2ALPHA- AMP-PNP COMPLEX. | i; i+1; | 2 | 12 | 488 | 499 | AFETSKFFTDLR | 97 | 2.50 |
| 2A45 | AB | A | CRYSTAL STRUCTURE OF THE COMPLEX BETWEEN THROMBIN AND THE CENTRAL "E" REGION OF FIBRIN | i; i+1; | 2 | 8 | 14 | 14 | ERELLESY | 98 | 3.65 |
| 2A4J | AB | B | SOLUTION STRUCTURE OF THE C-TERMINAL DOMAIN (T94-Y172) OF THE HUMAN CENTRIN 2 IN COMPLEX WITH A 17 RESIDUES PEPTIDE (P1-XPC) FROM XERODERMA PIGMENTOSUM GROUP C PROTEIN | i; i+3; | 4 | 8 | 2 | 9 | WKLLAKGL | 99 | NOT APP |
| 2AGH | BC | C | STRUCTURAL BASIS FOR COOPERATIVE TRANSCRIPTION FACTOR BINDING TO THE CBP COACTIVATOR | i; i+3; i+4; | 5 | 12 | 847 | 858 | SDMDFVLKNTP | 100 | NOT APP |
| 2BSL | AC | C | CRYSTAL STRUCTURE OF DDB1 IN COMPLEX WITH SIMIAN VIRUS 5 V PROTEIN | i; i+3; | 4 | 11 | 23 | 33 | TVEYFTSQQVT | 101 | 2.85 |
| 2C9W | AC | C | CRYSTAL STRUCTURE OF SOCS-2 IN COMPLEX WITH ELONGIN-B AND ELONGIN C AT 1.9A RESOLUTION | i; i+2; i+3; | 4 | 11 | 100 | 110 | ALELLMAANFL | 102 | 1.90 |

FIG. 1102

| A. PDB Code | B. Interface Chains | C. Chain | D. Title | E. Function | F. G$_{AVG,HELIX}$ (Kcal/mol) | G. G$_{SEM,HELIX}$ (Kcal/mol) | H. G$_{SEM,CHAIN}$ (Kcal/mol) | I. Helix Contribution | J. # Hotspot Residues | K. Hotspot Residues Residue #, G$_{(KCAL/MOL)}$ |
|---|---|---|---|---|---|---|---|---|---|---|
| 2CCL | CD | D | THE S45A, T46A MUTANT OF THE TYPE I COHESIN-DOCKERIN COMPLEX FROM THE CELLULOSOME OF CLOSTRIDIUM THERMOCELLUM | CELL ADHESION | 2.8 | 5.6 | 8.3 | 67% | 2 | K18, 1.9; R19, 3.7; |
| 2DWZ | AB | B | STRUCTURE OF THE ONCOPROTEIN GANKYRIN IN COMPLEX WITH S6 ATPASE OF THE 26S PROTEASOME | ONCOPROTEIN | 2.4 | 7.2 | 12.5 | 58% | 3 | R338, 2.1; R339, 1.4; R342, 3.7; |
| 2EHB | AD | D | THE STRUCTURE OF THE C-TERMINAL DOMAIN OF THE PROTEIN KINASE ATSOS2 BOUND TO THE CALCIUM SENSOR ATSOS3 | SIGNALLING PROTEIN/ TRANSFERASE | 3.0 | 8.9 | 17.9 | 50% | 3 | F313, 5.6; M315, 1.3; I316, 2.0; |
| 2EKV | AB | A | THE CRYSTAL STRUCTURE OF RIGOR LIKE SQUID MYOSIN S1 IN THE ABSENCE OF NUCLEOTIDE | CONTRACTILE PROTEIN | 2.9 | 8.6 | 16.3 | 53% | 3 | W828, 6.2; W829, 1.1; L831, 1.3; |
| 2EKV | AB | A | THE CRYSTAL STRUCTURE OF RIGOR LIKE SQUID MYOSIN S1 IN THE ABSENCE OF NUCLEOTIDE | CONTRACTILE PROTEIN | 3.0 | 5.9 | 16.3 | 36% | 2 | K819, 2.5; L821, 3.4; |
| 2ERJ | FH | H | CRYSTAL STRUCTURE OF THE HETEROTRIMERIC INTERLEUKIN-2 RECEPTOR IN COMPLEX WITH INTERLEUKIN-2 | IMMUNE SYSTEM/ CYTOKINE | 2.0 | 3.9 | 9.7 | 40% | 2 | H16, 2.9; L19, 1.0; |

FIG. 11P1

| A. | B. | C. | D. | L. | M. | N. | O. | P. | Q. | R. | S. |
|---|---|---|---|---|---|---|---|---|---|---|---|
| PDB Code | Interface Chains | Chain | Title | Hotspot Residue Helix Positions | Hotspot Residue End to End Length | Helix Length | Helix Start Residue # | Helix End Residue # | Helix Sequence | SEQ ID NO: | Resolution |
| 2CCL | CD | D | THE S45A, T46A MUTANT OF THE TYPE I COHESIN-DOCKERIN COMPLEX FROM THE CELLULOSOME OF CLOSTRIDIUM THERMOCELLUM | i;i+1; | 2 | 12 | 11 | 22 | STDLTMLKRSVL | 103 | 2.03 |
| 2DWZ | AB | B | STRUCTURE OF THE ONCOPROTEIN GANKYRIN IN COMPLEX WITH S6 ATPASE OF THE 26S PROTEASOME | i;i+1;i+4; | 5 | 14 | 338 | 351 | RRQKRLIFSTITSK | 104 | 2.40 |
| 2EHB | AD | D | THE STRUCTURE OF THE C-TERMINAL DOMAIN OF THE PROTEIN KINASE ATSOS2 BOUND TO THE CALCIUM SENSOR ATSOS3 | i;i+2;i+3; | 4 | 6 | 312 | 317 | AFEMIT | 105 | 2.10 |
| 2EKV | AB | A | THE CRYSTAL STRUCTURE OF RIGOR LIKE SQUID MYOSIN S1 IN THE ABSENCE OF NUCLEOTIDE | i;i+1;i+3; | 4 | 5 | 828 | 832 | WWRLF | 106 | 3.40 |
| 2EKV | AB | A | THE CRYSTAL STRUCTURE OF RIGOR LIKE SQUID MYOSIN S1 IN THE ABSENCE OF NUCLEOTIDE | i;i+3; | 3 | 11 | 815 | 825 | RNVRKWLVLRN | 107 | 3.40 |
| 2ERJ | FH | H | CRYSTAL STRUCTURE OF THE HETEROTRIMERIC INTERLEUKIN-2 RECEPTOR IN COMPLEX WITH INTERLEUKIN-2 | i;i+3; | 4 | 26 | 4 | 29 | SSSTKKTQLQLEHL LLDLQMILNGIN | 108 | 3.00 |

FIG. 11P2

| A. PDB Code | B. Interface Chains | C. Chain | D. Title | E. Function | F. $G_{AVG,HELIX}$ (Kcal/mol) | G. $G_{SEM,HELIX}$ (Kcal/mol) | H. $G_{SEM,CHAIN}$ (Kcal/mol) | I. Helix Contribution | J. # Hotspot Residues | K. Hotspot Residues Residue #, $G_{(KCAL/MOL)}$ |
|---|---|---|---|---|---|---|---|---|---|---|
| 2F93 | AB | B | K INTERMEDIATE STRUCTURE OF SENSORY RHODOPSIN II/TRANSDUCER COMPLEX IN COMBINATION WITH THE GROUND STATE STRUCTURE | MEMBRANE PROTEIN | 2.2 | 4.3 | 7.2 | 60% | 2 | I69, 2.1; I73, 2.2; |
| 2FM8 | BC | C | CRYSTAL STRUCTURE OF THE SALMONELLA SECRETION CHAPERONE INVB IN COMPLEX WITH SIPA | CHAPERONE/CELL INVASION | 2.2 | 4.3 | 4.3 | 100% | 2 | P54, 3.0; I58, 1.3; |
| 2FNJ | AC | A | CRYSTAL STRUCTURE OF A B30.2/SPRY DOMAIN-CONTAINING PROTEIN GUSTAVUS IN COMPLEX WITH ELONGIN B AND ELONGIN C | PROTEIN TRANSPORT/ SIGNALING PROTEIN | 3.1 | 6.1 | 6.1 | 100% | 2 | L241, 4.7; C245, 1.4; |
| 2FO1 | DE | D | CRYSTAL STRUCTURE OF THE CSL-NOTCH-MASTERMIND TERNARY COMPLEX BOUND TO DNA | GENE REGULATION/ SIGNALLING PROTEIN/DNA | 2.2 | 4.3 | 5.3 | 81% | 2 | L69, 3.1; H70, 1.2; |
| 2FOI | BD | D | SYNTHESIS, BIOLOGICAL ACTIVITY, AND X-RAY CRYSTAL STRUCTURAL ANALYSIS OF DIARYL ETHER INHIBITORS OF MALARIAL ENOYL ACP REDUCTASE. | OXIDOREDUCTASE | 2.9 | 5.7 | 8.9 | 64% | 2 | F368, 3.9; I369, 1.8; |
| 2G30 | AP | P | BETA APPENDAGE OF AP2 COMPLEXED WITH ARH PEPTIDE | ENDOCYTOSIS/ EXOCYTOSIS | 3.3 | 6.6 | 11.1 | 59% | 2 | L11, 1.5; F8, 5.1; |

FIG. 11Q1

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 2F93 | A B | B | K INTERMEDIATE STRUCTURE OF SENSORY RHODOPSIN II/TRANSDUCER COMPLEX IN COMBINATION WITH THE GROUND STATE STRUCTURE | i; i+4; | 5 | 27 | 53 | 79 | AAAVQEAAVSAILG LIILLGINLGLVA | 109 | 2.00 |
| 2FM8 | B C | C | CRYSTAL STRUCTURE OF THE SALMONELLA SECRETION CHAPERONE INVB IN COMPLEX WITH SIPA | i; i+4; | 5 | 17 | 54 | 70 | FPALIKQASLDALF KCG | 110 | 2.20 |
| 2FNJ | A C | A | CRYSTAL STRUCTURE OF A B30.2/SPRY DOMAIN-CONTAINING PROTEIN GUSTAVUS IN COMPLEX WITH ELONGIN B AND ELONGIN C | i; i+4; | 5 | 10 | 241 | 250 | LMDLCRRTIR | 111 | 1.80 |
| 2FO1 | D E | D | CRYSTAL STRUCTURE OF THE CSL-NOTCH-MASTERMIND TERNARY COMPLEX BOUND TO DNA | i; i+1; | 2 | 17 | 68 | 84 | ELHRQRSELARAN YEKA | 112 | 3.12 |
| 2FO1 | B D | D | SYNTHESIS, BIOLOGICAL ACTIVITY, AND X-RAY CRYSTAL STRUCTURAL ANALYSIS OF DIARYL ETHER INHIBITORS OF MALARIAL ENOYL ACP REDUCTASE. | i; i+1; | 2 | 12 | 368 | 379 | FIDYAIEYSEKY | 113 | 2.50 |
| 2G30 | A P | P | BETA APPENDAGE OF AP2 COMPLEXED WITH ARH PEPTIDE | i; i+3; | 4 | 11 | 5 | 15 | DEAFSRLAQSR | 114 | 1.60 |

FIG. 11Q2

| A. PDB Code | B. Interface Chains | C. Chain | D. Title | E. Function | F. $G_{AVG,HELIX}$ (Kcal/mol) | G. $G_{SUM,HELIX}$ (Kcal/mol) | H. $G_{SUM,CHAIN}$ (Kcal/mol) | I. Helix Contribution | J. # Hotspot Residues | K. Hotspot Residues Residue #, $G$ (KCAL/MOL) |
|---|---|---|---|---|---|---|---|---|---|---|
| 2G4D | A B | A | CRYSTAL STRUCTURE OF HUMAN SENP1 MUTANT (C603S) IN COMPLEX WITH SUMO- BINDING 1 | HYDROLASE/ PROTEIN | 3.6 | 10.8 | 17.9 | 60% | 3 | D468, 3.2; E469, 1.2; N472, 6.4; |
| 2GPV | A G | G | ESTROGEN RELATED RECEPTOR-GAMMA LIGAND BINDING DOMAIN COMPLEXED WITH 4-HYDROXY-TAMOXIFEN AND A SMRT PEPTIDE | TRANSCRIPTION | 2.1 | 4.2 | 4.2 | 100% | 2 | I1324, 2.0; L1328, 2.2; |
| 2HRK | A B | B | STRUCTURAL BASIS OF YEAST AMINOACYL-TRNA SYNTHETASE COMPLEX FORMATION REVEALED BY CRYSTAL STRUCTURES OF TWO BINARY SUB-COMPLEXES | LIGASE/ RNA BINDING PROTEIN | 2.7 | 5.3 | 8.9 | 60% | 2 | R102, 2.2; Y106, 3.1; |
| 2HUE | A B | B | STRUCTURE OF THE H3-H4 CHAPERONE ASF1 BOUND TO HISTONES H3 AND H4 | DNA BINDING PROTEIN | 2.1 | 4.2 | 7.2 | 58% | 2 | L126, 2.5; H130, 1.7; |
| 2HUE | B C | C | STRUCTURE OF THE H3-H4 CHAPERONE ASF1 BOUND TO HISTONES H3 AND H4 | DNA BINDING PROTEIN | 2.3 | 4.5 | 22.5 | 20% | 2 | R36, 1.8; L37, 2.7; |
| 2HWN | A E | E | CRYSTAL STRUCTURE OF RII ALPHA DIMERIZATION/DOCKING DOMAIN OF PKA BOUND TO THE D-AKAP2 PEPTIDE | TRANSFERASE | 2.1 | 4.1 | 4.1 | 100% | 2 | V13, 2.8; M17, 1.3; |
| 2I2R | A E | E | CRYSTAL STRUCTURE OF THE KCHIP1/KV4.3 T1 COMPLEX | TRANSPORT PROTEIN | 2.0 | 3.9 | 8.3 | 47% | 2 | I77, 1.5; Y78, 2.4; |

FIG. 11R1

| A. PDB Code | B. Interface Chains | C. Chain | D. Title | L. Hotpot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 2G4D | AB | A | CRYSTAL STRUCTURE OF HUMAN SENP1 MUTANT (C603S) IN COMPLEX WITH SUMO-1 | i; i+1; i+4; | 5 | 17 | 468 | 484 | DEINFYMNMLME RSKE | 115 | 2.80 |
| 2GPV | AG | G | ESTROGEN RELATED RECEPTOR-GAMMA LIGAND BINDING DOMAIN COMPLEXED WITH 4-HYDROXY-TAMOXIFEN AND A SMRT PEPTIDE | i; i+4; | 5 | 10 | 1321 | 1330 | EAIIRKALMG | 116 | 2.85 |
| 2HRK | AB | B | STRUCTURAL BASIS OF YEAST AMINOACYL-TRNA SYNTHETASE COMPLEX FORMATION REVEALED BY CRYSTAL STRUCTURES OF TWO BINARY SUB-COMPLEXES | i; i+4; | 5 | 14 | 98 | 111 | RHILRWDYMQNL L | 117 | 2.05 |
| 2HUE | AB | B | STRUCTURE OF THE H3-H4 CHAPERONE ASF1 BOUND TO HISTONES H3 AND H4 | i; i+4; | 5 | 11 | 121 | 131 | PKDIQLARRIR | 118 | 1.70 |
| 2HUE | BC | C | STRUCTURE OF THE H3-H4 CHAPERONE ASF1 BOUND TO HISTONES H3 AND H4 | i; i+1; | 2 | 11 | 31 | 41 | KPAIRRLARRG | 119 | 1.70 |
| 2HWN | AE | E | CRYSTAL STRUCTURE OF RII ALPHA DIMERIZATION/DOCKING DOMAIN OF PKA BOUND TO THE D-AKAP2 PEPTIDE | i; i+4; | 5 | 17 | 4 | 20 | LAWKIAKMIVSDV MQQC | 120 | 1.60 |
| 2I2R | AE | E | CRYSTAL STRUCTURE OF THE KCHIP1/KV4.3 F1 COMPLEX | i; i+1; | 2 | 12 | 71 | 82 | EDTFKQIYAQFF | 121 | 3.35 |

FIG. 11R2

| A. | B. | C. | D. | E. | F. | G. | H. | I. | J. | K. | |
|---|---|---|---|---|---|---|---|---|---|---|---|
| PDB Code | Interface Chains | Chain | Title | Function | $G_{AVG,HELIX}$ (Kcal/mol) | $G_{SEM,HELIX}$ (Kcal/mol) | $G_{SEM,CHAIN}$ (Kcal/mol) | Helix Contribution | # Hotspot Residues | Hotspot Residues Residue #, $G_{(KCAL/MOL)}$ | |
| 2I2R | BF | B | CRYSTAL STRUCTURE OF THE KCHIP1/KV4.3 T1 COMPLEX | TRANSPORT PROTEIN | 3.4 | 6.7 | 19.2 | 35% | 2 | F11, 1.7; W8, 5.0; | |
| 2I3S | CD | D | BUB3 COMPLEX WITH BUB1 GLEBS MOTIF | CELL CYCLE | 2.8 | 8.4 | 15.4 | 55% | 3 | E357, 3.3; E358, 1.9; L340, 3.0; | |
| 2I3T | CD | D | BUB3 COMPLEX WITH MAD3 (BUBR1) GLEBS MOTIF | CELL CYCLE | 2.8 | 5.5 | 17.7 | 31% | 2 | E383, 2.3; L385, 3.2; | |
| 2IV8 | AP | P | BETA APPENDAGE IN COMPLEX WITH B-ARRESTIN PEPTIDE | ENDOCYTOSIS/ REGULATOR | 2.7 | 5.4 | 9.1 | 59% | 2 | D3, 1.5; F6, 3.9; | |
| 2J59 | AM | M | CRYSTAL STRUCTURE OF THE ARF1:ARHGAP21-ARFBD COMPLEX | HYDROLASE | 2.1 | 4.2 | 4.2 | 100% | 2 | I1053, 2.0; H1057, 2.2; | |
| 2JTT | AC | C | SOLUTION STRUCTURE OF CALCIUM LOADED S100A6 BOUND TO C-TERMINAL SIAH-1 INTERACTING PROTEIN | CALCIUM BINDING PROTEIN/ANTITUMOR PROTEI | 2.5 | 5.0 | 5.0 | 100% | 2 | I211, 1.8; W215, 3.2; | |
| 2K8B | AB | B | SOLUTION STRUCTURE OF PLAA FAMILY UBIQUITIN BINDING DOMAIN (PFUC) CIS ISOMER IN COMPLEX WITH UBIQUITIN | PROTEIN BINDING | 2.1 | 6.4 | 6.4 | 100% | 3 | M105, 1.4; F106, 2.3; Q109, 2.7; | |
| 2KA6 | AB | B | NMR STRUCTURE OF THE CBP-TAZ2/STAT1-TAD COMPLEX | TRANSCRIPTION REGULATOR | 2.6 | 10.5 | 19.6 | 54% | 4 | E730, 1.8; F731, 4.5; E733, 3.0; V734, 1.2; | |
| 2OCF | AD | D | HUMAN ESTROGEN RECEPTOR ALPHA LIGAND-BINDING DOMAIN IN COMPLEX WITH ESTRADIOL AND THE E2/23 FN3 MONOBODY | HORMONE/GROWTH FACTOR | 2.2 | 4.4 | 4.4 | 100% | 2 | L78, 2.3; L82, 2.1; | |

FIG. 11S1

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 2I2R | B F | B | CRYSTAL STRUCTURE OF THE KCHIP1:KV4.3 T1 COMPLEX | i; i+3; | 4 | 8 | 8 | 15 | WLPFARAA | 122 | 3.35 |
| 2I3S | C D | D | BUB3 COMPLEX WITH BUB1 GLEBS MOTIF | i; i+1; i+3; | 4 | 9 | 336 | 344 | TEEILAMIK | 123 | 1.90 |
| 2I3T | C D | D | BUB3 COMPLEX WITH MAD3 (BUBR1) GLEBS MOTIF | i; i+2; | 3 | 9 | 381 | 389 | LEEVLAISR | 124 | 2.80 |
| 2IV8 | A P | P | BETA APPENDAGE IN COMPLEX WITH B-ARRESTIN PEPTIDE | i; i+3; | 4 | 12 | 2 | 13 | DDIVFEDEARQR | 125 | 2.80 |
| 2J59 | A M | M | CRYSTAL STRUCTURE OF THE ARF1:ARHGAP21-ARFBD COMPLEX | i; i+4; | 5 | 22 | 1042 | 1063 | EEDTGVTNRDLSRRIKEYNNL | 126 | 2.10 |
| 2JTT | A C | C | SOLUTION STRUCTURE OF CALCIUM LOADED S100A6 BOUND TO C-TERMINAL SIAH-1 INTERACTING PROTEIN | i; i+4; | 5 | 14 | 205 | 218 | DDMKRTINKAWVES | 127 | NOT APP |
| 2K8B | A B | B | SOLUTION STRUCTURE OF PLAA FAMILY UBIQUITIN BINDING DOMAIN (PFUC) CIS ISOMER IN COMPLEX WITH UBIQUITIN | i; i+1; i+4; | 5 | 17 | 104 | 120 | PMFLDQVAKFHDNTKG | 128 | NOT APP |
| 2KA6 | A B | B | NMR STRUCTURE OF THE CBP-TAZ2/STAT1-TAD COMPLEX | i; i+1; i+3; i+4; | 5 | 12 | 728 | 739 | PEEPDEVSRIVG | 129 | NOT APP |
| 2OCF | A D | D | HUMAN ESTROGEN RECEPTOR ALPHA LIGAND-BINDING DOMAIN IN COMPLEX WITH ESTRADIOL AND THE E2#23 FN3 MONOBODY | i; i+4; | 5 | 7 | 78 | 84 | LRLMLAG | 130 | 2.95 |

FIG. 11S2

| A. | B. | C. | D. | E. | F. | G. | H. | I. | J. | K. |
|---|---|---|---|---|---|---|---|---|---|---|
| PDB Code | Interface Chains | Chain | Title | Function | $G_{AVG,HELIX}$ (Kcal/mol) | $G_{SUM,HELIX}$ (Kcal/mol) | $G_{SUM,CHAIN}$ (Kcal/mol) | Helix Contribution | # Hotspot Residues | Hotspot Residues Residue #, $G$ (KCAL/MOL) |
| 2OF5 | C J | J | OLIGOMERIC DEATH DOMAIN COMPLEX | APOPTOSIS | 3.5 | 7.0 | 7.0 | 100% | 2 | D864, 5.2; E867, 1.8; |
| 2OZN | A B | B | THE COHESIN-DOCKERIN COMPLEX OF NAG1 AND NAGH FROM CLOSTRIDIUM PERFRINGENS | TOXIN | 2.3 | 4.5 | 7.0 | 64% | 2 | I1588, 3.1; L1591, 1.4; |
| 2P5T | E F | E | MOLECULAR AND STRUCTURAL CHARACTERIZATION OF THE PEZAT CHROMOSOMAL TOXIN-ANTITOXIN SYSTEM OF THE HUMAN PATHOGEN STREPTOCOCCUS PNEUMONIAE | TRANSCRIPTION REGULATOR | 2.1 | 4.2 | 17.9 | 23% | 2 | H123, 2.1; Y127, 2.1; |
| 2PHE | A C | C | MODEL FOR VP16 BINDING TO PC4 | TRANSCRIPTION | 2.5 | 7.6 | 7.6 | 100% | 3 | F475, 3.0; E476, 1.1; F479, 3.5; |
| 2PMS | A C | C | CRYSTAL STRUCTURE OF THE COMPLEX OF HUMAN LACTOFERRIN N-LOBE AND LACTOFERRIN-BINDING DOMAIN OF PNEUMOCOCCAL SURFACE PROTEIN A | METAL TRANSPORT, HYDROLASE | 2.0 | 4.0 | 8.1 | 49% | 2 | E182, 2.8; N183, 1.2; |
| 2POP | C D | C | THE CRYSTAL STRUCTURE OF TAB1 AND BIR1 COMPLEX | SIGNALING PROTEIN/APOPTOSIS | 2.3 | 7.0 | 7.0 | 100% | 3 | E2212, 2.4; D2213, 1.4; F2216, 3.2; |
| 2PQR | B D | D | CRYSTAL STRUCTURE OF YEAST FES1 COMPLEXED WITH A FRAGMENT OF YEAST CAF4 | APOPTOSIS | 2.9 | 5.7 | 22.6 | 25% | 2 | F101, 3.8; R102, 1.9; |

FIG. 11T1

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 2OF5 | CJ | J | OLIGOMERIC DEATH DOMAIN COMPLEX | i; i+3; | 4 | 12 | 863 | 874 | QDVAEEVRAVLE | 131 | 3.20 |
| 2OZN | AB | B | THE COHESIN-DOCKERIN COMPLEX OF NAG J AND NAG H FROM CLOSTRIDIUM PERFRINGENS | i; i+3; | 4 | 10 | 1588 | 1597 | IGDLAMVSKN | 132 | 1.60 |
| 2P5T | EF | E | MOLECULAR AND STRUCTURAL CHARACTERIZATION OF THE PEZAT CHROMOSOMAL TOXIN-ANTITOXIN SYSTEM OF THE HUMAN PATHOGEN STREPTOCOCCUS PNEUMONIAE | i; i+4; | 5 | 19 | 110 | 128 | PWILMSDDLSDLIH TNIYL | 133 | 3.20 |
| 2PHE | AC | C | MODEL FOR VP16 BINDING TO PC4 | i; i+1; i+4; | 5 | 6 | 475 | 480 | FEQMFT | 134 | NOT APP |
| 2PMS | AC | C | CRYSTAL STRUCTURE OF THE COMPLEX OF HUMAN LACTOFERRIN N- LOBE AND LACTOFERRIN-BINDING DOMAIN OF PNEUMOCOCCAL SURFACE PROTEIN A | i; i+1; | 2 | 19 | 174 | 192 | PQAKIAELENQVHR LEQEL | 135 | 2.91 |
| 2POP | CD | C | THE CRYSTAL STRUCTURE OF TAB1 AND BIR1 COMPLEX | i; i+1; i+4; | 5 | 11 | 2212 | 2222 | EDELFRLSQLG | 136 | 3.10 |
| 2PQR | BD | D | CRYSTAL STRUCTURE OF YEAST FSH COMPLEXED WITH A FRAGMENT OF YEAST CAF4 | i; i+1; | 2 | 9 | 97 | 105 | SATTFRILA | 137 | 1.88 |

FIG. 11T2

| A. | B. | C. | D. | E. | F. | G. | H. | I. | J. | K. | |
|---|---|---|---|---|---|---|---|---|---|---|---|
| PDB Code | Interface Chains | Chain | Title | Function | $G_{AVG,HELIX}$ (Kcal/mol) | $G_{SEM,HELIX}$ (Kcal/mol) | $G_{SEM,CHAIN}$ (Kcal/mol) | Helix Contribution | # Hotspot Residues | Hotspot Residues | |
| | | | | | | | | | | Residue #, $G$ (KCAL/MOL) | |
| 2PV2 | AE | E | CRYSTALLOGRAPHIC STRUCTURE OF SURA FIRST PEPTIDYL-PROLYL ISOMERASE DOMAIN COMPLEXED WITH PEPTIDE NFTLKFWDIFRK | ISOMERASE | 2.8 | 5.6 | 11.4 | 49% | 2 | F6, 4.6; 19, 1.0; |
| 2PV9 | AB | A | CRYSTAL STRUCTURE OF MURINE THROMBIN IN COMPLEX WITH THE EXTRACELLULAR FRAGMENT OF MURINE PAR4 | HYDROLASE | 2.2 | 4.4 | 8.5 | 52% | 2 | E14(E), 2.5; L14(F), 1.9; |
| 2QB0 | AD | D | STRUCTURE OF THE 2TEL CRYSTALLIZATION MODULE FUSED TO T4 LYSOZYME WITH AN ALA-GLY-PRO LINKER. | HYDROLASE REGULATOR | 2.1 | 4.2 | 10.6 | 40% | 2 | D79, 2.4; V80, 1.8; |
| 2RHK | AC | C | CRYSTAL STRUCTURE OF INFLUENZA A NS1A PROTEIN IN COMPLEX WITH F2F3 FRAGMENT OF HUMAN CELLULAR FACTOR CPSF30 | VIRAL PROTEIN/ NUCLEAR PROTEIN | 2.0 | 4.0 | 13.8 | 29% | 2 | Y97, 1.7; F98, 2.3; |
| 2UZ6 | EO | O | ACHBP-TARGETED A-CONOTOXIN CORRELATES DISTINCT BINDING ORIENTATIONS WITH NACHR SUBTYPE SELECTIVITY. | RECEPTOR | 4.2 | 8.4 | 10.6 | 79% | 2 | C8, 7.0; N11, 1.4; |

FIG. 11U1

| A. | B. | C. | D. | L. | M. | N. | O. | P. | Q. | R. | S. |
|---|---|---|---|---|---|---|---|---|---|---|---|
| PDB Code | Interface Chains | Chain | Title | Hotspot Residue Helix Positions | Hotspot Residue End to End Length | Helix Length | Helix Start Residue # | Helix End Residue # | Helix Sequence | SEQ ID NO: | Resolution |
| 2PV2 | A E | E | CRYSTALLOGRAPHIC STRUCTURE OF SURA FIRST PEPTIDYL-PROLYL ISOMERASE DOMAIN COMPLEXED WITH PEPTIDE NFTLKFWDIFRK | i; i+3; | 4 | 8 | 3 | 10 | TLKFWDIF | 138 | 1.30 |
| 2PV9 | A B | A | CRYSTAL STRUCTURE OF MURINE THROMBIN IN COMPLEX WITH THE EXTRACELLULAR FRAGMENT OF MURINE PAR4 | i; i+4; | 2 | 6 | 14E | 14F | EKELLD | 139 | 3.50 |
| 2QB0 | A D | D | STRUCTURE OF THE 2TEL CRYSTALLIZATION MODULE FUSED TO T4 LYSOZYME WITH AN ALA-GLY-PRO LINKER. | i; i+4; | 2 | 14 | 78 | 91 | GDVLYELLQHILKQ | 140 | 2.56 |
| 2RHK | A C | C | CRYSTAL STRUCTURE OF INFLUENZA A NS1A PROTEIN IN COMPLEX WITH F2F3 FRAGMENT OF HUMAN CELLULAR FACTOR CPSF30 | i; i+4; | 2 | 6 | 97 | 102 | YFYSKF | 141 | 1.95 |
| 2UZ6 | E O | O | ACHBP-TARGETED A-CONOTOXIN CORRELATES DISTINCT BINDING ORIENTATIONS WITH NACHR SUBTYPE SELECTIVITY. | i; i+3; | 4 | 7 | 6 | 12 | PPCCLNN | 142 | 2.40 |

FIG. 11U2

| A. PDB Code | B. Interface Chains | C. Chain | D. Title | E. Function | F. $G_{AVG,HELIX}$ (Kcal/mol) | G. $G_{SEM,HELIX}$ (Kcal/mol) | H. $G_{SEM,CHAIN}$ (Kcal/mol) | I. Helix Contribution | J. # Hotspot Residues | K. Hotspot Residues Residue #, $G$ (KCAL/MOL) |
|---|---|---|---|---|---|---|---|---|---|---|
| 2V1S | EL | L | CRYSTAL STRUCTURE OF RAF TOM2D-ALDH PRESEQUENCE COMPLEX | OXIDOREDUCTASE | 2.8 | 5.5 | 5.5 | 100% | 2 | R17, 2.0; Y21, 3.5; |
| 2V1Y | AB | B | STRUCTURE OF A PHOSPHOINOSITIDE 3-KINASE ALPHA ADAPTOR-BINDING DOMAIN (ABD) IN A COMPLEX WITH THE ISH2 DOMAIN FROM P85 ALPHA | TRANSFERASE | 2.7 | 5.3 | 7.8 | 68% | 2 | F494, 4.3; E496, 1.0; |
| 2V52 | BM | M | STRUCTURE OF MAL-RPEL2 COMPLEXED TO G-ACTIN | STRUCTURAL PROTEIN/ CONTRACTILE PROTEIN | 2.0 | 6.0 | 13.8 | 43% | 3 | L118, 2.7; K119, 1.6; H22, 1.7; |
| 2VGO | AD | D | CRYSTAL STRUCTURE OF AURORA B KINASE IN COMPLEX WITH REVERSINE INHIBITOR | TRANSFERASE | 2.0 | 3.9 | 20.1 | 19% | 2 | L833, 1.4; L836, 2.5; |
| 2VZD | BD | D | CRYSTAL STRUCTURE OF THE C-TERMINAL CALPONIN HOMOLOGY DOMAIN OF ALPHA PARVIN IN COMPLEX WITH PAXILLIN LD1 MOTIF | CELL ADHESION | 2.6 | 5.1 | 7.6 | 67% | 2 | L7, 3.1; L8, 2.0; |
| 2W2X | BC | B | COMPLEX OF RAC2 AND PLCG2 SPPH DOMAIN | SIGNALING PROTEIN/ HYDROLASE | 2.1 | 4.1 | 4.1 | 100% | 2 | L67, 2.5; L70, 1.6; |
| 2W2X | BC | C | COMPLEX OF RAC2 AND PLCG2 SPPH DOMAIN | SIGNALING PROTEIN/ HYDROLASE | 2.9 | 5.8 | 5.8 | 100% | 2 | F102, 3.5; V98, 2.3; |
| 2W84 | AB | B | STRUCTURE OF PEX14 IN COMPLEX WITH PEX5 | PROTEIN TRANSPORT | 4.1 | 8.1 | 8.1 | 100% | 2 | W103, 4.9; F107, 3.2; |

FIG. 11V1

| A. | B. | C. | D. | L. | M. | N. | O. | P. | Q. | R. | S. |
|---|---|---|---|---|---|---|---|---|---|---|---|
| PDB Code | Interface Chains | Chain | Title | Hotspot Residue Helix Positions | Hotspot Residue End to End Length | Helix Length | Helix Start Residue # | Helix End Residue # | Helix Sequence | SEQ ID NO: | Resolution |
| 2V1S | E L | L | CRYSTAL STRUCTURE OF RAT TOM20-ALDH PRESEQUENCE COMPLEX | i; i+4; | 5 | 9 | 15 | 23 | LSRLLSYAG | 143 | 2.05 |
| 2V1Y | A B | B | STRUCTURE OF A PHOSPHOINOSITIDE 3-KINASE ALPHA ADAPTOR-BINDING DOMAIN (ABD) IN A COMPLEX WITH THE ISH2 DOMAIN FROM P85 ALPHA | i; i+2; | 3 | 25 | 481 | 505 | RTAEEAFNETIKIFEEQCQTQERYS | 144 | 2.40 |
| 2V52 | B M | M | STRUCTURE OF MAL-RPEL2 COMPLEXED TO G-ACTIN | i; i+1; i+4; | 5 | 9 | 116 | 124 | DYLKRKIRS | 145 | 1.45 |
| 2VGO | A D | D | CRYSTAL STRUCTURE OF AURORA B KINASE IN COMPLEX WITH REVERSINE INHIBITOR | i; i+3; | 4 | 5 | 833 | 837 | LEELF | 146 | 1.70 |
| 2VZD | B D | D | CRYSTAL STRUCTURE OF THE C-TERMINAL CALPONIN HOMOLOGY DOMAIN OF ALPHA PARVIN IN COMPLEX WITH PAXILLIN LD1 MOTIF | i; i+1; | 2 | 10 | 2 | 11 | DDLDALLADL | 147 | 2.10 |
| 2W2X | B C | B | COMPLEX OF RAC2 AND PLCG2 SPPH DOMAIN | i; i+3; | 4 | 9 | 65 | 73 | DRLRPLSYP | 148 | 2.30 |
| 2W2X | B C | C | COMPLEX OF RAC2 AND PLCG2 SPPH DOMAIN | i; i+4; | 5 | 16 | 98 | 113 | VEELFEWFQSIREITW | 149 | 2.30 |
| 2W84 | A B | B | STRUCTURE OF PEX14 IN COMPLEX WITH PEX5 | i; i+4; | 5 | 17 | 94 | 110 | VADLALSENWAQEFLAA | 150 | NOT APP |

FIG. 11V2

| A. PDB Code | B. Interface Chains | C. Chain | D. Title | E. Function | F. $G_{AVG,HELIX}$ (Kcal/mol) | G. $G_{SUM,HELIX}$ (Kcal/mol) | H. $G_{SUM,CHAIN}$ (Kcal/mol) | I. Helix Contribution | J. # Hotspot Residues | K. Hotspot Residues Residue #, $G_{(KCAL/MOL)}$ |
|---|---|---|---|---|---|---|---|---|---|---|
| 2WAX | AB | B | STRUCTURE OF THE HUMAN DDX6 C-TERMINAL DOMAIN IN COMPLEX WITH AN EDC3-FDF PEPTIDE | HYDROLASE | 2.0 | 3.9 | 18.7 | 21% | 2 | F206, 2.3; L210, 1.6; |
| 2Z2S | GH | H | CRYSTAL STRUCTURE OF RHODOBACTER SPHAEROIDES SIGE IN COMPLEX WITH THE ANTI-SIGMA CHRR | TRANSCRIPTION | 2.0 | 3.9 | 9.5 | 41% | 2 | S65, 1.0; L66, 2.9; |
| 2ZFD | AB | B | THE CRYSTAL STRUCTURE OF PLANT SPECIFIC CALCIUM BINDING PROTEIN AtCBL2 IN COMPLEX WITH THE REGULATORY DOMAIN OF AtCIPK14 | SIGNALING PROTEIN/TRANSFERASE | 2.8 | 11.1 | 23.2 | 48% | 4 | F313, 5.1; D314, 1.0; I315, 2.1; I316, 2.9; |
| 2ZNV | AB | A | CRYSTAL STRUCTURE OF HUMAN AMSH-LP DUB DOMAIN IN COMPLEX WITH LYS63-LINKED UBIQUITIN DIMER | HYDROLASE/SIGNALING PROTEIN | 2.2 | 4.4 | 9.0 | 49% | 2 | E329, 1.4; F332, 3.0; |
| 2ZSH | AB | B | STRUCTURAL BASIS OF GIBBERELLIN(GA3)-INDUCED DELLA RECOGNITION BY THE GIBBERELLIN RECEPTOR | HORMONE RECEPTOR | 2.4 | 4.8 | 12.3 | 39% | 2 | L50, 2.1; E51, 2.7; |
| 3A1G | AB | B | HIGH-RESOLUTION CRYSTAL STRUCTURE OF RNA POLYMERASE PB1-PB2 SUBUNITS FROM INFLUENZA A VIRUS | TRANSFERASE | 2.1 | 6.4 | 9.1 | 70% | 3 | R3, 2.8; I4, 2.2; L7, 1.4; |

FIG. 11W1

| A. | B. | C. | D. | L. | M. | N. | O. | P. | Q. | R. | S. |
|---|---|---|---|---|---|---|---|---|---|---|---|
| PDB Code | Interface Chains | Chain | Title | Hotspot Residue Helix Positions | Hotspot Residue End to End Length | Helix Length | Helix Start Residue # | Helix End Residue # | Helix Sequence | SEQ ID NO: | Resolution |
| 2WAX | A,B | B | STRUCTURE OF THE HUMAN DDX6 C-TERMINAL DOMAIN IN COMPLEX WITH AN EDC3-FDF PEPTIDE | i; i+4; | 5 | 7 | 206 | 212 | FEGNLAL | 151 | 2.30 |
| 2Z2S | G,H | H | CRYSTAL STRUCTURE OF RHODOBACTER SPHAEROIDES SIGE IN COMPLEX WITH THE ANTI-SIGMA CHRR | i; i+1; | 2 | 5 | 65 | 69 | SLASV | 152 | 2.70 |
| 2ZFD | A,B | B | THE CRYSTAL STRUCTURE OF PLANT SPECIFIC CALCIUM BINDING PROTEIN ATCBL2 IN COMPLEX WITH THE REGULATORY DOMAIN OF ATCIPK14 | i; i+1; i+2; i+3; | 4 | 7 | 312 | 318 | AFDIISG | 153 | 1.20 |
| 2ZNV | A,B | A | CRYSTAL STRUCTURE OF HUMAN AMSH-LP DUB DOMAIN IN COMPLEX WITH LYS63-LINKED UBIQUITIN DIMER | i; i+3; | 4 | 10 | 329 | 338 | EELFWQDQH | 154 | 1.60 |
| 2ZSH | A,B | B | STRUCTURAL BASIS OF GIBBERELLIN(GA3)-INDUCED DELLA RECOGNITION BY THE GIBBERELLIN RECEPTOR | i; i+1; | 2 | 16 | 43 | 58 | MADVAQKLEQLEV MMS | 155 | 1.80 |
| 3A1G | A,B | B | HIGH-RESOLUTION CRYSTAL STRUCTURE OF RNA POLYMERASE PB1-PB2 SUBUNITS FROM INFLUENZA A VIRUS | i; i+1; i+4; | 5 | 8 | 3 | 10 | RIKELRNL | 156 | 1.70 |

*FIG. 11W2*

| A. PDB Code | B. Interface Chains | C. Chain | D. Title | E. Function | F. G_{AVG,HELIX} (Kcal/mol) | G. G_{SEM,HELIX} (Kcal/mol) | H. G_{SEM,CHAIN} (Kcal/mol) | I. Helix Contribution | J. # Hotspot Residues | K. Hotspot Residues Residue #, G (kcal/mol) |
|---|---|---|---|---|---|---|---|---|---|---|
| 3BLH | AB | B | CRYSTAL STRUCTURE OF HUMAN CDK9/CYCLINT1 | TRANSCRIPTION | 2.7 | 5.3 | 11.8 | 45% | 2 | F89, 2.2; K93, 3.1; |
| 3BS5 | AB | A | CRYSTAL STRUCTURE OF HCNK2-SAM/DHYP-SAM COMPLEX | SIGNALING PROTEIN/ MEMBRANE PROTEIN | 2.2 | 4.4 | 8.3 | 53% | 2 | R57, 2.4; R61, 2.0; |
| 3CJT | AB | A | RIBOSOMAL PROTEIN L11 METHYLTRANSFERASE (PRMA) IN COMPLEX WITH DIMETHYLATED RIBOSOMAL PROTEIN L11 | TRANSFERASE/ RIBOSOMAL PROTEIN | 4.0 | 8.0 | 24.6 | 33% | 2 | W59, 4.5; W63, 3.5; |
| 3CPH | GA | G | CRYSTAL STRUCTURE OF SEC4 IN COMPLEX WITH RAB-GDI | PROTEIN TRANSPORT | 2.4 | 4.8 | 8.8 | 55% | 2 | R248, 3.5; I252, 1.3; |
| 3CQX | BC | C | CHAPERONE COMPLEX | CHAPERONE | 2.2 | 4.4 | 7.4 | 59% | 2 | Q156, 1.6; I160, 2.8; |
| 3D24 | AB | B | CRYSTAL STRUCTURE OF LIGAND-BINDING DOMAIN OF ESTROGEN-RELATED RECEPTOR ALPHA (ERRALPHA) IN COMPLEX WITH THE PEROXISOME PROLIFERATORS-ACTIVATED RECEPTOR COACTIVATOR-1ALPHA BOX3 PEPTIDE (PGC-1ALPHA) | TRANSCRIPTION | 2.1 | 6.4 | 7.5 | 85% | 3 | L210, 2.6; Y213, 2.1; L214, 1.7; |

*FIG. 11X1*

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 3BLH | A B | B | CRYSTAL STRUCTURE OF HUMAN CDK9/CYCLINT1 | i; i+4; | 5 | 16 | 80 | 95 | GNSVAPAALFLAAKVE | 157 | 2.48 |
| 3BS3 | A B | A | CRYSTAL STRUCTURE OF HCNK2-SAM/HYP-SAM COMPLEX | i; i+4; | 5 | 7 | 56 | 62 | GRALLRI | 158 | 2.00 |
| 3CJT | A B | A | RIBOSOMAL PROTEIN L11 METHYLTRANSFERASE (PRMA) IN COMPLEX WITH DIMETHYLATED RIBOSOMAL PROTEIN L11 | i; i+4; | 5 | 8 | 59 | 66 | WLEAWRRD | 159 | 2.30 |
| 3CPH | G A | G | CRYSTAL STRUCTURE OF SEC4 IN COMPLEX WITH RAB-GDI | i; i+4; | 5 | 15 | 239 | 253 | LGELPQGFARLSAIY | 160 | 2.90 |
| 3CQX | B C | C | CHAPERONE COMPLEX | i; i+4; | 5 | 10 | 153 | 162 | QKFQSIVGC | 161 | 2.30 |
| 3D24 | A B | B | CRYSTAL STRUCTURE OF LIGAND-BINDING DOMAIN OF ESTROGEN-RELATED RECEPTOR ALPHA (ERRALPHA) IN COMPLEX WITH THE PEROXISOME PROLIFERATORS-ACTIVATED RECEPTOR COACTIVATOR-1ALPHA BOX3 PEPTIDE (PGC-1ALPHA) | i; i+3; i+4; | 5 | 8 | 208 | 215 | SELLKYLT | 162 | 2.11 |

*FIG. 11X2*

| A. PDB Code | B. Interface Chains | C. Chain | D. Title | E. Function | F. $G_{AVG,HELIX}$ (Kcal/mol) | G. $G_{SUM,HELIX}$ (Kcal/mol) | H. $G_{SUM,CHAIN}$ (Kcal/mol) | I. Helix Contribution | J. # Hotspot Residues | K. Hotspot Residues Residue #, G (KCAL/MOL) |
|---|---|---|---|---|---|---|---|---|---|---|
| 3D48 | PR | P | CRYSTAL STRUCTURE OF A PROLACTIN RECEPTOR ANTAGONIST BOUND TO THE EXTRACELLULAR DOMAIN OF THE PROLACTIN RECEPTOR | HORMONE/ HORMONE RECEPTOR | 2.4 | 7.2 | 16.3 | 44% | 3 | R177, 4.6; H180, 1.1; K181, 1.5; |
| 3DA7 | AD | D | A CONFORMATIONALLY STRAINED, CIRCULAR PERMUTANT OF BARNASE | PROTEIN BINDING | 3.6 | 7.1 | 14.6 | 49% | 2 | D36, 1.3; D40, 5.8; |
| 3DAB | AB | B | STRUCTURE OF THE HUMAN MDMX PROTEIN BOUND TO THE P53 TUMOR SUPPRESSOR TRANSACTIVATION DOMAIN | CELL CYCLE | 3.5 | 7.0 | 8.9 | 79% | 2 | F19, 2.8; W23, 4.2; |
| 3DAB | EF | F | STRUCTURE OF THE HUMAN MDMX PROTEIN BOUND TO THE P53 TUMOR SUPPRESSOR TRANSACTIVATION DOMAIN | CELL CYCLE | 3.5 | 6.9 | 8.2 | 84% | 2 | F19, 3.3; W23, 3.6; |
| 3DAW | AB | B | STRUCTURE OF THE ACTIN-DEPOLYMERIZING FACTOR HOMOLOGY DOMAIN IN COMPLEX WITH ACTIN | STRUCTURAL PROTEIN/ STRUCTURAL PROTEIN RE | 2.4 | 7.3 | 8.3 | 88% | 3 | R267, 1.2; R269, 4.7; M270, 1.4; |
| 3DD7 | AB | B | STRUCTURE OF DOCH6Y IN COMPLEX WITH THE C-TERMINAL DOMAIN OF PHD | RIBOSOME INHIBITOR | 3.6 | 7.1 | 12.2 | 58% | 2 | F56, 2.8; F60, 4.3; |
| 3EBA | AB | B | CABHU6 FGLW MUTANT (HUMANIZED) IN COMPLEX WITH HUMAN LYSOZYME | IMMUNE SYSTEM/ HYDROLASE | 3.6 | 7.2 | 11.4 | 63% | 2 | D94, 2.0; C95, 5.2; |
| 3ECH | AC | C | THE MARR-FAMILY REPRESSOR MEXR IN COMPLEX WITH ITS ANTIREPRESSOR ARMR | TRANSCRIPTION, TRANSCRIPTION REGULATION | 5.7 | 11.3 | 12.4 | 91% | 2 | W45, 7.0; Y48, 4.3; |

FIG. 11Y1

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 3D48 | PR | P | CRYSTAL STRUCTURE OF A PROLACTIN RECEPTOR ANTAGONIST BOUND TO THE EXTRACELLULAR DOMAIN OF THE PROLACTIN RECEPTOR | i; i+3; i+4; | 5 | 34 | 161 | 194 | EESRLSAYYNLLHC LRRDSHKIDNYLKL LKCRII | 163 | 2.50 |
| 3DA7 | AD | D | A CONFORMATIONALLY STRAINED, CIRCULAR PERMUTANT OF BARNASE | i; i+4; | 5 | 9 | 35 | 43 | LDALWDCLT | 164 | 2.25 |
| 3DAB | AB | B | STRUCTURE OF THE HUMAN MDMX PROTEIN BOUND TO THE P53 TUMOR SUPPRESSOR TRANSACTIVATION DOMAIN | i; i+4; | 5 | 8 | 19 | 26 | FSDLWKLL | 165 | 1.90 |
| 3DAB | EF | F | STRUCTURE OF THE HUMAN MDMX PROTEIN BOUND TO THE P53 TUMOR SUPPRESSOR TRANSACTIVATION DOMAIN | i; i+4; | 5 | 8 | 19 | 26 | FSDLWKLL | 166 | 1.90 |
| 3DAW | AB | B | STRUCTURE OF THE ACTIN-DEPOLYMERIZING FACTOR HOMOLOGY DOMAIN IN COMPLEX WITH ACTIN | i; i+2; i+3; | 4 | 10 | 266 | 275 | IRERMLYSSC | 167 | 2.55 |
| 3DD7 | AB | B | STRUCTURE OF DOCH6Y IN COMPLEX WITH THE C-TERMINAL DOMAIN OF PHD | i; i+4; | 5 | 9 | 55 | 63 | EFASLFDTL | 168 | 1.70 |
| 3EBA | AB | B | CABHUL6 FGLW MUTANT (HUMANIZED) IN COMPLEX WITH HUMAN LYSOZYME | i; i+4; | 5 | 11 | 90 | 100 | ADAVACAKRVV | 169 | 1.85 |
| 3ECH | AC | C | THE MARR-FAMILY REPRESSOR MEXR IN COMPLEX WITH ITS ANTIREPRESSOR ARMR | i; i+3; | 4 | 7 | 44 | 50 | AWDLYGE | 170 | 1.80 |

FIG. 11Y2

| A. | B. | C. | D. | E. | F. | G. | H. | I. | J. | K. |
|---|---|---|---|---|---|---|---|---|---|---|
| PDB Code | Interface Chains | Chain | Title | Function | $G_{AVG,HELIX}$ (Kcal/mol) | $G_{SUM,HELIX}$ (Kcal/mol) | $G_{SUM,CHAIN}$ (Kcal/mol) | Helix Contribution | # Hotspot Residues | Hotspot Residues Residue #, $G_{(KCAL/MOL)}$ |
| 3EG5 | A B | A | CRYSTAL STRUCTURE OF MDIA1-TSH GBD-FH3 IN COMPLEX WITH CDC42-GMPPNP | SIGNALING PROTEIN | 2.6 | 7.8 | 17.2 | 45% | 3 | R66, 4.7; L67, 1.3; L70, 1.8; |
| 3EJB | G H | G | CRYSTAL STRUCTURE OF P450BIO1 IN COMPLEX WITH TETRADECANOIC ACID LIGATED ACYL CARRIER PROTEIN | OXIDOREDUCTASE/LIPID TRANSPORT | 2.3 | 9.3 | 13.5 | 69% | 4 | L57, 3.4; D58, 1.9; V60, 1.3; E61, 2.7; |
| 3EZQ | C D | C | CRYSTAL STRUCTURE OF THE FAS/FADD DEATH DOMAIN COMPLEX | APOPTOSIS | 2.0 | 4.0 | 7.0 | 57% | 2 | Y291, 1.9; I295, 2.1; |
| 3F75 | A P | P | ACTIVATED TOXOPLASMA GONDII CATHEPSIN L (TGCPL) IN COMPLEX WITH ITS PROPEPTIDE | HYDROLASE | 2.6 | 5.1 | 19.6 | 26% | 2 | R170, 2.6; F173, 2.5; |
| 3F9K | B C | B | TWO DOMAIN FRAGMENT OF HIV-2 INTEGRASE IN COMPLEX WITH LEDGF IBD | VIRAL PROTEIN, RECOMBINATION | 2.0 | 3.9 | 5.4 | 72% | 2 | M128, 1.3; W131, 2.6; |
| 3FMP | A B | B | CRYSTAL STRUCTURE OF THE NUCLEOPORIN NUP214 IN COMPLEX WITH THE DEAD-BOX HELICASE DDX19 | ONCOPROTEIN/HYDROLASE | 2.1 | 6.2 | 8.7 | 71% | 3 | D255, 1.7; Q256, 1.2; R259, 3.3; |
| 3FUB | C D | C | CRYSTAL STRUCTURE OF GDNF-GFRALPHA1 COMPLEX | HORMONE | 2.1 | 4.2 | 5.3 | 79% | 2 | R171, 2.5; I175, 1.7; |

*FIG. 11Z1*

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 3EG5 | A B | A | CRYSTAL STRUCTURE OF MDIA1-TSH GBD-FH3 IN COMPLEX WITH CDC42-GMPPNP | i; i-1; i+4; | 5 | 9 | 65 | 73 | DRLRPLSYP | 171 | 2.70 |
| 3EJB | G H | G | CRYSTAL STRUCTURE OF P450BIOI IN COMPLEX WITH TETRADECANOIC ACID LIGATED ACYL CARRIER PROTEIN | i; i-1; i+3; i+4; | 5 | 14 | 57 | 70 | LDTVELVMALEEEF | 172 | 2.00 |
| 3EZQ | C D | C | CRYSTAL STRUCTURE OF THE FAS/FADD DEATH DOMAIN COMPLEX | i; i-4; | 5 | 33 | 287 | 319 | KKEAYDTLKDLKK ANLCTLAEKIQTIIL KDIT | 173 | 2.73 |
| 3F75 | A P | P | ACTIVATED TOXOPLASMA GONDII CATHEPSIN L (TGCPL) IN COMPLEX WITH ITS PROPEPTIDE | i; i-3; | 4 | 8 | 170 | 177 | RDEFRRKY | 174 | 1.99 |
| 3F9K | B C | B | TWO DOMAIN FRAGMENT OF HIV-2 INTEGRASE IN COMPLEX WITH LEDGF IBD | i; i-3; | 4 | 11 | 124 | 134 | QEVKMVAWWIG | 175 | 3.20 |
| 3FMP | A B | B | CRYSTAL STRUCTURE OF THE NUCLEOPORIN NUP214 IN COMPLEX WITH THE DEAD-BOX HELICASE DDX19 | i; i-1; i+4; | 5 | 11 | 253 | 263 | HQDQSIRIQRM | 176 | 3.19 |
| 3FUB | C D | C | CRYSTAL STRUCTURE OF GDNF-GFRALPHA1 COMPLEX | i; i-4; | 5 | 15 | 165 | 179 | DTCKKYRSAYTPC T | 177 | 2.35 |

FIG. 11Z2

| A. PDB Code | B. Interface Chains | C. Chain | D. Title | E. Function | F. $G_{AVG,HELIX}$ (Kcal/mol) | G. $G_{SUM,HELIX}$ (Kcal/mol) | H. $G_{SUM,CHAIN}$ (Kcal/mol) | I. Helix Contribution | J. # Hotspot Residues | K. Hotspot Residues Residue #, $G_i$ (KCAL/MOL) |
|---|---|---|---|---|---|---|---|---|---|---|
| 3G9V | A B | A | CRYSTAL STRUCTURE OF A SOLUBLE DECOY RECEPTOR IL-22BP BOUND TO INTERLEUKIN-22 | CYTOKINE/CYTOKINE RECEPTOR | 2.7 | 5.4 | 12.8 | 42% | 2 | W123, 1.3; E125, 4.1; |
| 3GCG | A B | B | CRYSTAL STRUCTURE OF MAP AND CDC42 COMPLEX | SIGNALING PROTEIN/ TRANSCRIPTION | 2.2 | 4.4 | 13.7 | 32% | 2 | I156, 1.3; F159, 3.1; |
| 3H2U | A B | A | HUMAN RAVER1 RRM1, RRM2, AND RRM3 DOMAINS IN COMPLEX WITH HUMAN VINCULIN TAIL DOMAIN VT | CELL ADHESION | 2.6 | 5.1 | 7.2 | 71% | 2 | L928, 1.2; E932, 3.9; |
| 3H9R | A B | A | CRYSTAL STRUCTURE OF THE KINASE DOMAIN OF TYPE I ACTIVIN RECEPTOR (ACVR1) IN COMPLEX WITH FKBP12 AND DORSOMORPHIN | ISOMERASE/ PROTEIN KINASE | 2.0 | 3.9 | 6.6 | 59% | 2 | W245, 2.1; F246, 1.8; |

*FIG. 11AA1*

| A. PDB Code | B. Interface Chains | C. Chain | D. Title | L. Hotspot Residue Helix Positions | M. Hotspot Residue End to End Length | N. Helix Length | O. Helix Start Residue # | P. Helix End Residue # | Q. Helix Sequence | R. SEQ ID NO: | S. Resolution |
|---|---|---|---|---|---|---|---|---|---|---|---|
| 3G9V | AB | A | CRYSTAL STRUCTURE OF A SOLUBLE DECOY RECEPTOR IL-22BP BOUND TO INTERLEUKIN-22 | i; i+2; | 3 | 5 | 122 | 126 | PWWET | 178 | 2.76 |
| 3GCG | AB | B | CRYSTAL STRUCTURE OF MAP AND CDC42 COMPLEX | i; i+3; | 4 | 24 | 155 | 178 | PITRFNTQTKMIEQ VSQEIFERNF | 179 | 2.30 |
| 3H2U | AB | A | HUMAN RAVER1 RRM1, RRM2, AND RRM3 DOMAINS IN COMPLEX WITH HUMAN VINCULIN TAIL DOMAIN VT | i; i+4; | 5 | 21 | 918 | 938 | DIAAAKRMALLM AEMSRLVR | 180 | 2.75 |
| 3H9R | AB | A | CRYSTAL STRUCTURE OF THE KINASE DOMAIN OF TYPE I ACTIVIN RECEPTOR (ACVRI) IN COMPLEX WITH FKBP12 AND DORSOMORPHIN | i; i+1; | 2 | 14 | 242 | 255 | EKSWFRETELYNTV | 181 | 2.35 |

FIG. 11AA2

```
                        SEQUENCE LISTING

<160> NUMBER OF SEQ ID NOS: 190

<210> SEQ ID NO 1
<211> LENGTH: 14
<212> TYPE: PRT
<213> ORGANISM: artificial
<220> FEATURE:
<223> OTHER INFORMATION: Alpha-helix sequence

<400> SEQUENCE: 1

Ala Ala Thr Leu Glu Glu Lys Leu Asn Lys Ile Phe Glu Lys
1               5                   10

<210> SEQ ID NO 2
<211> LENGTH: 12
<212> TYPE: PRT
<213> ORGANISM: artificial
<220> FEATURE:
<223> OTHER INFORMATION: Alpha-helix sequence

<400> SEQUENCE: 2

Glu Asp Asp Ile Thr Ala Val Leu Cys Phe Val Ile
1               5                   10

<210> SEQ ID NO 3
<211> LENGTH: 9
<212> TYPE: PRT
<213> ORGANISM: artificial
<220> FEATURE:
<223> OTHER INFORMATION: Alpha-helix sequence

<400> SEQUENCE: 3

Arg Tyr Thr His Phe Leu Thr Gln His
1               5

<210> SEQ ID NO 4
<211> LENGTH: 12
<212> TYPE: PRT
<213> ORGANISM: artificial
<220> FEATURE:
<223> OTHER INFORMATION: Alpha-helix sequence

<400> SEQUENCE: 4

Lys Glu Glu Leu Lys Arg Ser Leu Tyr Ala Leu Phe
1               5                   10

<210> SEQ ID NO 5
<211> LENGTH: 9
<212> TYPE: PRT
<213> ORGANISM: artificial
<220> FEATURE:
<223> OTHER INFORMATION: Alpha-helix sequence

<400> SEQUENCE: 5

Leu Asp Ala Leu Trp Asp Cys Leu Thr
1               5

<210> SEQ ID NO 6
<211> LENGTH: 11
<212> TYPE: PRT
<213> ORGANISM: artificial
<220> FEATURE:
<223> OTHER INFORMATION: Alpha-helix sequence
```

-continued

```
<400> SEQUENCE: 6

Pro Glu Glu Ile Arg Lys Tyr Leu Leu Leu Asn
1               5                   10

<210> SEQ ID NO 7
<211> LENGTH: 9
<212> TYPE: PRT
<213> ORGANISM: artificial
<220> FEATURE:
<223> OTHER INFORMATION: Alpha-helix sequence

<400> SEQUENCE: 7

Leu Asp Ala Leu Trp Asp Ala Leu Thr
1               5

<210> SEQ ID NO 8
<211> LENGTH: 14
<212> TYPE: PRT
<213> ORGANISM: artificial
<220> FEATURE:
<223> OTHER INFORMATION: Alpha-helix sequence

<400> SEQUENCE: 8

Val Ser Lys Cys Cys Glu Glu Phe Arg Asp Tyr Val Glu Glu
1               5                   10

<210> SEQ ID NO 9
<211> LENGTH: 15
<212> TYPE: PRT
<213> ORGANISM: artificial
<220> FEATURE:
<223> OTHER INFORMATION: Alpha-helix sequence

<400> SEQUENCE: 9

Trp Glu Asp Asn Val Gly Glu Trp Ile Glu Glu Met Lys Glu Glu
1               5                   10                  15

<210> SEQ ID NO 10
<211> LENGTH: 9
<212> TYPE: PRT
<213> ORGANISM: artificial
<220> FEATURE:
<223> OTHER INFORMATION: Alpha-helix sequence

<400> SEQUENCE: 10

Arg Gln Leu Ala Ile Ile Gly Asp Asp
1               5

<210> SEQ ID NO 11
<211> LENGTH: 7
<212> TYPE: PRT
<213> ORGANISM: artificial
<220> FEATURE:
<223> OTHER INFORMATION: Alpha-helix sequence

<400> SEQUENCE: 11

His Asn Ala Met Arg Leu Ile
1               5

<210> SEQ ID NO 12
<211> LENGTH: 12
<212> TYPE: PRT
<213> ORGANISM: artificial
<220> FEATURE:
<223> OTHER INFORMATION: Alpha-helix sequence
```

```
<400> SEQUENCE: 12

Ala Trp Pro Thr Lys Leu Glu Trp Glu Arg His Lys
1               5                   10

<210> SEQ ID NO 13
<211> LENGTH: 16
<212> TYPE: PRT
<213> ORGANISM: artificial
<220> FEATURE:
<223> OTHER INFORMATION: Alpha-helix sequence

<400> SEQUENCE: 13

Ala Glu Glu Thr Arg Arg Met Leu His Arg Ala Phe Asp Thr Leu Ala
1               5                   10                  15

<210> SEQ ID NO 14
<211> LENGTH: 5
<212> TYPE: PRT
<213> ORGANISM: artificial
<220> FEATURE:
<223> OTHER INFORMATION: Alpha-helix sequence

<400> SEQUENCE: 14

Asp Arg Leu Arg Pro
1               5

<210> SEQ ID NO 15
<211> LENGTH: 12
<212> TYPE: PRT
<213> ORGANISM: artificial
<220> FEATURE:
<223> OTHER INFORMATION: Alpha-helix sequence

<400> SEQUENCE: 15

Glu Ser Leu Arg Lys Tyr Lys Glu Ala Leu Leu Gly
1               5                   10

<210> SEQ ID NO 16
<211> LENGTH: 5
<212> TYPE: PRT
<213> ORGANISM: artificial
<220> FEATURE:
<223> OTHER INFORMATION: Alpha-helix sequence

<400> SEQUENCE: 16

Asp Arg Leu Arg Pro
1               5

<210> SEQ ID NO 17
<211> LENGTH: 6
<212> TYPE: PRT
<213> ORGANISM: artificial
<220> FEATURE:
<223> OTHER INFORMATION: Alpha-helix sequence

<400> SEQUENCE: 17

Phe Lys Asp Tyr Gly His
1               5

<210> SEQ ID NO 18
<211> LENGTH: 14
<212> TYPE: PRT
<213> ORGANISM: artificial
<220> FEATURE:
<223> OTHER INFORMATION: Alpha-helix sequence

<400> SEQUENCE: 18
```

```
Pro Thr Ala Arg Ala Ala Leu Trp Gln Gln Ile Cys Thr Tyr
1               5                   10

<210> SEQ ID NO 19
<211> LENGTH: 7
<212> TYPE: PRT
<213> ORGANISM: artificial
<220> FEATURE:
<223> OTHER INFORMATION: Alpha-helix sequence

<400> SEQUENCE: 19

Ser Asp Phe Gln Cys Lys Asp
1               5

<210> SEQ ID NO 20
<211> LENGTH: 7
<212> TYPE: PRT
<213> ORGANISM: artificial
<220> FEATURE:
<223> OTHER INFORMATION: Alpha-helix sequence

<400> SEQUENCE: 20

Ser Asp Phe Gln Cys Lys Asp
1               5

<210> SEQ ID NO 21
<211> LENGTH: 14
<212> TYPE: PRT
<213> ORGANISM: artificial
<220> FEATURE:
<223> OTHER INFORMATION: Alpha-helix sequence

<400> SEQUENCE: 21

Asp Thr Ile Ile Glu Phe Phe Met Lys Tyr Ile Glu Lys Ser
1               5                   10

<210> SEQ ID NO 22
<211> LENGTH: 10
<212> TYPE: PRT
<213> ORGANISM: artificial
<220> FEATURE:
<223> OTHER INFORMATION: Alpha-helix sequence

<400> SEQUENCE: 22

Ser Phe Phe Tyr Thr Asn Leu Ser Glu Arg
1               5                   10

<210> SEQ ID NO 23
<211> LENGTH: 9
<212> TYPE: PRT
<213> ORGANISM: artificial
<220> FEATURE:
<223> OTHER INFORMATION: Alpha-helix sequence

<400> SEQUENCE: 23

Ile Pro Ala Phe Leu Arg Lys Gln Ala
1               5

<210> SEQ ID NO 24
<211> LENGTH: 23
<212> TYPE: PRT
<213> ORGANISM: artificial
<220> FEATURE:
<223> OTHER INFORMATION: Alpha-helix sequence

<400> SEQUENCE: 24
```

```
Pro Ala Glu Val Glu Ala Leu Arg Glu Lys Val Tyr Ala Ser Leu Glu
1               5                   10                  15

Ala Tyr Cys Lys His Lys Tyr
            20

<210> SEQ ID NO 25
<211> LENGTH: 12
<212> TYPE: PRT
<213> ORGANISM: artificial
<220> FEATURE:
<223> OTHER INFORMATION: Alpha-helix sequence

<400> SEQUENCE: 25

Lys Tyr Pro Leu Leu Leu Arg Glu Leu Phe Ala Leu
1               5                   10

<210> SEQ ID NO 26
<211> LENGTH: 8
<212> TYPE: PRT
<213> ORGANISM: artificial
<220> FEATURE:
<223> OTHER INFORMATION: Alpha-helix sequence

<400> SEQUENCE: 26

Ile Lys Pro Ile Gln Arg Val Leu
1               5

<210> SEQ ID NO 27
<211> LENGTH: 8
<212> TYPE: PRT
<213> ORGANISM: artificial
<220> FEATURE:
<223> OTHER INFORMATION: Alpha-helix sequence

<400> SEQUENCE: 27

Lys Val Ala Ser His Ile Asn Glu
1               5

<210> SEQ ID NO 28
<211> LENGTH: 5
<212> TYPE: PRT
<213> ORGANISM: artificial
<220> FEATURE:
<223> OTHER INFORMATION: Alpha-helix sequence

<400> SEQUENCE: 28

Asp Arg Leu Arg Pro
1               5

<210> SEQ ID NO 29
<211> LENGTH: 8
<212> TYPE: PRT
<213> ORGANISM: artificial
<220> FEATURE:
<223> OTHER INFORMATION: Alpha-helix sequence

<400> SEQUENCE: 29

Lys Arg Trp Tyr Arg Leu Ala Ser
1               5

<210> SEQ ID NO 30
<211> LENGTH: 9
<212> TYPE: PRT
<213> ORGANISM: artificial
<220> FEATURE:
<223> OTHER INFORMATION: Alpha-helix sequence
```

```
<400> SEQUENCE: 30

Leu Pro Glu Leu Leu Lys Val Ser Gly
1               5

<210> SEQ ID NO 31
<211> LENGTH: 7
<212> TYPE: PRT
<213> ORGANISM: artificial
<220> FEATURE:
<223> OTHER INFORMATION: Alpha-helix sequence

<400> SEQUENCE: 31

Glu Glu Leu Leu Arg Ala Leu
1               5

<210> SEQ ID NO 32
<211> LENGTH: 12
<212> TYPE: PRT
<213> ORGANISM: artificial
<220> FEATURE:
<223> OTHER INFORMATION: Alpha-helix sequence

<400> SEQUENCE: 32

Lys Lys Lys Leu Gln Asp Leu Val Arg Glu Val Asp
1               5                   10

<210> SEQ ID NO 33
<211> LENGTH: 15
<212> TYPE: PRT
<213> ORGANISM: artificial
<220> FEATURE:
<223> OTHER INFORMATION: Alpha-helix sequence

<400> SEQUENCE: 33

Lys Glu Ala Phe Trp Asp Arg Cys Leu Ser Val Ile Asn Leu Met
1               5                   10                  15

<210> SEQ ID NO 34
<211> LENGTH: 7
<212> TYPE: PRT
<213> ORGANISM: artificial
<220> FEATURE:
<223> OTHER INFORMATION: Alpha-helix sequence

<400> SEQUENCE: 34

Pro Leu His Ala Leu Leu His
1               5

<210> SEQ ID NO 35
<211> LENGTH: 12
<212> TYPE: PRT
<213> ORGANISM: artificial
<220> FEATURE:
<223> OTHER INFORMATION: Alpha-helix sequence

<400> SEQUENCE: 35

Arg Ala Asp Ala Glu Asn Ala Met Arg Tyr Ile Asn
1               5                   10

<210> SEQ ID NO 36
<211> LENGTH: 5
<212> TYPE: PRT
<213> ORGANISM: artificial
<220> FEATURE:
<223> OTHER INFORMATION: Alpha-helix sequence

<400> SEQUENCE: 36
```

```
Leu Gln Gln Trp Gly
1               5

<210> SEQ ID NO 37
<211> LENGTH: 13
<212> TYPE: PRT
<213> ORGANISM: artificial
<220> FEATURE:
<223> OTHER INFORMATION: Alpha-helix sequence

<400> SEQUENCE: 37

Val Arg Ala Lys Trp Tyr Pro Glu Val Arg His His Cys
1               5                   10

<210> SEQ ID NO 38
<211> LENGTH: 5
<212> TYPE: PRT
<213> ORGANISM: artificial
<220> FEATURE:
<223> OTHER INFORMATION: Alpha-helix sequence

<400> SEQUENCE: 38

Asp Arg Leu Arg Pro
1               5

<210> SEQ ID NO 39
<211> LENGTH: 12
<212> TYPE: PRT
<213> ORGANISM: artificial
<220> FEATURE:
<223> OTHER INFORMATION: Alpha-helix sequence

<400> SEQUENCE: 39

Glu Ser Leu Arg Lys Tyr Lys Glu Ala Leu Leu Gly
1               5                   10

<210> SEQ ID NO 40
<211> LENGTH: 14
<212> TYPE: PRT
<213> ORGANISM: artificial
<220> FEATURE:
<223> OTHER INFORMATION: Alpha-helix sequence

<400> SEQUENCE: 40

Leu Lys Glu Arg Cys Leu Gln Val Val Arg Ser Leu Val Lys
1               5                   10

<210> SEQ ID NO 41
<211> LENGTH: 9
<212> TYPE: PRT
<213> ORGANISM: artificial
<220> FEATURE:
<223> OTHER INFORMATION: Alpha-helix sequence

<400> SEQUENCE: 41

Phe Glu Glu Leu Tyr Lys Ile Thr Gly
1               5

<210> SEQ ID NO 42
<211> LENGTH: 7
<212> TYPE: PRT
<213> ORGANISM: artificial
<220> FEATURE:
<223> OTHER INFORMATION: Alpha-helix sequence

<400> SEQUENCE: 42
```

```
Lys Lys Leu Ala Asp Met Tyr
1               5

<210> SEQ ID NO 43
<211> LENGTH: 11
<212> TYPE: PRT
<213> ORGANISM: artificial
<220> FEATURE:
<223> OTHER INFORMATION: Alpha-helix sequence

<400> SEQUENCE: 43

Ala Ala Glu Leu Arg His Val Met Thr Asn Leu
1               5                   10

<210> SEQ ID NO 44
<211> LENGTH: 18
<212> TYPE: PRT
<213> ORGANISM: artificial
<220> FEATURE:
<223> OTHER INFORMATION: Alpha-helix sequence

<400> SEQUENCE: 44

Arg Glu Ala Glu Glu Arg Arg Gly Glu Lys Gly Arg Ala Leu Ser Thr
1               5                   10                  15

Arg Ala

<210> SEQ ID NO 45
<211> LENGTH: 7
<212> TYPE: PRT
<213> ORGANISM: artificial
<220> FEATURE:
<223> OTHER INFORMATION: Alpha-helix sequence

<400> SEQUENCE: 45

Arg Pro Leu Trp Arg His Tyr
1               5

<210> SEQ ID NO 46
<211> LENGTH: 6
<212> TYPE: PRT
<213> ORGANISM: artificial
<220> FEATURE:
<223> OTHER INFORMATION: Alpha-helix sequence

<400> SEQUENCE: 46

Ala Asp Val Lys Ser Ser
1               5

<210> SEQ ID NO 47
<211> LENGTH: 8
<212> TYPE: PRT
<213> ORGANISM: artificial
<220> FEATURE:
<223> OTHER INFORMATION: Alpha-helix sequence

<400> SEQUENCE: 47

Ile Pro Glu Leu Val Asn Gln Gly
1               5

<210> SEQ ID NO 48
<211> LENGTH: 7
<212> TYPE: PRT
<213> ORGANISM: artificial
<220> FEATURE:
<223> OTHER INFORMATION: Alpha-helix sequence

<400> SEQUENCE: 48
```

```
Leu Arg Pro Leu Ser Tyr Pro
1               5

<210> SEQ ID NO 49
<211> LENGTH: 8
<212> TYPE: PRT
<213> ORGANISM: artificial
<220> FEATURE:
<223> OTHER INFORMATION: Alpha-helix sequence

<400> SEQUENCE: 49

Gln Tyr Ala Asn Asn Leu Ala Gly
1               5

<210> SEQ ID NO 50
<211> LENGTH: 11
<212> TYPE: PRT
<213> ORGANISM: artificial
<220> FEATURE:
<223> OTHER INFORMATION: Alpha-helix sequence

<400> SEQUENCE: 50

Glu Glu Leu Leu Arg Ala Leu Asp Gln Val Asn
1               5                   10

<210> SEQ ID NO 51
<211> LENGTH: 7
<212> TYPE: PRT
<213> ORGANISM: artificial
<220> FEATURE:
<223> OTHER INFORMATION: Alpha-helix sequence

<400> SEQUENCE: 51

Leu Arg Pro Leu Ser Tyr Pro
1               5

<210> SEQ ID NO 52
<211> LENGTH: 19
<212> TYPE: PRT
<213> ORGANISM: artificial
<220> FEATURE:
<223> OTHER INFORMATION: Alpha-helix sequence

<400> SEQUENCE: 52

Pro Asp Ser Leu Glu Asn Ile Pro Glu Lys Trp Thr Pro Glu Val Lys
1               5                   10                  15

His Phe Cys

<210> SEQ ID NO 53
<211> LENGTH: 11
<212> TYPE: PRT
<213> ORGANISM: artificial
<220> FEATURE:
<223> OTHER INFORMATION: Alpha-helix sequence

<400> SEQUENCE: 53

Ala Leu Glu Leu Leu Met Ala Ala Asn Phe Leu
1               5                   10

<210> SEQ ID NO 54
<211> LENGTH: 11
<212> TYPE: PRT
<213> ORGANISM: artificial
<220> FEATURE:
<223> OTHER INFORMATION: Alpha-helix sequence
```

```
<400> SEQUENCE: 54

Leu Lys Glu Arg Cys Leu Gln Val Val Arg Ser
1               5                   10

<210> SEQ ID NO 55
<211> LENGTH: 18
<212> TYPE: PRT
<213> ORGANISM: artificial
<220> FEATURE:
<223> OTHER INFORMATION: Alpha-helix sequence

<400> SEQUENCE: 55

Glu Asn Val Leu Leu Lys Glu Leu Glu Leu Val Gln Asn Ala Phe Phe
1               5                   10                  15

Thr Asp

<210> SEQ ID NO 56
<211> LENGTH: 7
<212> TYPE: PRT
<213> ORGANISM: artificial
<220> FEATURE:
<223> OTHER INFORMATION: Alpha-helix sequence

<400> SEQUENCE: 56

Arg Ala Asp Val Phe Asn Ser
1               5

<210> SEQ ID NO 57
<211> LENGTH: 18
<212> TYPE: PRT
<213> ORGANISM: artificial
<220> FEATURE:
<223> OTHER INFORMATION: Alpha-helix sequence

<400> SEQUENCE: 57

Gln Asp Glu Ser Gly Ala Ala Ala Ile Phe Thr Val Gln Leu Asp Asp
1               5                   10                  15

Tyr Leu

<210> SEQ ID NO 58
<211> LENGTH: 10
<212> TYPE: PRT
<213> ORGANISM: artificial
<220> FEATURE:
<223> OTHER INFORMATION: Alpha-helix sequence

<400> SEQUENCE: 58

Val Phe Thr Trp Ser Leu Pro Phe Val Gly
1               5                   10

<210> SEQ ID NO 59
<211> LENGTH: 9
<212> TYPE: PRT
<213> ORGANISM: artificial
<220> FEATURE:
<223> OTHER INFORMATION: Alpha-helix sequence

<400> SEQUENCE: 59

Lys Ile Leu His Arg Leu Leu Gln Asp
1               5

<210> SEQ ID NO 60
<211> LENGTH: 9
<212> TYPE: PRT
<213> ORGANISM: artificial
```

```
<220> FEATURE:
<223> OTHER INFORMATION: Alpha-helix sequence

<400> SEQUENCE: 60

Leu Ala Arg Ile Lys Lys Ile Met Lys
1               5

<210> SEQ ID NO 61
<211> LENGTH: 9
<212> TYPE: PRT
<213> ORGANISM: artificial
<220> FEATURE:
<223> OTHER INFORMATION: Alpha-helix sequence

<400> SEQUENCE: 61

Lys Ile Leu His Arg Leu Leu Gln Glu
1               5

<210> SEQ ID NO 62
<211> LENGTH: 8
<212> TYPE: PRT
<213> ORGANISM: artificial
<220> FEATURE:
<223> OTHER INFORMATION: Alpha-helix sequence

<400> SEQUENCE: 62

Glu Arg Glu Leu Leu Glu Ser Tyr
1               5

<210> SEQ ID NO 63
<211> LENGTH: 9
<212> TYPE: PRT
<213> ORGANISM: artificial
<220> FEATURE:
<223> OTHER INFORMATION: Alpha-helix sequence

<400> SEQUENCE: 63

Ser Trp Phe Glu Glu Lys Ala Asn Leu
1               5

<210> SEQ ID NO 64
<211> LENGTH: 7
<212> TYPE: PRT
<213> ORGANISM: artificial
<220> FEATURE:
<223> OTHER INFORMATION: Alpha-helix sequence

<400> SEQUENCE: 64

Glu Arg Glu Leu Leu Glu Ser
1               5

<210> SEQ ID NO 65
<211> LENGTH: 20
<212> TYPE: PRT
<213> ORGANISM: artificial
<220> FEATURE:
<223> OTHER INFORMATION: Alpha-helix sequence

<400> SEQUENCE: 65

Val Gly Thr Val Arg Ser Arg Ile Phe Arg Ala Arg Glu Ala Ile Asp
1               5                   10                  15

Asn Lys Val Gln
            20

<210> SEQ ID NO 66
<211> LENGTH: 11
```

```
<212> TYPE: PRT
<213> ORGANISM: artificial
<220> FEATURE:
<223> OTHER INFORMATION: Alpha-helix sequence

<400> SEQUENCE: 66

Gln Lys Ala Phe Asn Leu Leu Val Val Arg Tyr
1               5                   10

<210> SEQ ID NO 67
<211> LENGTH: 8
<212> TYPE: PRT
<213> ORGANISM: artificial
<220> FEATURE:
<223> OTHER INFORMATION: Alpha-helix sequence

<400> SEQUENCE: 67

Ala Leu Leu Arg Tyr Leu Leu Asp
1               5

<210> SEQ ID NO 68
<211> LENGTH: 9
<212> TYPE: PRT
<213> ORGANISM: artificial
<220> FEATURE:
<223> OTHER INFORMATION: Alpha-helix sequence

<400> SEQUENCE: 68

Met Val Ser Ala Phe Leu Lys Gln Ala
1               5

<210> SEQ ID NO 69
<211> LENGTH: 15
<212> TYPE: PRT
<213> ORGANISM: artificial
<220> FEATURE:
<223> OTHER INFORMATION: Alpha-helix sequence

<400> SEQUENCE: 69

Thr Glu Phe Glu Tyr Leu Arg Lys Val Leu Phe Glu Tyr Met Met
1               5                   10                  15

<210> SEQ ID NO 70
<211> LENGTH: 8
<212> TYPE: PRT
<213> ORGANISM: artificial
<220> FEATURE:
<223> OTHER INFORMATION: Alpha-helix sequence

<400> SEQUENCE: 70

Arg Pro Leu Trp Arg His Tyr Phe
1               5

<210> SEQ ID NO 71
<211> LENGTH: 14
<212> TYPE: PRT
<213> ORGANISM: artificial
<220> FEATURE:
<223> OTHER INFORMATION: Alpha-helix sequence

<400> SEQUENCE: 71

Leu Glu Lys Lys Val Lys Glu Leu Lys Glu Lys Ile Glu Lys
1               5                   10

<210> SEQ ID NO 72
<211> LENGTH: 7
<212> TYPE: PRT
```

```
<213> ORGANISM: artificial
<220> FEATURE:
<223> OTHER INFORMATION: Alpha-helix sequence

<400> SEQUENCE: 72

Leu Arg Tyr Ile Tyr Ser Gln
1               5

<210> SEQ ID NO 73
<211> LENGTH: 7
<212> TYPE: PRT
<213> ORGANISM: artificial
<220> FEATURE:
<223> OTHER INFORMATION: Alpha-helix sequence

<400> SEQUENCE: 73

Arg Phe Ala Tyr Ala Val Leu
1               5

<210> SEQ ID NO 74
<211> LENGTH: 23
<212> TYPE: PRT
<213> ORGANISM: artificial
<220> FEATURE:
<223> OTHER INFORMATION: Alpha-helix sequence

<400> SEQUENCE: 74

Pro Lys Glu Thr Leu Ser Glu Arg Leu Ser Ala Leu Gln Asp Lys Ile
1               5                   10                  15

Ile Asp His Tyr Glu Asn Asp
            20

<210> SEQ ID NO 75
<211> LENGTH: 14
<212> TYPE: PRT
<213> ORGANISM: artificial
<220> FEATURE:
<223> OTHER INFORMATION: Alpha-helix sequence

<400> SEQUENCE: 75

Phe Ile Thr Phe Leu Gly Ala Leu Lys Ser Phe Leu Lys Gly
1               5                   10

<210> SEQ ID NO 76
<211> LENGTH: 6
<212> TYPE: PRT
<213> ORGANISM: artificial
<220> FEATURE:
<223> OTHER INFORMATION: Alpha-helix sequence

<400> SEQUENCE: 76

Asp Asp Phe Asp Ala Gln
1               5

<210> SEQ ID NO 77
<211> LENGTH: 15
<212> TYPE: PRT
<213> ORGANISM: artificial
<220> FEATURE:
<223> OTHER INFORMATION: Alpha-helix sequence

<400> SEQUENCE: 77

Lys Ser Ala Arg Ile Tyr Leu Val Phe His Lys Leu Glu Glu Leu
1               5                   10                  15

<210> SEQ ID NO 78
```

```
<211> LENGTH: 10
<212> TYPE: PRT
<213> ORGANISM: artificial
<220> FEATURE:
<223> OTHER INFORMATION: Alpha-helix sequence

<400> SEQUENCE: 78

Gln Ala Met Val Ile Glu Ala Ile Lys Ala
1               5                   10

<210> SEQ ID NO 79
<211> LENGTH: 5
<212> TYPE: PRT
<213> ORGANISM: artificial
<220> FEATURE:
<223> OTHER INFORMATION: Alpha-helix sequence

<400> SEQUENCE: 79

Leu Asp Asp Phe Phe
1               5

<210> SEQ ID NO 80
<211> LENGTH: 7
<212> TYPE: PRT
<213> ORGANISM: artificial
<220> FEATURE:
<223> OTHER INFORMATION: Alpha-helix sequence

<400> SEQUENCE: 80

Gln Ala Glu Ile Asp Ala Leu
1               5

<210> SEQ ID NO 81
<211> LENGTH: 15
<212> TYPE: PRT
<213> ORGANISM: artificial
<220> FEATURE:
<223> OTHER INFORMATION: Alpha-helix sequence

<400> SEQUENCE: 81

Pro Glu Ile Ala Leu Glu Leu Leu Met Ala Ala Asn Phe Leu Asp
1               5                   10                  15

<210> SEQ ID NO 82
<211> LENGTH: 5
<212> TYPE: PRT
<213> ORGANISM: artificial
<220> FEATURE:
<223> OTHER INFORMATION: Alpha-helix sequence

<400> SEQUENCE: 82

Asp Arg Leu Arg Pro
1               5

<210> SEQ ID NO 83
<211> LENGTH: 7
<212> TYPE: PRT
<213> ORGANISM: artificial
<220> FEATURE:
<223> OTHER INFORMATION: Alpha-helix sequence

<400> SEQUENCE: 83

Leu Arg Pro Leu Ser Tyr Pro
1               5

<210> SEQ ID NO 84
<211> LENGTH: 10
```

```
<212> TYPE: PRT
<213> ORGANISM: artificial
<220> FEATURE:
<223> OTHER INFORMATION: Alpha-helix sequence

<400> SEQUENCE: 84

Lys Ile Leu His Arg Leu Leu Gln Glu Gly
1               5                   10

<210> SEQ ID NO 85
<211> LENGTH: 6
<212> TYPE: PRT
<213> ORGANISM: artificial
<220> FEATURE:
<223> OTHER INFORMATION: Alpha-helix sequence

<400> SEQUENCE: 85

Phe Trp Gln Phe Phe Ser
1               5

<210> SEQ ID NO 86
<211> LENGTH: 29
<212> TYPE: PRT
<213> ORGANISM: artificial
<220> FEATURE:
<223> OTHER INFORMATION: Alpha-helix sequence

<400> SEQUENCE: 86

Arg Phe Ala Lys Leu Leu Leu Arg Leu Pro Ala Leu Arg Ser Ile Gly
1               5                   10                  15

Leu Lys Cys Leu Glu His Leu Phe Phe Phe Lys Leu Ile
            20                  25

<210> SEQ ID NO 87
<211> LENGTH: 7
<212> TYPE: PRT
<213> ORGANISM: artificial
<220> FEATURE:
<223> OTHER INFORMATION: Alpha-helix sequence

<400> SEQUENCE: 87

Lys Ile Leu His Arg Leu Leu
1               5

<210> SEQ ID NO 88
<211> LENGTH: 6
<212> TYPE: PRT
<213> ORGANISM: artificial
<220> FEATURE:
<223> OTHER INFORMATION: Alpha-helix sequence

<400> SEQUENCE: 88

Trp Tyr Asp Phe Leu Met
1               5

<210> SEQ ID NO 89
<211> LENGTH: 6
<212> TYPE: PRT
<213> ORGANISM: artificial
<220> FEATURE:
<223> OTHER INFORMATION: Alpha-helix sequence

<400> SEQUENCE: 89

Phe Ser Asp Leu Trp Lys
1               5
```

```
<210> SEQ ID NO 90
<211> LENGTH: 9
<212> TYPE: PRT
<213> ORGANISM: artificial
<220> FEATURE:
<223> OTHER INFORMATION: Alpha-helix sequence

<400> SEQUENCE: 90

Ala Leu Leu Arg Tyr Leu Leu Asp Lys
1               5

<210> SEQ ID NO 91
<211> LENGTH: 5
<212> TYPE: PRT
<213> ORGANISM: artificial
<220> FEATURE:
<223> OTHER INFORMATION: Alpha-helix sequence

<400> SEQUENCE: 91

Asp Arg Leu Arg Pro
1               5

<210> SEQ ID NO 92
<211> LENGTH: 6
<212> TYPE: PRT
<213> ORGANISM: artificial
<220> FEATURE:
<223> OTHER INFORMATION: Alpha-helix sequence

<400> SEQUENCE: 92

Arg Ala Met Met Val Thr
1               5

<210> SEQ ID NO 93
<211> LENGTH: 6
<212> TYPE: PRT
<213> ORGANISM: artificial
<220> FEATURE:
<223> OTHER INFORMATION: Alpha-helix sequence

<400> SEQUENCE: 93

Thr Asp Leu Ile Tyr Tyr
1               5

<210> SEQ ID NO 94
<211> LENGTH: 13
<212> TYPE: PRT
<213> ORGANISM: artificial
<220> FEATURE:
<223> OTHER INFORMATION: Alpha-helix sequence

<400> SEQUENCE: 94

Pro Gln Gln Gln Gln Gln Val Leu Asn Ile Leu Lys Ser
1               5                   10

<210> SEQ ID NO 95
<211> LENGTH: 12
<212> TYPE: PRT
<213> ORGANISM: artificial
<220> FEATURE:
<223> OTHER INFORMATION: Alpha-helix sequence

<400> SEQUENCE: 95

Pro Gln Leu Met Ala Ala Phe Ile Lys Gln Arg Thr
1               5                   10

<210> SEQ ID NO 96
```

```
<211> LENGTH: 8
<212> TYPE: PRT
<213> ORGANISM: artificial
<220> FEATURE:
<223> OTHER INFORMATION: Alpha-helix sequence

<400> SEQUENCE: 96

Ile Met Gly Leu Met Ser Leu Ala
1               5

<210> SEQ ID NO 97
<211> LENGTH: 12
<212> TYPE: PRT
<213> ORGANISM: artificial
<220> FEATURE:
<223> OTHER INFORMATION: Alpha-helix sequence

<400> SEQUENCE: 97

Ala Phe Glu Thr Ser Lys Phe Phe Thr Asp Leu Arg
1               5                   10

<210> SEQ ID NO 98
<211> LENGTH: 8
<212> TYPE: PRT
<213> ORGANISM: artificial
<220> FEATURE:
<223> OTHER INFORMATION: Alpha-helix sequence

<400> SEQUENCE: 98

Glu Arg Glu Leu Leu Glu Ser Tyr
1               5

<210> SEQ ID NO 99
<211> LENGTH: 8
<212> TYPE: PRT
<213> ORGANISM: artificial
<220> FEATURE:
<223> OTHER INFORMATION: Alpha-helix sequence

<400> SEQUENCE: 99

Trp Lys Leu Leu Ala Lys Gly Leu
1               5

<210> SEQ ID NO 100
<211> LENGTH: 12
<212> TYPE: PRT
<213> ORGANISM: artificial
<220> FEATURE:
<223> OTHER INFORMATION: Alpha-helix sequence

<400> SEQUENCE: 100

Ser Asp Ile Met Asp Phe Val Leu Lys Asn Thr Pro
1               5                   10

<210> SEQ ID NO 101
<211> LENGTH: 11
<212> TYPE: PRT
<213> ORGANISM: artificial
<220> FEATURE:
<223> OTHER INFORMATION: Alpha-helix sequence

<400> SEQUENCE: 101

Thr Val Glu Tyr Phe Thr Ser Gln Gln Val Thr
1               5                   10

<210> SEQ ID NO 102
<211> LENGTH: 11
```

```
<212> TYPE: PRT
<213> ORGANISM: artificial
<220> FEATURE:
<223> OTHER INFORMATION: Alpha-helix sequence

<400> SEQUENCE: 102

Ala Leu Glu Leu Leu Met Ala Ala Asn Phe Leu
1               5                   10

<210> SEQ ID NO 103
<211> LENGTH: 12
<212> TYPE: PRT
<213> ORGANISM: artificial
<220> FEATURE:
<223> OTHER INFORMATION: Alpha-helix sequence

<400> SEQUENCE: 103

Ser Thr Asp Leu Thr Met Leu Lys Arg Ser Val Leu
1               5                   10

<210> SEQ ID NO 104
<211> LENGTH: 14
<212> TYPE: PRT
<213> ORGANISM: artificial
<220> FEATURE:
<223> OTHER INFORMATION: Alpha-helix sequence

<400> SEQUENCE: 104

Arg Arg Gln Lys Arg Leu Ile Phe Ser Thr Ile Thr Ser Lys
1               5                   10

<210> SEQ ID NO 105
<211> LENGTH: 6
<212> TYPE: PRT
<213> ORGANISM: artificial
<220> FEATURE:
<223> OTHER INFORMATION: Alpha-helix sequence

<400> SEQUENCE: 105

Ala Phe Glu Met Ile Thr
1               5

<210> SEQ ID NO 106
<211> LENGTH: 5
<212> TYPE: PRT
<213> ORGANISM: artificial
<220> FEATURE:
<223> OTHER INFORMATION: Alpha-helix sequence

<400> SEQUENCE: 106

Trp Trp Arg Leu Phe
1               5

<210> SEQ ID NO 107
<211> LENGTH: 11
<212> TYPE: PRT
<213> ORGANISM: artificial
<220> FEATURE:
<223> OTHER INFORMATION: Alpha-helix sequence

<400> SEQUENCE: 107

Arg Asn Val Arg Lys Trp Leu Val Leu Arg Asn
1               5                   10

<210> SEQ ID NO 108
<211> LENGTH: 26
<212> TYPE: PRT
```

```
<213> ORGANISM: artificial
<220> FEATURE:
<223> OTHER INFORMATION: Alpha-helix sequence

<400> SEQUENCE: 108

Ser Ser Ser Thr Lys Lys Thr Gln Leu Gln Leu Glu His Leu Leu Leu
1               5                   10                  15

Asp Leu Gln Met Ile Leu Asn Gly Ile Asn
            20                  25

<210> SEQ ID NO 109
<211> LENGTH: 27
<212> TYPE: PRT
<213> ORGANISM: artificial
<220> FEATURE:
<223> OTHER INFORMATION: Alpha-helix sequence

<400> SEQUENCE: 109

Ala Ala Ala Val Gln Glu Ala Ala Val Ser Ala Ile Leu Gly Leu Ile
1               5                   10                  15

Ile Leu Leu Gly Ile Asn Leu Gly Leu Val Ala
            20                  25

<210> SEQ ID NO 110
<211> LENGTH: 17
<212> TYPE: PRT
<213> ORGANISM: artificial
<220> FEATURE:
<223> OTHER INFORMATION: Alpha-helix sequence

<400> SEQUENCE: 110

Phe Pro Ala Leu Ile Lys Gln Ala Ser Leu Asp Ala Leu Phe Lys Cys
1               5                   10                  15

Gly

<210> SEQ ID NO 111
<211> LENGTH: 10
<212> TYPE: PRT
<213> ORGANISM: artificial
<220> FEATURE:
<223> OTHER INFORMATION: Alpha-helix sequence

<400> SEQUENCE: 111

Leu Met Asp Leu Cys Arg Arg Thr Ile Arg
1               5                   10

<210> SEQ ID NO 112
<211> LENGTH: 17
<212> TYPE: PRT
<213> ORGANISM: artificial
<220> FEATURE:
<223> OTHER INFORMATION: Alpha-helix sequence

<400> SEQUENCE: 112

Glu Leu His Arg Gln Arg Ser Glu Leu Ala Arg Ala Asn Tyr Glu Lys
1               5                   10                  15

Ala

<210> SEQ ID NO 113
<211> LENGTH: 12
<212> TYPE: PRT
<213> ORGANISM: artificial
<220> FEATURE:
<223> OTHER INFORMATION: Alpha-helix sequence
```

```
<400> SEQUENCE: 113

Phe Ile Asp Tyr Ala Ile Glu Tyr Ser Glu Lys Tyr
1               5                   10

<210> SEQ ID NO 114
<211> LENGTH: 11
<212> TYPE: PRT
<213> ORGANISM: artificial
<220> FEATURE:
<223> OTHER INFORMATION: Alpha-helix sequence

<400> SEQUENCE: 114

Asp Glu Ala Phe Ser Arg Leu Ala Gln Ser Arg
1               5                   10

<210> SEQ ID NO 115
<211> LENGTH: 17
<212> TYPE: PRT
<213> ORGANISM: artificial
<220> FEATURE:
<223> OTHER INFORMATION: Alpha-helix sequence

<400> SEQUENCE: 115

Asp Glu Ile Ile Asn Phe Tyr Met Asn Met Leu Met Glu Arg Ser Lys
1               5                   10                  15

Glu

<210> SEQ ID NO 116
<211> LENGTH: 10
<212> TYPE: PRT
<213> ORGANISM: artificial
<220> FEATURE:
<223> OTHER INFORMATION: Alpha-helix sequence

<400> SEQUENCE: 116

Glu Ala Ile Ile Arg Lys Ala Leu Met Gly
1               5                   10

<210> SEQ ID NO 117
<211> LENGTH: 14
<212> TYPE: PRT
<213> ORGANISM: artificial
<220> FEATURE:
<223> OTHER INFORMATION: Alpha-helix sequence

<400> SEQUENCE: 117

Arg His Ile Leu Arg Trp Ile Asp Tyr Met Gln Asn Leu Leu
1               5                   10

<210> SEQ ID NO 118
<211> LENGTH: 11
<212> TYPE: PRT
<213> ORGANISM: artificial
<220> FEATURE:
<223> OTHER INFORMATION: Alpha-helix sequence

<400> SEQUENCE: 118

Pro Lys Asp Ile Gln Leu Ala Arg Arg Ile Arg
1               5                   10

<210> SEQ ID NO 119
<211> LENGTH: 11
<212> TYPE: PRT
<213> ORGANISM: artificial
<220> FEATURE:
<223> OTHER INFORMATION: Alpha-helix sequence
```

```
<400> SEQUENCE: 119

Lys Pro Ala Ile Arg Arg Leu Ala Arg Arg Gly
1               5                   10

<210> SEQ ID NO 120
<211> LENGTH: 17
<212> TYPE: PRT
<213> ORGANISM: artificial
<220> FEATURE:
<223> OTHER INFORMATION: Alpha-helix sequence

<400> SEQUENCE: 120

Leu Ala Trp Lys Ile Ala Lys Met Ile Val Ser Asp Val Met Gln Gln
1               5                   10                  15

Cys

<210> SEQ ID NO 121
<211> LENGTH: 12
<212> TYPE: PRT
<213> ORGANISM: artificial
<220> FEATURE:
<223> OTHER INFORMATION: Alpha-helix sequence

<400> SEQUENCE: 121

Glu Asp Thr Phe Lys Gln Ile Tyr Ala Gln Phe Phe
1               5                   10

<210> SEQ ID NO 122
<211> LENGTH: 8
<212> TYPE: PRT
<213> ORGANISM: artificial
<220> FEATURE:
<223> OTHER INFORMATION: Alpha-helix sequence

<400> SEQUENCE: 122

Trp Leu Pro Phe Ala Arg Ala Ala
1               5

<210> SEQ ID NO 123
<211> LENGTH: 9
<212> TYPE: PRT
<213> ORGANISM: artificial
<220> FEATURE:
<223> OTHER INFORMATION: Alpha-helix sequence

<400> SEQUENCE: 123

Thr Glu Glu Ile Leu Ala Met Ile Lys
1               5

<210> SEQ ID NO 124
<211> LENGTH: 9
<212> TYPE: PRT
<213> ORGANISM: artificial
<220> FEATURE:
<223> OTHER INFORMATION: Alpha-helix sequence

<400> SEQUENCE: 124

Leu Glu Glu Val Leu Ala Ile Ser Arg
1               5

<210> SEQ ID NO 125
<211> LENGTH: 12
<212> TYPE: PRT
<213> ORGANISM: artificial
<220> FEATURE:
```

```
<223> OTHER INFORMATION: Alpha-helix sequence

<400> SEQUENCE: 125

Asp Asp Ile Val Phe Glu Asp Phe Ala Arg Gln Arg
1               5                   10

<210> SEQ ID NO 126
<211> LENGTH: 22
<212> TYPE: PRT
<213> ORGANISM: artificial
<220> FEATURE:
<223> OTHER INFORMATION: Alpha-helix sequence

<400> SEQUENCE: 126

Glu Glu Asp Thr Gly Val Thr Asn Arg Asp Leu Ile Ser Arg Arg Ile
1               5                   10                  15

Lys Glu Tyr Asn Asn Leu
            20

<210> SEQ ID NO 127
<211> LENGTH: 14
<212> TYPE: PRT
<213> ORGANISM: artificial
<220> FEATURE:
<223> OTHER INFORMATION: Alpha-helix sequence

<400> SEQUENCE: 127

Asp Asp Met Lys Arg Thr Ile Asn Lys Ala Trp Val Glu Ser
1               5                   10

<210> SEQ ID NO 128
<211> LENGTH: 17
<212> TYPE: PRT
<213> ORGANISM: artificial
<220> FEATURE:
<223> OTHER INFORMATION: Alpha-helix sequence

<400> SEQUENCE: 128

Pro Met Phe Leu Asp Gln Val Ala Lys Phe Ile Ile Asp Asn Thr Lys
1               5                   10                  15

Gly

<210> SEQ ID NO 129
<211> LENGTH: 12
<212> TYPE: PRT
<213> ORGANISM: artificial
<220> FEATURE:
<223> OTHER INFORMATION: Alpha-helix sequence

<400> SEQUENCE: 129

Pro Glu Glu Phe Asp Glu Val Ser Arg Ile Val Gly
1               5                   10

<210> SEQ ID NO 130
<211> LENGTH: 7
<212> TYPE: PRT
<213> ORGANISM: artificial
<220> FEATURE:
<223> OTHER INFORMATION: Alpha-helix sequence

<400> SEQUENCE: 130

Leu Arg Leu Met Leu Ala Gly
1               5

<210> SEQ ID NO 131
```

```
<211> LENGTH: 12
<212> TYPE: PRT
<213> ORGANISM: artificial
<220> FEATURE:
<223> OTHER INFORMATION: Alpha-helix sequence

<400> SEQUENCE: 131

Gln Asp Val Ala Glu Glu Val Arg Ala Val Leu Glu
1               5                   10

<210> SEQ ID NO 132
<211> LENGTH: 10
<212> TYPE: PRT
<213> ORGANISM: artificial
<220> FEATURE:
<223> OTHER INFORMATION: Alpha-helix sequence

<400> SEQUENCE: 132

Ile Gly Asp Leu Ala Met Val Ser Lys Asn
1               5                   10

<210> SEQ ID NO 133
<211> LENGTH: 19
<212> TYPE: PRT
<213> ORGANISM: artificial
<220> FEATURE:
<223> OTHER INFORMATION: Alpha-helix sequence

<400> SEQUENCE: 133

Pro Trp Ile Leu Met Ser Asp Asp Leu Ser Asp Leu Ile His Thr Asn
1               5                   10                  15

Ile Tyr Leu

<210> SEQ ID NO 134
<211> LENGTH: 6
<212> TYPE: PRT
<213> ORGANISM: artificial
<220> FEATURE:
<223> OTHER INFORMATION: Alpha-helix sequence

<400> SEQUENCE: 134

Phe Glu Gln Met Phe Thr
1               5

<210> SEQ ID NO 135
<211> LENGTH: 19
<212> TYPE: PRT
<213> ORGANISM: artificial
<220> FEATURE:
<223> OTHER INFORMATION: Alpha-helix sequence

<400> SEQUENCE: 135

Pro Gln Ala Lys Ile Ala Glu Leu Glu Asn Gln Val His Arg Leu Glu
1               5                   10                  15

Gln Glu Leu

<210> SEQ ID NO 136
<211> LENGTH: 11
<212> TYPE: PRT
<213> ORGANISM: artificial
<220> FEATURE:
<223> OTHER INFORMATION: Alpha-helix sequence

<400> SEQUENCE: 136

Glu Asp Glu Leu Phe Arg Leu Ser Gln Leu Gly
1               5                   10
```

```
<210> SEQ ID NO 137
<211> LENGTH: 9
<212> TYPE: PRT
<213> ORGANISM: artificial
<220> FEATURE:
<223> OTHER INFORMATION: Alpha-helix sequence

<400> SEQUENCE: 137

Ser Ala Thr Thr Phe Arg Ile Leu Ala
1               5

<210> SEQ ID NO 138
<211> LENGTH: 8
<212> TYPE: PRT
<213> ORGANISM: artificial
<220> FEATURE:
<223> OTHER INFORMATION: Alpha-helix sequence

<400> SEQUENCE: 138

Thr Leu Lys Phe Trp Asp Ile Phe
1               5

<210> SEQ ID NO 139
<211> LENGTH: 6
<212> TYPE: PRT
<213> ORGANISM: artificial
<220> FEATURE:
<223> OTHER INFORMATION: Alpha-helix sequence

<400> SEQUENCE: 139

Glu Lys Glu Leu Leu Asp
1               5

<210> SEQ ID NO 140
<211> LENGTH: 14
<212> TYPE: PRT
<213> ORGANISM: artificial
<220> FEATURE:
<223> OTHER INFORMATION: Alpha-helix sequence

<400> SEQUENCE: 140

Gly Asp Val Leu Tyr Glu Leu Leu Gln His Ile Leu Lys Gln
1               5                   10

<210> SEQ ID NO 141
<211> LENGTH: 6
<212> TYPE: PRT
<213> ORGANISM: artificial
<220> FEATURE:
<223> OTHER INFORMATION: Alpha-helix sequence

<400> SEQUENCE: 141

Tyr Phe Tyr Ser Lys Phe
1               5

<210> SEQ ID NO 142
<211> LENGTH: 7
<212> TYPE: PRT
<213> ORGANISM: artificial
<220> FEATURE:
<223> OTHER INFORMATION: Alpha-helix sequence

<400> SEQUENCE: 142

Pro Pro Cys Ile Leu Asn Asn
1               5
```

```
<210> SEQ ID NO 143
<211> LENGTH: 9
<212> TYPE: PRT
<213> ORGANISM: artificial
<220> FEATURE:
<223> OTHER INFORMATION: Alpha-helix sequence

<400> SEQUENCE: 143

Leu Ser Arg Leu Leu Ser Tyr Ala Gly
1               5

<210> SEQ ID NO 144
<211> LENGTH: 25
<212> TYPE: PRT
<213> ORGANISM: artificial
<220> FEATURE:
<223> OTHER INFORMATION: Alpha-helix sequence

<400> SEQUENCE: 144

Arg Thr Ala Ile Glu Ala Phe Asn Glu Thr Ile Lys Ile Phe Glu Glu
1               5                   10                  15

Gln Cys Gln Thr Gln Glu Arg Tyr Ser
            20                  25

<210> SEQ ID NO 145
<211> LENGTH: 9
<212> TYPE: PRT
<213> ORGANISM: artificial
<220> FEATURE:
<223> OTHER INFORMATION: Alpha-helix sequence

<400> SEQUENCE: 145

Asp Tyr Leu Lys Arg Lys Ile Arg Ser
1               5

<210> SEQ ID NO 146
<211> LENGTH: 5
<212> TYPE: PRT
<213> ORGANISM: artificial
<220> FEATURE:
<223> OTHER INFORMATION: Alpha-helix sequence

<400> SEQUENCE: 146

Leu Glu Glu Leu Phe
1               5

<210> SEQ ID NO 147
<211> LENGTH: 10
<212> TYPE: PRT
<213> ORGANISM: artificial
<220> FEATURE:
<223> OTHER INFORMATION: Alpha-helix sequence

<400> SEQUENCE: 147

Asp Asp Leu Asp Ala Leu Leu Ala Asp Leu
1               5                   10

<210> SEQ ID NO 148
<211> LENGTH: 9
<212> TYPE: PRT
<213> ORGANISM: artificial
<220> FEATURE:
<223> OTHER INFORMATION: Alpha-helix sequence

<400> SEQUENCE: 148

Asp Arg Leu Arg Pro Leu Ser Tyr Pro
```

```
1               5
```

<210> SEQ ID NO 149
<211> LENGTH: 16
<212> TYPE: PRT
<213> ORGANISM: artificial
<220> FEATURE:
<223> OTHER INFORMATION: Alpha-helix sequence

<400> SEQUENCE: 149

```
Val Glu Glu Leu Phe Glu Trp Phe Gln Ser Ile Arg Glu Ile Thr Trp
1               5                   10                  15
```

<210> SEQ ID NO 150
<211> LENGTH: 17
<212> TYPE: PRT
<213> ORGANISM: artificial
<220> FEATURE:
<223> OTHER INFORMATION: Alpha-helix sequence

<400> SEQUENCE: 150

```
Val Ala Asp Leu Ala Leu Ser Glu Asn Trp Ala Gln Glu Phe Leu Ala
1               5                   10                  15

Ala
```

<210> SEQ ID NO 151
<211> LENGTH: 7
<212> TYPE: PRT
<213> ORGANISM: artificial
<220> FEATURE:
<223> OTHER INFORMATION: Alpha-helix sequence

<400> SEQUENCE: 151

```
Phe Glu Gly Asn Leu Ala Leu
1               5
```

<210> SEQ ID NO 152
<211> LENGTH: 5
<212> TYPE: PRT
<213> ORGANISM: artificial
<220> FEATURE:
<223> OTHER INFORMATION: Alpha-helix sequence

<400> SEQUENCE: 152

```
Ser Leu Ala Ser Val
1               5
```

<210> SEQ ID NO 153
<211> LENGTH: 7
<212> TYPE: PRT
<213> ORGANISM: artificial
<220> FEATURE:
<223> OTHER INFORMATION: Alpha-helix sequence

<400> SEQUENCE: 153

```
Ala Phe Asp Ile Ile Ser Gly
1               5
```

<210> SEQ ID NO 154
<211> LENGTH: 10
<212> TYPE: PRT
<213> ORGANISM: artificial
<220> FEATURE:
<223> OTHER INFORMATION: Alpha-helix sequence

<400> SEQUENCE: 154

Glu Glu Leu Phe Asn Val Gln Asp Gln His
1               5                   10

<210> SEQ ID NO 155
<211> LENGTH: 16
<212> TYPE: PRT
<213> ORGANISM: artificial
<220> FEATURE:
<223> OTHER INFORMATION: Alpha-helix sequence

<400> SEQUENCE: 155

Met Ala Asp Val Ala Gln Lys Leu Glu Gln Leu Glu Val Met Met Ser
1               5                   10                  15

<210> SEQ ID NO 156
<211> LENGTH: 8
<212> TYPE: PRT
<213> ORGANISM: artificial
<220> FEATURE:
<223> OTHER INFORMATION: Alpha-helix sequence

<400> SEQUENCE: 156

Arg Ile Lys Glu Leu Arg Asn Leu
1               5

<210> SEQ ID NO 157
<211> LENGTH: 16
<212> TYPE: PRT
<213> ORGANISM: artificial
<220> FEATURE:
<223> OTHER INFORMATION: Alpha-helix sequence

<400> SEQUENCE: 157

Gly Asn Ser Val Ala Pro Ala Ala Leu Phe Leu Ala Ala Lys Val Glu
1               5                   10                  15

<210> SEQ ID NO 158
<211> LENGTH: 7
<212> TYPE: PRT
<213> ORGANISM: artificial
<220> FEATURE:
<223> OTHER INFORMATION: Alpha-helix sequence

<400> SEQUENCE: 158

Gly Arg Ala Leu Leu Arg Ile
1               5

<210> SEQ ID NO 159
<211> LENGTH: 8
<212> TYPE: PRT
<213> ORGANISM: artificial
<220> FEATURE:
<223> OTHER INFORMATION: Alpha-helix sequence

<400> SEQUENCE: 159

Trp Leu Glu Ala Trp Arg Arg Asp
1               5

<210> SEQ ID NO 160
<211> LENGTH: 15
<212> TYPE: PRT
<213> ORGANISM: artificial
<220> FEATURE:
<223> OTHER INFORMATION: Alpha-helix sequence

<400> SEQUENCE: 160

Leu Gly Glu Leu Pro Gln Gly Phe Ala Arg Leu Ser Ala Ile Tyr

<210> SEQ ID NO 161
<211> LENGTH: 10
<212> TYPE: PRT
<213> ORGANISM: artificial
<220> FEATURE:
<223> OTHER INFORMATION: Alpha-helix sequence

<400> SEQUENCE: 161

Gln Lys Phe Gln Ser Ile Val Ile Gly Cys
1               5                   10

<210> SEQ ID NO 162
<211> LENGTH: 8
<212> TYPE: PRT
<213> ORGANISM: artificial
<220> FEATURE:
<223> OTHER INFORMATION: Alpha-helix sequence

<400> SEQUENCE: 162

Ser Glu Leu Leu Lys Tyr Leu Thr
1               5

<210> SEQ ID NO 163
<211> LENGTH: 34
<212> TYPE: PRT
<213> ORGANISM: artificial
<220> FEATURE:
<223> OTHER INFORMATION: Alpha-helix sequence

<400> SEQUENCE: 163

Glu Glu Ser Arg Leu Ser Ala Tyr Tyr Asn Leu Leu His Cys Leu Arg
1               5                   10                  15

Arg Asp Ser His Lys Ile Asp Asn Tyr Leu Lys Leu Leu Lys Cys Arg
            20                  25                  30

Ile Ile

<210> SEQ ID NO 164
<211> LENGTH: 9
<212> TYPE: PRT
<213> ORGANISM: artificial
<220> FEATURE:
<223> OTHER INFORMATION: Alpha-helix sequence

<400> SEQUENCE: 164

Leu Asp Ala Leu Trp Asp Cys Leu Thr
1               5

<210> SEQ ID NO 165
<211> LENGTH: 8
<212> TYPE: PRT
<213> ORGANISM: artificial
<220> FEATURE:
<223> OTHER INFORMATION: Alpha-helix sequence

<400> SEQUENCE: 165

Phe Ser Asp Leu Trp Lys Leu Leu
1               5

<210> SEQ ID NO 166
<211> LENGTH: 8
<212> TYPE: PRT
<213> ORGANISM: artificial
<220> FEATURE:
<223> OTHER INFORMATION: Alpha-helix sequence

```
<400> SEQUENCE: 166

Phe Ser Asp Leu Trp Lys Leu Leu
1               5

<210> SEQ ID NO 167
<211> LENGTH: 10
<212> TYPE: PRT
<213> ORGANISM: artificial
<220> FEATURE:
<223> OTHER INFORMATION: Alpha-helix sequence

<400> SEQUENCE: 167

Ile Arg Glu Arg Met Leu Tyr Ser Ser Cys
1               5                   10

<210> SEQ ID NO 168
<211> LENGTH: 9
<212> TYPE: PRT
<213> ORGANISM: artificial
<220> FEATURE:
<223> OTHER INFORMATION: Alpha-helix sequence

<400> SEQUENCE: 168

Glu Phe Ala Ser Leu Phe Asp Thr Leu
1               5

<210> SEQ ID NO 169
<211> LENGTH: 11
<212> TYPE: PRT
<213> ORGANISM: artificial
<220> FEATURE:
<223> OTHER INFORMATION: Alpha-helix sequence

<400> SEQUENCE: 169

Ala Asp Ala Val Ala Cys Ala Lys Arg Val Val
1               5                   10

<210> SEQ ID NO 170
<211> LENGTH: 7
<212> TYPE: PRT
<213> ORGANISM: artificial
<220> FEATURE:
<223> OTHER INFORMATION: Alpha-helix sequence

<400> SEQUENCE: 170

Ala Trp Asp Leu Tyr Gly Glu
1               5

<210> SEQ ID NO 171
<211> LENGTH: 9
<212> TYPE: PRT
<213> ORGANISM: artificial
<220> FEATURE:
<223> OTHER INFORMATION: Alpha-helix sequence

<400> SEQUENCE: 171

Asp Arg Leu Arg Pro Leu Ser Tyr Pro
1               5

<210> SEQ ID NO 172
<211> LENGTH: 14
<212> TYPE: PRT
<213> ORGANISM: artificial
<220> FEATURE:
<223> OTHER INFORMATION: Alpha-helix sequence
```

```
<400> SEQUENCE: 172

Leu Asp Thr Val Glu Leu Val Met Ala Leu Glu Glu Glu Phe
1               5                   10

<210> SEQ ID NO 173
<211> LENGTH: 33
<212> TYPE: PRT
<213> ORGANISM: artificial
<220> FEATURE:
<223> OTHER INFORMATION: Alpha-helix sequence

<400> SEQUENCE: 173

Lys Lys Glu Ala Tyr Asp Thr Leu Ile Lys Asp Leu Lys Lys Ala Asn
1               5                   10                  15

Leu Cys Thr Leu Ala Glu Lys Ile Gln Thr Ile Ile Leu Lys Asp Ile
            20                  25                  30

Thr

<210> SEQ ID NO 174
<211> LENGTH: 8
<212> TYPE: PRT
<213> ORGANISM: artificial
<220> FEATURE:
<223> OTHER INFORMATION: Alpha-helix sequence

<400> SEQUENCE: 174

Arg Asp Glu Phe Arg Arg Lys Tyr
1               5

<210> SEQ ID NO 175
<211> LENGTH: 11
<212> TYPE: PRT
<213> ORGANISM: artificial
<220> FEATURE:
<223> OTHER INFORMATION: Alpha-helix sequence

<400> SEQUENCE: 175

Gln Glu Val Lys Met Val Ala Trp Trp Ile Gly
1               5                   10

<210> SEQ ID NO 176
<211> LENGTH: 11
<212> TYPE: PRT
<213> ORGANISM: artificial
<220> FEATURE:
<223> OTHER INFORMATION: Alpha-helix sequence

<400> SEQUENCE: 176

His Gln Asp Gln Ser Ile Arg Ile Gln Arg Met
1               5                   10

<210> SEQ ID NO 177
<211> LENGTH: 15
<212> TYPE: PRT
<213> ORGANISM: artificial
<220> FEATURE:
<223> OTHER INFORMATION: Alpha-helix sequence

<400> SEQUENCE: 177

Asp Thr Cys Lys Lys Tyr Arg Ser Ala Tyr Ile Thr Pro Cys Thr
1               5                   10                  15

<210> SEQ ID NO 178
<211> LENGTH: 5
<212> TYPE: PRT
```

```
<213> ORGANISM: artificial
<220> FEATURE:
<223> OTHER INFORMATION: Alpha-helix sequence

<400> SEQUENCE: 178

Pro Trp Trp Glu Thr
1               5

<210> SEQ ID NO 179
<211> LENGTH: 24
<212> TYPE: PRT
<213> ORGANISM: artificial
<220> FEATURE:
<223> OTHER INFORMATION: Alpha-helix sequence

<400> SEQUENCE: 179

Pro Ile Thr Arg Phe Asn Thr Gln Thr Lys Met Ile Glu Gln Val Ser
1               5                   10                  15

Gln Glu Ile Phe Glu Arg Asn Phe
            20

<210> SEQ ID NO 180
<211> LENGTH: 21
<212> TYPE: PRT
<213> ORGANISM: artificial
<220> FEATURE:
<223> OTHER INFORMATION: Alpha-helix sequence

<400> SEQUENCE: 180

Asp Ile Ile Ala Ala Ala Lys Arg Met Ala Leu Leu Met Ala Glu Met
1               5                   10                  15

Ser Arg Leu Val Arg
            20

<210> SEQ ID NO 181
<211> LENGTH: 14
<212> TYPE: PRT
<213> ORGANISM: artificial
<220> FEATURE:
<223> OTHER INFORMATION: Alpha-helix sequence

<400> SEQUENCE: 181

Glu Lys Ser Trp Phe Arg Glu Thr Glu Leu Tyr Asn Thr Val
1               5                   10

<210> SEQ ID NO 182
<211> LENGTH: 29
<212> TYPE: PRT
<213> ORGANISM: Artificial Sequence
<220> FEATURE:
<223> OTHER INFORMATION: Endoplasmic reticulum signal peptide

<400> SEQUENCE: 182

Met Met Ser Phe Val Ser Leu Leu Leu Val Gly Ile Leu Phe Tyr Ala
1               5                   10                  15

Thr Glu Ala Glu Gln Leu Thr Lys Cys Glu Val Phe Gln
            20                  25

<210> SEQ ID NO 183
<211> LENGTH: 4
<212> TYPE: PRT
<213> ORGANISM: Artificial Sequence
<220> FEATURE:
<223> OTHER INFORMATION: Endoplasmic reticulum retention signal peptide

<400> SEQUENCE: 183
```

-continued

```
Lys Glu Asp Leu
1

<210> SEQ ID NO 184
<211> LENGTH: 8
<212> TYPE: PRT
<213> ORGANISM: Artificial Sequence
<220> FEATURE:
<223> OTHER INFORMATION: nuclear transport peptide

<400> SEQUENCE: 184

Pro Pro Lys Lys Lys Arg Lys Val
1               5

<210> SEQ ID NO 185
<211> LENGTH: 25
<212> TYPE: PRT
<213> ORGANISM: Artificial Sequence
<220> FEATURE:
<223> OTHER INFORMATION: mitochondrial signal peptide

<400> SEQUENCE: 185

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 186
<211> LENGTH: 12
<212> TYPE: PRT
<213> ORGANISM: Artificial
<220> FEATURE:
<223> OTHER INFORMATION: Alpha-helix sequence

<400> SEQUENCE: 186

Glu Thr Phe Ser Asp Leu Trp Lys Leu Leu Pro Glu
1               5                   10

<210> SEQ ID NO 187
<211> LENGTH: 8
<212> TYPE: PRT
<213> ORGANISM: Artificial
<220> FEATURE:
<223> OTHER INFORMATION: Alpha-helix sequence

<400> SEQUENCE: 187

Glu Leu Leu Arg Ala Leu Asp Gln
1               5

<210> SEQ ID NO 188
<211> LENGTH: 13
<212> TYPE: PRT
<213> ORGANISM: Artificial
<220> FEATURE:
<223> OTHER INFORMATION: Alpha-helix sequence

<400> SEQUENCE: 188

Arg Ile Lys Glu Leu Glu Leu Leu Leu Met Ser Thr Glu
1               5                   10

<210> SEQ ID NO 189
<211> LENGTH: 12
<212> TYPE: PRT
<213> ORGANISM: Artificial
<220> FEATURE:
<223> OTHER INFORMATION: Alpha-helix sequence
```

```
<400> SEQUENCE: 189

Asp Glu Arg Ala Leu Leu Asp Gln Leu His Thr Leu
1               5                   10

<210> SEQ ID NO 190
<211> LENGTH: 10
<212> TYPE: PRT
<213> ORGANISM: Artificial
<220> FEATURE:
<223> OTHER INFORMATION: Alpha-helix sequence

<400> SEQUENCE: 190

Leu Arg Ala Leu Val Glu Met Ala Arg Val
1               5                   10
```

OLIGOOXOPIPERAZINES AND METHODS OF MAKING AND USING THEM

This application is a continuation of U.S. patent application Ser. No. 12/917,176, filed Nov. 1, 2010, which claims the priority benefit of U.S. Provisional Patent Application Ser. No. 61/373,108, filed Aug. 12, 2010, which are hereby incorporated by reference in their entirety.

This invention was made with government support under National Science Foundation grant number CHE-0848410. The government has certain rights in this invention.

FIELD OF THE INVENTION

This invention is directed generally to oligooxopiperazines and methods for preparing oligooxopiperazines from amino acids.

BACKGROUND OF THE INVENTION

A fundamental limitation of current drug development centers on the inability of traditional pharmaceuticals to target spatially extended protein interfaces. The majority of modern pharmaceuticals are small molecules that target enzymes or protein receptors with defined pockets. However, in general they cannot target protein-protein interactions involving large contact areas with the required specificity. Examination of complexes of proteins with other biomolecules reveals that proteins tend to interact with partners via folded sub-domains, in which the backbone possesses secondary structure. These protein sub-domains rarely remain structured once excised from the protein; much of their ability to specifically bind their intended targets is lost because they assume a manifold of shapes rather than the biologically relevant one. The α-helix is the most prevalent protein secondary structure.

α-Helices play fundamental roles in mediating protein-protein interactions. Several approaches for stabilizing peptides in helical conformations or mimicking this conformation with nonnatural oligomers have been described (Henchey et al., *Curr. Opin. Chem. Biol.* 12: 692-697 (2008); Home et al., *Acc. Chem. Res.* 41: 1399-1408 (2008); Seebach et al., *J. Acc. Chem. Res.* 41: 1366-1375 (2008); Patgiri et al., *Acc. Chem. Res.* 41: 1289-1300 (2008); Garner et al., *Org. Biomol. Chem.* 5: 3577-3585 (2007); Goodman et al., *Nat. Chem. Biol.* 3: 252-262 (2007); Chin et al., *Am. Chem. Soc.* 123: 2929-2930 (2001)). Examination of complexes of proteins with other biomolecules reveals that often one face of the helix featuring the i, i+4 and i+7 residues is involved in binding. Synthetic scaffolds that display protein-like functionality and reproduce the arrangement of key side chains on an α-helix would be invaluable as inhibitors of selective protein interactions.

The present invention is directed to overcoming these and other deficiencies in the art.

SUMMARY OF THE INVENTION

One aspect of the present invention relates to an oligooxopiperazine of Formula I:

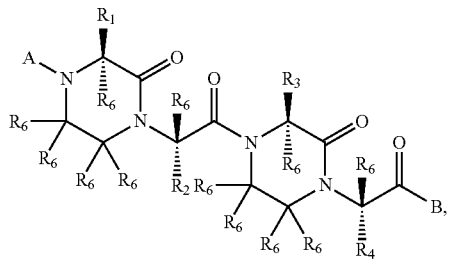

wherein:

each of $R_1$, $R_2$, $R_3$, and $R_4$ is independently an amino acid side chain, H, $N(R)_2$, OR, halogen, an alkyl, or an aryl; wherein each R is independently H, an alkyl, or an aryl;

each $R_6$ is independently H, $N(R)_2$, OR, halogen, an alkyl, or an aryl; wherein each R is independently H, an alkyl, or an aryl;

A is $X_1$ or C, wherein:

$X_1$ is H, COR', $CO_2R'$, CONR', an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and C is a moiety of the formula

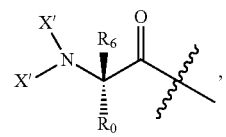

wherein:

each X' is independently H, COR', $CO_2R'$, CONR', $N(R'')_2$, an alkyl, an aryl, an arylalkyl, a cycloalkyl, a heteroaryl, a targeting moiety, or a tag; wherein:

R' is H, an alkyl, an aryl, an arylalkyl, a cycloalkyl, a heteroaryl, a targeting moiety, or a tag; and each R'' is independently H, an alkyl, an aryl, an arylalkyl, a cycloalkyl, a heteroaryl, a targeting moiety, or a tag;

$R_0$ is an amino acid side chain, H, $N(R)_2$, OR, halogen, an alkyl, or an aryl; wherein each R is independently H, an alkyl, or an aryl; and $R_6$ is H, $N(R)_2$, OR, halogen, an alkyl, or an aryl; wherein each R is independently H, an alkyl, or an aryl; and B is Y or D, wherein:

Y is OR', COR', $N(R''')_2$, an alkyl, an aryl, an arylalkyl, a cycloalkyl, a heteroaryl, a protecting group for protection of a carboxylic acid, a targeting moiety, or a tag; wherein:

R' is H, an alkyl, an aryl, an arylalkyl, a cycloalkyl, a heteroaryl, a targeting moiety, or a tag; and each R''' is independently H, $CO_2R'$, CONR', an alkyl, an aryl, an arylalkyl, a cycloalkyl, a heteroaryl, a targeting moiety, or a tag; and D is a moiety of the formula

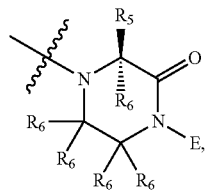

wherein:
$R_5$ is an amino acid side chain, H, $N(R)_2$, OR, halogen, an alkyl, or an aryl; wherein each R is independently H, an alkyl, or an aryl;
$R_6$ is H, $N(R)_2$, OR, halogen, an alkyl, or an aryl; wherein each R is independently H, an alkyl, or an aryl; and
E is $X_2$ or F, wherein:
$X_2$ is H, COR', $CO_2R'$, CONR', an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and
F is a moiety of the formula

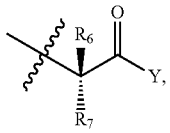

wherein:
$R_6$ is H, $N(R)_2$, OR, halogen, an alkyl, or an aryl; wherein each R is independently H, an alkyl, or an aryl;
$R_7$ is an amino acid side chain; and
Y is OR', COR', $N(R'')_2$, an alkyl, an aryl, an arylalkyl, a cycloalkyl, a heteroaryl, a protecting group for protection of a carboxylic acid, a targeting moiety, or a tag; wherein:
R' is H, an alkyl, an aryl, an arylalkyl, a cycloalkyl, a heteroaryl, a targeting moiety, or a tag; and
each R''' is independently H, $CO_2R'$, CONR', an alkyl, an aryl, an arylalkyl, a cycloalkyl, a heteroaryl, a targeting moiety, or a tag;
with the proviso that A and B are not both, respectively, C and D.

The present invention is further directed to pharmaceutical formulations containing the oligooxopiperazine of Formula I and methods of inhibiting protein activity or protein-protein interactions using the oligooxopiperazine of Formula I.

Another aspect of the present invention relates to a method of inhibiting a protein-protein interaction. This method involves contacting at least one of the proteins involved in the protein-protein interaction with an oligooxopiperazine under conditions effective to inhibit the protein-protein interaction. In one embodiment of this aspect of the present invention, the protein-protein interaction is mediated by a first hot spot amino acid residue and a second hot spot amino acid residue, and the oligooxopiperazine comprises an oligooxopiperazine of Formula II:

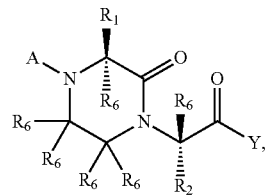

wherein:
$R_1$ and $R_2$ are independently an amino acid side chain, H, $N(R)_2$, OR, halogen, an alkyl, or an aryl; wherein each R is independently H, an alkyl, or an aryl;
each $R_6$ is independently H, $N(R)_2$, OR, halogen, an alkyl, or an aryl; wherein each R is independently H, an alkyl, or an aryl;
A is $X_1$ or C, wherein:
$X_1$ is H, COR', $CO_2R'$, CONR', an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and
C is a moiety of the formula

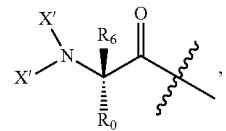

wherein:
each X' is independently H, COR', $CO_2R'$, CONR', $N(R'')_2$, an alkyl, an aryl, an arylalkyl, a cycloalkyl, a heteroaryl, a targeting moiety, or a tag; wherein:
R' is H, an alkyl, an aryl, an arylalkyl, a cycloalkyl, a heteroaryl, a targeting moiety, or a tag; and
each R'' is independently H, $CO_2R'$, CONR', an alkyl, an aryl, an arylalkyl, a cycloalkyl, a heteroaryl, a targeting moiety, or a tag;
$R_0$ is an amino acid side chain, H, $N(R)_2$, OR, halogen, an alkyl, or an aryl; wherein each R is independently H, an alkyl, or an aryl; and
$R_6$ is H, $N(R)_2$, OR, halogen, an alkyl, or an aryl; wherein each R is independently H, an alkyl, or an aryl; and
Y is OR', COR', $N(R''')_2$, an alkyl, an aryl, an arylalkyl, a cycloalkyl, a heteroaryl, a protecting group for protection of a carboxylic acid, a targeting moiety, or a tag;
wherein:
R' is H, an alkyl, an aryl, an arylalkyl, a cycloalkyl, a heteroaryl, a targeting moiety, or a tag; and
each R''' is independently H, $CO_2R'$, CONR', an alkyl, an aryl, an arylalkyl, a cycloalkyl, a heteroaryl, a targeting moiety, or a tag.

The present invention is further directed to methods of solid phase and solution phase synthesis of the oligooxopiperazines of the present invention.

A fundamental limitation of current drug development centers on the inability of traditional pharmaceuticals to target spatially extended protein surfaces. The intrinsic conformational and chemical instabilities of peptides limit their potential as reagents in molecular biology and drug discovery. Accordingly, there is a need to develop nonpeptidic oligomers that display protein-like side chains as alternatives to peptides and have superior pharmacological properties. The present invention describes the design and synthesis of non-peptidic oxopiperazine oligomers that are non-aromatic helix mimetics that are easily synthesized from α-amino acids. These scaffolds present chiral backbones, as compared to the aromatic templates, that are more effective in discriminating between chiral protein pockets Importantly, because the oligooxopiperazines of the present invention are obtained by linking neighboring amide nitrogen atoms in peptides with ethylene bridges, the amide bond, that may be the chief culprit leading to the poor cellular uptake of peptides, is removed. Molecular modeling studies, 2D NMR, and circular dichroism provide strong support for the design features of the oligooxopiperazines described herein.

BRIEF DESCRIPTION OF THE DRAWINGS

FIGS. 1A-1H depict suitable methods of coupling and cyclizing amino acid residues using various alkylating agents. FIGS. 1A-1B show the steps of coupling and cyclizing amino acid residues using X—$CH_2$—CH═CH (designated as alkylating agent A) in the solid phase (designated Sd) or solution phase (designated Sn) synthesis of the oligooxopiperazines of the present invention. FIGS. 1C-1D show the steps of coupling and cyclizing amino acid residues using X—$CH_2$—$CH(OR_{11})_2$ (designated as alkylating agent B) in the solid phase (designated Sd) or solution phase (designated Sn) synthesis schemes of the present invention. FIGS. 1E-1F show the steps of coupling and cyclizing amino acid residues using X—$(CH_2)_2$—X (designated as alkylating agent C) in the solid phase (designated Sd) or solution phase (designated Sn) synthesis schemes of the present invention. FIGS. 1G-1H shows the steps of coupling and cyclizing amino acid residues using X—$(CH_2)_2$—OH (designated as alkylating agent D) in the solid phase (designated Sd) or solution phase (designated Sn) synthesis schemes of the present invention.

FIG. 2B shows an 8mer canonical α-helix with side chain residues depicted as dark grey spheres (left). The predicted structure of an oligooxopiperazine dimer with side chain residues depicted as light grey spheres (FIG. 2B, right) and an overlay of the piperazine dimer and the α-helix (FIG. 2B, center) is also shown. FIG. 2C (left) and FIG. 2C (right) show a top-down view of the structures shown in FIG. 2B (left) and FIG. 2B (center), respectively.

FIG. 8B shows the predicted structure of an oligooxopiperazine trimer. An overlay of the trimer and the α-helix (gray stick model) is shown in FIG. 8C. The spheres represent amino acid side chains. FIG. 8D illustrates the numbering of side chain residues on the oligooxopiperazine trimer.

FIG. 10B shows an overlay of oligooxopiperazine 38 and the p53 helix. FIG. 10C shows the structures of oligooxopiperazine 38 (FIG. 10C; left), and the negative control oligooxopiperazine 39 (FIG. 10C; right), which lacks the key tryptophan residue.

FIGS. 11A1-11AA2 contain a table of α-helices involved in modulating protein-protein interactions that are suitable targets for oligooxopiperazines design. The table sets forth the α-helices by, inter alia, their RSC Protein Data Bank (an online database that includes proteins involved in protein-protein interactions; "PDB") code (column A), title (column D), function (column E), the chains in the protein-protein complex featuring a helix at the interface (column B), and the chain containing the candidate helix to be mimicked (column C). Also shown in the table are the number of hot spot residues in the helix (column J), the relative position of the hot spot residues within the chain (column K) and within the helix (column L), the length of the candidate helix to be mimicked (column N), the first (column O) and last (column P) residue of the helix to be mimicked, and the amino acid sequence of the helix to be mimicked (column Q).

DETAILED DESCRIPTION OF THE INVENTION

Figure 1B:
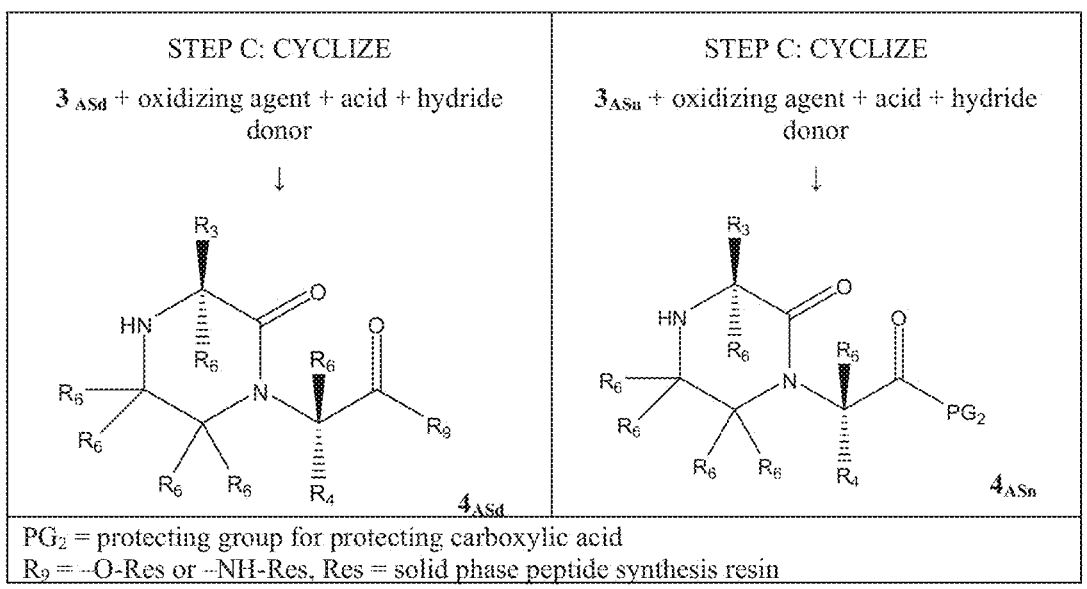

A first aspect of the present invention is directed to an oligooxopiperazine of Formula I:

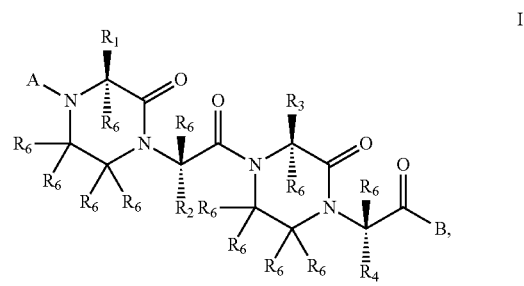

wherein:
each of $R_1$, $R_2$, $R_3$, and $R_4$ is independently an amino acid side chain, H, $N(R)_2$, OR, halogen, an alkyl, or an aryl; wherein each R is independently H, an alkyl, or an aryl;
each $R_6$ is independently H, $N(R)_2$, OR, halogen, an alkyl, or an aryl; wherein each R is independently H, an alkyl, or an aryl;
A is $X_1$ or C, wherein:
 $X_1$ is H, COR', $CO_2R'$, CONR, an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and
 C is a moiety of the formula

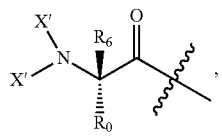

wherein:
 each X' is independently H, COR', $CO_2R'$, CONR', $N(R'')_2$, an alkyl, an aryl, an arylalkyl, a cycloalkyl, a heteroaryl, a targeting moiety, or a tag; wherein:
  R' is H, an alkyl, an aryl, an arylalkyl, a cycloalkyl, a heteroaryl, a targeting moiety, or a tag; and
  each R" is independently H, $CO_2R'$, CONR', an alkyl, an aryl, an arylalkyl, a cycloalkyl, a heteroaryl, a targeting moiety, or a tag;
 $R_0$ is an amino acid side chain, H, $N(R)_2$, OR, halogen, an alkyl, or an aryl; wherein each R is independently H, an alkyl, or an aryl; and
 $R_6$ is H, $N(R)_2$, OR, halogen, an alkyl, or an aryl; wherein each R is independently H, an alkyl, or an aryl; and
B is Y or D, wherein:
 Y is OR', COR', $N(R''')_2$, an alkyl, an aryl, an arylalkyl, a cycloalkyl, a heteroaryl, a protecting group for protection of a carboxylic acid, a targeting moiety, or a tag; wherein:
  R' is H, an alkyl, an aryl, an arylalkyl, a cycloalkyl, a heteroaryl, a targeting moiety, or a tag; and
  each R''' is independently H, $CO_2R'$, CONR', an alkyl, an aryl, an arylalkyl, a cycloalkyl, a heteroaryl, a targeting moiety, or a tag; and
 D is a moiety of the formula

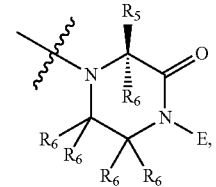

wherein:
 $R_5$ is an amino acid side chain, H, $N(R)_2$, OR, halogen, an alkyl, or an aryl; wherein each R is independently H, an alkyl, or an aryl;
 $R_6$ is H, $N(R)_2$, OR, halogen, an alkyl, or an aryl; wherein each R is independently H, an alkyl, or an aryl; and E is $X_2$ or F, wherein:
 $X_2$ is H, COR', $CO_2R'$, CONR', an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and
 F is a moiety of the formula

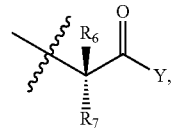

wherein:
 $R_6$ is H, $N(R)_2$, OR, halogen, an alkyl, or an aryl; wherein each R is independently H, an alkyl, or an aryl;
 $R_7$ is an amino acid side chain; and
 Y is OR', COR', $N(R''')_2$, an alkyl, an aryl, an arylalkyl, a cycloalkyl, a heteroaryl, a protecting group for protection of a carboxylic acid, a targeting moiety, or a tag; wherein:
  R' is H, an alkyl, an aryl, an arylalkyl, a cycloalkyl, a heteroaryl, a targeting moiety, or a tag; and
  each R''' is independently H, $CO_2R'$, CONR', an alkyl, an aryl, an arylalkyl, a cycloalkyl, a heteroaryl, a targeting moiety, or a tag;
with the proviso that A and B are not both, respectively, C and D.

Amino acid side chains according to this and all aspects of the present invention can be any amino acid side chain—from natural or nonnatural amino acids—including alpha amino acids, beta amino acids, gamma amino acids, L-amino acids, and D-amino acids.

As used herein, the term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

As used herein, "cycloalkyl" refers to a non-aromatic saturated or unsaturated mono- or polycyclic ring system which may contain 3 to 6 carbon atoms, and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

As used herein, the term "aryl" refers to an aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" refers to a radical of the formula $-R^aR^b$ where $R^a$ is an alkyl radical as defined above and $R^b$ is an aryl radical as defined above. The alkyl radical and the cycloalkyl radical may be optionally substituted as defined above.

As used herein, "heteroaryl" refers to an aromatic ring radical which consists of carbon atoms and from one to five heteroatoms selected from the group consisting of nitrogen, oxygen, and sulfur. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. Additional heteroaryls are described in COMPREHENSIVE HETEROCYCLIC CHEMISTRY: THE STRUCTURE, REACTIONS, SYNTHESIS AND USE OF HETEROCYCLIC COMPOUNDS (Katritzky et al. eds., 1984), which is hereby incorporated by reference in its entirety.

The oligooxopiperazines of Formula I may comprise a protecting group that is suitable for the protection of an amine or a carboxylic acid. Such protecting groups function primarily to protect or mask the reactivity of functional groups. Protecting groups that are suitable for the protection of an amine group are well known in the art, including without limitation, carbamates, amides, N-alkyl and N-aryl amines, imine derivatives, enamine derivatives, and N-hetero atom derivatives as described by THEODORA W. GREENE & PETER G. M. WUTS, PROTECTIVE GROUPS IN ORGANIC SYNTHESIS 494-615 (1999), which is hereby incorporated by reference in its entirety. Protecting groups that are suitable for the protection of a carboxylic acid are also well known in the art. Suitable carboxylic acid protecting groups include, without limitation, esters (e.g., substituted methyl esters, 2-substituted ethyl esters, 2,6-dialkylphenyl esters, substituted benzyl esters, silyl esters, and stannyl esters), amides, and hydrazides as described by THEODORA W. GREENE & PETER G. M. WUTS, PROTECTIVE GROUPS IN ORGANIC SYNTHESIS 372-450 (1999), which is hereby incorporated by reference in its entirety. Methods of protecting and deprotecting amine and carboxylic acids vary depending on the chosen protecting group; however, these methods are well known in the art and described in THEODORA W. GREENE & PETER G. M. WUTS, PROTECTIVE GROUPS IN ORGANIC SYNTHESIS 372-450 and 494-615 (1999), which is hereby incorporated by reference in its entirety.

A "tag" as used herein includes any labeling moiety that facilitates the detection, quantitation, separation, and/or purification of the oligooxopiperazine of the present invention. Suitable tags include purification tags, radioactive or fluorescent labels, and enzymatic tags.

Purification tags, such as poly-histidine ($His_{6-}$), a glutathione-S-transferase (GST-), or maltose-binding protein (MBP-), can assist in oligomer purification or separation but can later be removed, i.e., cleaved from the oligooxopiperazine following recovery. Protease-specific cleavage sites can be used to facilitate the removal of the purification tag. The desired oligooxopiperazine product can be purified further to remove the cleaved purification tags.

Other suitable tags include radioactive labels, such as, $^{125}I$, $^{131}I$, $^{111}In$, or $^{99}TC$. Methods of radiolabeling compounds, are known in the art and described in U.S. Pat. No. 5,830,431 to Srinivasan et al., which is hereby incorporated by reference in its entirety. Radioactivity is detected and quantified using a scintillation counter or autoradiography. Alternatively, the oligooxopiperazine can be conjugated to a fluorescent tag. Suitable fluorescent tags include, without limitation, chelates (europium chelates), fluorescein and its derivatives, rhodamine and its derivatives, dansyl, Lissamine, phycoerythrin and Texas Red. The fluorescent labels can be conjugated to the oligooxopiperazine using techniques disclosed in CURRENT PROTOCOLS IN IMMUNOLOGY (Coligen et al. eds., 1991), which is hereby incorporated by reference in its entirety. Fluorescence can be detected and quantified using a fluorometer.

Enzymatic tags generally catalyze a chemical alteration of a chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Examples of suitable enzymatic tags include luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like. Techniques for conjugating enzymes to proteins and peptides are described in O'Sullivan et al., Methods for the Preparation of Enzyme—Antibody Conjugates for Use in Enzyme Immunoassay, in METHODS IN ENZYMOLOGY 147-66 (Langone et al. eds., 1981), which is hereby incorporated by reference in its entirety. Such tags may be particularly useful for detecting inhibition of protein-protein interactions using the oligooxopiperazine of the present invention, as described more fully, infra.

A targeting moiety according to the present invention functions to (i) promote the cellular uptake of the oligooxopiperazine, (ii) target the oligooxopiperazine to a particular cell or tissue type (e.g., signaling peptide sequence), or (iii) target the oligooxopiperazine to a specific sub-cellular localization after cellular uptake (e.g., transport peptide sequence).

To promote the cellular uptake of an oligooxopiperazine of the present invention, the targeting moiety may be a cell penetrating peptide (CPP). CPPs translocate across the plasma membrane of eukaryotic cells by a seemingly energy-independent pathway and have been used successfully for intracellular delivery of macromolecules, including antibodies, peptides, proteins, and nucleic acids, with molecular weights several times greater than their own. Several commonly used CPPs, including polyarginines, transportant, protamine, maurocalcine, and M918, are suitable targeting moieties for use in the present invention and are well known in the art (see Stewart et al., "Cell-Penetrating Peptides as Delivery Vehicles for Biology and Medicine," *Organic Biomolecular Chem* 6:2242-2255 (2008), which is hereby incorporated by reference in its entirety). Additionally, methods of making CPP are described in U.S. Patent Application Publication No. 20080234183 to Hallbrink et al., which is hereby incorporated by reference in its entirety.

Another suitable targeting moiety useful for enhancing the cellular uptake of the oligooxopiperazine is an "importation competent" signal peptide as disclosed by U.S. Pat. No. 6,043,339 to Lin et al., which is hereby incorporated by reference in its entirety. An importation competent signal peptides is generally about 10 to about 50 amino acid residues in length, typically hydrophobic residues, that render the oligooxopiperazine capable of penetrating through the cell membrane from outside the cell to the interior of the cell. An exemplary importation competent signal peptide includes the signal peptide from Kaposi fibroblast growth factor (see U.S.

Pat. No. 6,043,339 to Lin et al., which is hereby incorporated by reference in its entirety). Other suitable peptide sequences can be selected from the SIGPEP database (see von Heijne G., "SIGPEP: A Sequence Database for Secretory Signal Peptides," *Protein Seq. Data Anal.* 1(1):41-42 (1987), which is hereby incorporated by reference in its entirety).

Another suitable targeting moiety is a signal peptide sequence capable of targeting the oligooxopiperazine to a particular tissue or cell type. The signaling peptide can include at least a portion of a ligand binding protein. Suitable ligand binding proteins include high-affinity antibody fragments (e.g., Fab, Fab' and F(ab)$_2$), single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins. For cell specific targeting, the signaling peptide is preferably a ligand binding domain of a cell specific membrane receptor. Thus, when the modified oligooxopiperazine is delivered intravenously or otherwise introduced into blood or lymph, the oligooxopiperazine will adsorb to the targeted cell, and the targeted cell will internalize the oligooxopiperazine. For example, if the target cell is a cancer cell, the oligooxopiperazine may be conjugated to an anti-C3B(I) antibody as disclosed by U.S. Pat. No. 6,572,856 to Taylor et al., which is hereby incorporated by reference in its entirety. Alternatively, the oligooxopiperazine may be conjugated to an alphafeto protein receptor as disclosed by U.S. Pat. No. 6,514,685 to Moro, or to a monoclonal GAH antibody as disclosed by U.S. Pat. No. 5,837,845 to Hosokawa, which are hereby incorporated by reference in their entirety. For targeting an oligooxopiperazine to a cardiac cell, the oligooxopiperazine may be conjugated to an antibody recognizing elastin microfibril interfacer (EMILIN2) (Van Hoof et al., "Identification of Cell Surface for Antibody-Based Selection of Human Embryonic Stem Cell-Derived Cardiomyocytes," *J Proteom Res* 9:1610-18 (2010), which is hereby incorporated by reference in its entirety), cardiac troponin I, connexin-43, or any cardiac cell-surface membrane receptor that is known in the art. For targeting an oligooxopiperazine to a hepatic cell, the signaling peptide may include a ligand domain specific to the hepatocyte-specific asialoglycoprotein receptor. Methods of preparing such chimeric proteins and peptides are described in U.S. Pat. No. 5,817,789 to Heartlein et al., which is hereby incorporated by reference in its entirety.

Another suitable targeting moiety is a transport peptide that directs intracellular compartmentalization of the oligooxopiperazine once it is internalized by a target cell or tissue. For example, if the protein activity or protein-protein interaction that is sought to be inhibited occurs in the endoplasmic reticulum (ER), the oligooxopiperazine can be conjugated to an ER transport peptide sequence. A number of such signal peptides are known in the art, including the signal peptide MMSFVSLLLVGILFYATEAEQLTKCEVFQ (SEQ ID NO:182). Other suitable ER signal peptides include the N-terminus endoplasmic reticulum targeting sequence of the enzyme 17β-hydroxysteroid dehydrogenase type 11 (Horiguchi et al., "Identification and Characterization of the ER/Lipid Droplet-Targeting Sequence in 17β-hydroxysteroid Dehydrogenase Type 11," *Arch. Biochem. Biophys.* 479(2):121-30 (2008), which is hereby incorporated by reference in its entirety), or any of the ER signaling peptides (including the nucleic acid sequences encoding the ER signal peptides) disclosed in U.S. Patent Publication No. 20080250515 to Reed et al., which is hereby incorporated by reference in its entirety. Additionally, the oligooxopiperazine of the present invention can contain an ER retention signal, such as the retention signal KEDL (SEQ ID NO:183). Methods of modifying the oligooxopiperazines of the present invention to incorporate transport peptides for localization of the oligomers to the ER can be carried out as described in U.S. Patent Publication No. 20080250515 to Reed et al., which is hereby incorporated by reference in its entirety.

If the protein activity or protein-protein interaction that is sought to be inhibited occurs in the nucleus, the oligooxopiperazine can include a nuclear localization transport signal. Suitable nuclear transport peptide sequences are known in the art, including the nuclear transport peptide PPKKKRKV (SEQ ID NO:184). Other nuclear localization transport signals include, for example, the nuclear localization sequence of acidic fibroblast growth factor and the nuclear localization sequence of the transcription factor NF-KB p50 as disclosed by U.S. Pat. No. 6,043,339 to Lin et al., which is hereby incorporated by reference in its entirety. Other nuclear localization peptide sequences known in the art are also suitable for use in the accordance with this aspect of the invention.

Suitable transport peptide sequences for targeting to the mitochondria include MLSLRQSIRFFKPATRTLCSSRYLL (SEQ ID NO:185). Other suitable transport peptide sequences suitable for selectively targeting the oligooxopiperazine of the present invention to the mitochondria are disclosed in U.S. Published Patent Application No. 20070161544 to Wipf, which is hereby incorporated by reference in its entirety.

In one embodiment of the present invention, the oligooxopiperazine of Formula I has a formula of Formula IA:

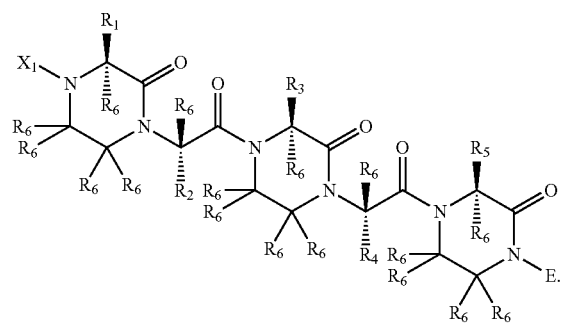

Exemplary oligooxopiperazine compounds of Formula IA include, without limitation,

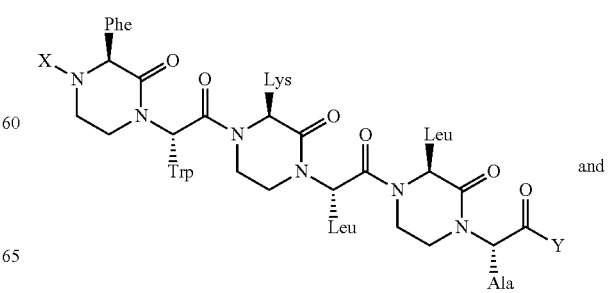

and

-continued

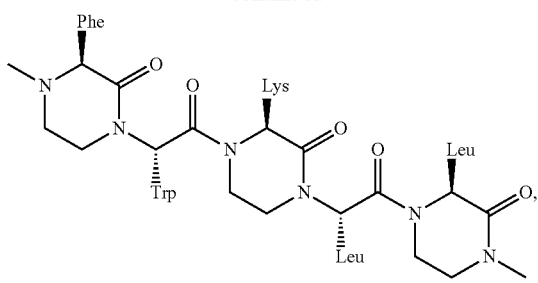

where X is H, COCH$_3$, or any amino acid, and Y is OH, NH$_2$, OMe, or any amino acid.

In another embodiment of the present invention, the oligooxopiperazine of Formula I has a formula of Formula IB:

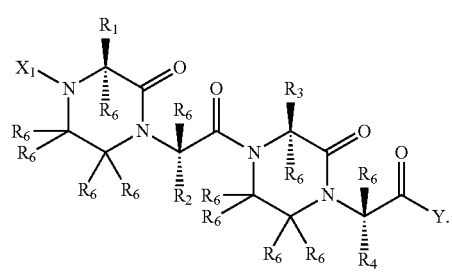

IB

Exemplary oligooxopiperazine compounds of Formula IB include, without limitation,

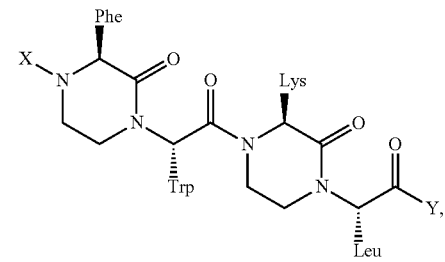

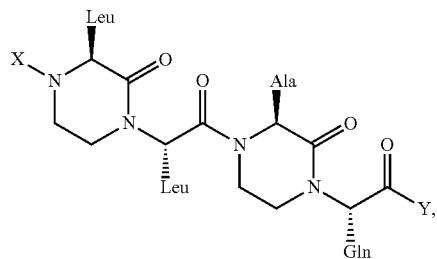

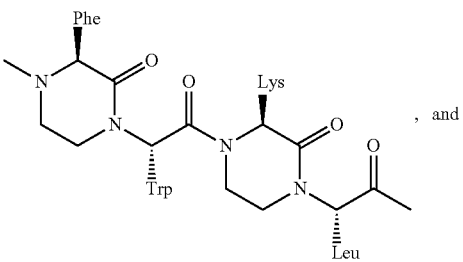

, and

-continued

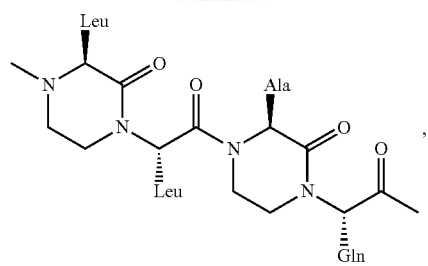

where X is H, COCH$_3$, or any amino acid, and Y is OH, NH$_2$, OMe, or any amino acid.

In another embodiment of the present invention, the oligooxopiperazine of Formula I has a formula of Formula IC:

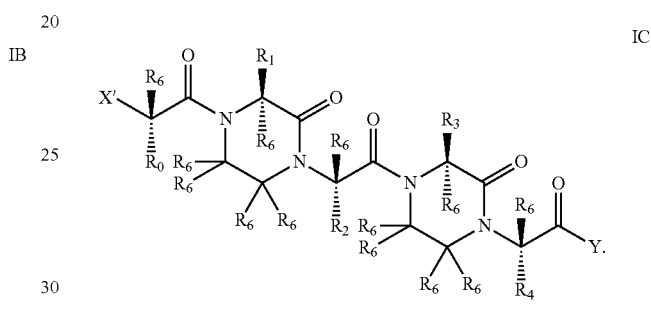

IC

Exemplary oligooxopiperazine compounds of Formula IC include, without limitation,

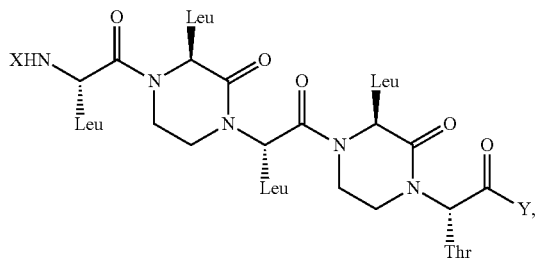

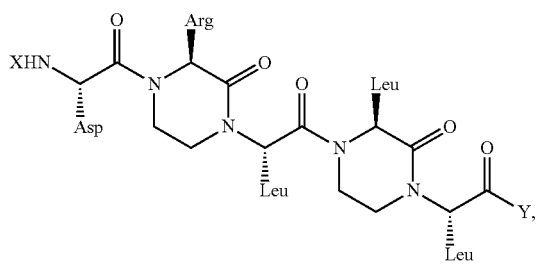

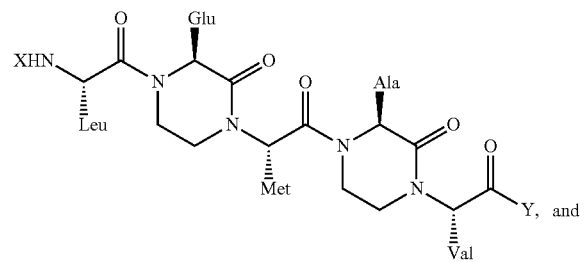

, and

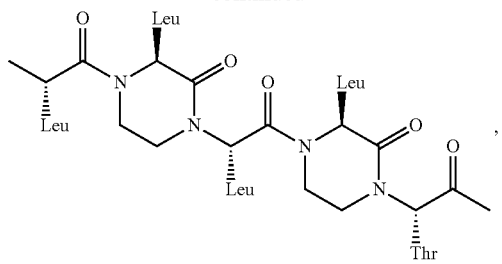

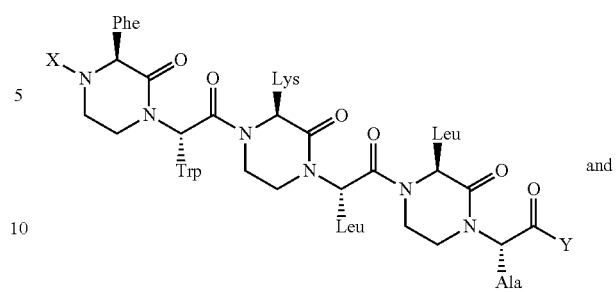

where X is H, COCH₃, or any amino acid, and Y is OH, NH₂, OMe, or any amino acid.

In a preferred embodiment of the present invention, the oligooxopiperazine of Formula I, including oligooxopiperazines of Formulas IA, IB, and IC, are designed to mimic an α-helix that is involved in a protein-protein interaction. α-Helices involved in modulating protein-protein interactions that are suitable for mimicking are shown in the table of FIGS. 11A1-11AA2. This table sets forth predicted targets by, inter alia, their RSC Protein Data Bank (an online database that includes proteins involved in protein-protein interactions; "PDB") code (column A), title (column D), function (column E), the chains in the protein-protein complex featuring a helix at the interface (column B), and the chain containing the candidate helix to be mimicked (column C). Also shown in the table of FIGS. 11A1-11AA2 are the number of hot spot residues in the helix (column J), the relative position of the hot spot residues within the chain (column K) and within the helix (column L), the length of the candidate helix to be mimicked (column N), the first (column O) and last (column P) residue of the helix to be mimicked, and the amino acid sequence of the helix to be mimicked (column Q). Additional α-helices suitable for mimicking are disclosed in Jochim et al., "Assessment of Helical Interfaces in Protein-Protein Interactions," *Mol. Biosyst.* 5(9):924-26 (2009), which is hereby incorporated by reference in its entirety, which describes the identification and classification of over 2,500 helical interface protein-protein interactions and the hot spot residues involved in these interactions.

Oligooxopiperazines of the present invention that are designed to mimic an α-helix of a protein, e.g., an α-helix involved in a protein-protein interaction, can be designed to mimic every side chain of the α-helix. Alternatively, if the hot spot residues of the α-helix are known, the oligooxopiperazine can be designed to mimic only the hot spot residues, in which case the remaining oligooxopiperazine side groups can be any side group that does not interfere with the oligooxopiperazine's function.

In accordance with this embodiment of the present invention, $R_1$, $R_2$, $R_4$, and $R_5$ of the oligooxopiperazine of Formula IA can mimic the amino acid side chain of, respectively, residues i, i+4, i+6, and i+7, of the α-helix. Suitable oligooxopiperazines of Formula IA that mimic an α-helix involved in a protein-protein interaction include, without limitation,

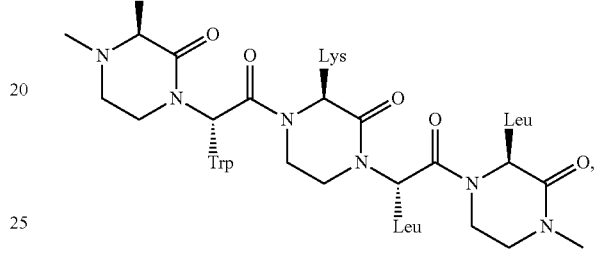

where X is H, COCH₃, or any amino acid, and Y is OH, NH₂, OMe, or any amino acid.

The oligooxopiperazine of Formula IB can also be designed to mimic an α-helix involved in a protein-protein interaction. In one embodiment, $R_1$, $R_2$, and $R_4$ of the oligooxopiperazine of Formula IB can mimic the amino acid side chain of, respectively, residues i, i+4, and i+7, of the α-helix. Such suitable oligooxopiperazines of Formula IB include, without limitation,

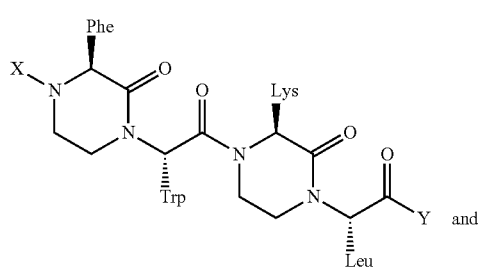

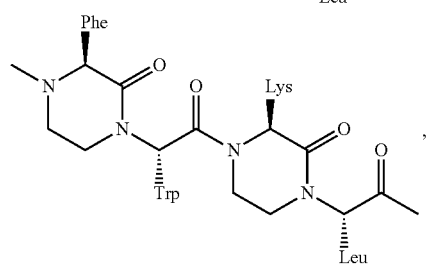

where X is H, COCH₃, or any amino acid, and Y is OH, NH₂, OMe, or any amino acid. Alternatively, $R_1$, $R_2$, and $R_4$ can mimic the amino acid side chain of, respectively, residues i, i+4, and i+6 of the α-helix. Such suitable oligooxopiperazines of Formula IB include, without limitation,

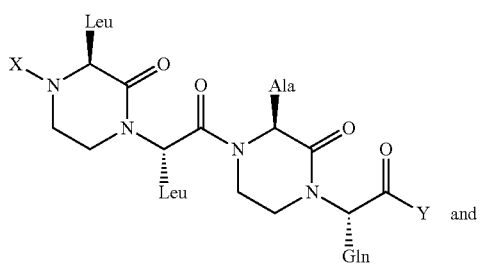

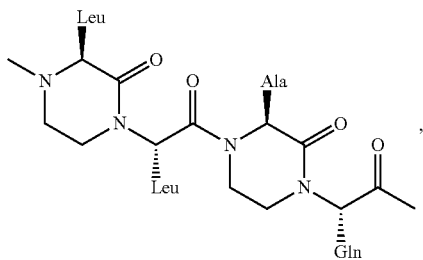

where X is H, COCH₃, or any amino acid, and Y is OH, NH₂, OMe, or any amino acid.

The oligooxopiperazine of Formula IC can also be designed to mimic an α-helix involved in protein-protein interactions. For example, $R_0$, $R_1$, $R_2$, $R_3$, and $R_4$ of Formula IC can mimic the amino acid side chain of, respectively, residues i, i+2, i+3, i+4, and i+7 of the α-helix. Suitable oligooxopiperazines of Formula IC that mimic an α-helix involved in a protein-protein interaction include, without limitation,

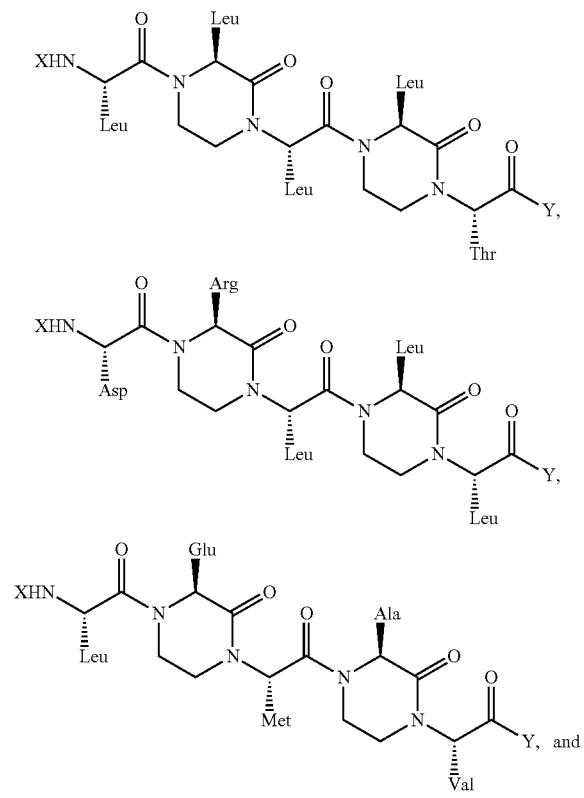

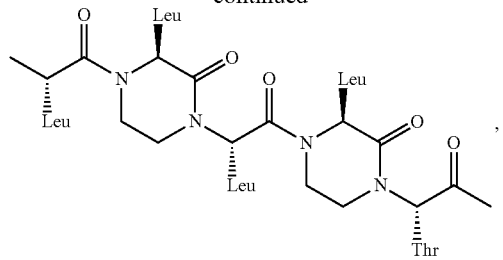

where X is H, COCH₃, or any amino acid, and Y is OH, NH₂, OMe, or any amino acid.

Another aspect of the present invention relates to pharmaceutical formulations comprising any of the above described oligooxopiperazines of Formula I, including the oligooxopiperazines of Formulas IA, IB, and IC of the present invention and a pharmaceutically acceptable carrier. Acceptable pharmaceutical carriers include solutions, suspensions, emulsions, excipients, powders, or stabilizers. The carrier should be suitable for the desired mode of delivery.

In addition, the pharmaceutical formulations of the present invention may further comprise one or more pharmaceutically acceptable diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

Another aspect of the present invention relates to a method of inhibiting activity of a protein that involves contacting the protein with an oligooxopiperazine of the present invention under conditions effective to inhibit activity of the protein. The oligooxopiperazine according to this aspect of the present invention is an oligooxopiperazine of Formula I (e.g, an oligooxopiperazine of Formula IA, IB, or IC), preferably designed to mimic an α-helix involved in a protein-protein interaction as described supra.

Another aspect of the present invention relates to a method of inhibiting a protein-protein interaction that involves contacting at least one of the proteins involved in the protein-protein interaction with an oligooxopiperazine under conditions effective to inhibit the protein-protein interaction. The oligooxopiperazine according to this aspect of the present invention is an oligooxopiperazine of Formula I (e.g, an oligooxopiperazine of Formula IA, IB, or IC), or, if the protein-protein interaction is mediated by a first hot spot residue and a second hot spot residue, an oligooxopiperazine Formula II:

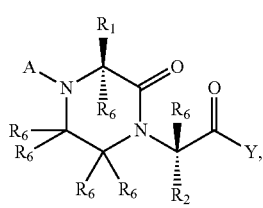

wherein:
$R_1$ and $R_2$ are independently an amino acid side chain, H, $N(R)_2$, OR, halogen, an alkyl, or an aryl; wherein each R is independently H, an alkyl, or an aryl;
each $R_6$ is independently H, $N(R)_2$, OR, halogen, an alkyl, or an aryl; wherein each R is independently H, an alkyl, or an aryl;
A is $X_1$ or C, wherein:
$X_1$ is H, COR', $CO_2R'$, CONR', an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and
C is a moiety of the formula

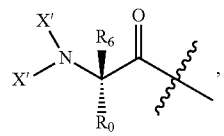

wherein:
each X' is independently H, COR', $CO_2R'$, CONR', $N(R'')_2$, an alkyl, an aryl, an arylalkyl, a cycloalkyl, a heteroaryl, a targeting moiety, or a tag; wherein:
R' is H, an alkyl, an aryl, an arylalkyl, a cycloalkyl, a heteroaryl, a targeting moiety, or a tag; and
each R'' is independently H, $CO_2R'$, CONR', an alkyl, an aryl, an arylalkyl, a cycloalkyl, a heteroaryl, a targeting moiety, or a tag;
$R_0$ is an amino acid side chain, H, $N(R)_2$, OR, halogen, an alkyl, or an aryl; wherein each R is independently H, an alkyl, or an aryl; and
$R_6$ is H, $N(R)_2$, OR, halogen, an alkyl, or an aryl; wherein each R is independently H, an alkyl, or an aryl; and
Y is OR', COR', $N(R''')_2$, an alkyl, an aryl, an arylalkyl, a cycloalkyl, a heteroaryl, a protecting group for protection of a carboxylic acid, a targeting moiety, or a tag; wherein:
R' is H, an alkyl, an aryl, an arylalkyl, a cycloalkyl, a heteroaryl, a targeting moiety, or a tag; and
each R''' is independently H, $CO_2R'$, CONR', an alkyl, an aryl, an arylalkyl, a cycloalkyl, a heteroaryl, a targeting moiety, or a tag.
Preferably, the oligooxopiperazine is designed to mimic an α-helix involved in the protein-protein interaction. Oligooxopiperazines of Formula I can be used to mimic α-helices containing 3-5 hot spot residues, such as the α-helices identified in FIGS. 11A1-11AA2. Oligooxopiperazines of Formula II can be used to mimic α-helices containing only 2 hot spot residues. For example, the first and second hot spot residues can be, respectively, residues i and i+4 of an alpha helix, and $R_1$ and $R_2$ of Formula II can mimic the amino acid side chain of, respectively, residues i and i+4 of the α-helix.

Another aspect of the present invention is directed to a method of treating a disorder in a subject, where the disorder is mediated by p53. This method involves administering to the subject a pharmaceutical composition containing an oligooxopiperazine that mimics the α-helix of p53 under conditions effective to treat the disorder. In accordance with this aspect of the invention, the oligooxopiperazine is preferably an oligooxopiperazine of Formula IA, where $R_1$, $R_2$, $R_4$, and $R_5$ mimic the amino acid side chain of, respectively, residues i, i+4, i+6, and i+7 of a p53 α-helix.

Figure 10A:
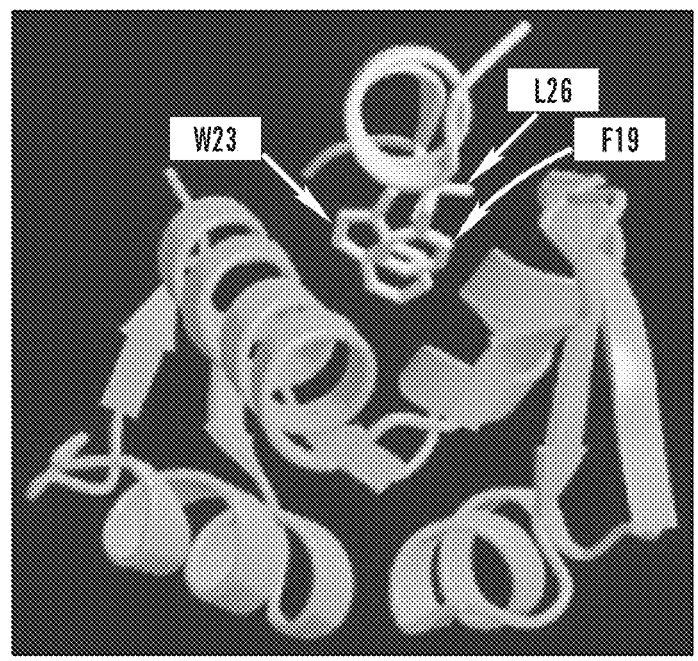
FIGS. 10A-10C show oligooxopiperazine 38 of the present invention designed to target the p53 transactivation domain, which adopts a helical conformation to target Mdm2. Three key hydrophobic residues of p53 (F19, W23, and L26) bind in the Mdm2 pocket as depicted in FIG. 10A.
Figure 10B:
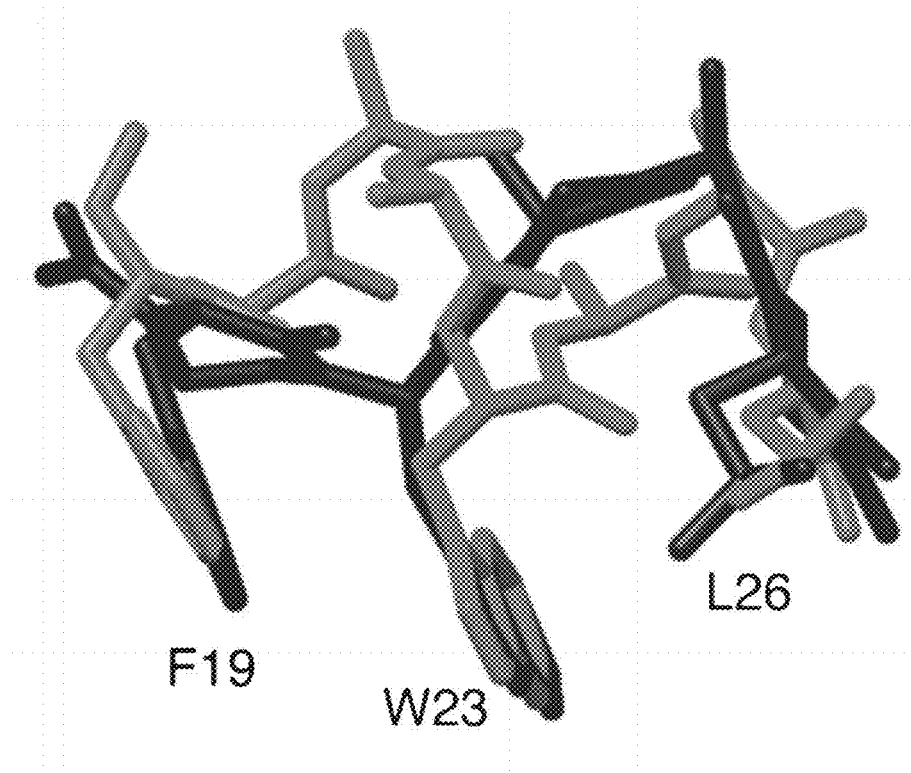
Figure 10C:
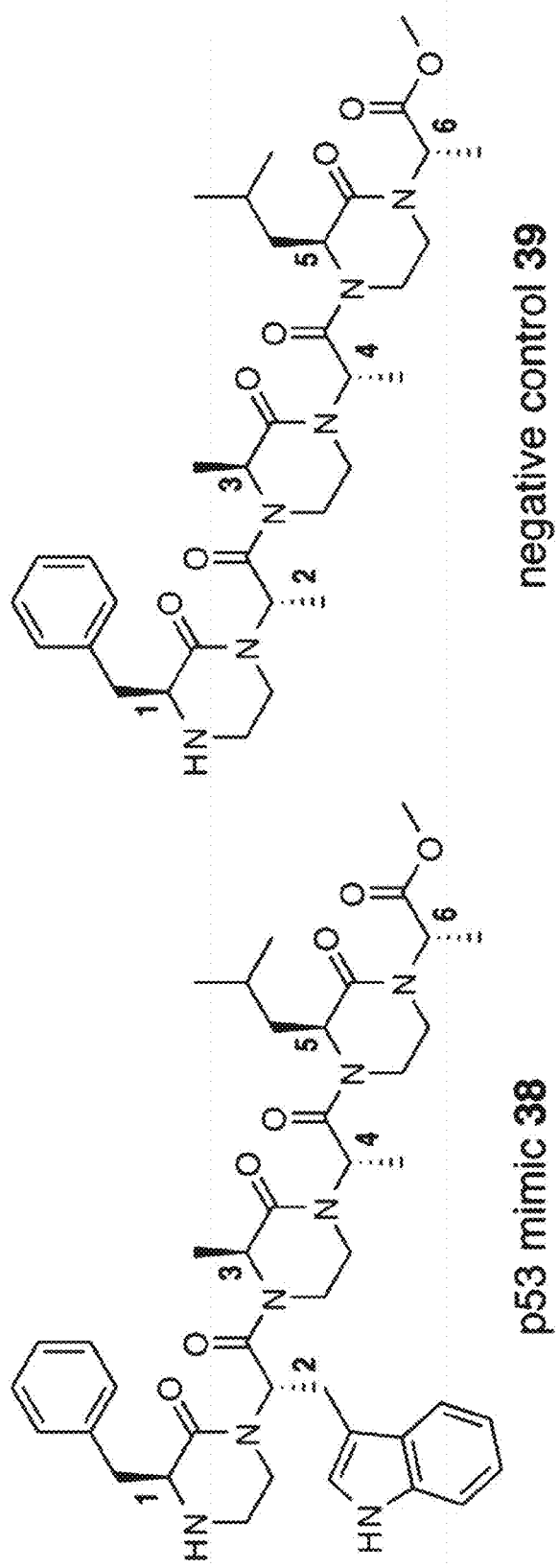

In accordance with this aspect of the invention, an oligooxopiperazine of Formula IA that is suitable for treating a disorder mediated by p53 in a subject is oligooxopiperazine 38 as described in the Examples herein and shown in FIG. 10C. Oligooxopiperazines mimicking an α-helix of p53 that disrupt p53 complex formation with, for example, Mdm2, would be suitable for treating cancer. Therapeutic inhibition of p53 is also suitable for the treatment of ischemia induced apoptosis, myocardial infarction, cholestasis, and a variety of neurodegenerative diseases including AID-associated neurodegeneration, stroke, Parkinson's disease, Alzheimer's disease, and Huntington's disease (see Amaral J., "The Role of p53 in Apoptosis," *Discov. Med.* 9(45):145-53 (2010), which is hereby incorporated by reference in its entirety).

Another aspect of the present invention is directed to methods of making oligooxopiperazines, including the oligooxopiperazines of Formulas IA, IB, and IC. The oligooxopiperazines can be synthesized via solution phase synthesis, or alternatively, via solid phase synthesis.

Accordingly, one aspect of the present invention is directed to a method of solid phase synthesis of the oligooxopiperazine of Formula IA. This method of synthesis involves providing a compound of Formula III:

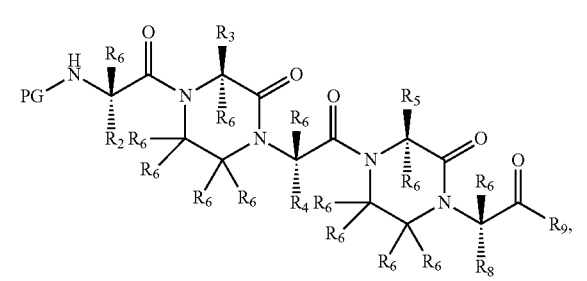

where PG is a protecting group for the protection of an amine; $R_8$ is an amino acid side chain, H, $N(R)_2$, OR, halogen, an alkyl, or an aryl, where each R is independently H, an alkyl, or an aryl; and $R_9$ is —O-Res or —NH-Res, where Res is a solid phase peptide synthesis resin. This method further involves providing a compound of Formula $IV_1$:

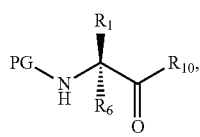

PG is a protecting group for the protection of an amine and where $R_{10}$ is —OH or a halide. The compound of Formula III is reacted with a first alkylating agent and the compound of Formula $IV_1$ under conditions effective to produce a compound of Formula V:

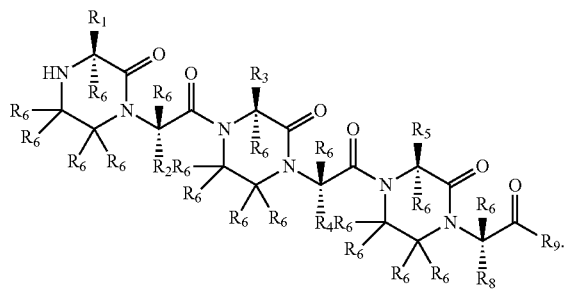

If necessary, —$CR_6R_8$—CO—$R_9$ in the compound of Formula V can be converted to E of Formula IA using standard methods known in the art. In addition, if necessary the N-terminal hydrogen in the compound of Formula V can be converted to $X_1$ of Formula IA. As will be appreciated by one of skill in the art, according to this and all aspects of the present invention that call for converting a first moiety to a second moiety, said converting can be carried out, for example, by chemically transforming the first moiety to the second moiety or by entirely replacing the first moiety with the second moiety.

This and other synthesis methods described herein include the use of individual amino acid residues. Typically, individual amino acid residues are obtained protected at the N-terminal and unprotected at the C-terminal. The C-terminal can then be protected using standard methods known in the art (see e.g., THEODORA W. GREENE & PETER G. M. WUTS, PROTECTIVE GROUPS IN ORGANIC SYNTHESIS 372-450 and 494-615 (1999), which is hereby incorporated by reference in its entirety). If desired, the N-terminal protecting group in the amino acid residue can be replaced with a different amino protecting group for use in these methods.

In accordance with this and subsequent solid phase synthesis embodiments of the invention, solid phase peptide synthesis resins suitable for use include, without limitation, polystyrene resins, polyamide resins, PEG hybrid polystyrene resins, and PEG-based resins as described in Fluka Chemie GmbH, "Resins for Solid-Phase Peptide Synthesis," *ChemFiles* 3(4):5-6 (2003), which is hereby incorporated by reference in its entirety.

In this and all synthesis methods described herein, suitable protecting groups for the protection of an amine include any of those described supra. Exemplary protecting groups include Boc, Cbz, Ns, and Fmoc. Likewise, in all synthesis methods described herein, suitable protecting groups for the protection of a carboxylic acid include any of those described supra.

In accordance with this and all aspects of the present invention, suitable halides include Br, Cl, and F. Preferably, the halide is Br.

In all the synthesis methods described herein involving the use of an alkylating agent, suitable alkylating agents include those selected from the group consisting of X—$CH_2$—CH=CH, X—$CH_2$—CH(OR$_{11}$)$_2$, X—$(CH_2)_2$—X and X—$(CH_2)_2$—OH wherein each X is independently a leaving group and each $R_{11}$ is independently an alkyl (e.g., halogens, OMs, or OTs). Suitable methods of using the above alkylating agents are depicted in FIGS. 1A-1H and are described infra. Where more than one alkylating step is called for, the alkylating agent for each step can be the same or different.

In accordance with the above method of making the oligooxopiperazine of Formula IA, the compound of Formula III can be provided by providing a compound of Formula VI:

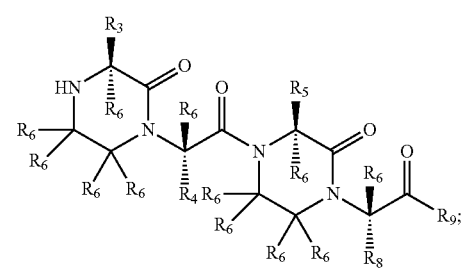

and a compound of Formula $IV_2$:

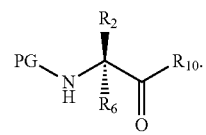

The compound of Formula VI is reacted with the compound of Formula $IV_2$ under conditions effective to produce a compound of Formula III using methods that will be apparent to one of ordinary skill in the art.

The compound of Formula VI above can be provided by providing a compound of Formula VII:

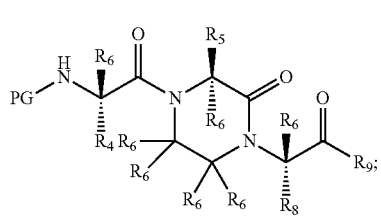

and a compound of Formula IV₃:

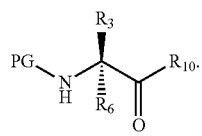

The compound of Formula VII is reacted with a second alkylating agent and the compound of Formula IV₃ under conditions effective to produce a compound of Formula VI using methods that will be apparent to one of ordinary skill in the art.

The compound of Formula VII above can be provided by providing and reacting a compound of Formula VIII:

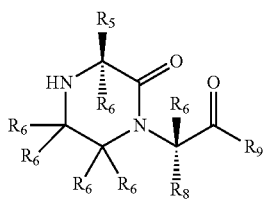

and a compound of Formula IV₄:

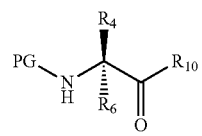

under conditions effective to produce a compound of Formula VII using methods that will be apparent to one of ordinary skill in the art.

The compound of Formula VIII above can be provided by providing a compound of Formula IX:

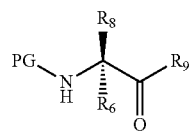

and a compound of Formula IV₅:

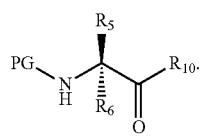

The compound of Formula IX is reacted with a third alkylating agent and the compound of Formula IV₅ under conditions effective to produce a compound of Formula VIII using methods that will be apparent to one of ordinary skill in the art.

Another aspect of the present invention is directed to the solid phase synthesis of the oligooxopiperazines of Formula IB and IC. This method of synthesis involves providing a compound of Formula VII':

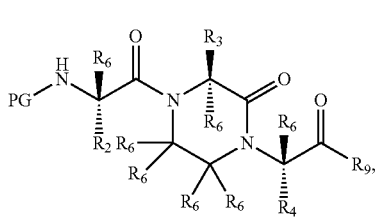

where PG is a protecting group for the protection of an amine, and R₉ is —O-Res or —NH-Res. The method further involves providing a compound of Formula IV₁:

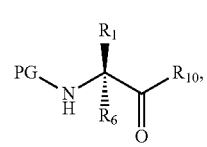

where PG is a protecting group for the protection of an amine and R₁₀ is —OH or a halide. The compound of Formula VII' is reacted with a first alkylating agent and the compound of Formula IV₁ under conditions effective to produce a compound of Formula VI':

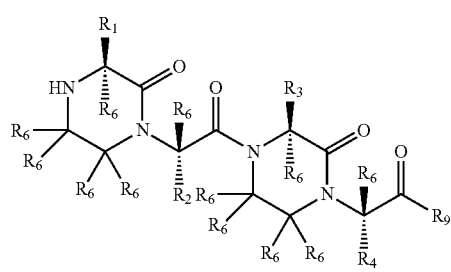

using methods that will be apparent to one of ordinary skill in the art.

If necessary, —R₉ of Formula VI' can be converted to Y using standard methods known in the art. Further, when synthesizing an oligooxopiperazine of Formula 1B, if necessary, the N-terminal hydrogen in the compound of Formula VI' can be converted to X₁ using standard methods known in the art; when synthesizing an oligooxopiperazine of Formula IC, the N-terminal hydrogen in the compound of Formula VI' can be converted to a moiety of formula

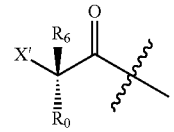

using standard methods.

In accordance with the above method of making the oligooxopiperazines of Formulas IB and IC, the compound of Formula VII' can be provided by providing a compound of Formula VIII':

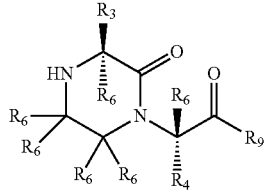

VIII' and providing a compound of Formula IV$_2$:

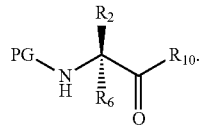

IV$_2$

The compound of Formula VIII' is reacted with the compound of Formula IV$_2$ under conditions effective to produce a compound of Formula VII' using methods that will be apparent to one of ordinary skill in the art.

A compound of Formula VIII' can be provided by providing a compound of Formula IX':

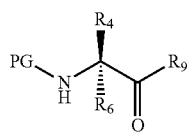

IX' and providing a compound of Formula IV$_3$:

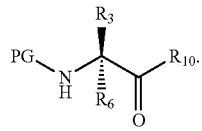

IV$_3$

The compound of Formula IX' is reacted with a second alkylating agent and the compound of Formula IV$_3$ under conditions effective to produce a compound of Formula VIII' using methods that will be apparent to one of ordinary skill in the art.

Another aspect of the present invention is directed to a method of solution phase synthesis of the oligooxopiperazines of Formula IA. This method of synthesis involves providing a compound of Formula X:

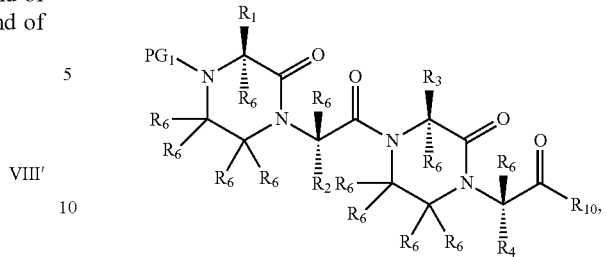

X where PG$_1$ is a protecting group for the protection of an amine and R$_{10}$ is —OH or a halide, and providing a compound of Formula XI$_{5/8}$:

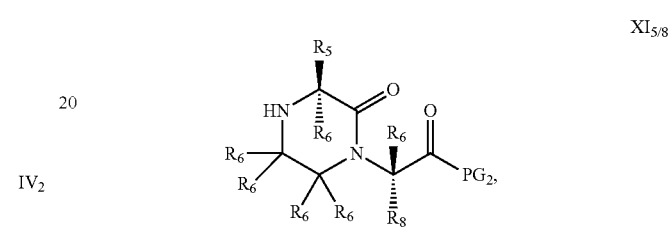

XI$_{5/8}$ where PG$_2$ is a protecting group for the protection of a carboxylic acid; and R$_8$ is an amino acid side chain, H, N(R)$_2$, OR, halogen, an alkyl, or an aryl, where each R is independently H, an alkyl, or an aryl. The compound of Formula X is reacted with the compound of Formula XI$_{5/8}$ under conditions effective to produce a compound of Formula XII:

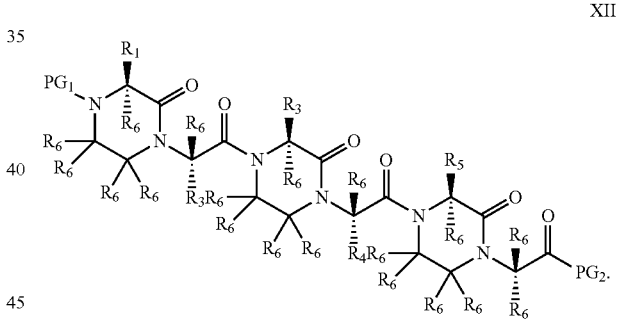

XII

If necessary, —CR$_6$R$_8$—CO—PG$_2$ in the compound of Formula XII can be converted to E of Formula IA using standard methods known in the art. Additionally, if necessary PG$_1$ in the compound of Formula XII can be converted to X$_1$ of Formula IA using standard methods known in the art.

The compound of Formula X above can be provided by providing a compound of Formula X':

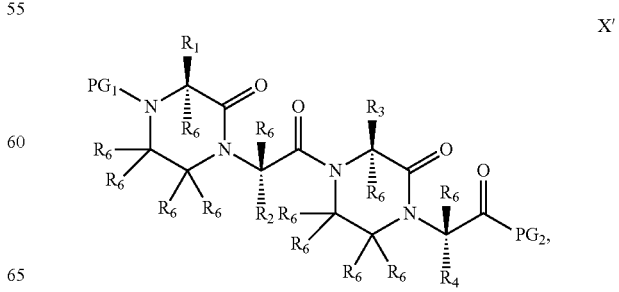

X' and converting PG$_1$ of Formula X' to hydrogen and converting PG$_2$ of Formula X' to R$_{10}$. Methods for removing protecting groups are well known in the art (see e.g., THEODORA W. GREENE & PETER G. M. WUTS, PROTECTIVE GROUPS IN ORGANIC SYNTHESIS 372-450 and 494-615 (1999), which is hereby incorporated by reference in its entirety).

The compound of Formula X' above can be provided by providing a compound of Formula XIII:

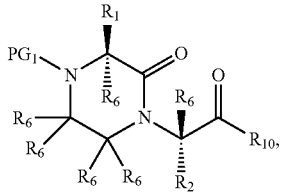

XIII and providing a compound of Formula XI$_{3/4}$:

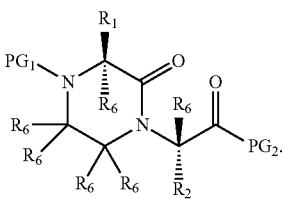

XI$_{3/4}$

The compound of Formula XIII is reacted with the compound of Formula XI$_{3/4}$ under conditions effective to produce a compound of Formula X' using methods that will be apparent to one of ordinary skill in the art.

The compound of Formula XIII above can be provided by providing a compound of Formula XI$_{1/2}$:

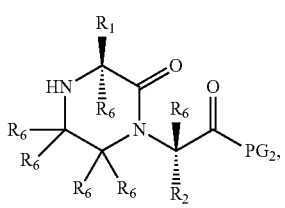

XI$_{1/2}$ and reacting it with a protecting group under conditions effective to produce a compound of Formula XIII using methods that will be apparent to one of ordinary skill in the art. Suitable methods for adding protecting groups are well known in the art (see e.g., THEODORA W. GREENE & PETER G. M. WUTS, PROTECTIVE GROUPS IN ORGANIC SYNTHESIS 372-450 and 494-615 (1999), which is hereby incorporated by reference in its entirety).

The compound of Formula XI$_{1/2}$ can be provided by providing a compound of Formula XIV:

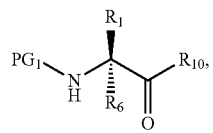

XIV and providing a compound of Formula XV:

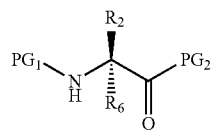

XV

The compound of Formula XIV is reacted with an alkylating agent and the compound of Formula XV under conditions effective to produce a compound of Formula XI$_{1/2}$.

Another aspect of the present invention is directed to the solution phase synthesis of the oligooxopiperazines of Formula IB and IC. This method of synthesis involves providing a compound of Formula XIII:

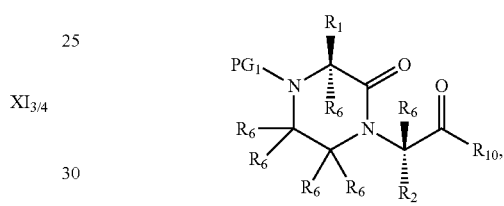

XIII where PG$_1$ is a protecting group for the protection of an amine and R$_{10}$ is —OH or a halide. Suitable methods of making the compound of Formula XIII are described supra. A compound of Formula XI$_{3/4}$:

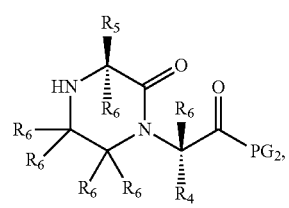

XI$_{3/4}$ where PG$_2$ is a protecting group for the protection of a carboxylic acid, is also provided. The compound of Formula XIII is reacted with the compound of Formula XI$_{3/4}$ under conditions effective to produce a compound of Formula X':

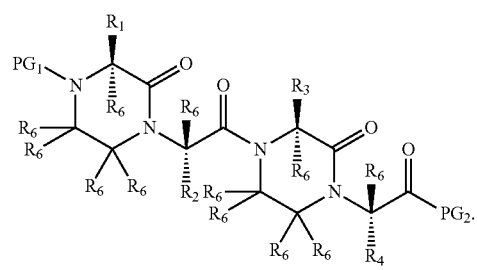

X'

If necessary, PG$_2$ in the compound of Formula X' can be converted to Y using standard methods known in the art.

Further, when synthesizing the oligooxopiperazine of Formula IB, if necessary, PG$_1$ in the compound of Formula X' can be converted to X$_1$ using standard methods; when synthesizing the oligooxopiperazine of Formula IC, PG$_1$ in the compound of Formula X' can be converted to a moiety of formula

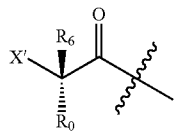

using standard methods.

The above described solid phase and solution phase methods of oligooxopiperazine synthesis sometimes call for reacting compounds with an alkylating agent. The alkylating agent is used to facilitate coupling and cyclization of the oligooxopiperazine. Suitable methods of coupling and cyclization using the exemplary alkylating agents disclosed herein include the methods shown in FIGS. 1A-1H.

In particular, FIGS. 1A-1B depict coupling and cyclization using X—CH$_2$—CH=CH as the alkylating agent (alkylating agent A) in solid phase (Sd; left) and solution phase (Sn; right) methods of synthesis. Step A involves the alkylation of the amino acid residue ($1_{ASd}$ or $1_{ASn}$). PG$_3$, which is a protecting group for the protection of an amine, allows the alkylating agent to react with the hydrogen on the amine. Ns is a preferred protecting group for this purpose. PG$_3$ can then be replaced with hydrogen to facilitate coupling with another residue. Typically, a mild base is used during alkylation to facilitate hydrogen removal. Suitable bases include triethylamine, N,N-diisopropylethylamine, 1,8-Diazabicyclo[5.4.0]undec-7-ene (DBU), 2,4,6-trimethylpyridine, potassium carbonate, and cesium carbonate.

Step B involves the coupling of a second amino acid residue ($2_{ASd}$ or $2_{ASn}$) to the alkylated amino acid residue ($1'_{ASd}$ or $1'_{ASn}$). In Step C, the coupled amino acid residues ($3_{ASd}$ or $3_{ASn}$) are cyclized upon the simultaneous or sequential addition of an oxidizing agent, an acid, and a hydride donor. The oxidizing agent, preferably ozone, converts the allyl to an aldehyde. The acid is one that removes the protecting group to provide for cyclization with the aldehyde. Suitable acids include TFA, HCl, HBr, HCOOH, and CH$_3$COOH. The hydride donor ensures that the cyclization reaction takes place in excess hydrogen so the resulting ring is saturated. Suitable hydride donors include triethylsilane and NaBH$_3$CN.

Figure 1D:
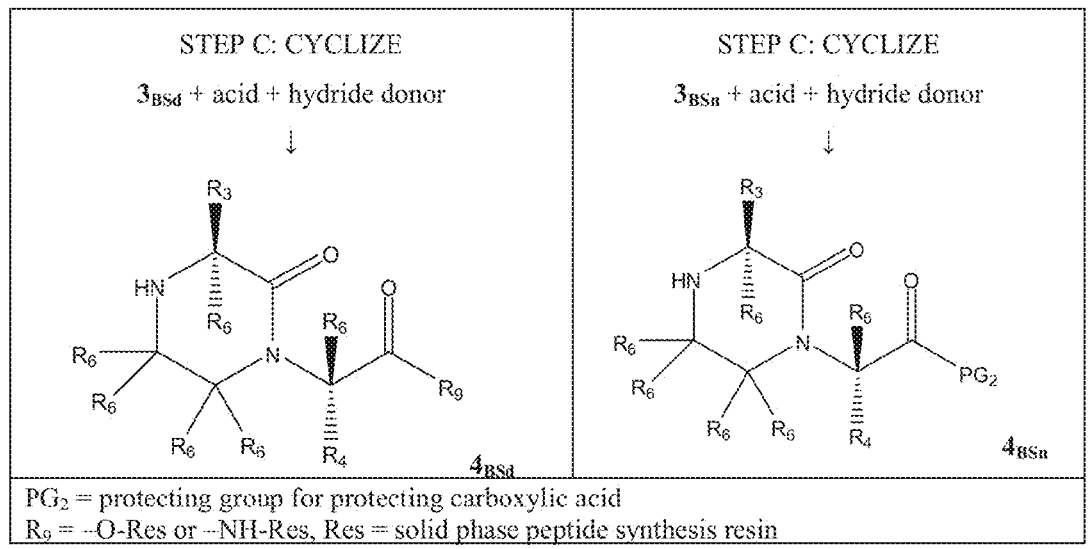
Figure 1E:
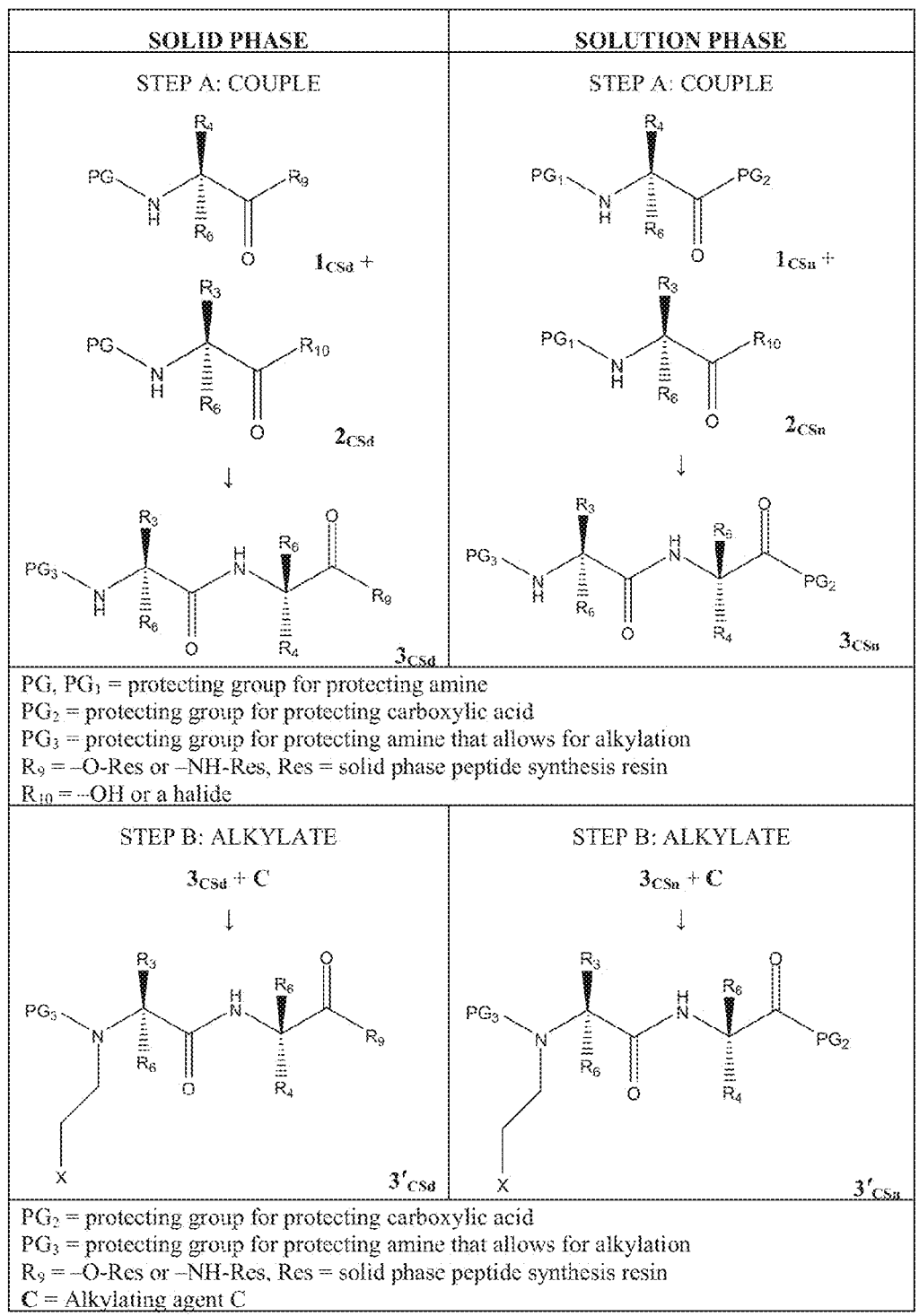
Figure 1F:
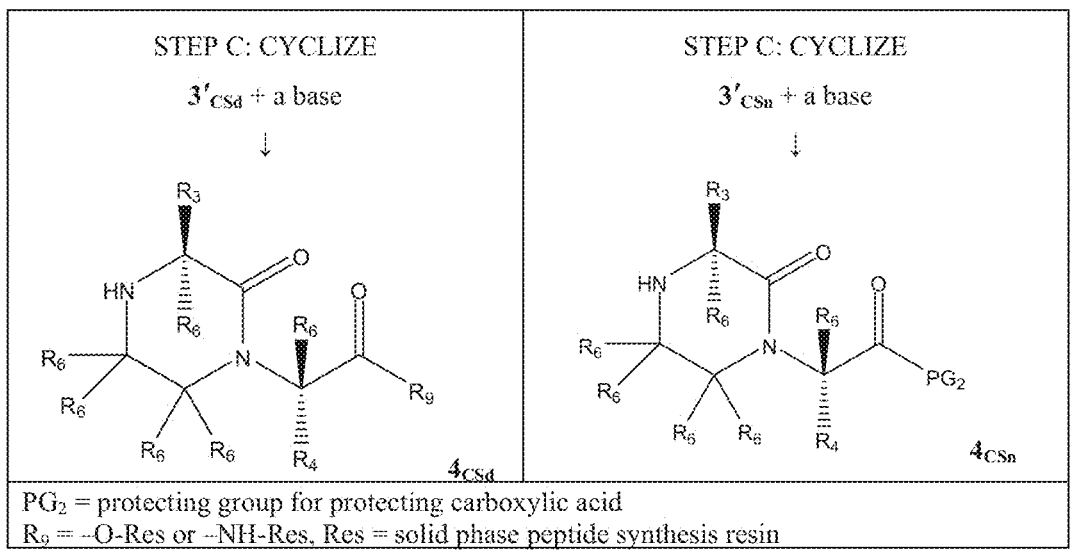
Figure 1H:
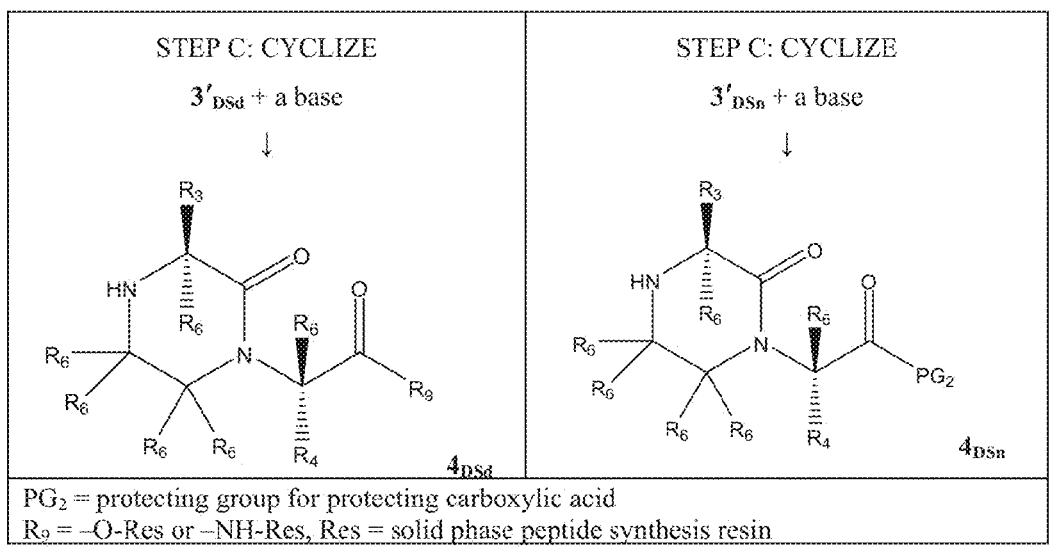

FIGS. 1C-1D depict coupling and cyclization using X—CH$_2$—CH(OR$_{11}$)$_2$ as the alkylating agent (alkylating agent B) in solid phase (Sd; left) and solution phase (Sn; right) methods of synthesis. These steps are similar to the steps of coupling and cyclization using alkylating agent A described above. Step A involves the alkylation of the amino acid residue ($1_{BSd}$ or $1_{BSn}$). As in FIGS. 1A-1B, PG$_3$, which is a protecting group for the protection of an amine, allows the alkylating agent to react with the hydrogen on the amine. Ns is a preferred protecting group for this purpose. PG$_3$ can then be replaced with hydrogen to facilitate coupling with another residue. Typically, a mild base is used during alkylation to facilitate hydrogen removal. Suitable bases include those described supra.

Step B in FIG. 1C involves the coupling of a second amino acid residue ($2_{BSd}$ or $2_{BSn}$) to the alkylated amino acid residue ($1'_{BSd}$ or $1'_{BSn}$). In step C, the coupled amino acid residues ($3_{BSd}$ or $3_{BSn}$) are cyclized upon the simultaneous or sequential addition of an acid and a hydride donor. The acid is one that removes the protecting group to provide for cyclization with the aldehyde. Suitable acids include TFA, HCl, HBr, HCOOH, and CH$_3$COOH. The hydride donor ensures that the cyclization reaction takes place in excess hydrogen so the resulting ring is saturated. Suitable hydride donors include triethylsilane and NaBH$_3$CN.

FIGS. 1E-1F and 1G-1H depict coupling and cyclization using X—(CH$_2$)$_2$—X) (alkylating agent C) or X—(CH$_2$)$_2$—OH (alkylating agent D), respectively, in solid phase (Sd; left) and solution phase (Sn; right) methods of synthesis. Using either agent C or D, step A involves the coupling of two amino acid residues ($1_{CSd/CSn}+2_{CSd/CSn}\rightarrow 3_{CSd/CSn}$; $1_{DSd/DSn}+2_{DSd/DSn}\rightarrow 3_{DSd/DS}$). Similar to the previous methods, PG$_3$ allows the alkylating agent to react with the hydrogen on the amine during alkylation. Ns is preferred. PG$_3$ can be present as PG in compound $2_{CSd}$ or PG$_1$ in compound $2_{CSn}$, or can be added after coupling.

Step B involves the alkylation of one of the coupled amino acid residues ($3_{CSd/CSn}$ or $3_{DSd/DSn}$). Typically, a mild base is used during alkylation to facilitate hydrogen removal. Suitable bases include triethylamine, N,N-diisopropylethylamine, 1,8-Diazabicyclo[5.4.0]undec-7-ene (DBU), 2,4,6-trimethylpyridine, potassium carbonate, and cesium carbonate. In Step C, the alkylated coupled amino acid residues ($3'_{CSd/CSn}$ or $3'_{DSd/DSn}$) are cyclized upon the addition of a base. Suitable bases include triethylamine, N,N-diisopropylethylamine, 1,8-Diazabicyclo[5.4.0]undec-7-ene (DBU), 2,4,6-trimethylpyridine, potassium carbonate, and cesium carbonate.

The present invention may be further illustrated by reference to the following examples.

EXAMPLES

Example 1

Materials and Reagents

Commercial-grade reagents and solvents were used without further purification except as indicated. All reactions were stirred magnetically; moisture-sensitive reactions were performed under nitrogen in flame-dried glassware. Unless indicated, all reactions were performed at 25° C. Thin-layer chromatography (TLC), using ethyl acetate: hexane, diethyl ether: ethyl acetate, diethyl ether: hexane, DCM: methanol as solvent systems, was used to monitor reactions. Visualization was accomplished by either ultraviolet light or immersing the plate in 1% aqueous solution of potassium permanganate followed by heating. Flash chromatography with silica gel was performed following the conditions described by Still et al., *J. Org. Chem.* 43, 2923-2925 (1978), which is hereby incorporated by reference in its entirety. Solvents were removed by rotary evaporation under reduced pressure. Where appropriate, the residue was further dried using vacuum. One-dimensional Proton (400 MHz) and carbon (100 MHz) NMR spectra were obtained on a Bruker AV-400 spectrometer. Two-dimensional $^1$H NMR spectra were obtained on a Bruker AV-600 (600 MHz) spectrometer. Proton chemical shifts are reported as values relative to tetramethylsilane (0.00 ppm) or the particular solvent used in the experiment. Carbon chemical shifts are reported as values relative to the solvent used in the experiment (CDCl$_3$; 77.0 ppm). Data is reported as follows: chemical shift, multiplicity (s=singlet, d=doublet, t=triplet, q=quartet, m=multiplet, dd=doublet of doublet, ddt=doublet of doublet of triplet, and br=broad), coupling constant, and integration. The following abbreviations are used in the examples described infra: DCM=dichloromethane, THF=tetrahydrofuran, DIPEA=N, Ndiisopropylethylamine, TEA=triethylamine, TFA=trifluoroacetic acid, HOBt=hydroxybenzotriazole, DCC=N,N'-dicyclohexylcarbodiimide.

Example 2

Synthesis of Oligooxopiperazine 1a

A schematic of oligooxopiperazine 1a synthesis via the reductive amination route (Tong et al., *J. Org. Chem.* 65:2484-2493 (2000), which is hereby incorporated by reference in its entirety), is shown in Scheme 1 below.

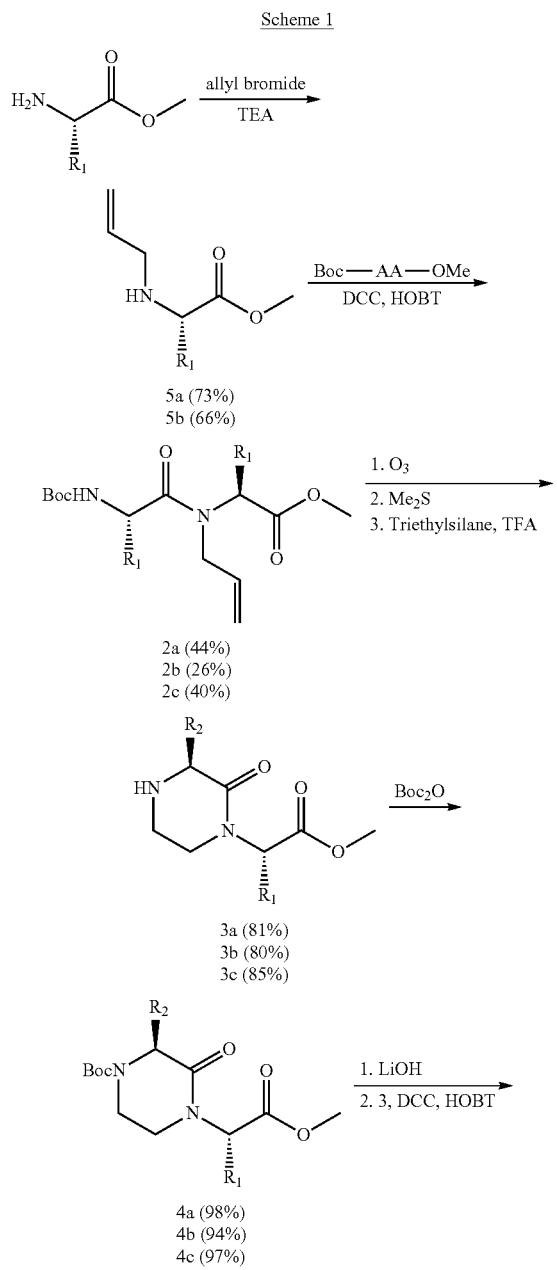

1a (73%)
1b (70%)
1c (71%)

a: $R_1$ = $CH_2CH(CH_3)_2$, $R_2$ = $CH_3$
   $R_1'$ = $CH_2Ph$, $R_2'$ = $(CH_2)_4NHCbz$
b: $R_1$ = $CH_2Ph$, $R_2$ = $(CH_2)_4NHCbz$
   $R_1'$ = $CH_2CH(CH_3)_2$, $R_2'$ = $CH_3$
c: $R_1$ = $R_2$ = $R_1'$ = $R_2'$ = $CH_2CH(CH_3)_2$

The synthesis of (S)—N-Allyl-Leu-OMe (5a) was carried out as follows. Allyl bromide (137.0 mmol, 11.6 mL) was added to a solution of H-Leu-OMe (55.0 mmol, 10.0 g), DMF (120 mL) and TEA (192.0 mmol, 26.5 mL) at 0° C. The resulting mixture was warmed to 25° C. and stirred for 48 h. The reaction mixture was diluted with water (250 mL) and extracted with diethyl ether (3×, 250 mL). The combined organic layers were washed with saturated aqueous sodium bicarbonate and saturated brine, dried with $MgSO_4$ and concentrated under vacuum. The residue was purified by column chromatography (15% ethyl acetate in hexane) to afford compound 5a as a light yellow oil (7.4 g, 73%). $^1$H NMR (400 MHz, $CDCl_3$) 5.88 (ddt, J=17.1, 10.2, 6.1 Hz, 1H), 5.19 (dd, J=17.1, 1.5 Hz, 1H), 5.09 (dd, J=10.2, 1.5 Hz, 1H), 3.65 (s, 3H), 3.25 (t, J=7.4 Hz, 1H), 3.15 (ddt, J=6.2, 1.4 Hz, 1H), 2.96 (ddt, J=6.2, 1.4 Hz, 1H), 1.72 (m, 1H), 1.42 (t, J=6.7 Hz, 2H), 0.88 (d, J=6.6 Hz, 3H), 0.78 (d, J=6.7 Hz, 3H); $^{13}$C NMR (100 MHz, $CDCl_3$) 176.4, 136.3, 116.4, 59.0, 51.5, 50.7, 42.8, 24.9, 22.6, 22.3; HRMS m/z for $C_{10}H_{19}NO_2[M+H]^+$, calcd 186.1494. found 186.1486.

The synthesis of Boc-Ala-N(allyl)-Leu-OMe (2a) was carried out as follows. A solution of Boc-Ala-OH (80.0 mmol, 15.1 g), HOBt (80.0 mmol, 10.8 g) and DCC (80.0 mmol, 16.5 g) in DMF (200 mL) was stirred at 25° C. After 15 min, a solution of 5a (40.0 mmol, 7.4 g) in DMF (5 mL) was added, and the resulting mixture heated at reflux overnight. The reaction mixture was cooled to 25° C., diluted with 400 mL of water and extracted with diethyl ether (250 mL, 3×). The combined organic layers were sequentially washed with 1M NaOH (250 mL, 3×), water (250 mL, 3×), 1M HCl (250 mL, 3×), and saturated brine (250 mL), dried with anhydrous $MgSO_4$ and concentrated under vacuum. The residue was purified by column chromatography using 20% ethyl acetate in hexane. The purified product yielded compound 2a as a yellow oil (6.2 g, 44%). $^1$H NMR (400 MHz, $CDCl_3$) 5.90-5.80 (m, 1H), 5.25-5.15 (m, 2H), 5.04 (q, J=5.2 Hz, 1H), 4.55 (t, J=7.3 Hz, 1H), 3.94 (d, J=5.3 Hz, 2H), 3.62 (s, 3H), 1.73-1.60 (m, 2H), 1.60-1.50 (m, 1H), 1.45 (s, 9H), 1.21 (d, J=6.8 Hz, 3H), 0.84 (d, J=7.9 Hz, 3H), 0.78 (d, J=6.7 Hz, 3H); $^{13}$C NMR (100 MHz, $CDCl_3$) 174.4, 172.2, 155.1, 134.2, 117.7, 79.6, 55.5, 52.1, 48.4, 46.7, 37.7, 28.3, 24.7, 22.9, 21.8, 19.0; HRMS m/z for $C_{18}H_{32}N_2O_5$ $[M+Na]^+$, calcd 379.2209. found 379.2210.

The synthesis of (AlaLeu)Oxopiperazine methyl ester (3a) was carried out as follows. Ozone was bubbled into a solution of 2a (17.4 mmol, 6.21 g) in anhydrous methanol (200 mL) at −78° C. and ambient pressure. The reaction mixture turned light blue after 2 h. After an additional 30 min, nitrogen was bubbled into the solution until the blue color disappeared. Dimethyl sulfide (61.0 mmol, 4.5 g) was added and the mixture was stirred at room temperature. After 16 h, the mixture was concentrated under vacuum, and the residue (6.2 g) was dissolved in DCM (125 mL), and triethylsilane (34.6 mmol, 5.5 mL) and TFA (260.0 mmol, 19.3 mL) was added. The reaction mixture was stirred for 24 h at 25° C. and then concentrated under vacuum. The residue was redissolved in DCM (60 mL) and TEA (60 mL) at 0° C. and stirred at 25° C. After one hour, the solvent was concentrated under vacuum. The residue was dissolved in DCM and the organic layer was washed with saturated aqueous sodium bicarbonate. The aqueous layer was washed 3× with DCM. The residue was purified by column chromatography (95% diethyl ether 5% methanol and 0.1% TEA) to obtain compound 3a as a colorless oil (2.6 g, 81%). $^1$H NMR (400 MHz, CDCl$_3$) 5.20 (t, J=8.2 Hz, 1H), 3.68 (s, 3H), 3.53 (q, J=6.8 Hz, 1H), 3.28-3.20 (m, 2H), 3.10-3.02 (m, 2H), 1.63 (t, J=7.5 Hz, 2H), 1.52-1.46 (septet, J=7.8 Hz, 1H), 1.32 (d, J=6.9 Hz, 3H), 0.88 (d, J=6.7 Hz, 3H), 0.78 (d, J=6.5 Hz, 3H); $^{13}$C NMR (100 MHz, CDCl$_3$) 172.3, 171.4, 55.4, 53.8, 52.2, 44.9, 42.2, 36.7, 24.9, 23.2, 21.3, 18.99; HRMS m/z for C$_{12}$H$_{22}$N$_2$O$_3$[M+Na]$^+$, calcd 265.1528. found 265.1523.

The synthesis of Boc-(AlaLeu)oxopiperazine-methyl ester (4a) was carried out as follows. To a solution of 3a (6.6 mmol, 1.6 g) in DCM (22 mL) at 0° C. was added 4-methylmorpholine (10.0 mmol, 1.1 mL) and ditert-butyl dicarbonate (16.6 mmol, 3.6 g) in 50 mL of DCM. The mixture was allowed to warm to 25° C. and then heated at reflux. After 6 h, the mixture was concentrated and the residue purified by column chromatography (40% hexane in diethyl ether) to yield 2.2 g (98%) of compound 4a as a colorless oil. $^1$H NMR (400 MHz, CDCl$_3$) 5.21 (q, J=5.72 Hz, 1H), 4.51 (br, 1H), 3.89 (br, 1H), 3.64 (s, 3H), 3.46-3.35 (m, 1H), 3.26 (br, 1H), 3.16-3.11 (m, 1H), 1.73-1.60 (m, 2H), 1.45 (br, 1H), 0.41 (s, 9H), 1.3 (d, J=6.9 Hz, 3H), 0.88 (d, J=6.7 Hz, 3H), 0.78 (d, J=6.8 Hz, 3H); $^{13}$C NMR (100 MHz, CDCl$_3$) 172.2, 168.0, 151.3, 78.3, 52.1, 40.3, 34.2, 25.8, 22.5, 20.6, 18.8, 15.5; HRMS m/z for C$_{17}$H$_{30}$N$_2$O$_5$ [M+Na]$^+$, calcd 365.2052. found 365.2049.

The synthesis of oxopiperazine dimer (1a) was carried out as follows. To solution of 4a (6.5 mmol, 2.2 g) in THF/MeOH/H$_2$O (12:4:1, total volume of 120 mL) at 0° C. was added lithium hydroxide monohydrate (16.3 mmol, 0.7 g). The mixture was stirred for 2 h at 0° C. and then acidified to pH 3 with saturated sodium bisulfate. The mixture was concentrated and the residue was dissolved in ethyl acetate and washed with brine (2:1). The aqueous layer was extracted 3× with ethyl acetate, the combined organic layers were dried with anhydrous sodium sulfate, and concentrated under vacuum to yield 2.2 g of product. The residue was used in the next step without further purification.

A portion of the residue from above (1.3 mmol, 0.40 g), HOBt (2.6 mmol, 0.40 g) and DCC (1.3 mmol, 0.30 g) were dissolved in 50 mL of DMF. The reaction mixture was stirred for 15 min at room temperature followed by the addition of 3b (0.6 mmol, 0.3 g) in DMF (5 mL). The reaction mixture was heated at 55° C. for 48 h. Then, the reaction mixture was cooled to 25° C. and diluted with 100 mL of water and extracted with diethyl ether (100 mL, 3×). The combined organic layers were washed sequentially with 1M NaOH (50 mL, 3×), water (50 mL), 1M HCl (50 mL, 3×), and brine (50 mL). The solution was dried with anhydrous MgSO$_4$ and concentrated under vacuum. The residue was purified by column chromatography with 20% ethyl acetate in hexane to yield compound 1a as a yellow oil (0.2 g, 73%). $^1$H NMR (400 MHz, CDCl$_3$) 7.29-7.08 (m, 10H), 5.31 (t, J=7.2 Hz, 1H), 5.25-5.15 (m, 1H), 5.03 (s, 2H), 4.65 (t, J=7.0 Hz, 1H), 4.46 (br, 1H), 3.77-3.72 (m, 2H), 3.69 (s, 3H), 3.38-3.33 (m, 2H), 3.31-3.15 (m, 4.5H), 3.15-2.92 (m, 3.5H), 1.50 (t, J=7.1 Hz, 2H), 1.38 (s, 9H), 1.34 (d, J=7.0 Hz, 3H), 1.34-1.15 (m, 5H), 1.02-0.93 (m, 2H), 0.87 (d, J=6.6 Hz, 3H), 0.83 (d, J=6.6 Hz, 3H); $^{13}$C NMR (100 MHz, CDCl$_3$) 168.0, 167.2, 166.1, 166.0, 153.9, 151.1, 134.2, 133.6, 126.3, 126.2, 126.0, 125.6, 124.6, 113.4, 76.4, 64.1, 54.9, 53.3, 50.8, 50.0, 47.2, 41.1, 39.0, 38.3, 38.2, 35.3, 34.9, 32.0, 29.2, 25.8, 22.3, 20.4, 20.2, 19.8, 15.6; HRMS m/z for C$_{42}$H$_{59}$N$_5$O$_9$ [M+Na]$^+$, calcd 800.4210. found 800.4248.

Example 3

Synthesis of Oligooxopiperazine 1b

The synthesis of oligooxopiperazine dimer 1b of the present invention is illustrated in Scheme 1 above.

The synthesis of (S)—N-allyl-Phe-OMe (5b) was carried out as follows. Allyl bromide (140.0 mmol, 9.8 mL) was added to a solution of H-Phe-OMe (46.0 mmol, 10.0 g), DMF (130 mL) and TEA (164.0 mmol, 22.6 mL) at 0° C., and the reaction mixture was warmed to 25° C. After 48 h, the reaction mixture was diluted with 250 mL of water and extracted with diethyl ether (200 mL, 3×). The combined organic layers were washed with saturated aqueous sodium bicarbonate and saturated brine, dried with MgSO$_4$ and concentrated under vacuum. The residue was purified with column chromatography (15% ethyl acetate in hexane) to afford compound 5b as a light yellow oil 6.7 g (66%). $^1$H NMR (400 MHz, CDCl$_3$) 7.32-7.16 (m, 5H), 5.83 (ddt, J=17.1, 10.2, 6.1 Hz, 1H), 5.14 (dd, J=17.1, 1.5 Hz, 1H), 5.09 (dd, J=10.2, 1.5 Hz, 1H), 3.64 (s, 3H), 3.56 (t, J=6.8 Hz, 1H), 3.26 (ddt, J=6.8, 1.4 Hz, 1H), 3.15 (ddt, J=6.8, 1.4 Hz, 1H), 2.96 (d, J=6.9 Hz, 2H), 1.59 (br, 1H); $^{13}$C NMR (100 MHz, CDCl$_3$) 175.0, 137.2, 136.0, 129.2, 128.4, 126.8, 116.5, 62.0, 51.6, 50.6, 39.7; HRMS m/z for C$_{13}$H$_{17}$NO$_2$ [M+H]$^+$, calcd 220.1338. found 220.1344.

The synthesis of Boc-Lys(Z)—N(allyl)-Phe-OMe (2b) was carried out as follows. A solution of Boc-Lys(Z)—OH (29.7 mmol, 11.3 g), HOBt (29.7 mmol, 4.0 g) and DCC (29.7 mmol, 6.1 g) in 200 mL of DMF was stirred at 25° C. After 15 min, a solution of 5b (22.8 mmol, 5.0 g) in DMF (5 mL) was added. The mixture was heated at 55° C. After 48 h, the mixture was cooled to 25° C., diluted with 400 mL of water and extracted with diethyl ether (300 mL, 3×). The combined organic layers were sequentially washed with 1M NaOH (400 mL, 3×), water (400 mL), 1M HCl (400 mL, 3×), and brine (400 mL). The organic layer was dried with MgSO$_4$ and concentrated under vacuum. The residue was purified by column chromatography using 20% ethyl acetate in hexane. The purified product yielded compound 2b as a yellow oil (3.5 g, 26%). $^1$H NMR (400 MHz, CDCl$_3$) 7.37-7.14 (m, 10H), 5.63-5.53 (m, 1H), 5.22-5.08 (m, 4H), 5.07 (s, 2H), 5.01 (br, 1H), 4.47-4.39 (m, 2H) 3.91-3.81 (br, 1H), 3.69 (s, 3H), 3.50-3.31 (m, 2H), 3.21-3.09 (m, 2H), 1.77 (br, 2H), 1.57-1.48 (m, 4H), 1.41 (s, 9H); $^{13}$C NMR (100 MHz, CDCl$_3$) 170.8, 168.9, 154.5, 153.6, 135.7, 134.7, 131.2, 127.6, 127.4, 126.9, 126.6, 126.3, 126.2, 125.0, 116.8, 114.5, 77.8, 64.7, 58.7, 50.4, 49.4, 48.3, 38.9, 32.9, 31.3, 27.4, 26.4, 20.6. HRMS m/z for C$_{32}$H$_{43}$N$_3$O$_7$ [M+Na]$^+$, calcd 604.2999. found 604.3005.

The synthesis of (Lys$^z$Phe)Oxopiperazine-methylester (3b) was carried out as follows. Ozone was bubbled through a solution of 2b (3.3 mmol, 1.9 g) in anhydrous methanol (12 mL) at −78° C. and ambient pressure. The reaction mixture turned light blue after 2 h. After an additional 30 min, nitrogen was bubbled through until the blue color disappeared. Dimethyl sulfide (11.6 mmol, 0.9 mL) was added to the mixture and the reaction was stirred for 12 h at 25° C. The reaction mixture was concentrated under vacuum, and the residue (1.9 g) was redissolved in 23.7 mL of DCM, and triethylsilane (6.7 mmol, 1.1 mL) and TFA (49.9 mmol, 3.7 mL) were added. The mixture was stirred for 24 h at 25° C. and then concentrated under vacuum. The residue was dissolved in DCM (12 mL) and TEA (12 mL) at 0° C. and stirred for 1 h at 25° C. The solution was re-concentrated under vacuum and the residue dissolved in DCM (200 mL). The DCM solution was washed with saturated aqueous sodium bicarbonate (150 mL). The aqueous layer was extracted with DCM (150 mL) The organic layers were combined, dried over anhydrous $MgSO_4$, and concentrated. The residue was purified with column chromatography (95% diethyl ether, 5% methanol and 0.1% of TEA) to obtain compound 3b as a colorless oil (0.9 g, 80%). $^1H$ NMR (400 MHz, $CDCl_3$) 7.26-7.09 (m, 10H), 5.07-5.03 (m, 1H), 5.00 (s, 2H), 4.84 (br, 1H), 3.64 (s, 3H), 3.45-3.26 (m, 2H), 3.26-3.21 (m, 1H), 3.19-3.17 (m, 3H), 3.03-2.99 (m, 2H), 2.96-2.86 (m, 1H), 1.58-1.45 (m, 3H), 1.34-1.31 (m, 2H), 1.16-0.95 (br, 2H); $^{13}C$ NMR (100 MHz, $CDCl_3$) 170.0, 169.5, 155.4, 135.9, 135.7, 127.8, 127.7, 127.5, 127.4, 127.1, 127.0, 125.8, 65.5, 58.0, 57.2, 51.3, 45.6, 40.8, 39.6, 33.1, 30.7, 28.6, 21.1; HRMS m/z for $C_{26}H_{33}N_3O_5$ [M+H]$^+$, calcd 468.2498. found 468.2500.

The synthesis of Boc-Oxopiperazine-methylester (4b) was carried out as follows. To a solution of 3b (3.2 mmol, 1.5 g) in 11.7 mL of DCM at 0° C. was added 4-methylmorpholine (4.8 mmol, 0.5 mL) and di-tert-butyl dicarbonate (8.0 mmol, 1.8 g) in 24 mL of DCM. The mixture was allowed to warm to 25° C. and then heated at reflux for 6 h. The mixture was concentrated and the residue was purified by column chromatography (40% hexane in diethyl ether) to yield 1.7 g (94%) of compound 5c as a colorless oil. $^1H$ NMR (400 MHz, $CDCl_3$) 7.41-7.08 (m, 10H), 5.30-5.26 (m, 1H), 5.02 (s, 2H), 4.74 (br, 1H), 4.32 (br, 1H), 3.68 (s, 3H), 3.35-3.29 (m, 1H), 3.16-3.08 (m, 1H), 3.07-2.93 (m, 5H), 1.45-1.29 (m, 5H), 1.34 (s, 9H), 1.13-0.93 (br, 2H); 13C NMR (100 MHz, $CDCl_3$) 170.7, 168.9, 156.4, 153.9, 136.7, 136.4, 128.9, 128.6, 128.5, 128.1, 128.0, 127.0, 80.6, 66.6, 57.2, 52.5, 43.3, 40.8, 34.4, 32.2, 28.3, 22.8; HRMS m/z for $C_{31}H_{41}N_3O_7$ [M+Na]$^+$, calcd 590.2842. found 590.2845.

The synthesis of oxopiperazine dimer (1b) was carried out as follows. Lithium hydroxide monohydrate (4.4 mmol, 0.2 g) was added to solution of 4b (1.8 mmol, 1 g) in 12:4:1 THF/MeOH/$H_2O$ (32 mL) at 0° C. The reaction mixture was stirred for 2 h at 0° C. and then acidified to pH 3 with saturated aqueous sodium bisulfate. The reaction mixture was concentrated and the residue was dissolved in ethyl acetate (15 mL) and washed with brine (10 mL). The aqueous layer was extracted with ethyl acetate (15 mL), and the combined organic layers were dried with anhydrous sodium sulfate and concentrated under vacuum to yield 1.1 g of residue. The residue was used in the next step without further purification.

A portion of the residue from above (0.6 mmol, 0.3 g), HOBt (1.2 mmol, 0.2 g) and DCC (0.6 mmol, 0.1 g) were dissolved in 100 mL of DMF. The reaction mixture was stirred for 15 min at 25° C. and 3a (0.3 mmol, 0.1 g) in DMF (5 mL) was added. The mixture was heated at 55° C. After 48 h, the solution was cooled to room temperature and diluted with 100 mL of water and extracted with diethyl ether (100 mL, 3×). The combined organic layers were washed sequentially with 1M NaOH (50 mL, 3×), water (50 mL), 1M HCl (50 mL, 3×) and brine (50 mL), dried with $MgSO_4$ and concentrated under vacuum. The residue was purified by column chromatography with 20% ethyl acetate in hexane to obtain compound 1b as a yellow oil (0.1 g, 70%). $^1H$ NMR (400 MHz, $CDCl_3$) 7.29-7.11 (m, 10H), 5.72-5.63 (m, 1H), 5.22-5.16 (m, 1H), 5.02 (s, 2H), 4.88-4.80 (m, 1H), 4.34 (br, 1H), 3.91 (br, 1H), 3.64 (s, 3H), 3.59-3.54 (m, 2H), 3.46-3.41 (m, 1H), 3.38-3.21 (m, 2H), 3.15-2.90 (m, 6H), 1.93-1.57 (m, 5H), 1.36-1.22 (m, 15H), 1.19-1.06 (m, 2H), 0.87 (d, J=6.6 Hz, 3H), 0.81 (d, J=6.6 Hz, 3H); $^{13}C$ NMR (100 MHz, $CDCl_3$) 170.6, 168.5, 168.2, 167.5, 166.2, 135.2, 134.9, 128.4, 128.3, 128.2, 127.6, 127.5, 127.48, 127.46, 127.1, 126.0, 79.9, 65.6, 52.4, 51.4, 51.3, 51.2, 41.3, 39.8, 39.4, 35.9, 35.8, 34.1, 33.9, 28.9, 28.7, 27.3, 27.27, 24.0, 22.2, 22.1, 21.9, 20.2; HRMS m/z for $C_{42}H_{59}N_5O_9$ [M+Na]$^+$, calcd 800.4210. found 800.4233.

Example 4

Synthesis of Oligooxopiperazine 1c

The synthesis of oligooxopiperazine dimer 1c of the present invention is illustrated in Scheme 1 above.

The synthesis of Boc-Leu-N(allyl)-Leu-OMe (2c) was carried out as follows. A solution of Boc-Leu-OH (78.6 mmol, 24.1 g), HOBt (78.6 mmol, 10.6 g) and DCC (78.6 mmol, 16.2 g) in 200 mL of DMF was stirred at 25° C. After 15 min, a solution of 5a (39.3 mmol, 7.3 g) was added in DMF (5 mL), and the resulting mixture was heated at 55° C. for 12 h. The mixture was cooled to 25° C., diluted with 400 mL of water and extracted with diethyl ether (300 mL, 3×). The combined organic layers were washed sequentially with 1M NaOH (500 mL, 3×), water (500 mL), 1M HCl (500 mL, 3×), and brine (500 mL). The organic layer was dried with anhydrous $MgSO_4$ and concentrated under vacuum. The residue was purified by column chromatography (20% ethyl acetate in hexane) to afford 2c as a yellow oil (6.2 g, 40%). $^1H$ NMR (400 MHz, $CDCl_3$) 5.92-5.74 (m, 1H), 5.22-5.16 (m, 2H), 5.06-4.97 (m, 2H), 4.57-4.54 (m, 1H), 4.01-3.91 (br, 2H), 3.65 (s, 3H), 1.79-1.56 (m, 3H), 1.54-1.43 (m, 3H), 1.35 (s, 9H), 0.93-0.74 (m, 12H); $^{13}C$ NMR (100 MHz, $CDCl_3$) 174.4, 172.2, 155.5, 134.2, 117.7, 79.4, 55.4, 52.1, 49.3, 48.3, 42.4, 37.8, 28.3, 24.6, 23.5, 22.9, 21.7; HRMS m/z for $C_{21}H_{38}N_2O_5$ [M+H]$^+$, calcd 398.2859. found 399.2862.

The synthesis of (LeuLeu)Oxopiperazine methyl ester (3c) was carried out as follows. Ozone was bubbled through a solution of 2c (11.0 mmol, 4.4 g) in anhydrous methanol (75 mL) at −78° C. and ambient pressure. The reaction mixture turned light blue after 2 h. After an additional 30 min, nitrogen was bubbled through until the blue color disappeared. Dimethyl sulfide (38.5 mmol, 2.8 mL) was added and the mixture stirred for 12 h at 25° C. The mixture was concentrated under vacuum, and the residue was redissolved in DCM (78 mL), triethylsilane (21.9 mmol, 3.5 mL) and TFA (165.0 mmol, 12.2 mL). The reaction mixture was stirred for 24 h at 25° C. and then concentrated under vacuum. The residue was dissolved in 39 mL of DCM and 39 mL of TEA at 0° C. and stirred for h at 25° C. The solvent was then concentrated under vacuum. The residue was redissolved in DCM (300 mL), and the solution washed with saturated aqueous sodium bicarbonate (300 mL). The aqueous layer was extracted with DCM (200 mL, ×3). The combined organic layers were concentrated and the residue was purified with column chromatography (95% diethyl ether, 5% methanol, and 0.1% of TEA) to obtain compound 3c as a colorless oil (2.2 g, 85%). $^1H$ NMR (400 MHz, $CDCl_3$) 5.26-5.22 (t, J=7.8 Hz, 1H), 3.65 (s, 3H), 3.48-3.38 (m, 1H), 3.27-3.17 (m, 2H), 3.14-3.09 (m, 1H), 3.02-2.95 (m, 1H), 1.83-1.76 (m, 1H), 1.74-1.61 (m, 4H), 1.52-1.41 (m, 2H), 0.89-0.85 (m, 12H); $^{13}C$ NMR (100 MHz, $CDCl_3$) 172.3, 171.5, 57.7, 53.8, 52.1, 44.7, 42.0, 41.6, 36.7, 24.9, 24.5, 23.5, 23.2, 21.3, 21.1; HRMS m/z for $C_{15}H_{28}N_2O_3$ [M+H]$^+$, calcd 285.2178. found 285.2182.

The synthesis of Boc-(LeuLeu)oxopiperazine-methyl ester (4c) was carried out as follows. To a solution of 3c (7.7 mmol, 2.2 g) in 25 mL of DCM at 0° C. was added 4-methylmorpholine (11.5 mmol, 1.3 mL) and ditert-butyl dicarbonate (19.2 mmol, 4.2 g) in 50 mL of DCM. The mixture was allowed to warm to 25° C., and then heated at reflux. After 6 h, the mixture was concentrated and the residue was purified by column chromatography (40% hexane in diethyl ether) to yield 2.9 g (97%) of compound 4c as a colorless oil. $^1$H NMR (400 MHz, CDCl$_3$) 5.21-5.17 (m, 1H), 4.53 (br, 1H), 3.95 (br, 1H), 3.66 (s, 3H), 3.44-3.34 (m, 1H), 3.23 (br, 1H), 3.15-3.10 (m, 1H), 1.70-1.62 (m, 3H), 1.60-1.52 (m, 3H), 1.45 (s, 9H), 0.91-0.81 (m, 12H); $^{13}$C NMR (100 MHz, CDCl$_3$) 171.6, 169.7, 154.1, 80.7, 56.2, 53.6, 52.1, 41.9, 41.8, 37.7, 36.8, 28.3, 24.9, 24.6, 23.2, 22.8, 22.3, 21.2; HRMS m/z for $C_{20}H_{36}N_2O_5$ [M+Na]$^+$, calcd 407.2522. found 407.2510.

The synthesis of oxopiperazine dimer (1c) was carried out as follows. To solution of 4c (5.4 mmol, 1.9 g) in 12:4:1 THF/MeOH/H$_2$O (100 mL) at 0° C. was added lithium hydroxide monohydrate (16.4 mmol, 0.7 g). The reaction mixture was stirred for 2 h at 0° C. and then acidified to pH 3 with saturated aqueous sodium bisulfate. The reaction mixture was concentrated and the residue was dissolved in ethyl acetate (100 mL) and washed with brine (50 mL). The aqueous layer was extracted with ethyl acetate (100 mL), and the combined organic layers were dried with anhydrous sodium sulfate and concentrated to yield 2 g of product residue. The residue was used in the next step without further purification.

A portion of the residue from above (1.8 mmol, 0.70 g), HOBt (3.5 mmol, 0.50 g) and DCC (1.8 mmol, 0.40 g) were dissolved in 50 mL of DMF. The solution was stirred for 15 min at 25° C., and 3c (0.9 mmol, 0.3 g) was added in DMF (5 mL). The mixture was heated at 55° C. for 48 h and then cooled to 25° C. and diluted with water (100 mL) and extracted with diethyl ether (100 mL, 3×). The combined organic layers were washed sequentially with 1M NaOH (50 mL, 3×), water (50 mL), 1M HCl (50 mL, 3×) and brine (50 mL), dried with MgSO$_4$, and concentrated under vacuum. The residue was purified by column chromatography with 20% ethyl acetate in hexane to obtain compound 1c as a yellow oil (0.2 g, 71%). $^1$H NMR (400 MHz, CDCl$_3$) 5.60-5.58 (t, J=7.4 Hz, 1H), 5.28-5.25 (m, 1H), 5.12-5.08 (m, 1H), 4.58 (br, 1H), 4.23 (br, 1H), 4.12 (br, 1H), 3.66 (s, 3H), 3.48-3.42 (m, 1H), 3.39-3.24 (m, 4H), 3.20-3.11 (m, 1H), 1.73-1.49 (m, 10H), 1.45 (s, 9H), 1.44-1.36 (m, 2H), 0.97-0.88 (m, 24H); $^{13}$C NMR (100 MHz, CDCl3) 171.8, 171.7, 169.6, 169.2, 154.1, 54.9, 54.5, 53.5, 53.3, 52.3, 52.2, 42.5, 42.2, 41.7, 41.5, 41.4, 41.2, 40.6, 39.5, 37.6, 37.4, 37.0, 36.8, 28.3, 28.0, 25.1, 25.0, 24.9, 24.8, 24.7; HRMS m/z for $C_{34}H_{60}N_4O_7$ [M+Na]+, calcd 659.4360. found 659.4350.

Example 5

Two-Dimensional NMR Spectroscopy of Oligooxopiperazine 1a

COSY spectrum of 1a was recorded on a Bruker Avance 400 at 20° C. by collecting 2048 complex data points in the t$_2$ domain by averaging 32 scans and 256 increments in the t$_1$ domain with States-TPPI mode. The original free induction decays (FIDs) were zero-filled to give a final matrix of 1024 by 1024 real data points. A 0° sine-bell window function was applied in both dimensions. NOESY spectrum of 1a was recorded on a Bruker Avance 600 at 20° C. by collecting 4096 complex data points in the t$_2$ domain by averaging 48 scans and 512 increments in the t$_1$ domain with States-TPPI mode and the mixing time of 750 ms. The original free induction decays (FIDs) were zero-filled to give a final matrix of 2048 by 1024 real data points. A 90° sine-square window function was applied in both dimensions. All the data were processed and analyzed using Bruker TOPSPIN 1.3 program.

Example 6

Circular Dichroism (CD) Spectroscopy Studies

CD spectra were recorded on AVIV 202SF CD spectrometer equipped with a temperature controller using 1 mm length cells and a scan speed of 15 nm/min. The spectra were averaged over 10 scans with the baseline subtracted from analogous conditions as that for the samples. The samples were prepared in acetonitrile or methanol with the final peptide concentration of 100 M. The amount of oxopiperazines were determined by dry weight.

Example 7

Conformational Analysis of Oligooxopiperazines

The present invention relates to the design and synthesis of nonaromatic helix mimetics which feature a chiral backbone and are easily synthesized from α-amino acids. The piperazine skeleton was an attractive design choice because it is considered a privileged scaffold for peptidomimetic research and drug discovery (Patchett et al., *Ann. Rep. Med. Chem.* 35: 289-298 (2000), which is hereby incorporated by reference in its entirety). Specifically, the 2-oxopiperazine and the diketopiperazines have a rich history in medicinal chemistry and are considered to be "drug-like" scaffolds (Herrero et al., *J. Org. Chem.* 67:3866-3873 (2002); Kitamura et al., *J. Med. Chem.* 44:2438-2450 (2001); Gante, J., "Peptidomimetics—Tailored Enzyme-Inhibitors," *Angew. Chem. Int. Ed. Engl.* 33:1699-1720 (1994); Giannis et al., *Angew. Chem. Int. Ed.* 32:1244-1267 (1993), which are hereby incorporated by reference in their entirety). Initial computational studies of the oligooxopiperazines predicted stable structures due to the conformational constraints inherent in the system. Molecular modeling studies indicate that an oxopiperazine dimer spans the length of an 8mer α-helix and superimposes amino acid functionality onto the i, i+4, and i+7 residues of the helix (FIG. 2B). Oligooxopiperazines do not contain hydrogen bond donors in the backbone; however, this omission is not expected to be detrimental for helix mimetics because helices typically do not utilize backbone hydrogen bonding functionality for interaction with other biomolecules.

Figure 3A:
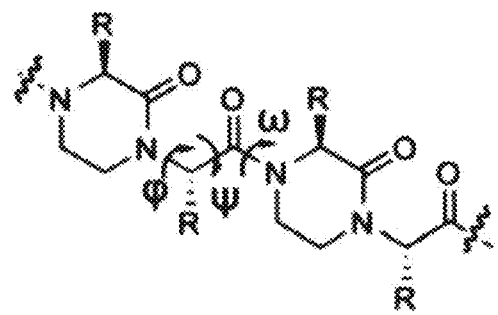
FIGS. 3A-3C depict the rotatable bonds and favored geometries of an oligooxopiperazine dimer. The rotatable bonds (i.e., φ, ψ, and ω) of an oligooxopiperazine dimer are show in FIG. 3A. The favored chair and amide bond geometries are shown in FIGS. 3B and 3C, respectively. The values were calculated with Macromodel MMFF force field in chloroform.

The analysis of oligooxopiperazines was started by searching the Cambridge Structural Database for examples of oxopiperazine derivatives. This search resulted in five hits (CSD codes: KEMXUV, ZOZTUD, ZARZOH, FOBFEH, and KEMXUV) of single piperazine ring systems relevant to the system. Although this is a narrow set to base hypotheses upon, these hits provided invaluable insights regarding the φ and ψ dihedral angles favored in the amino acid residue linking two piperazine rings and corroborated the molecular modeling calculations (FIGS. 3A-3C).

Figure 3B:
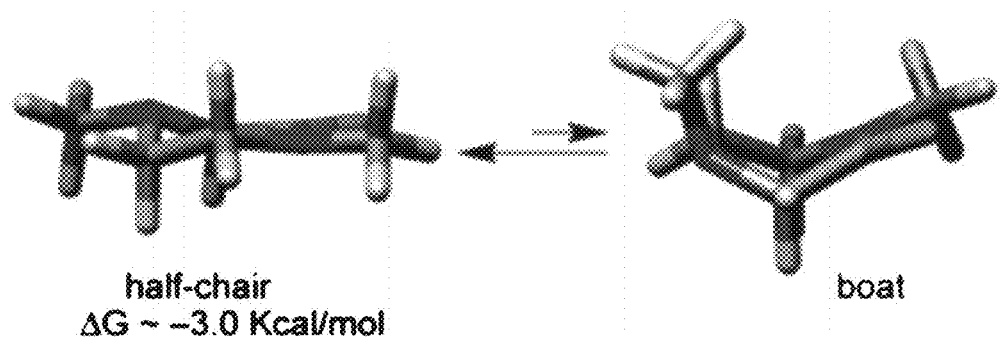
Figure 3C:
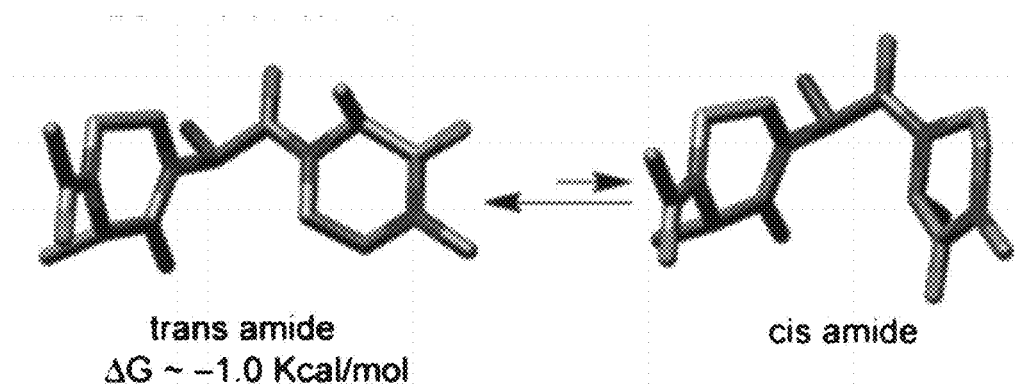

The oxopiperazine rings may adopt the half-chair or the boat conformation, but the half-chair conformation is substantially lower in energy, ~2.9 Kcal/mol (FIG. 3B). A dimer of oxopiperazines contains three rotatable bonds φ, ψ, and ω. The tertiary amide bond may adopt a cis or trans amide conformation like proline as shown in FIG. 3C. Macromodel calculations suggest that the trans conformation is roughly 1

Kcal/mol more stable than the cis conformation in tetraalanine systems. The trans to cis ratio is expected to increase in dimers built from bulkier amino acid residues.

To examine the preferred φ and ψ dihedral angles in an oxopiperazine dimer, dimer 30 (see FIG. 7), the "dihedral drive" functionality in Macromodel was utilized (Mohamadi et al., *J. Comp. Chem.* 11:440-467 (1990), which is hereby incorporated by reference in its entirety). The results of these calculations intimate a limited number and a narrow range of φ and ψ values in the lowest energy conformations (Table 1 below and FIGS. 7A-7B). Importantly, the dihedral angles predicted by Macromodel were also found in the crystal structures of relevant compounds in CSD (Table 1). The calculations indicate that oligooxopiperazines will favor φ and ψ angles of −128°±25° and 76°±15°, respectively. The favored φ values show direct correlation with allyl 1,2 and 1,3 strains.

TABLE 1

Calculated Low Energy and Values for Oxopiperazine Dimer 30.

30

| | Dihedral angle (°) | Relative energy (Kcal/mol) | Cambridge structure database code* |
|---|---|---|---|
| φ | −150 | 0.95 | — |
| | −128 | 0 | KEMXUV, ZOZTUD |
| | −90 | 1.26 | ZARZOH |
| ψ | 60 | 0.64 | — |
| | 76.76 | 0 | ZARZOH |
| | 90 | 0.34 | — |
| | 120 | 1.87 | — |

*the corresponding dihedral value was found in the indicated CSD structure.

Figure 2A:
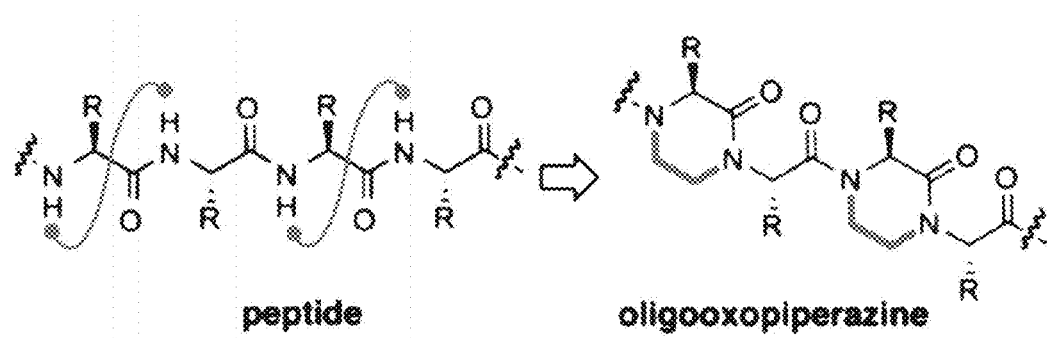
FIGS. 2A-2C illustrate the design and predicted structure of amino acid-derived oligooxopiperazines. The oligooxopiperazines are obtained by linking neighboring amide nitrogen atoms in peptides with ethylene bridges as depicted in FIG. 2A.
Figure 2B:
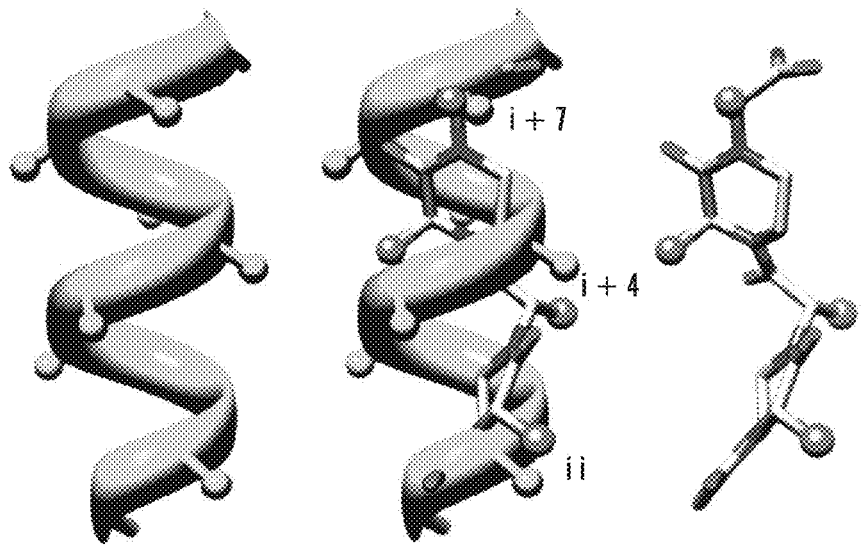
Figure 2C:
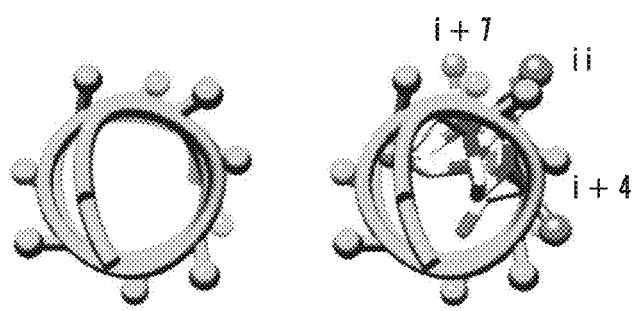

The predicted low energy structure of the oxopiperazine dimer arrays functionality to match side chain patterns on a canonical α-helix (FIG. 2). Similarly, the predicted low energy structure of the oxopiperazine trimer arrays functionality to match side chain patterns on a canonical α-helix (FIG. 8). Positions 1, 2, 3, and 4 overlay well onto the i+1, i+2, i+3 and i+7 residues on a 10mer α-helix; while the i+1, i+4 and i+7 positions are best mimicked by positions 1, 2, and 5 of an oligooxopiperazine (FIG. 8). This level of structural versatility has not been observed with other nonpeptidic helix mimetics, which typically only mimic one face of the helix (Davis et al., *Chem. Soc. Rev.* 36:326-334 (2007); Yin et al., *Angew. Chem. Int. Ed.*, 44: 4130-4163 (2005), which are hereby incorporated by reference in their entirety.

Figure 4A:
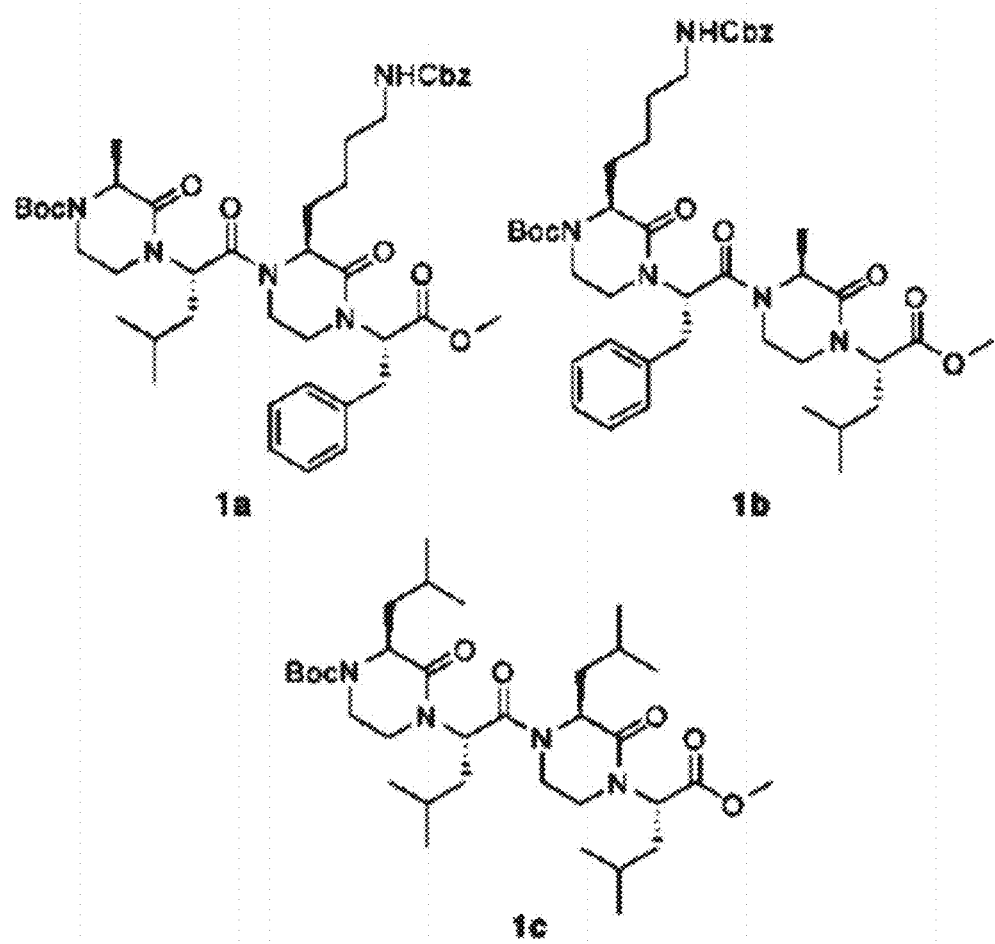
FIGS. 4A-4B show three oligooxopiperazine helix mimetics of the present invention (FIG. 4A; oxopiperazine 1a, 1b, and 1c) and their synthesis via reductive amination (FIG. 4B). Synthesis of dimers 1a-c: (a) $O_3$, (b) $Me_2S$, (c) TFA and triethylsilane. Combined yield for steps a-c: 3a, 81%; 3b, 80%; 3c, 85%; (d) $Boc_2O$: 4a, 98%; 4b, 94%; 4c, 97%; (e) $LiOH_3$, DCC, HOBt: 1a, 73%; 1b, 70%; 1c, 71%.
a: $R^1$═$CH_2CH(CH_3)_2$, $R^2$═$CH_3$. b: $R^1$═$CH_2Ph$, $R^2$═$(CH_2)_4NHCbz$. c: $R^1$═$CH_2CH(CH_3)_2$, $R^2$═$CH_2CH(CH_3)_2$.
Figure 4B:
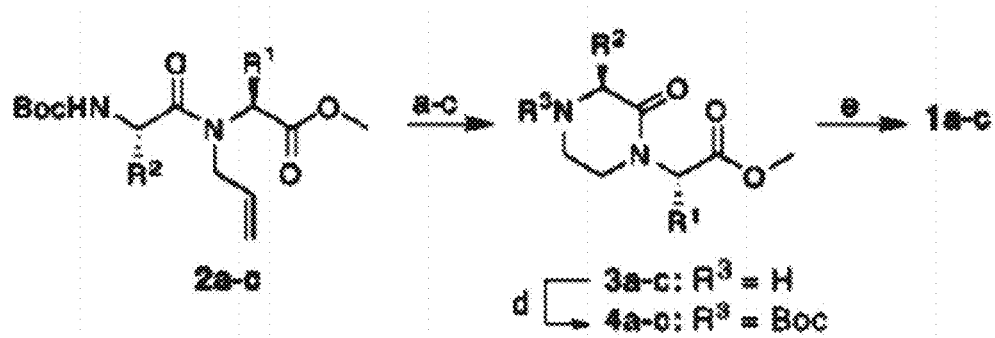

Oligooxopiperazines 1a-c were designed to test the impact of different side chain combinations on the stability of the oxopiperazine dimer conformation. Several synthetic routes to piperazines are known, which were anticipated to allow rapid synthesis and evaluation of the desired compounds (Franceschini et al., *Org. Biomol. Chem.* 3:787-793 (2005); Tong et al., *J. Org. Chem.* 65:2484-2493 (2000); Sugihara et al., *J. Med. Chem.* 41:489-502 (1998), which are hereby incorporated by reference in their entirety). While a number of these synthetic routes were evaluated, it was discovered that the reductive amination route described by Tong et al., *J. Org. Chem.*, 65:2484-93 (2000), which is hereby incorporated by reference in its entirety, can afford short oligomers in respectable yields (FIG. 4B and Scheme 1).

Figure 5A:
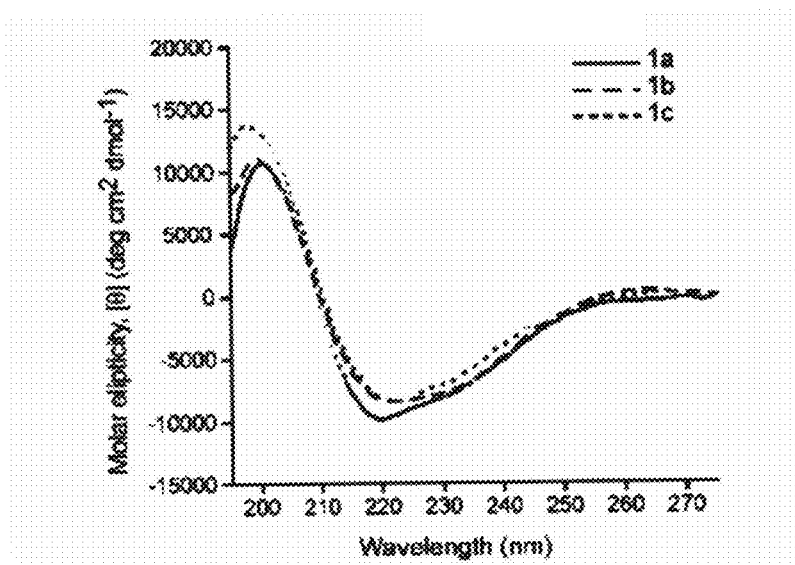
FIGS. 5A-5C show the solution conformation and thermal stabilities of oligooxopiperazines 1a, 1b, and 1c shown in FIG. 4A. The circular dichroism (CD) spectra of oxopiperazines 1a-1c in acetonitrile and methanol is depicted in FIGS. 5A and 5C, respectively. The effect of temperature on the stability of compounds 1a-1c is shown in FIG. 5B.
Figure 5B:
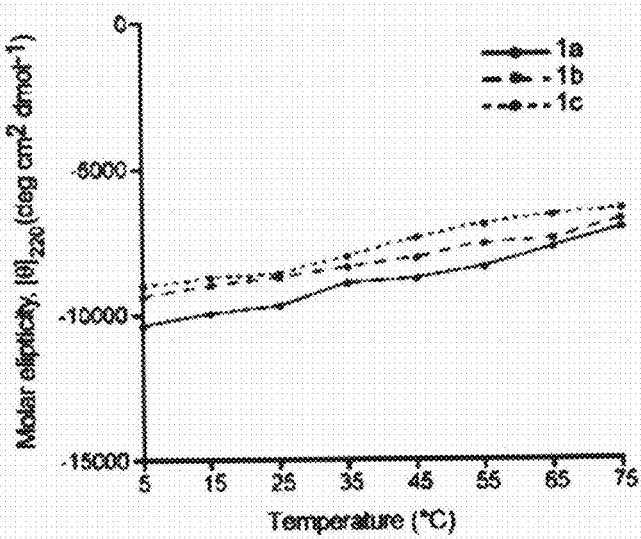
Figure 5C:
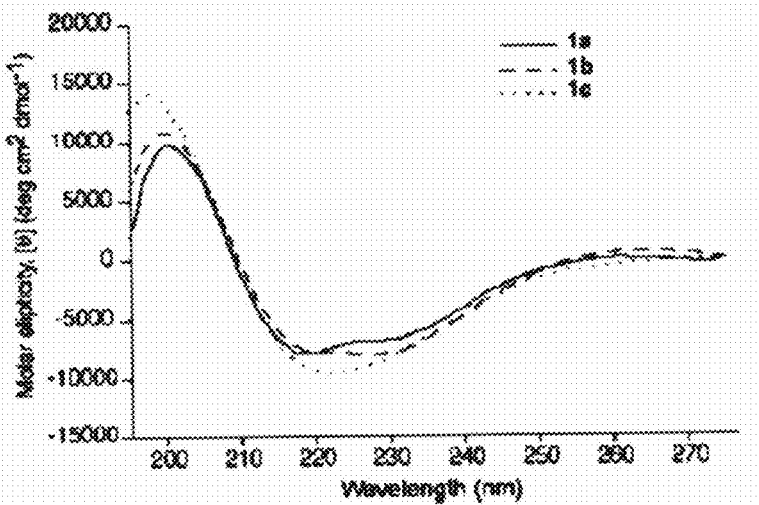

The solution conformation of dimers 1a-c was investigated by CD spectroscopy in methanol and acetonitrile solutions. FIGS. 5A and 5C show CD spectra of oxopiperazine 1a, 1b, and 1c in acetonitrile and methanol, respectively. The CD spectra of 1a-c display double minima near 220 and 230 nm and maxima at 200 nm. Surprisingly, the overall shape is reminiscent of CD spectra of α-helices; although, the maxima and minima are red-shifted by 10 nm. Although CD spectra of artificial systems are often difficult to interpret (Driver et al., *Org. Lett.* 11:3092-3095 (2009), which is hereby incorporated by reference in its entirety), the spectra of 1a-c indicate a high degree of preorganization. The thermal stabilities of 1a-c were investigated by monitoring the temperature-dependent change in the intensity of the 220 nm bands in the CD spectra (FIG. 5B). A gradual increase in the signal intensity was observed at 220 nm with temperature, but the dimers retain over 70% of their room-temperature elipticity at 75° C. Similar non-cooperative denaturation behavior has been observed with other conformationally defined oligomers (Saludes et al., *Am. Chem. Soc.* 131:5495-5505 (2009); Wang et al., *Org. Biomol. Chem.* 4:4074-4081 (2006). Overall, the CD studies demonstrate that helix mimetics 1a-c adopt stable conformations confirming the molecular modeling analysis.

Figure 6A:
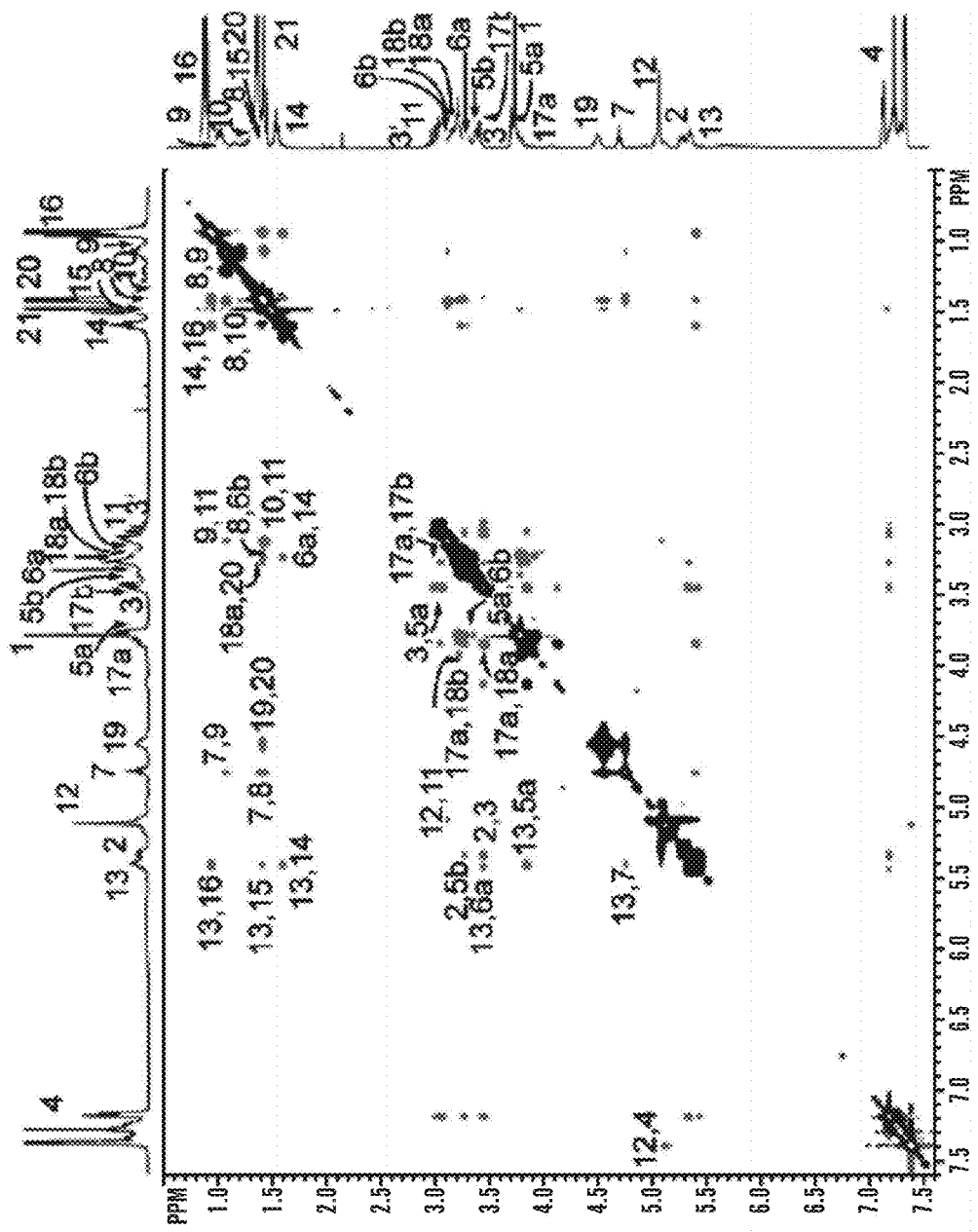
FIGS. 6A-6B show a cross-section of the NOESY spectra of oligooxopiperazine 1a in $CDCl_3$ (FIG. 6A) and an overlay of key NOEs on the predicted oligooxopiperazine conformation (FIG. 6B) (Side chain groups not shown for clarity.)
Figure 6B:
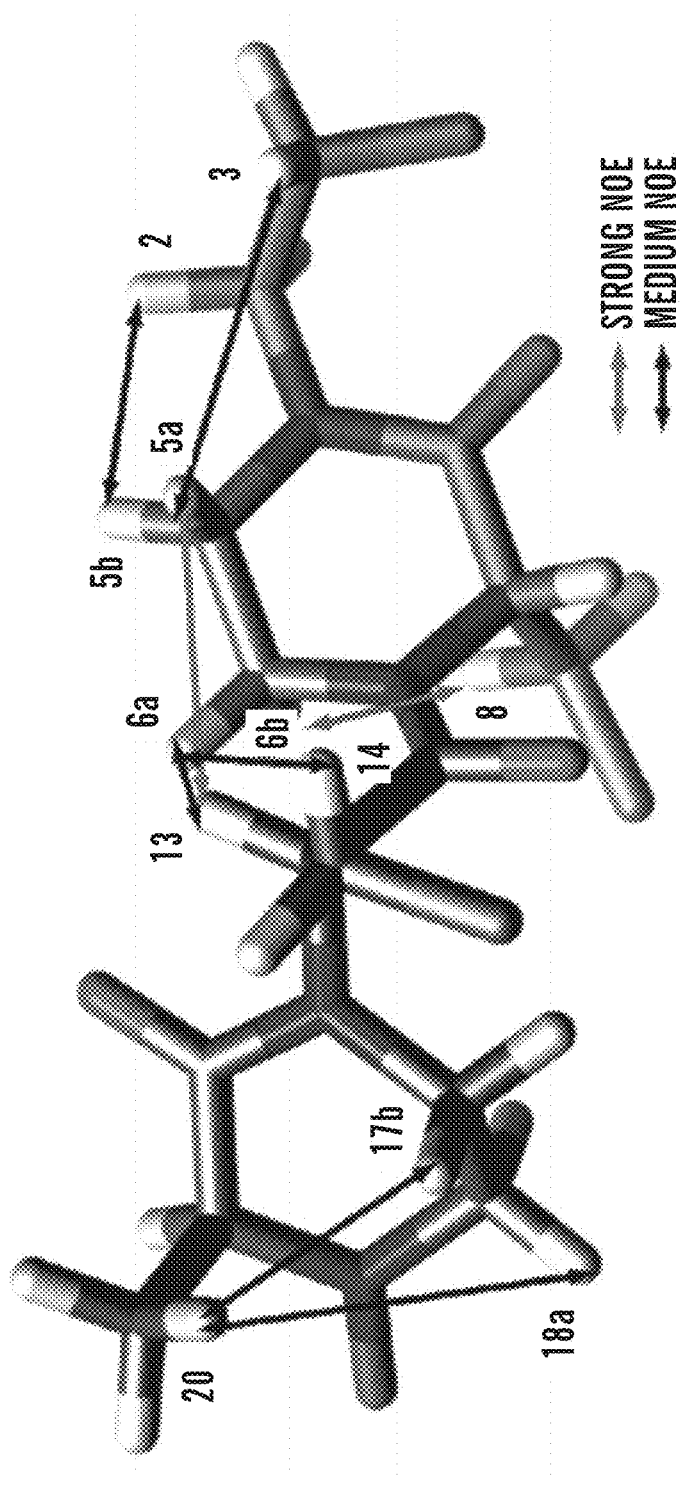
Figures 7A, 7B:
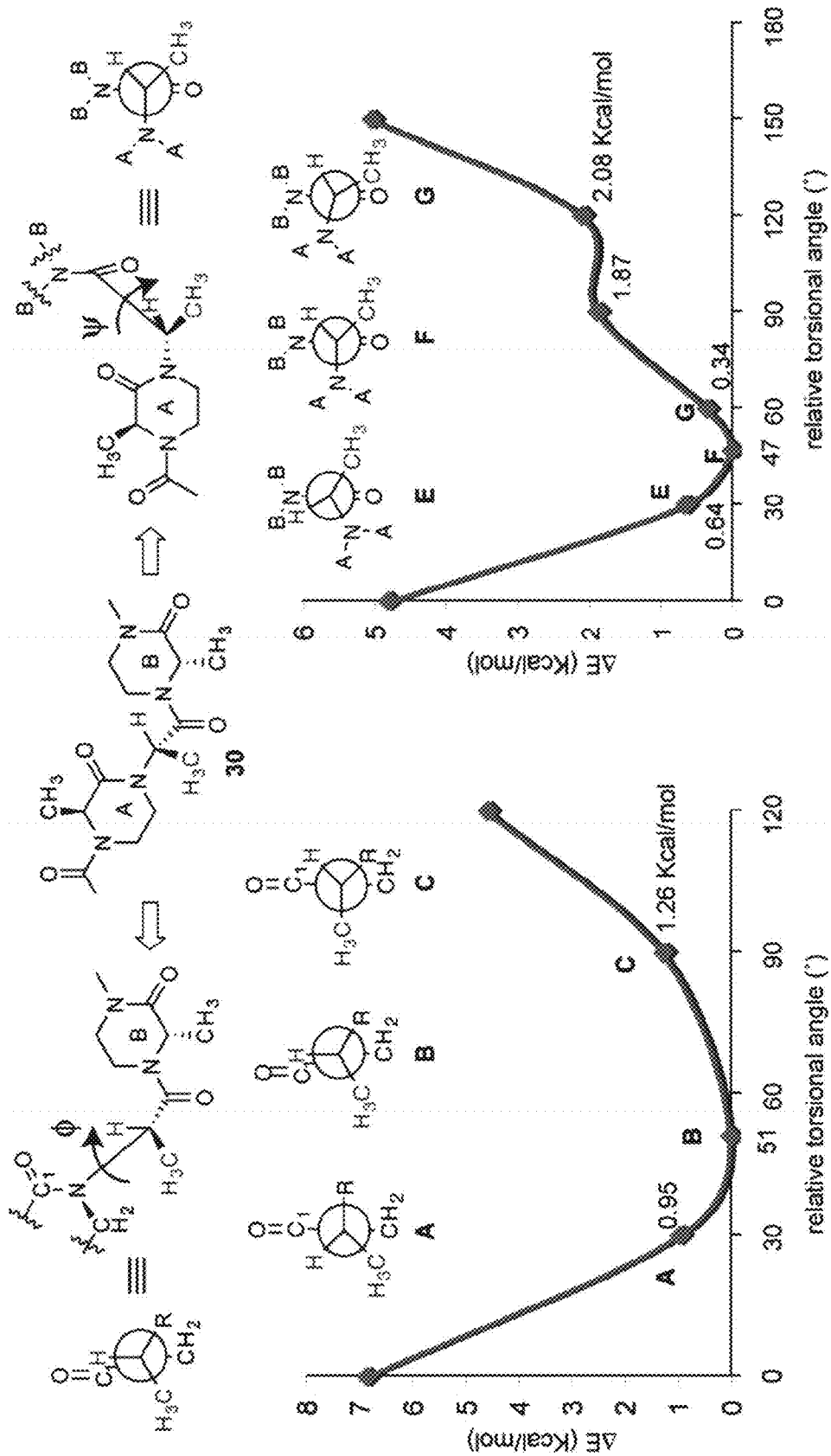
FIGS. 7A-7B are graphs showing the low energy φ (FIG. 7A) and ψ (FIG. 7B) angles for oligooxopiperazine dimer 30 calculated using the macromodel "dihedral drive" function.
Figure 8D:
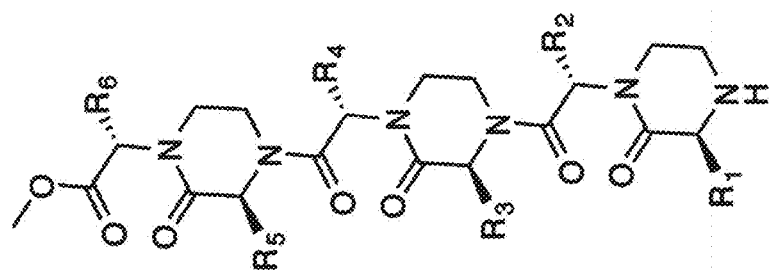
FIGS. 8A-8D depict a 10mer alpha helix and the predicted structure of an oligooxopiperazine trimer. The 10mer alpha helix of FIG. 8A displays i and i+1, and i and i+4 distances.
Figure 8C:
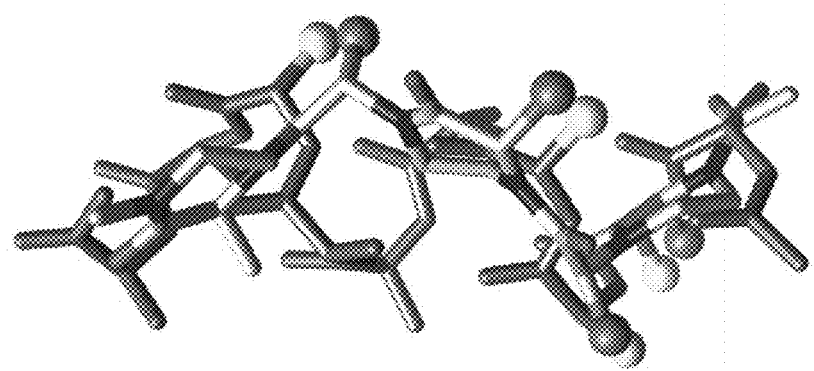
Figure 8B:
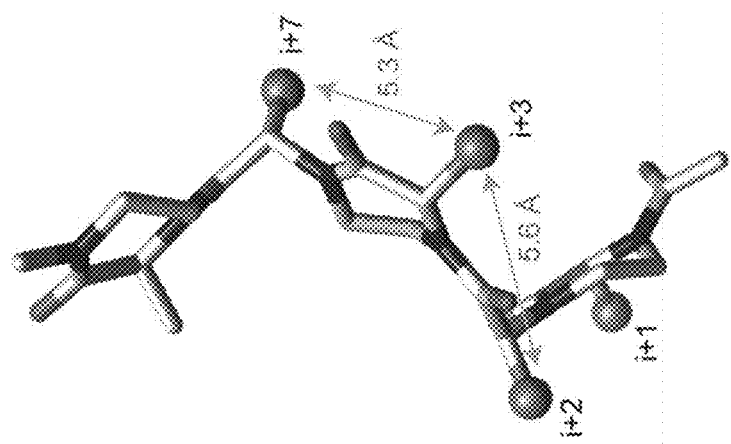
Figure 8A:
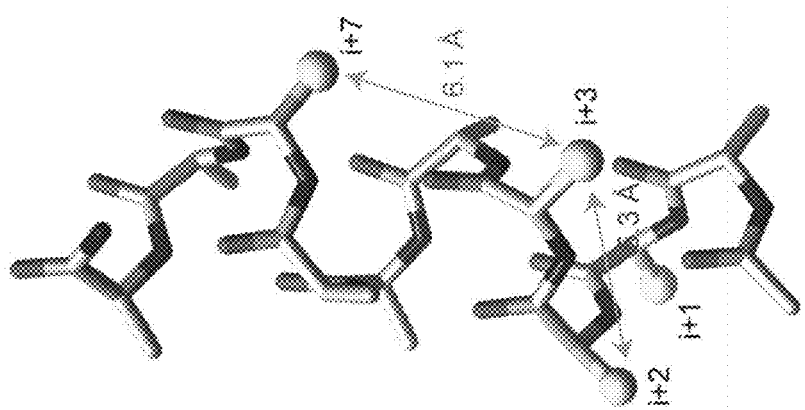
Figure 9A:
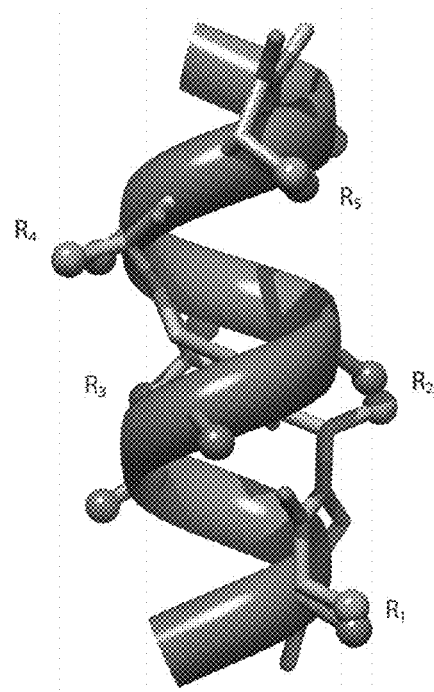
FIGS. 9A-9D show the design and structure of model oligooxopiperazine dimers A-C (FIGS. 9B-9D) and a model oligooxopiperazine trimer (FIG. 9A) of the present invention. An overlay of the predicted structure of each model oligooxopiperazine and its target α-helix is also shown.
Figure 9A:
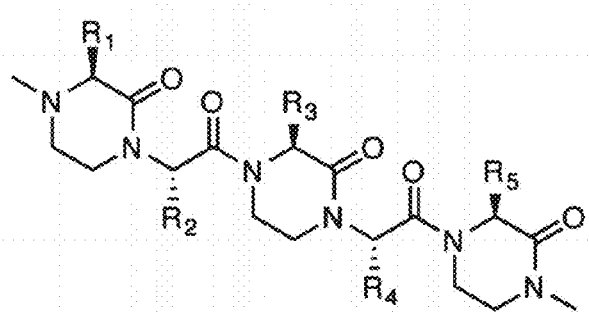
Figure 9B:
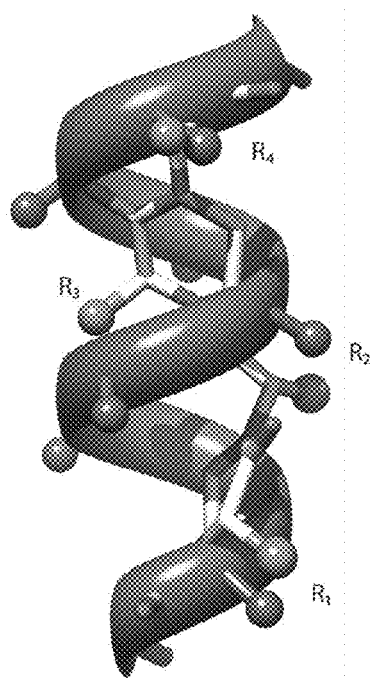
Figure 9B:
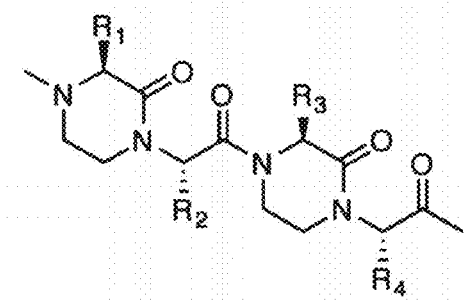
Figure 9C:
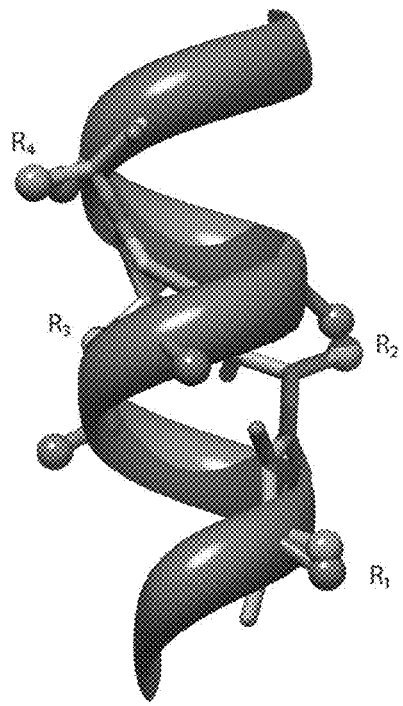
Figure 9C:
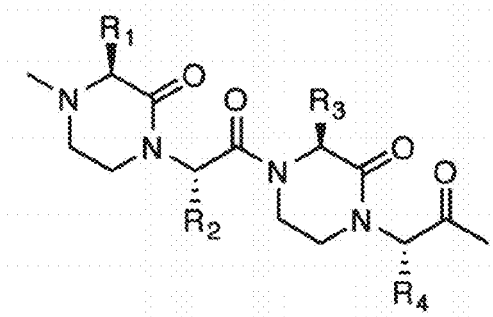
Figure 9D:
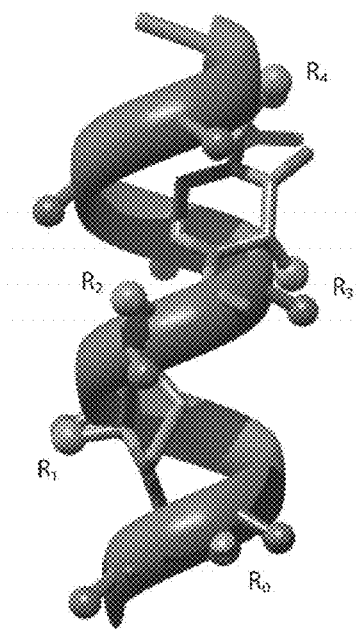
Figure 9D:
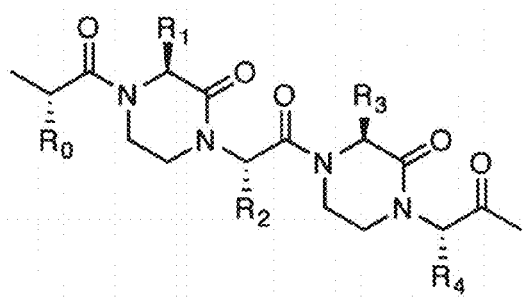

Two-dimensional NMR spectroscopy was also utilized to analyze the conformations adopted by 1a as a model oxopiperazine helix mimetic, specifically to determine the geometry adopted by the tertiary amide bond linking two piperazine rings. A combination of COSY and NOESY spectroscopy was used to assign $^1$H NMR resonances for 1a. The NOESY spectrum reveals several NOEs in the two-ring system, which would be expected from a trans-amide geometry in 1a but not from the cis-amide conformation (FIG. 6A). NOE crosspeaks were not observed between protons on neighboring piperazine rings (FIG. 6B). This absence of NOEs is expected based on the proposed low energy conformation in which these protons lie outside the 5 Å distance typically required to observe the nuclear Overhauser effect. Thus, the NOESY studies strongly corroborate the modeling analysis. Significantly, the NMR spectra did not display peaks indicative of a minor cis-amide isomer, suggesting that the trans conformation is substantially more stable than the cis analog.

Example 8

Representative Solid Phase Synthesis of Oligooxopiperazines

An alternative route of oligooxopiperazine synthesis was investigated. Scheme 2 below illustrates a representative solid phase synthesis scheme for the synthesis of oligooxopiperazine dimers (i.e., dimers A, B, and C) and trimers. FIGS. 9A-9D show the predicted structures of the oligooxopiperazine dimers A, B, and C, and trimer as they overlay with the target α-helix. Exemplary dimers and trimers produced via this synthesis approach are shown in Tables 2 and 3 below. The biological protein target of the oligooxopiperazine, the helical sequence of the target protein, and the oligooxopiperazine structure are provided in Tables 2 and 3.
Representative Solid Phase Synthesis of Oxopiperazine Dimer A-D and Trimer
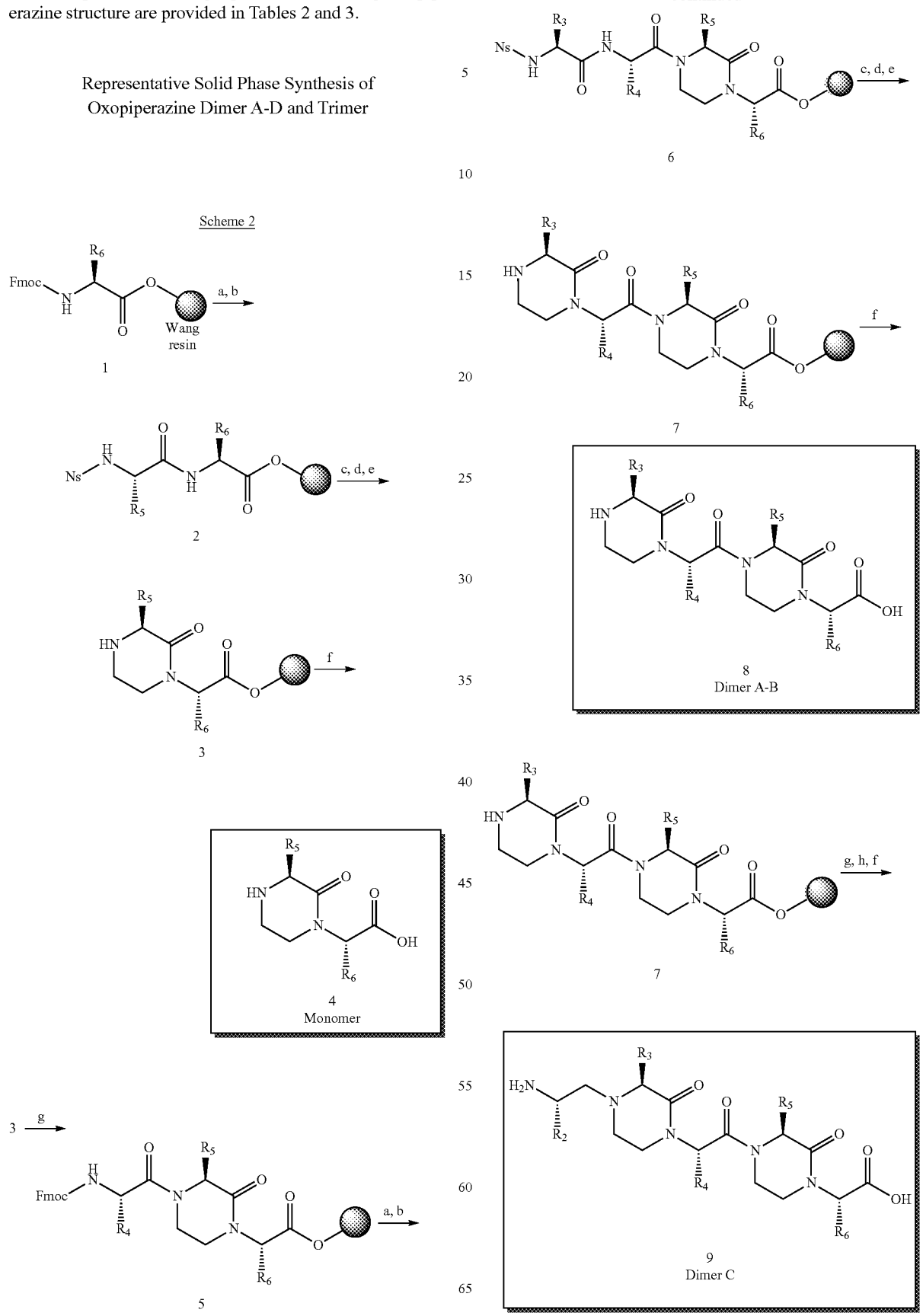

-continued

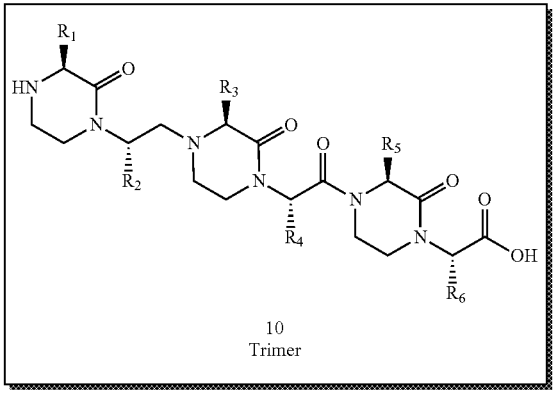

10
Trimer

Repeat steps g, a, b, c, d, e, f →

-continued

Reaction Conditions a = 1. 20% piperidine/DMF
    2. Fmoc—AA—OH, HBTU, DIEA, DMF
b = 1. 20% piperidine/DMF
    2. o-nitrobenzenesulfonyl chloride, collidine, DCM
c = PPh₃, DIAD, 2-bromoethanol, THF
d = DBU, THF
e = DBU, 2-mercaptoethanol, DMF
f = 95% TFA/2.5% TIPS/2.5% H₂O
g = Fmoc—AA—OH, triphosgene, collidine, THF
h = 20% piperidine/DMF

TABLE 2

Exemplary Oligooxopiperazines and their Helical Targets

| Target | Model Type | Sequence of Helical Partner | Oligooxopiperazine Structure |
|---|---|---|---|
| HDM2 | Trimer | p53$_{17-28}$ ETFSDLWKLLPE (SEQ ID NO: 186) | [Structure with Phe, Trp, Lys, Leu, Leu, Ala substituents] |
| HDM2 | Dimer A | p53$_{17-28}$ ETFSDLWKLLPE (SEQ ID NO: 186) | [Structure with Phe, Lys, Trp, Leu substituents] |
| p300-TAZ1 | Dimer B | Hif1$_{140-147}$ ELLRALDQ (SEQ ID NO: 187) | [Structure with Leu, Leu, Ala, Gln substituents] |

TABLE 2-continued

Exemplary Oligooxopiperazines and their Helical Targets

| Target | Model Type | Sequence of Helical Partner | Oligooxopiperazine Structure |
|---|---|---|---|
| p300-KIX | Dimer C | cMyb$_{91-103}$<br>RIKELELLLMSTE<br>(SEQ ID NO: 188) | (structure with residues Leu, Leu, Leu, Leu, Thr) |
| p300-SID | Dimer C | p16$_{05-16}$<br>DERALLDQLHTL<br>(SEQ ID NO: 189) | (structure with residues Asp, Arg, Leu, Leu, Leu) |
| p300-IBid | Dimer C | IRF3$_{372-381}$<br>LRALVEMARV<br>(SEQ ID NO: 190) | (structure with residues Leu, Glu, Met, Ala, Val) |

X = H, COCH$_3$, amino acid;
Y = OH, NH$_2$, OMe, amino acid
bold residues indicate key residues for binding.

TABLE 3

Exemplary Oligooxopiperazines and their Helical Targets

| Target | Model Type | Wild Type Sequence Helical Domain* | Oligooxopiperazine Structure* |
|---|---|---|---|
| p53/MDM2 | Trimer | p53$_{17-28}$<br>ETFSDLWKLLPE<br>(SEQ ID NO: 186) | (structure with residues Phe, Trp, Lys, Leu, Leu) |

TABLE 3-continued

Exemplary Oligooxopiperazines and their Helical Targets

| Target | Model Type | Wild Type Sequence Helical Domain* | Oligooxopiperazine Structure* |
|---|---|---|---|
| p53/MDM2 | Dimer A | p53$_{17-28}$<br><br>ETFSDLWKLLPE<br><br>(SEQ ID NO: 186) | Structure displaying Phe, Trp, Lys, Leu side chains |
| Hif1/p300 | Dimer B | Hif1$_{140-147}$<br><br>ELLRALDQ<br><br>(SEQ ID NO: 187) | Structure displaying Leu, Leu, Ala, Gln side chains |
| cMyb/KIX | Dimer C | cMyb$_{91-103}$<br><br>RIKELELLLMSTE<br><br>(SEQ ID NO: 188) | Structure displaying Leu, Leu, Leu, Leu, Thr side chains |

*bold residues are critical for binding of the helix to the protein partner

Example 9

Biological Potential of Oligooxopiperazines

The potential of the oligooxopiperazine molecules of the present invention to inhibit protein-protein interactions in which helices play key roles at the interfaces will be tested using the Bcl-xL/Bak-BH3 (Sattler et al., *Science* 275:983-986 (1997), which is hereby incorporated by reference in its entirety) and p53/Mdm2 (Kussie et al., *Science* 274:948-953 (1996), which is hereby incorporated by reference in its entirety) complexes as targets. Both of these complexes are intimately involved in regulating the crucial process of programmed cell death. These complexes have been chosen for the initial foray into the control of protein-protein interactions with oligooxopiperazines because these protein complexes have been targeted with several different strategies, including small molecules, allowing the evaluation of the suitability of this approach (Murray et al., *Biopolymers* 88:657-686 (2007); Ernst et al., *Angew. Chem. Int. Ed. Engl.* 42: 535-539 (2003); Walensky et al., *Science* 305:1466-70 (2004); Gemperli et al., *J. Am. Chem. Soc.* 127:1596-7 (2005); Sadowsky et al., *J. Am. Chem. Soc.* 129: 139-154 (2007); Davis et al., *Chem. Soc. Rev.* 36:326-334 (2007), which are hereby incorporated by reference in their entirety).

Oligooxopiperazine 38 (FIG. 10C) has been designed and synthesized to mimic the p53 helix. This helix features three hydrophobic residues phenylalanine, tryptophan, and leucine on the same face (at positions i, i+4, and i+7) and it binds in a deep hydrophobic cleft of Mdm2 (FIG. 10A). Modeling studies suggest that oligooxopiperazine trimer positions 1, 2, and 5, respectively, would overlay well onto i, i+4, and i+7 positions of an α-helix (FIG. 10B). Accordingly, oligooxopiperazine 38 was designed to display phenylalanine, tryptophan and leucine side chains at position 1, 2, and 5 of the trimer, respectively (FIG. 10C). For these preliminary studies, oligooxopiperazine trimer 39, which lacks the key tryptophan residue at position 2, has also been synthesized. This negative control will allow assessment of the specificity of oligooxopiperazines for their targets. A oxopiperazine trimer has the potential to display six residues and mimic a 10-mer helix. In this first generation study only three key residues from p53 will be imported into the oligoxopiperazine scaffold; in subsequent studies the other residues from the p53 sequence will also be introduced and studied in an iterative manner.

In summary, through rational design and synthesis, a new class of nonpeptidic α-helix mimetics have been developed. NMR and circular dichroism spectroscopies provide compelling evidence that oligooxopiperazine dimers adopt stable conformations that reproduce the arrangement of i, i+4, and i+7 residues on an α-helix. Given the importance of the helix conformation in protein-protein interactions, and the potential of nonpeptidic scaffolds that mimic this conformation, these oxopiperazine scaffolds will offer attractive new tools for chemical biology (Jochim and Arora, *Mol. BioSyst.* 5:924-926 (2009); *Jones and Thornton, Proc. Natl. Acad. Sci U.S.A.* 93:13-20(1996), which are hereby incorporated by reference in their entirety). Oxopiperazine helix mimetics have the potential to disrupt chosen protein-protein interactions.

What is claimed:

1. A pharmaceutical formulation comprising:
   (i) an oligooxopiperazine of Formula I:

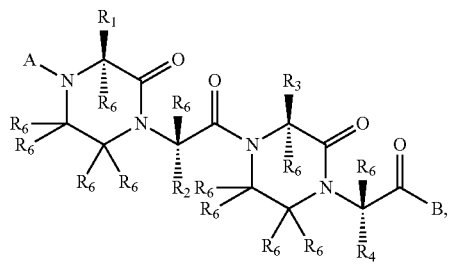

wherein:
each of $R_1$, $R_2$, $R_3$, and $R_4$ is independently an amino acid side chain, H, $N(R)_2$, OR, halogen, an alkyl, or an aryl; wherein each R is independently H, an alkyl, or an aryl;
each $R_6$ is independently H, $N(R)_2$, OR, halogen, an alkyl, or an aryl; wherein each R is independently H, an alkyl, or an aryl;
A is $X_1$ or C, wherein:
  $X_1$ is H, COR', $CO_2R'$, CONHR', an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and
  C is a moiety of the formula

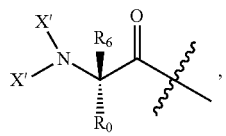

wherein:
  each X' is independently H, COR', $CO_2R'$, CONHR', $N(R'')_2$, an alkyl, an aryl, an arylalkyl, a cycloalkyl, a heteroaryl, a targeting moiety, or a tag; wherein: R' is H, an alkyl, an aryl, an arylalkyl, a cycloalkyl, a heteroaryl, a targeting moiety, or a tag; and
  each R'' is independently H, $CO_2R'$, CONHR', an alkyl, an aryl, an arylalkyl, a cycloalkyl, a heteroaryl, a targeting moiety, or a tag;

$R_0$ is an amino acid side chain, H, $N(R)_2$, OR, halogen, an alkyl, or an aryl;
  wherein each R is independently H, an alkyl, or an aryl; and
$R_6$ is H, $N(R)_2$, OR, halogen, an alkyl, or an aryl; wherein each R is independently H, an alkyl, or an aryl; and B is Y or D, wherein:
  Y is OR', COR', $N(R''')_2$, an alkyl, an aryl, an arylalkyl, a cycloalkyl, a heteroaryl, a protecting group for protection of a carboxylic acid, a targeting moiety, or a tag; wherein:
    R' is H, an alkyl, an aryl, an arylalkyl, a cycloalkyl, a heteroaryl, a targeting moiety, or a tag; and
    each R''' is independently H, $CO_2R'$, CONHR', an alkyl, an aryl, an arylalkyl, a cycloalkyl, a heteroaryl, a targeting moiety, or a tag; and
  D is a moiety of the formula

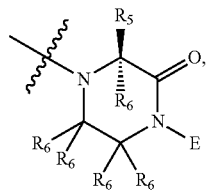

wherein:
$R_5$ is an amino acid side chain, H, $N(R)_2$, OR, halogen, an alkyl, or an aryl; wherein each R is independently H, an alkyl, or an aryl;
$R_6$ is H, $N(R)_2$, OR, halogen, an alkyl, or an aryl; wherein each R is independently H, an alkyl, or an aryl; and
E is $X_2$ or F, wherein:
  $X_2$ is H, COR', $CO_2R'$, CONHR', an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and F is a moiety of the formula

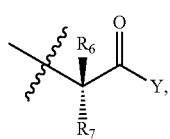

wherein:

$R_6$ is H, $N(R)_2$, OR, halogen, an alkyl, or an aryl; wherein each R is independently H, an alkyl, or an aryl;

$R_7$ is an amino acid side chain; and

Y is OR', COR', $N(R''')_2$, an alkyl, an aryl, an arylalkyl, a cycloalkyl, a heteroaryl, a protecting group for protection of a carboxylic acid, a targeting moiety, or a tag; wherein:

R' is H, an alkyl, an aryl, an arylalkyl, a cycloalkyl, a heteroaryl, a targeting moiety, or a tag; and each R''' is independently H, $CO_2R'$, CONHR', an alkyl, an aryl, an arylalkyl, a cycloalkyl, a heteroaryl, a targeting moiety, or a tag;

with the proviso that A and B are not both, respectively, C and D, and (ii) a pharmaceutically acceptable vehicle.

2. The pharmaceutical formulation according to claim 1, wherein the oligooxopiperazine is an oligooxopiperazine of Formula IA:

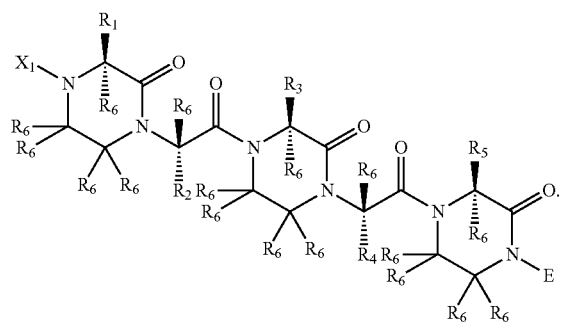

3. The pharmaceutical formulation according to claim 2, wherein the oligooxopiperazine is selected from the group consisting of

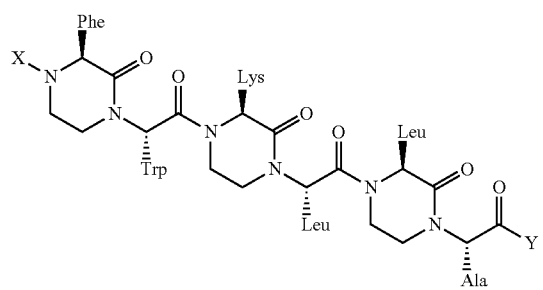

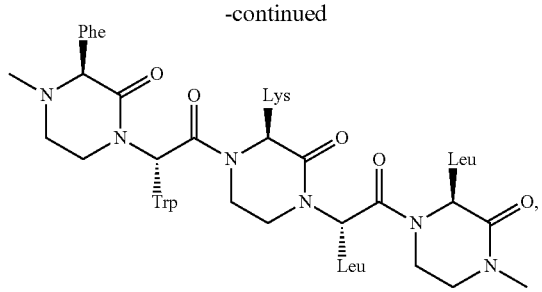

wherein X is H, $COCH_3$, or any amino acid, and Y is OH, $NH_2$, OMe, or any amino acid.

4. The pharmaceutical formulation according to claim 1, wherein the oligooxopiperazine is an oligooxopiperazine of Formula IB:

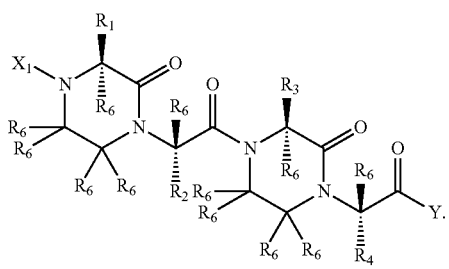

5. The pharmaceutical formulation according to claim 4, wherein the oligooxopiperazine is selected from the group consisting of

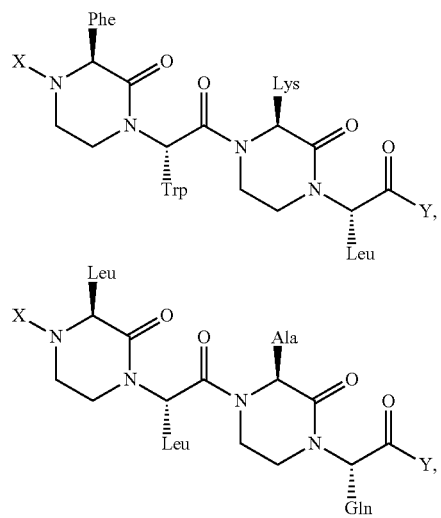

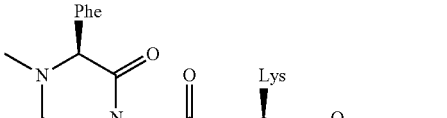

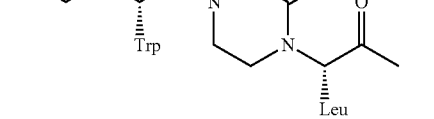

-continued

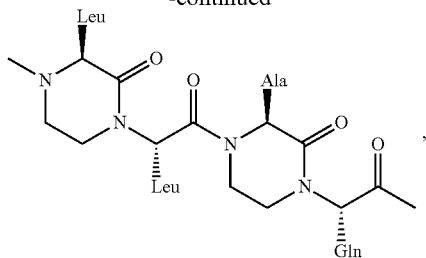

wherein X is H, COCH₃, or any amino acid, and Y is OH, NH₂, OMe, or any amino acid.

6. The pharmaceutical formulation according to claim 1, wherein the oligooxopiperazine is an oligooxopiperazine of Formula IC:

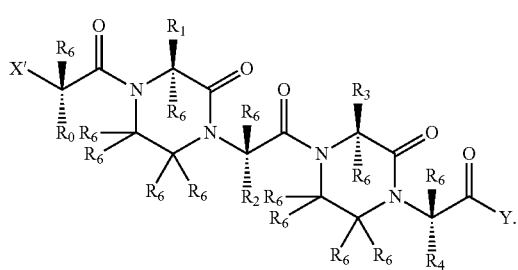

7. The pharmaceutical formulation according to claim 6, wherein the oligooxopiperazine is selected from the group consisting of

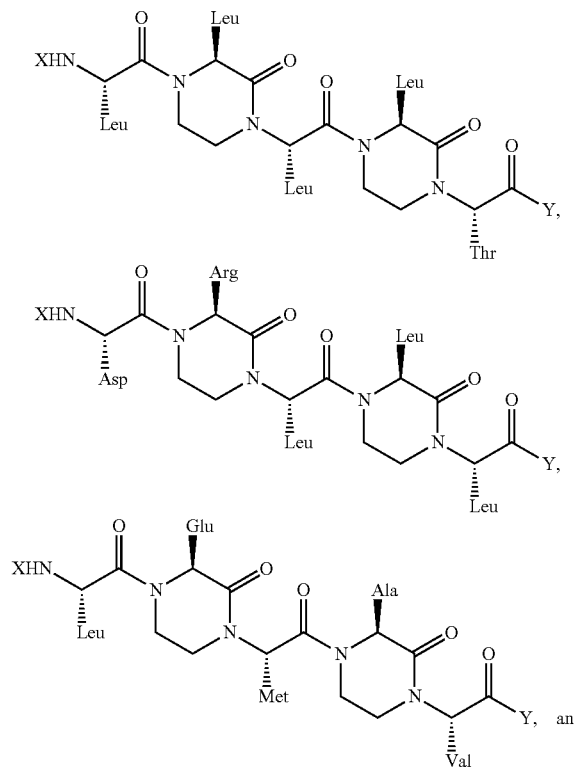

-continued

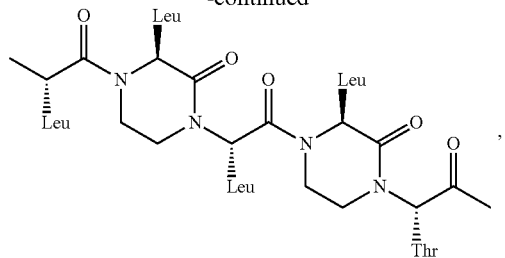

wherein X is H, COCH₃, or any amino acid, and Y is OH, NH₂, OMe, or any amino acid.

8. The pharmaceutical formulation according to claim 1, wherein the oligooxopiperazine mimics an α-helix involved in a protein-protein interaction.

9. The pharmaceutical formulation according to claim 2, wherein $R_1$, $R_2$, $R_4$, and $R_5$ mimic the amino acid side chain of, respectively, residues i, i+4, i+6, and i+7 of an α-helix involved in a protein-protein interaction.

10. The pharmaceutical formulation according to claim 4, wherein $R_1$, $R_2$, and $R_4$ mimic the amino acid side chain of, respectively, residues i, i+4, and i+7 of an α-helix involved in a protein-protein interaction.

11. The pharmaceutical formulation according to claim 4, wherein $R_1$, $R_2$, and $R_4$ mimic the amino acid side chain of, respectively, residues i, i+4, and i+6 of an α-helix involved in a protein-protein interaction.

12. The pharmaceutical formulation according to claim 6, wherein $R_0$, $R_1$, $R_2$, $R_3$, and $R_4$ mimic the amino acid side chain of, respectively, residues i, i+2, i+3, i+4, and i+7 of an α-helix involved in a protein-protein interaction.

13. The pharmaceutical formulation according to claim 8, wherein the α-helix is selected from the group consisting of those identified in FIGS. 11A-11I.

14. A method of making an oligooxopiperazine of Formula IA:

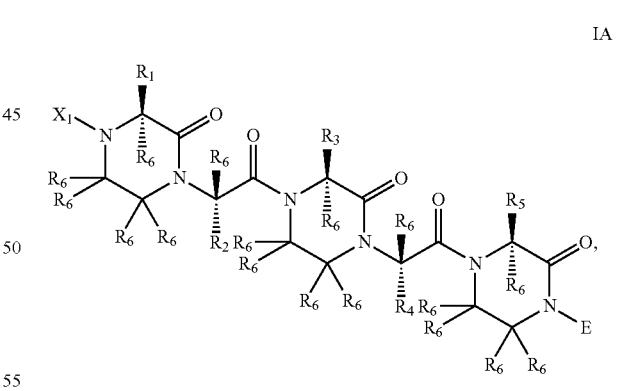

wherein:
each of $R_1$, $R_2$, $R_3$, $R_4$, and $R_5$ is independently an amino acid side chain, H, N(R)₂, OR, halogen, an alkyl, or an aryl; wherein each R is independently H, an alkyl, or an aryl;
each $R_6$ is independently H, N(R)₂, OR, halogen, an alkyl, or an aryl; wherein each R is independently H, an alkyl, or an aryl;
$X_1$ is H, COR', CO₂R', CONHR', an alkyl, an aryl, an arylalkyl, a cycloalkyl, a heteroaryl, a protecting group for protection of an amine, a targeting moiety, or a tag;

wherein R' is H, an alkyl, an aryl, an arylalkyl, a cycloalkyl, a heteroaryl, a targeting moiety, or a tag; and E is $X_2$ or F, wherein:

$X_2$ is H, COR', $CO_2R'$, CONHR', an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and F is a moiety of the formula

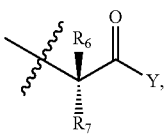

wherein:

$R_6$ is H, $N(R)_2$, OR, halogen, an alkyl, or an aryl; wherein each R is independently H, an alkyl, or an aryl;

$R_7$ is an amino acid side chain; and

Y is OR', COR', $N(R''')_2$, an alkyl, an aryl, an arylalkyl, a cycloalkyl, a heteroaryl, a protecting group for protection of a carboxylic acid, a targeting moiety, or a tag; wherein:

R' is H, an alkyl, an aryl, an arylalkyl, a cycloalkyl, a heteroaryl, a targeting moiety, or a tag; and each R''' is independently H, $CO_2R'$, CONHR', an alkyl, an aryl, an arylalkyl, a cycloalkyl, a heteroaryl, a targeting moiety, or a tag;

(i) wherein said method comprises:

providing a compound of Formula III:

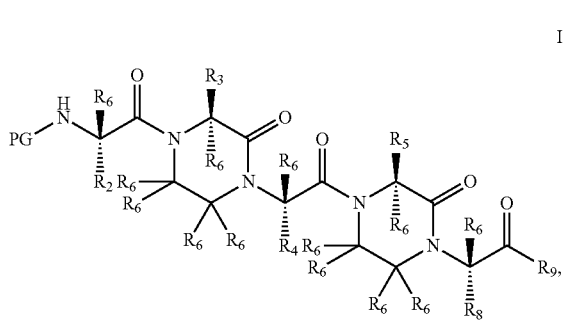

wherein:

PG is a protecting group for the protection of an amine;

$R_8$ is an amino acid side chain, H, $N(R)_2$, OR, halogen, an alkyl, or an aryl; wherein each R is independently H, an alkyl, or an aryl; and $R_9$ is —O-Res or —NH-Res, wherein Res is a solid phase peptide synthesis resin;

providing a compound of Formula $IV_1$:

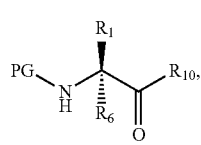

wherein $R_{10}$ is —OH or a halide; and reacting the compound of Formula III with a first alkylating agent and the compound of Formula $IV_1$ under conditions effective to produce a compound of Formula V:

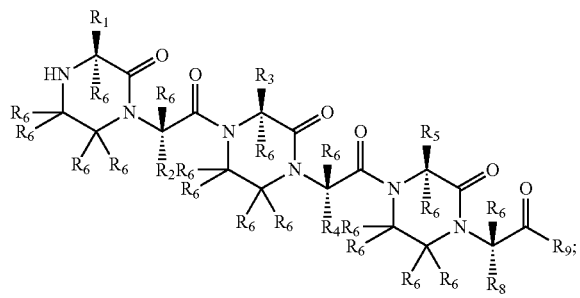

wherein:

if E is not —$CR_6R_7$—CO—Y, where $R_7$ is the same as $R_8$ and Y is the same as $R_9$, said method further comprises converting —$CR_6R_8$—CO—$R_9$ in the compound of Formula V to E; and if $X_1$ is not hydrogen, said method further comprises converting the N-terminal hydrogen in the compound of Formula V to $X_1$;

or (ii) wherein said method comprises:

providing a compound of Formula X:

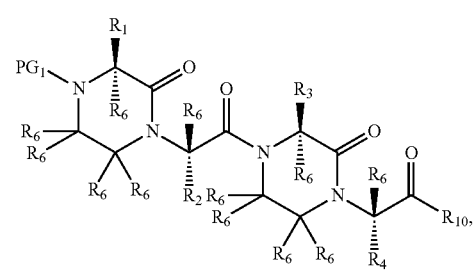

wherein:

$PG_1$ is a protecting group for the protection of an amine, and $R_{10}$ is —OH or a halide;

providing a compound of Formula $XI_{5/8}$:

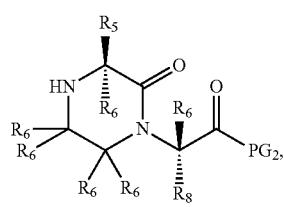

wherein:

$PG_2$ is a protecting group for the protection of a carboxylic acid; and $R_8$ is an amino acid side chain, H, $N(R)_2$, OR, halogen, an alkyl, or an aryl; wherein each R is independently H, an alkyl, or an aryl; and reacting the compound of Formula X with the compound of Formula $XI_{5/8}$ under conditions effective to produce a compound of Formula XII:

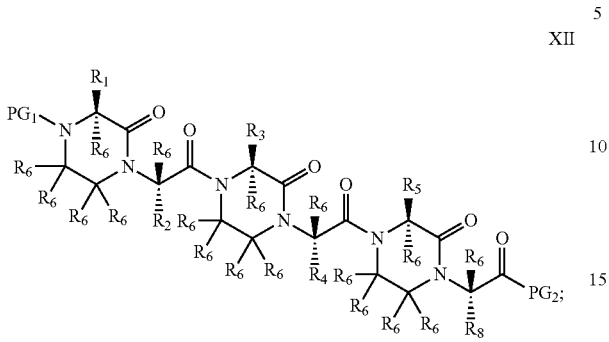

wherein:
  if E is not —$CR_6R_7$—CO—Y, where $R_7$ is the same as $R_8$ and Y is the same as $PG_2$, said method further comprises converting —$CR_6R_8$—CO—$PG_2$ in the compound of Formula XII to E; and wherein if $X_1$ is not $PG_1$, said method further comprises converting $PG_1$ in the compound of Formula XII to $X_1$.

15. The method according to claim 14, wherein the first alkylating agent is selected from the group consisting of X—$CH_2$—CH=CH, X—$CH_2$—$CH(OR_{11})_2$, X—$(CH_2)_2$—X, and X—$(CH_2)_2$—OH, wherein each X is independently a leaving group and each $R_{11}$ is independently an alkyl.

16. The method according to claim 14, wherein said providing a compound of Formula III comprises:

providing a compound of Formula VI:

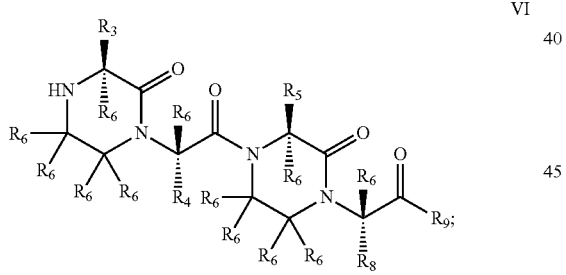

providing a compound of Formula $IV_2$:

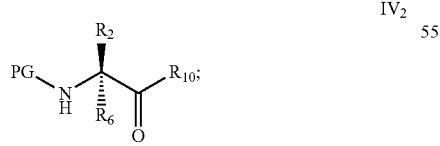

and reacting the compound of Formula VI with the compound of Formula $IV_2$ under conditions effective to produce a compound of Formula III.

17. The method according to claim 16, wherein said providing a compound of Formula VI comprises:

providing a compound of Formula VII:

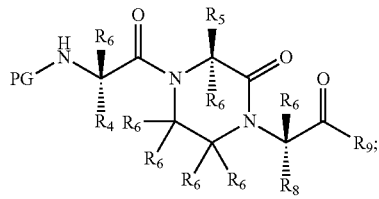

providing a compound of Formula $IV_3$:

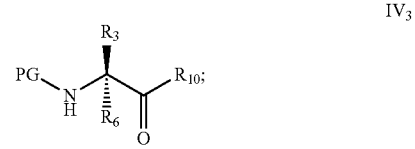

and reacting the compound of Formula VII with a second alkylating agent and the compound of Formula $IV_3$ under conditions effective to produce a compound of Formula VI.

18. The method according to claim 17, wherein the second alkylating agent is selected from the group consisting of X—$CH_2$—CH=CH, X—$CH_2$—$CH(OR_{11})_2$, X—$(CH_2)_2$—X, and X—$(CH_2)_2$—OH, wherein each X is independently a leaving group and each $R_{11}$ is independently an alkyl.

19. The method according to claim 17, wherein said providing a compound of Formula VII comprises:

providing a compound of Formula VIII:

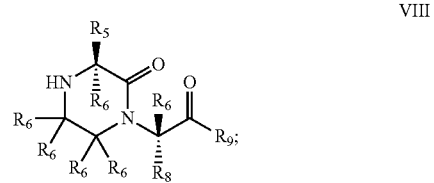

providing a compound of Formula $IV_4$:

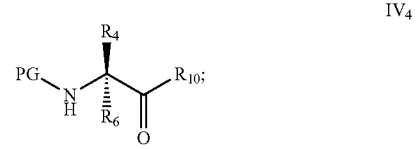

and reacting the compound of Formula XIII with the compound of Formula $IV_4$ under conditions effective to produce a compound of Formula VII.

20. The method according to claim 19, wherein said providing a compound of Formula VIII comprises:

providing a compound of Formula IX:

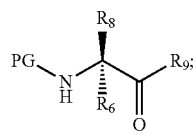

providing a compound of Formula IV$_5$:

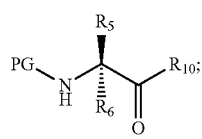

and
reacting the compound of Formula IX with a third alkylating agent and the compound of Formula IV$_5$ under conditions effective to produce a compound of Formula VIII.

21. The method according to claim 20, wherein the third alkylating agent is selected from the group consisting of X—CH$_2$—CH=CH, X—CH$_2$—CH(OR$_{11}$)$_2$, X—(CH$_2$)$_2$—X, and X—(CH$_2$)$_2$—OH, wherein each X is independently a leaving group and each R$_{if}$ is independently an alkyl.

22. A method of making an oligooxopiperazine of Formula IB:

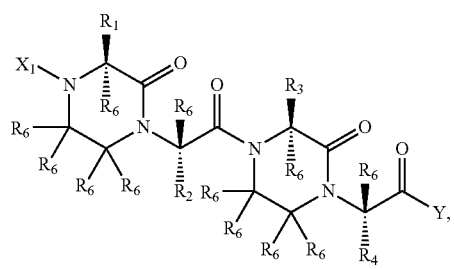

wherein:
each of R$_1$, R$_2$, R$_3$, and R$_4$ is independently an amino acid side chain, H, N(R)$_2$, OR, halogen, an alkyl, or an aryl; wherein each R is independently H, an alkyl, or an aryl;
each R$_6$ is independently H, N(R)$_2$, OR, halogen, an alkyl, or an aryl; wherein each R is independently H, an alkyl, or an aryl;
X$_1$ is H, COR', CO$_2$R', CONHR', an alkyl, an aryl, an arylalkyl, a cycloalkyl, a heteroaryl, a protecting group for protection of an amine, a targeting moiety, or a tag; wherein R' is H, an alkyl, an aryl, an arylalkyl, a cycloalkyl, a heteroaryl, a targeting moiety, or a tag; and
Y is OR', COR', N(R''')$_2$, an alkyl, an aryl, an arylalkyl, a cycloalkyl, a heteroaryl, a protecting group for protection of a carboxylic acid, a targeting moiety, or a tag; wherein:
R' is H, an alkyl, an aryl, an arylalkyl, a cycloalkyl, a heteroaryl, a targeting moiety, or a tag; and
each R''' is independently H, CO$_2$R', CONHR', an alkyl, an aryl, an arylalkyl, a cycloalkyl, a heteroaryl, a targeting moiety, or a tag;

(i) wherein said method comprises:
providing a compound of Formula VII':

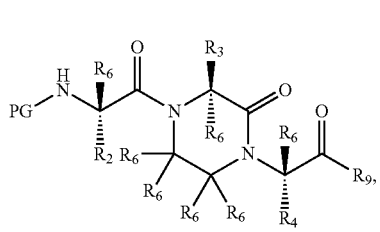

wherein:
PG is a protecting group for the protection of an amine; and
R$_9$ is —O-Res or —NH-Res, wherein Res is a solid phase peptide synthesis resin;
providing a compound of Formula IV$_1$:

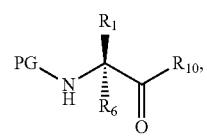

wherein R$_{10}$ is —OH or a halide;
reacting the compound of Formula VII' with a first alkylating agent and the compound of Formula IV$_1$ under conditions effective to produce a compound of Formula VI':

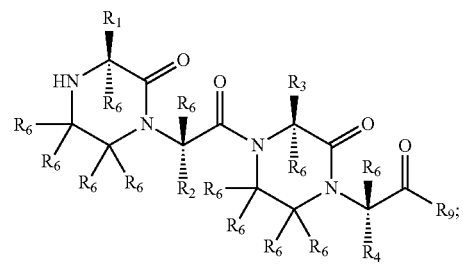

and
converting —R$_9$ in the compound of Formula VI' to Y;
wherein if X$_1$ is not hydrogen, said method further comprises converting the N-terminal hydrogen in the compound of Formula VI' to X$_1$;
or (ii) wherein said method comprises:
providing a compound of Formula XIII:

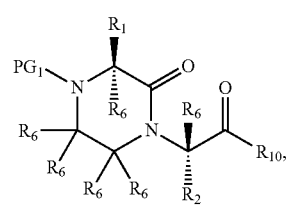

wherein:

PG$_1$ is a protecting group for the protection of an amine, and

R$_{10}$ is —OH or a halide;

providing a compound of Formula XI$_{3/4}$:

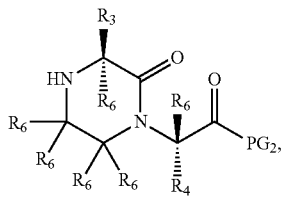

XI$_{3/4}$ wherein PG$_2$ is a protecting group for the protection of a carboxylic acid; and reacting the compound of Formula XIII with the compound of Formula XI$_{3/4}$ under conditions effective to produce a compound of Formula X':

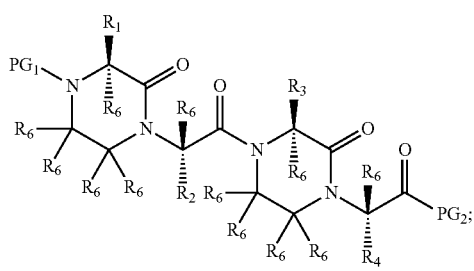

X' and converting —PG$_2$ in the compound of Formula X' to Y;

wherein if X$_1$ is not PG$_1$, said method further comprises converting PG$_1$ in the compound of Formula X' to X$_1$.

23. The method according to claim 22, wherein the first alkylating agent is selected from the group consisting of X—CH$_2$—CH=CH, X—CH$_2$—CH(OR$_{11}$)$_2$, X—(CH$_2$)$_2$—X, and X—(CH$_2$)$_2$—OH, wherein each X is independently a leaving group and each R$_{ii}$ is independently an alkyl.

24. The method according to claim 22, wherein said providing a compound of Formula VII' comprises:

providing a compound of Formula VIII':

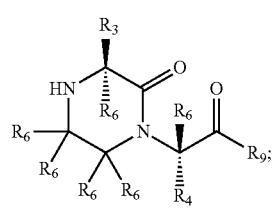

VIII' providing a compound of Formula IV$_2$:

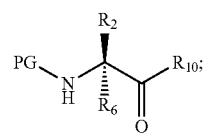

IV$_2$ and reacting the compound of Formula VIII' with the compound of Formula IV$_2$ under conditions effective to produce a compound of Formula VII'.

25. The method according to claim 24, wherein said providing a compound of Formula VIII' comprises:

providing a compound of Formula IX':

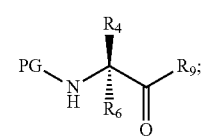

IX' providing a compound of Formula IV$_3$:

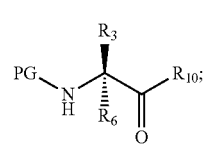

IV$_3$ and reacting the compound of Formula IX' with a second alkylating agent and the compound of Formula IV$_3$ under conditions effective to produce a compound of Formula VIII'.

26. The method according to claim 25, wherein the second alkylating agent is selected from the group consisting of X—CH$_2$—CH=CH, X—CH$_2$—CH(OR$_{11}$)$_2$, X—(CH$_2$)$_2$—X, and X—(CH$_2$)$_2$—OH, wherein each X is independently a leaving group and each R$_{ii}$ is independently an alkyl.

27. A method of making an oligooxopiperazine of Formula IC:

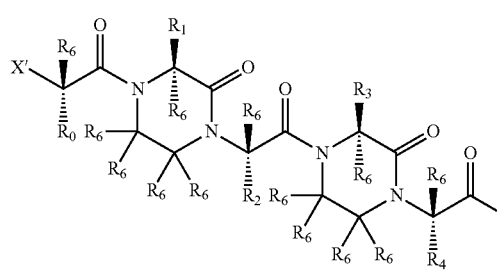

IC wherein:

each of R$_0$, R$_1$, R$_2$, R$_3$, and R$_4$ is independently an amino acid side chain, H, N(R)$_2$, OR, halogen, an alkyl, or an aryl; wherein each R is independently H, an alkyl, or an aryl;

each $R_6$ is independently H, $N(R)_2$, OR, halogen, an alkyl, or an aryl; wherein each R is independently H, an alkyl, or an aryl;

X' is H, COR', $CO_2R'$, CONHR', $N(R'')_2$, an alkyl, an aryl, an arylalkyl, a cycloalkyl, a heteroaryl, a targeting moiety, or a tag; wherein:
  R' is H, an alkyl, an aryl, an arylalkyl, a cycloalkyl, a heteroaryl, a targeting moiety, or a tag; and
  each R" is independently H, $CO_2R'$, CONHR', an alkyl, an aryl, an arylalkyl, a cycloalkyl, a heteroaryl, a targeting moiety, or a tag; and Y is OR', COR', $N(R''')_2$, an alkyl, an aryl, an arylalkyl, a cycloalkyl, a heteroaryl, a protecting group for protection of a carboxylic acid, a targeting moiety, or a tag; wherein:
  R' is H, an alkyl, an aryl, an arylalkyl, a cycloalkyl, a heteroaryl, a targeting moiety, or a tag; and
  each R''' is independently H, $CO_2R'$, CONHR', an alkyl, an aryl, an arylalkyl, a cycloalkyl, a heteroaryl, a targeting moiety, or a tag;

(i) wherein said method comprises:
providing a compound of Formula VII':

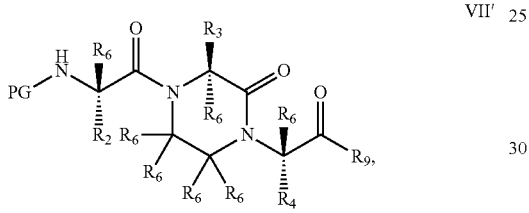

VII' wherein:
PG is a protecting group for the protection of an amine; and
$R_9$ is —O-Res or —NH-Res, wherein Res is a solid phase peptide synthesis resin;
providing a compound of Formula $IV_1$:

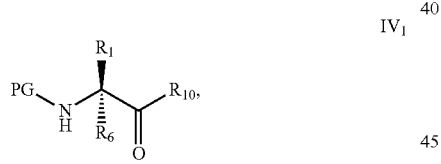

$IV_1$ wherein $R_{10}$ is —OH or a halide;
reacting the compound of Formula VII' with a first alkylating agent and the compound of Formula $IV_1$ under conditions effective to produce a compound of Formula VI':

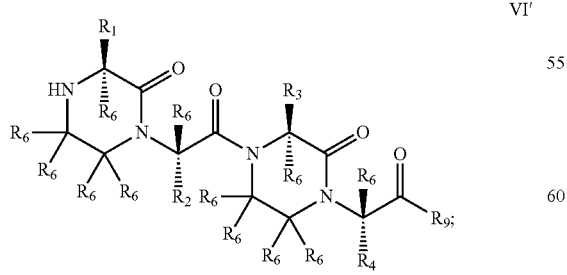

VI' converting —$R_9$ in the compound of Formula VI' to Y; and
converting the N-terminal hydrogen in the compound of Formula VI' to a moiety of formula

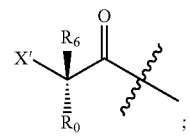

;

or (ii) wherein said method comprises:
providing a compound of Formula XIII:

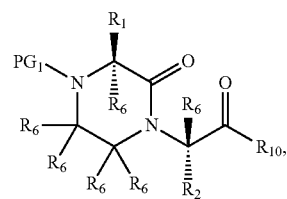

XIII wherein:
$PG_1$ is a protecting group for the protection of an amine, and
$R_{10}$ is —OH or a halide;
providing a compound of Formula $XI_{3/4}$:

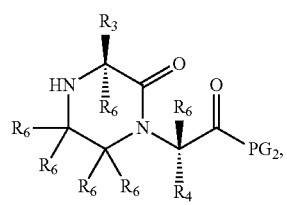

$XI_{3/4}$ wherein $PG_2$ is a protecting group for the protection of a carboxylic acid; and
reacting the compound of Formula XIII with the compound of Formula $XI_{3/4}$ under conditions effective to produce a compound of Formula X':

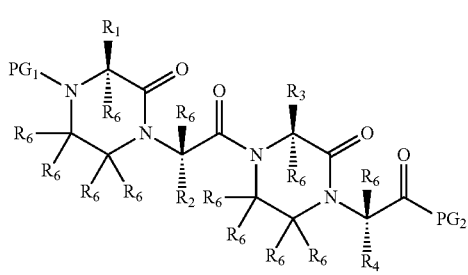

X' converting —$PG_2$ in the compound of Formula X' to Y; and
converting $PG_1$ in the compound of Formula X' to a moiety of formula

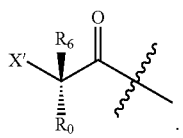

28. The method according to claim 27, wherein the first alkylating agent is selected from the group consisting of X—CH$_2$—CH=CH, X—CH$_2$—CH(OR$_{11}$)$_2$, X—(CH$_2$)$_2$—X, and X—(CH$_2$)$_2$—OH, wherein each X is independently a leaving group and each R$_{11}$ is independently an alkyl.

29. The method according to claim 27, wherein said providing a compound of Formula VII' comprises:

providing a compound of Formula VIII':

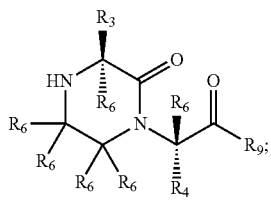

providing a compound of Formula IV$_2$:

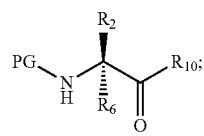

and reacting the compound of Formula VIII' with the compound of Formula IV$_2$ under conditions effective to produce a compound of Formula VII'.

30. The method according to claim 29, wherein said providing a compound of Formula VIII' comprises:

providing a compound of Formula IX':

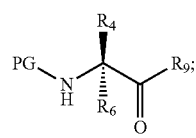

providing a compound of Formula IV$_3$:

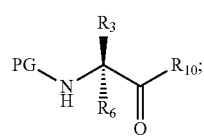

and reacting the compound of Formula IX' with a second alkylating agent and the compound of Formula IV$_3$ under conditions effective to produce a compound of Formula VIII'.

31. The method according to claim 14, wherein said providing a compound of Formula X comprises:

providing a compound of Formula X':

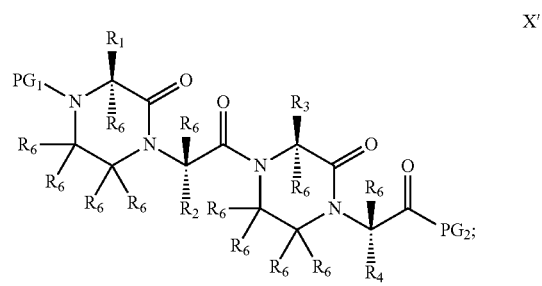

and converting PG$_1$ in the compound of Formula X' to hydrogen and converting PG$_2$ in the compound of Formula X' to R$_{10}$ to produce a compound of Formula X.

32. The method according to claim 31, wherein said providing a compound of Formula X' comprises:

providing a compound of Formula XIII:

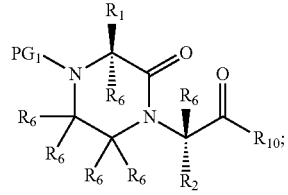

providing a compound of Formula XI$_{3/4}$:

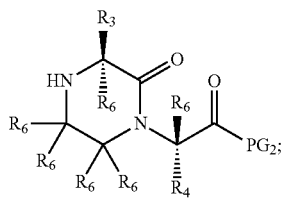

and reacting the compound of Formula XIII with the compound of Formula XI$_{3/4}$ under conditions effective to produce a compound of Formula X'.

33. The method according to claim 32, wherein said providing a compound of Formula XIII comprises:

providing a compound of Formula XI$_{1/2}$:

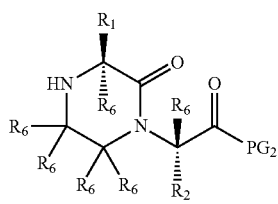

XI$_{1/2}$ and reacting the compound of Formula XI$_{1/2}$ with a protecting group under conditions effective to produce a compound of Formula XIII.

34. The method according to claim 33, wherein said providing a compound of Formula XI$_{1/2}$ comprises:

providing a compound of Formula XIV:

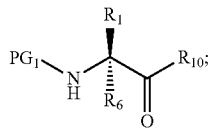

XIV providing a compound of Formula XV:

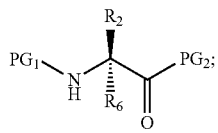

XV and reacting the compound of Formula XIV with an alkylating agent and the compound of Formula XV under conditions effective to produce a compound of Formula XI$_{1/2}$.

35. The method according to claim 34, wherein the alkylating agent is selected from the group consisting of X—CH$_2$—CH=CH, X—CH$_2$—CH(OR$_{11}$)$_2$, X—(CH$_2$)$_2$—X, and X—(CH$_2$)$_2$—OH, wherein each X is independently a leaving group and each R$_{11}$ is independently an alkyl.

36. The method according to claim 22, wherein said providing a compound of Formula XIII comprises:

providing a compound of Formula XI$_{1/2}$:

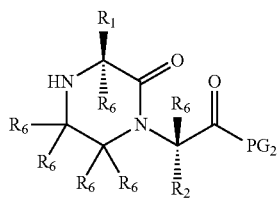

XI$_{1/2}$ and reacting the compound of Formula XI$_{1/2}$ with a protecting group under conditions effective to produce a compound of Formula XIII.

37. The method according to claim 36, wherein said providing a compound of Formula XI$_{1/2}$ comprises:

providing a compound of Formula XIV:

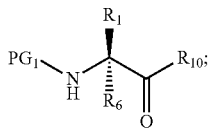

XIV providing a compound of Formula XV:

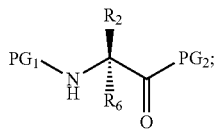

XV and reacting the compound of Formula XIV with an alkylating agent and the compound of Formula XV under conditions effective to produce a compound of Formula XI$_{1/2}$.

38. The method according to claim 37, wherein the alkylating agent is selected from the group consisting of X—CH$_2$—CH=CH, X—CH$_2$—CH(OR$_{11}$)$_2$, X—(CH$_2$)$_2$—X, and X—(CH$_2$)$_2$—OH, wherein each X is independently a leaving group and each R$_{11}$ is independently an alkyl.

39. The method according to claim 27, wherein said providing a compound of Formula XIII comprises:

providing a compound of Formula XI$_{1/2}$:

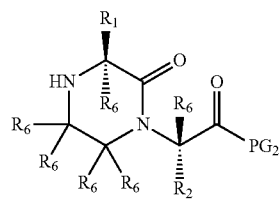

XI$_{1/2}$ and reacting the compound of Formula XI$_{1/2}$ with a protecting group under conditions effective to produce a compound of Formula XIII.

40. The method according to claim 39, wherein said providing a compound of Formula XI$_{1/2}$ comprises:

providing a compound of Formula XIV:

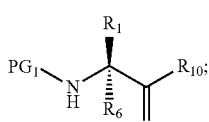

XIV providing a compound of Formula XV:

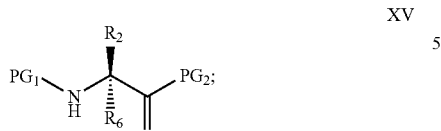

and
reacting the compound of Formula XIV with an alkylating agent and the compound of Formula XV under conditions effective to produce a compound of Formula $XI_{1/2}$.

41. The method according to claim 40, wherein the alkylating agent is selected from the group consisting of $X-CH_2-CH=CH$, $X-CH_2-CH(OR_{11})_2$, $X-(CH_2)_2-X$, and $X-(CH_2)_2-OH$, wherein each X is independently a leaving group and each $R_{11}$ is independently an alkyl.

* * * * *